United States Patent
Pan et al.

(10) Patent No.: US 10,441,596 B2
(45) Date of Patent: *Oct. 15, 2019

(54) METHODS AND COMPOSITIONS RELATED TO GLUCOCORTICOID RECEPTOR ANTAGONISTS AND BREAST CANCER

(71) Applicant: The University of Chicago, Chicago, IL (US)

(72) Inventors: Deng Pan, Chicago, IL (US); Masha Kocherginsky, Chicago, IL (US); Suzanne D. Conzen, Park Ridge, IL (US)

(73) Assignee: The University of Chicago, Chicago, IL (US)

( * ) Notice: Subject to any disclaimer, the term of this patent is extended or adjusted under 35 U.S.C. 154(b) by 217 days.

This patent is subject to a terminal disclaimer.

(21) Appl. No.: 15/448,827

(22) Filed: Mar. 3, 2017

(65) Prior Publication Data

US 2017/0182066 A1  Jun. 29, 2017

Related U.S. Application Data

(63) Continuation of application No. 14/296,127, filed on Jun. 4, 2014, now Pat. No. 9,623,032, which is a continuation of application No. 14/172,051, filed on Feb. 4, 2014, now Pat. No. 9,149,485, which is a continuation of application No. 13/071,363, filed on Mar. 24, 2011, now Pat. No. 8,710,035.

(60) Provisional application No. 61/317,182, filed on Mar. 24, 2010.

(51) Int. Cl.

| | |
|---|---|
| *A61K 31/575* | (2006.01) |
| *A61K 31/00* | (2006.01) |
| *A61K 45/06* | (2006.01) |
| *A61K 31/282* | (2006.01) |
| *A61K 31/337* | (2006.01) |
| *A61K 31/357* | (2006.01) |
| *A61K 31/4745* | (2006.01) |
| *A61K 31/7068* | (2006.01) |
| *A61K 33/24* | (2019.01) |
| *A61K 39/395* | (2006.01) |
| *A61N 5/00* | (2006.01) |
| *A61J 1/00* | (2006.01) |
| *A61K 31/567* | (2006.01) |
| *A61K 31/58* | (2006.01) |

(52) U.S. Cl.
CPC .............. *A61K 31/575* (2013.01); *A61J 1/00* (2013.01); *A61K 31/282* (2013.01); *A61K 31/337* (2013.01); *A61K 31/357* (2013.01); *A61K 31/4745* (2013.01); *A61K 31/567* (2013.01); *A61K 31/58* (2013.01); *A61K 31/7068* (2013.01); *A61K 33/24* (2013.01); *A61K 39/3955* (2013.01); *A61K 45/06* (2013.01); *A61N 5/00* (2013.01)

(58) Field of Classification Search
CPC .............................. A61K 31/575; A61K 31/00
USPC ............................................... 514/171; 435/4
See application file for complete search history.

(56) References Cited

U.S. PATENT DOCUMENTS

| | | | |
|---|---|---|---|
| 8,003,689 B2 | 8/2011 | Veverka | |
| 8,658,128 B2 † | 2/2014 | Altschul | |
| 8,710,035 B2 | 4/2014 | Pan et al. | |
| 9,114,147 B2 † | 8/2015 | Altschul | |
| 9,149,485 B2 | 10/2015 | Pan et al. | |
| 9,623,032 B2 | 4/2017 | Pan et al. | |
| 2002/0115613 A1 | 8/2002 | Kumar | |
| 2005/0124533 A1 | 6/2005 | Schatzberg et al. | |
| 2006/0063748 A1 | 3/2006 | Belanoff | |
| 2008/0287419 A1 | 11/2008 | Bruncko et al. | |
| 2010/0135956 A1 | 6/2010 | Gant et al. | |
| 2014/0315866 A1 | 10/2014 | Pan et al. | |

FOREIGN PATENT DOCUMENTS

WO     2009064738 A2     5/2009

OTHER PUBLICATIONS

Gura (Science. 1997; 278: 1041-1042).*
Dennis (Nature. Aug. 7, 2006; 442: 739-741).*
Reagan-Shaw et al. (FASEB J, 2007, 22: 659-61).*
Data Sheet: Glucocorticoid Receptor mouse monoclonal antibody NCL-GCR, Novocastra Laboratories Ltd., available at http://www.ebiotrade.com/buyf/Novocastra/data/hrerp/gcr.pdf, accessed on Jun. 7, 2011.
Identification of Glucocorticoid Receptor (GR) signatures in primary human breast cancer: Association with relapse-free survival time, poster presented by S.D. Conzen as a short talk, presented at Nuclear Receptors: Signaling, Gene Regulation and Cancer, Keystone Symposia on Molecular and Cellular Biology, Keystone Resort, Keystone, Colorado, Mar. 25, 2010.
Belanoff et al., Selective glucocorticoid receptor {type II} antagonists prevent weight gain caused by olanzapine in rats, Eur. J. Pharmacal., vol. 655, 2011, pp. 117-120.

(Continued)

*Primary Examiner* — Yan Xiao

(74) *Attorney, Agent, or Firm* — Kilpatrick Townsend & Stockton LLP

(57) ABSTRACT

Embodiments of the invention are directed to methods of determining the prognosis of a breast cancer patient by evaluating the activity of the glucocorticoid receptor in tumor cells. Other embodiment include methods of treating breast cancer cells, particularly, chemo-resistant cells, with a glucocorticoid receptor antagonist and an anticancer agent or compound.

20 Claims, 12 Drawing Sheets

Specification includes a Sequence Listing.

(56) References Cited

OTHER PUBLICATIONS

Belova et al., Glucocorticoid receptor expression in breast cancer associates with older patient age, Breast Cancer Res Treat, vol. 116, 2009, pp. 441-447.
Cho et al., Role of activation function domain-1, DNA binding, and coactivator GRIP1 in the expression of partial agonist activity of glucocorticoid receptor-antagonist complexes, Biochemistry, vol. 44, issue 9, 2005, pp. 3547-3561.
Clark, Glucocorticoid Receptor Antagonists, Current Topics in Medicinal Chemistry, vol. 8, 2008, pp. 813-838.
Colleoni et al., Response to primary chemotherapy in breast cancer patients with tumors not expressing estrogen and progesterone receptors, Annals of Oncology, vol. 11, issue 8, 2000, pp. 1057-1059.
Desmedt et al., Strong time dependence of the 76-gene prognostic signature for node-negative breast cancer patients in the TRANSBIG multicenter independent validation series, Clin Cancer Res., vol. 13, 2007, pp. 3207-3214.
Gaddy et al., Mifepristone Induces Growth Arrest, Caspase Activation, and Apoptosis of Estrogen Receptor-Expressing, Antiestrogen-Resistant Breast Cancer Cells, Clin Cancer Res., vol. 10, 2004, pp. 5215-5225.
Grover et al., The initiation of breast and prostate cancer, Carcinogenesis, vol. 23, issue 7, 2002, pp. 1095-1102.
Hein et al., Click Chemistry, A powerful Tool for Pharmaceutical Sciences, Pharmaceutical Research, vol. 25, issue 10, 2008, pp. 2216-2230.
Henderson et al., Estrogens as a cause of human cancer: the Richard and Hinda Rosenthal Foundation award lecture, Cancer Res., vol. 48, 1988, pp. 246-253.
Huang et al., Reversal effect of mifepristone on adriamycin resistance in human breast cancer cell Abstract only line MCF-7/ADM in vitro and in vivo, J Cent South Univ (Med Sci), vol. 35, issue 6, Jun. 2010, pp. 576-583.
Keen et al., The biology of breast carcinoma, Cancer, vol. 97, 3 Supp, 2003, pp. 825-833.
Kriaucionis et al., The nuclear DNA base 5-hydroxymethylcytosine is present in Purkinje neurons and the brain, Science, vol. 15, 2009, pp. 929-930.
Loi et al., Definition of Clinically Distinct Molecular Subtypes in Estrogen Receptor-Positive Breast Carcinomas Through Genomic Grade, Journal of Clinical Oncology, vol. 25, 2006, pp. 1239-1246.
Loi et al., Predicting prognosis using molecular profiling in estrogen receptor-positive breast cancer treated with tamoxifen, BMC Genomics, vol. 9:239, 2008, 12 pages.
Lucci et al., Modification of ceramide metabolism increases cancer cell sensitivity to cytotoxics, Int J. Onco., vol. 15, 1999, pp. 541-546.
Ma et al., IL-21 activates both innate and adaptive immunity to generate potent antitumor responses that require perforin but are independent of IFN-gamma, J. Jmmunol, vol. 171, issue 2, 2003, pp. 608-615.
Melhem et al., Administration of glucocorticoids to ovarian cancer patients is associated with expression of the anti-apoptotic genes SGK1 and MKP1/DUSP1 in ovarian tissues, Clin. Cancer Res., vol. 15, issue 9, 2009, pp. 3196-3204.
Mikosz et al., Glucocorticoid Receptor-mediated Protection from Apoptosis Is Associated with Induction of the Serine/Threonine Survival Kinase Gene, sgk-1, J. Biol. Chem., vol. 276, No. 20, 2001, pp. 16649-16654.
Minn et al., Genes that mediate breast cancer metastasis to lung, Nature. vol. 436(7050)., Jul. 28, 2005, pp. 518-524.
Moran et al., The glucocorticoid receptor mediates a survival signal in human mammary epithelial cells, Cancer Res., vol. 60, issue 4, 2000, pp. 867-872.
Moses et al., The Growing Applications of Click Chemistry, Chern Soc Rev vol. 36, 2007, pp. 1249-1262.
Pan et al., Activation of the glucocorticoid receptor is associated with poor prognosis in estrogen receptor-negative breast cancer, Cancer Research, vol. 71, Aug. 25, 2011, pp. 6360-6370.
Pang et al., Dexamethasone decreases xenograft response to paclitaxel through inhibition of tumor cell apoptosis, Cancer Biology & Therapy, vol. 5, Issue 8, 2006, pp. 933-940.
Peeters et al., Differential effects of the new glucocorticoid receptor antagonist ORG 34517 and RU486 (mifepristone) on glucocorticoid receptor nuclear translocation in the AtT20 cell line, Ann. NY Acad. Sci., vol. 1148, 2008, pp. 536-541.
Pike et al., Estrogens, progestogens, normal breast cell proliferation, and breast cancer risk, Epidemiologic Rev., vol. 15, issue 1, 1993, pp. 17-35.
Robinson et al., Octahydrophenanthrene-2, 7-diol Analogues as dissociated Glucocorticoid Receptor Agonists Discovery and Lead Exploration, J. Med. Chem., vol. 52, 2009, pp. 1731-1743.
Sims et al., The removal of multiplicative, systematic bias allows integration of breast cancer gene expression datasets—improving meta-analysis and prediction of prognosis, BMC Medical Genomics, 1:42, 2008, 14 pages.
Smith et al., Expression of glucocorticoid and progesterone nuclear receptor genes in archival breast cancer tissue, Breast Cancer Res., vol. 5, issue 1, 2003, pp. R9-RI2.
Smith et al., Progesterone, glucocorticoid, but not estrogen receptor mRNA is altered in breast cancer stroma, Cancer Lett., vol. 255, 2007, pp. 77-84.
Sorlie et al., Gene expression patterns of breast carcinomas distinguish tumor subclasses with clinical implications, Proc. Natl. Acad. Sci., vol. 98, 2001, pp. 10869-10874.
Sotiriou et al., Gene expression profiling in breast cancer: understanding the molecular basis of histologic grade to improve prognosis, J. Nat/. Cancer Inst, vol. 98, 2006, pp. 262-272.
Srinivas et al., Proteomics for cancer biomarker discovery, Clin. Chem., vol. 48, issue 8, 2002, pp. 1160-1169.
Sui et al., Estrogen Receptor a Mediates Breast Cancer Cell Resistance to Paclitaxel through Inhibition of Apoptotic Cell Death, Cancer Res., vol. 67, issue 11, 2007, pp. 5337-5344.
Wang et al., Gene-expression profiles to predict distant metastasis of lymph-node-negative primary breast cancer, The Lancet, vol. 365, No. 9460, Feb. 19, 2005, pp. 671-679.
Wu et al., Glucocorticoid receptor activation signals through forkhead transcription factor 3a in breast cancer cells, Mol. Endocrinol, vol. 20, issue 10, 2006, pp. 2304-2314.
Wu et al., Microarray Analysis Reveals Glucocorticoid-Regulated Survival Genes That Are Associated With Inhibition of Apoptosis in Breast Epithelial Cells, Cancer Research, vol. 64, 2004, pp. 1757-1764.
Wu et al., Prevalent expression of the immunostimulatory MHC class I chain-related molecule is counteracted by shedding in prostate cancer, J. Clin. Investigation, vol. 114, issue 4, 2004, pp. 560-568.
U.S. Appl. No. 61/317,182, filed Mar. 24, 2010.†
U.S. Appl. No. 14/451,207; Non-Final Office Action dated Feb. 24, 2016.†
U.S. Appl. No. 14/451,207; Notice of Withdrawal from Issue under 37 CFR 1.313(b) dated Feb. 4, 2016.†

\* cited by examiner
† cited by third party

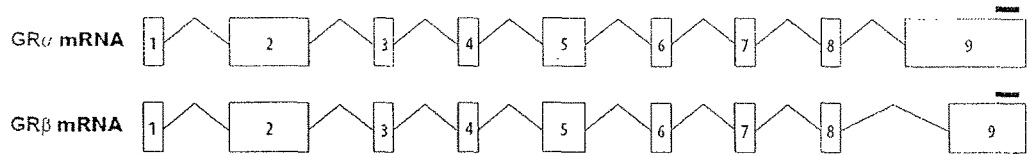

```
Query = GR alpha
Length=6784

18665 = GR beta

ALIGNMENTS

Query   1    GGCGCCGCCTCCACCCGCTCCCCGCTCGGTCCCGCTCGCTCGCCCAGGCCGGGCTGCCCT   60
18665   1    GGCGCCGCCTCCACCCGCTCCCCGCTCGGTCCCGCTCGCTCGCCCAGGCCGGGCTGCCCT   60

Query   61   TTCGCGTGTCCGCGCTCTCTTCCCTCCGCCGCCGCCTCCTCCATTTTGCGAGCTCGTGTC   120
18665   61   TTCGCGTGTCCGCGCTCTCTTCCCTCCGCCGCCGCCTCCTCCATTTTGCGAGCTCGTGTC   120

Query   121  TGTGACGGGAGCCCGAGTCACCGCCTGCCCGTCGGGGACGGATTCTGTGGGTGGAAGGAG   180
18665   121  TGTGACGGGAGCCCGAGTCACCGCCTGCCCGTCGGGGACGGATTCTGTGGGTGGAAGGAG   180

Query   181  ACGCCGCAGCCGGAGCGGCCGAAGCAGCTGGGACCGGGACGGGGCACGCGCGCCCGGAAC   240
18665   181  ACGCCGCAGCCGGAGCGGCCGAAGCAGCTGGGACCGGGACGGGGCACGCGCGCCCGGAAC   240

Query   241  CTCGACCCGCGGAGCCCGGCGCGGGGCGGAGGGCTGGCTTGTCAGCTGGGCAATGGGAGA   300
18665   241  CTCGACCCGCGGAGCCCGGCGCGGGGCGGAGGGCTGGCTTGTCAGCTGGGCAATGGGAGA   300

Query   301  CTTTCTTAAATAGGGGCTCTCCCCCCACCCATGGAGAAAGGGGCGGCTGTTTACTTCCtt   360
18665   301  CTTTCTTAAATAGGGGCTCTCCCCCCACCCATGGAGAAAGGGGCGGCTGTTTACTTCCTT   360

Query   361  ttttAGaaaaaaaaaaTATATTTCCCTCCTGCTCCTTCTGCGTTCACAAGCTAAGTTGT   420
18665   361  TTTTTAGAAAAAAAAAATATATTTCCCTCCTGCTCCTTCTGCGTTCACAAGCTAAGTTGT   420

Query   421  TTATCTCGGCTGCGGCGGGAACTGCGGACGGTGGCGGGCGAGCGGCTCCTCTGCCAGAGT   480
18665   421  TTATCTCGGCTGCGGCGGGAACTGCGGACGGTGGCGGGCGAGCGGCTCCTCTGCCAGAGT   480

Query   481  TGATATTCACTGATGGACTCCAAAGAATCATTAACTCCTGGTAGAGAAGAAAACCCCAGC   540
18665   481  TGATATTCACTGATGGACTCCAAAGAATCATTAACTCCTGGTAGAGAAGAAAACCCCAGC   540

Query   541  AGTGTGCTTGCTCAGGAGAGGGGAGATGTGATGGACTTCTATAAAACCCTAAGAGGAGGA   600
18665   541  AGTGTGCTTGCTCAGGAGAGGGGAGATGTGATGGACTTCTATAAAACCCTAAGAGGAGGA   600

Query   601  GCTACTGTGAAGGTTTCTGCGTCTTCACCCTCACTGGCTGTCGCTTCTCAATCAGACTCC   660
18665   601  GCTACTGTGAAGGTTTCTGCGTCTTCACCCTCACTGGCTGTCGCTTCTCAATCAGACTCC   660

Query   661  AAGCAGCGAAGACTTTTGGTTGATTTTCCAAAAGGCTCAGTAAGCAATGCGCAGCAGCCA   720
18665   661  AAGCAGCGAAGACTTTTGGTTGATTTTCCAAAAGGCTCAGTAAGCAATGCGCAGCAGCCA   720

Query   721  GATCTGTCCAAAGCAGTTTCACTCTCAATGGGACTGTATATGGGAGAGACAGAAACAAAA   780
18665   721  GATCTGTCCAAAGCAGTTTCACTCTCAATGGGACTGTATATGGGAGAGACAGAAACAAAA   780

Query   781  GTGATGGGAAATGACCTGGGATTCCCACAGCAGGGCCAAATCAGCCTTTCCTCGGGGAA   840
18665   781  GTGATGGGAAATGACCTGGGATTCCCACAGCAGGGCCAAATCAGCCTTTCCTCGGGGAA   840

Query   841  ACAGACTTAAAGCTTTTGGAAGAAAGCATTGCAAACCTCAATAGGTCGACCAGTGTTCCA   900
18665   841  ACAGACTTAAAGCTTTTGGAAGAAAGCATTGCAAACCTCAATAGGTCGACCAGTGTTCCA   900
```

FIG. 7A

```
Query    901   GAGAACCCCAAGAGTTCAGCATCCACTGCTGTGTCTGCTGCCCCCACAGAGAAGGAGTTT   960
18665    901   GAGAACCCCAAGAGTTCAGCATCCACTGCTGTGTCTGCTGCCCCCACAGAGAAGGAGTTT   960

Query    961   CCAAAAACTCACTCTGATGTATCTTCAGAACAGCAACATTTGAAGGGCCAGACTGGCACC   1020
18665    961   CCAAAAACTCACTCTGATGTATCTTCAGAACAGCAACATTTGAAGGGCCAGACTGGCACC   1020

Query    1021  AACGGTGGCAATGTGAAATTGTATACCACAGACCAAAGCACCTTTGACATTTTGCAGGAT   1080
18665    1021  AACGGTGGCAATGTGAAATTGTATACCACAGACCAAAGCACCTTTGACATTTTGCAGGAT   1080

Query    1081  TTGGAGTTTTCTTCTGGGTCCCCAGGTAAAGAGACGAATGAGAGTCCTTGGAGATCAGAC   1140
18665    1081  TTGGAGTTTTCTTCTGGGTCCCCAGGTAAAGAGACGAATGAGAGTCCTTGGAGATCAGAC   1140

Query    1141  CTGTTGATAGATGAAAACTGTTTGCTTTCTCCTCTGGCGGGAGAAGACGATTCATTCCTT   1200
18665    1141  CTGTTGATAGATGAAAACTGTTTGCTTTCTCCTCTGGCGGGAGAAGACGATTCATTCCTT   1200

Query    1201  TTGGAAGGAAACTCGAATGAGGACTGCAAGCCTCTCATTTTACCGGACACTAAACCCAAA   1260
18665    1201  TTGGAAGGAAACTCGAATGAGGACTGCAAGCCTCTCATTTTACCGGACACTAAACCCAAA   1260

Query    1261  ATTAAGGATAATGGAGATCTGGTTTTGTCAAGCCCCAGTAATGTAACACTGCCCCAAGTG   1320
18665    1261  ATTAAGGATAATGGAGATCTGGTTTTGTCAAGCCCCAGTAATGTAACACTGCCCCAAGTG   1320

Query    1321  AAAACAGAAAAGAAGATTTCATCGAACTCTGCACCCCTGGGGTAATTAAGCAAGAGAAA   1380
18665    1321  AAAACAGAAAAGAAGATTTCATCGAACTCTGCACCCCTGGGGTAATTAAGCAAGAGAAA   1380

Query    1381  CTGGGCACAGTTTACTGTCAGGCAAGCTTTCCTGGAGCAAATATAATTGGTAATAAAATG   1440
18665    1381  CTGGGCACAGTTTACTGTCAGGCAAGCTTTCCTGGAGCAAATATAATTGGTAATAAAATG   1440

Query    1441  TCTGCCATTTCTGTTCATGGTGTGAGTACCTCTGGAGGACAGATGTACCACTATGACATG   1500
18665    1441  TCTGCCATTTCTGTTCATGGTGTGAGTACCTCTGGAGGACAGATGTACCACTATGACATG   1500

Query    1501  AATACAGCATCCCTTTCTCAACAGCAGGATCAGAAGCCTATTTTTAATGTCATTCCACCA   1560
18665    1501  AATACAGCATCCCTTTCTCAACAGCAGGATCAGAAGCCTATTTTTAATGTCATTCCACCA   1560

Query    1561  ATTCCCGTTGGTTCCGAAAATTGGAATAGGTGCCAAGGATCTGGAGATGACAACTTGACT   1620
18665    1561  ATTCCCGTTGGTTCCGAAAATTGGAATAGGTGCCAAGGATCTGGAGATGACAACTTGACT   1620

Query    1621  TCTCTGGGGACTCTGAACTTCCCTGGTCGAACAGTTTTTTCTAATGGCTATTCAAGCCCC   1680
18665    1621  TCTCTGGGGACTCTGAACTTCCCTGGTCGAACAGTTTTTTCTAATGGCTATTCAAGCCCC   1680

Query    1681  AGCATGAGACCAGATGTAAGCTCTCCTCCATCCAGCTCCTCAACAGCAACAACAGGACCA   1740
18665    1681  AGCATGAGACCAGATGTAAGCTCTCCTCCATCCAGCTCCTCAACAGCAACAACAGGACCA   1740

Query    1741  CCTCCCAAACTCTGCCTGGTGTGCTCTGATGAAGCTTCAGGATGTCATTATGGAGTCTTA   1800
18665    1741  CCTCCCAAACTCTGCCTGGTGTGCTCTGATGAAGCTTCAGGATGTCATTATGGAGTCTTA   1800

Query    1801  ACTTGTGGAAGCTGTAAAGTTTTCTTCAAAAGAGCAGTGGAAGGACAGCACAATTACCTA   1860
18665    1801  ACTTGTGGAAGCTGTAAAGTTTTCTTCAAAAGAGCAGTGGAAGGACAGCACAATTACCTA   1860

Query    1861  TGTGCTGGAAGGAATGATTGCATCATCGATAAAATTCGAAGAAAAACTGCCCAGCATGC   1920
18665    1861  TGTGCTGGAAGGAATGATTGCATCATCGATAAAATTCGAAGAAAAACTGCCCAGCATGC   1920

Query    1921  CGCTATCGAAAATGTCTTCAGGCTGGAATGAACCTGGAAGCTCGaaaaacaaagaaaaaa   1980
18665    1921  CGCTATCGAAAATGTCTTCAGGCTGGAATGAACCTGGAAGCTCGAAAAACAAAGAAAAAA   1980

Query    1981  ataaaaGGAATTCAGCAGGCCACTACAGGAGTCTCACAAGAAACCTCTGAAAATCCTGGT   2040
18665    1981  ATAAAAGGAATTCAGCAGGCCACTACAGGAGTCTCACAAGAAACCTCTGAAAATCCTGGT   2040

Query    2041  AACAAAACAATAGTTCCTGCAACGTTACCACAACTCACCCCTACCCTGGTGTCACTGTTG   2100
18665    2041  AACAAAACAATAGTTCCTGCAACGTTACCACAACTCACCCCTACCCTGGTGTCACTGTTG   2100

Query    2101  GAGGTTATTGAACCTGAAGTGTTATATGCAGGATATGATAGCTCTGTTCCAGACTCAACT   2160
18665    2101  GAGGTTATTGAACCTGAAGTGTTATATGCAGGATATGATAGCTCTGTTCCAGACTCAACT   2160
```

FIG. 7B

```
Query  2161  TGGAGGATCATGACTACGCTCAACATGTTAGGAGGGCGGCAAGTGATTGCAGCAGTGAAA  2220
18665  2161  TGGAGGATCATGACTACGCTCAACATGTTAGGAGGGCGGCAAGTGATTGCAGCAGTGAAA  2220

Query  2221  TGGGCAAAGGCAATACCAGGTTTCAGGAACTTACACCTGGATGACCAAATGACCCTACTG  2280
18665  2221  TGGGCAAAGGCAATACCAGGTTTCAGGAACTTACACCTGGATGACCAAATGACCCTACTG  2280

Query  2281  CAGTACTCCTGGATGTTTCTTATGGCATTTGCTCTGGGGTGGAGATCATATAGACAATCA  2340
18665  2281  CAGTACTCCTGGATGTTTCTTATGGCATTTGCTCTGGGGTGGAGATCATATAGACAATCA  2340

Query  2341  AGTGCAAACCTGCTGTGTTTTGCTCCTGATCTGATTATTAATGAGCAGAGAATGACTCTA  2400
18665  2341  AGTGCAAACCTGCTGTGTTTTGCTCCTGATCTGATTATTAATGAGCAGAGAATGACTCTA  2400

Query  2401  CCCTGCATGTACGACCAATGTAAACACATGCTGTATGTTTCCTCTGAGTTACACAGGCTT  2460
18665  2401  CCCTGCATGTACGACCAATGTAAACACATGCTGTATGTTTCCTCTGAGTTACACAGGCTT  2460

Query  2461  CAGGTATCTTATGAAGAGTATCTCTGTATGAAAACCTTACTGCTTCTCTCTTCAGTTCCT  2520
18665  2461  CAGGTATCTTATGAAGAGTATCTCTGTATGAAAACCTTACTGCTTCTCTCTTCAGTTCCT  2520

Query  2521  AAGGACGGTCTGAAGAGCCAAGAGCTATTTGATGAAATTAGAATGACCTACATCAAAGAG  2580
18665  2521  AAGGACGGTCTGAAGAGCCAAGAGCTATTTGATGAAATTAGAATGACCTACATCAAAGAG  2580

Query  2581  CTAGGAAAAGCCATTGTCAAGAGGGAAGGAAACTCCAGCCAGAACTGGCAGCGGTTTTAT  2640
18665  2581  CTAGGAAAAGCCATTGTCAAGAGGGAAGGAAACTCCAGCCAGAACTGGCAGCGGTTTTAT  2640

Query  2641  CAACTGACAAAACTCTTGGATTCTATGCATGAAGTGGTTGAAATCTCCTTAACTATTGC  2700
18665  2641  CAACTGACAAAACTCTTGGATTCTATGCATGAA                            2673

Query  2701  TTCCAAACATTTTTGGATAAGACCATGAGTATTGAATTCCCCGAGATGTTAGCTGAAATC  2760

Query  2761  ATCACCAATCAGATACCAAAATATTCAAATGGAAATATCAAAAAACTTCTGTTTCATCAA  2820

Query  2821  AAGTGACTGCCTTAATAAGAATGGTTGCCTTAAAGAAAGTCGAATTAATAGCTTTTATTG  2880

Query  2881  TATAAACTATCAGTTTGTCCTGTAGAGgttttgttgttttattttttattgttttcatct  2940

Query  2941  gttgttttgttttAAATACGCACTACATGTGGTTTATAGAGGGCCAAGACTTGGCAACAG  3000

Query  3001  AAGCAGTTGAGTCGTCATCACTTTTCAGTGATGGGAGAGTAGATGGTGAAATTTATTAGT  3060

Query  3061  TAATATATCCCAGAAATTAGAAACCTTAATATGTGGACGTAATCTCCACAGTCAAAGAAG  3120

Query  3121  GATGGCACCTAAACCACCAGTGCCCAAAGTCTGTGTGATGAACTTTCTCTTCATACtttt  3180

Query  3181  tttCACAGTTGGCTGGATGAAATTTTCTAGACTTTCTGTTGGTGTATccccccccTGTAT  3240

Query  3241  AGTTAGGATAGCATTTTTGATTTATGCATGGAAACCTGaaaaaaaaGTTTACAAGTGTATA  3300

Query  3301  TCAGAAAAGGGAAGTTGTGCCTTTTATAGCTATTACTGTCTGGTTTTAACAATTTCCTTT  3360

Query  3361  ATATTTAGTGAACTACGCTTGCTCATTTTTTCTTACATAATTTTTTATTCAAGTTATTGT  3420

Query  3421  ACAGCTGTTTAAGATGGGCAGCTAGTTCGTAGCTTTCCCAAATAAACTCTAAACATTAAT  3480

Query  3481  CAATCATCTGTGTGAAAATGGGTTGGTGCTTCTAACCTGATGGCACTTAGCTATCAGAAG  3540

Query  3541  ACCACAAAAATTGACTCAAATCTCCAGTATTCTTGTCaaaaaaaaaaaaaaaaaaGCTCA  3600

Query  3601  TATTTTGTATATATCTGCTTCAGTGGAGAATTATATAGGTTGTGCAAATTAACAGTCCTA  3660

Query  3661  ACTGGTATAGAGCACCTAGTCCAGTGACCTGCTGGGTAAACTGTGGATGATGGTTGCAAA  3720

Query  3721  AGACTAATTTAAAAAATAACTACCAAGAGGCCCTGTCTGTACCTAACGCCCTATTTTTGC  3780
```

FIG. 7C

| | | | |
|---|---|---|---|
| Query | 3781 | AATGGCTATATGGCAAGAAAGCTGGTAAACTATTTGTCTTTCAGGACCTTTTGAAGTAGT | 3840 |
| Query | 3841 | TTGTATAACTTCTTAAAAGTTGTGATTCCAGATAACCAGCTGTAACACAGCTGAGAGACT | 3900 |
| Query | 3901 | TTTAATCAGACAAAGTAATTCCTCTCACTAAACTTTACCCAAAAACTAAATCTCTAATAT | 3960 |
| Query | 3961 | GGCAAAAATGGCTAGACACCCATTTTCACATTCCCATCTGTCACCAATTGGTTAATCTTT | 4020 |
| Query | 4021 | CCTGATGGTACAGGAAAGCTCAGCTACTGATTTTTGTGATTTAGAACTGTATGTCAGACA | 4080 |
| Query | 4081 | TCCATGTTTGTAAAACTACACATCCCTAATGTGTGCCATAGAGTTTAACACAAGTCCTGT | 4140 |
| Query | 4141 | GAATTTCTTCACTGTTGAAAATTATTTTAAACAAAATAGAAGCTGTAGTAGCCCTTTCTG | 4200 |
| Query | 4201 | TGTGCACCTTACCAACTTTCTGTAAACTCAAAACTTAACATATTTACTAAGCCACAAGAA | 4260 |
| Query | 4261 | ATTTGATTTCTATTCAAGGTGGCCAAATTATTTGTGTAATAGAAAACTGAAAATCTAATA | 4320 |
| Query | 4321 | TTAAAAATATGGAACTTCTAatatattttttatatttagttatagtttcagatatatatca | 4380 |
| Query | 4381 | tatTGGTATTCACTAATCTGGGAAGGGAAGGGCTACTGCAGCTTTACATGCAATTTATTA | 4440 |
| Query | 4441 | AAATGATTGTAAAATAGCTTGTATAGTGTAAAATAAGAATGATTTTTAGATGAGATTGTT | 4500 |
| Query | 4501 | TTATCATGACATGTTATATATTTTTTGTAGGGGTCAAAGAAATGCTGATGGATAACCTAT | 4560 |
| Query | 4561 | ATGATTTATAGTTTGTACATGCATTCATACAGGCAGCGATGGTCTCAGAAACCAAACAGT | 4620 |
| Query | 4621 | TTGCTCTAGGGGAAGAGGGAGATGGAGACTGGTCCTGTGTGCAGTGAAGGTTGCTGAGGC | 4680 |
| Query | 4681 | TCTGACCCAGTGAGATTACAGAGGAAGTTATCCTCTGCCTCCCATTCTGACCACCCTTCT | 4740 |
| Query | 4741 | CATTCCAACAGTGAGTCTGTCAGCGCAGGTTTAGTTTACTCAATCTCCCCTTGCACTAAA | 4800 |
| Query | 4801 | GTATGTAAAGTATGTAAACAGGAGACAGGAAGGTGGTGCTTACATCCTTAAAGGCACCAT | 4860 |
| Query | 4861 | CTAATAGCGGGTTACTTTCACATACAGCCCTCCCCCAGCAGTTGAATGACAACAGAAGCT | 4920 |
| Query | 4921 | TCAGAAGTTTGGCAATAGTTTGCATAGAGGTACCAGCAATATGTAAATAGTGCAGAATCT | 4980 |
| Query | 4981 | CATAGGTTGCCAATAATACACTAATTCCTTTCTATCCTACAACAAGAGTTTATTTCCAAA | 5040 |
| Query | 5041 | TAAAATGAGGACAtgttttttgttttctttgaatgcttttttgaatgttatttgttattttc | 5100 |
| Query | 5101 | agtattttggagaaattatttAAtaaaaaaaCAATCATTTGCTTTTTGAATGCTCTCTAA | 5160 |
| Query | 5161 | AAGGGAATGTAATATTTTAAGATGGTGTGTAACCCGGCTGGATAAATTTTTGGTGCCTAA | 5220 |
| Query | 5221 | GAAAACTGCTTGAATATTCTTATCAATGACAGTGTTAAGTTTCAAAAGAGCTTCTAAAA | 5280 |
| Query | 5281 | CGTAGATTATCATTCCTTTATAGAATGTTATGTGGTTAAAACCAGAAAGCACATCTCACA | 5340 |
| 18665 | 2674 |                     AATGTTATGTGGTTAAAACCAGAAAGCACATCTCACA | 2710 |
| Query | 5341 | CATTAATCTGATTTTCATCCCAACAATCTTGGCGCTCAAAAAATAGAACTCAATGAGAAA | 5400 |
| 18665 | 2711 | CATTAATCTGATTTTCATCCCAACAATCTTGGCGCTCAAAAAATAGAACTCAATGAGAAA | 2770 |
| Query | 5401 | AAGAAGATTATGTGCACTTCGTTGTCAATAATAAGTCAACTGATGCTCATCGACAACTAT | 5460 |
| 18665 | 2771 | AAGAAGATTATGTGCACTTCGTTGTCAATAATAAGTCAACTGATGCTCATCGACAACTAT | 2830 |
| Query | 5461 | AGGAGGCTTTTCATTAAATGGGAAAAGAAGCTGTGCCCTTTTAGGATACGTGGGGGAAAA | 5520 |
| 18665 | 2831 | AGGAGGCTTTTCATTAAATGGGAAAAGAAGCTGTGCCCTTTTAGGATACGTGGGGGAAAA | 2890 |
| Query | 5521 | GAAAGTCATCTTAATTATGTTTAATTGTGGATTTAAGTGCTATATGGTGGTGCTGTTTGA | 5580 |

FIG. 7D

```
18665  2891  GAAAGTCATCTTAATTATGTTTAATTGTGGATTTAAGTGCTATATGGTGGTGCTGTTTGA  2950

Query  5581  AAGCAGATTTATTTCCTATGTATGTGTTATCTGGCCATCCCAACCCAAACTGTTGAAGTT  5640
18665  2951  AAGCAGATTTATTTCCTATGTATGTGTTATCTGGCCATCCCAACCCAAACTGTTGAAGTT  3010

Query  5641  TGTAGTAACTTCAGTGAGAGTTGGTTACTCACAACAAATCCTGAAAAGTATTTTTAGTGT  5700
18665  3011  TGTAGTAACTTCAGTGAGAGTTGGTTACTCACAACAAATCCTGAAAAGTATTTTTAGTGT  3070

Query  5701  TTGTAGGTATTCTGTGGGATACTATACAAGCAGAACTGAGGCACTTAGGACATAACACTT  5760
18665  3071  TTGTAGGTATTCTGTGGGATACTATACAAGCAGAACTGAGGCACTTAGGACATAACACTT  3130

Query  5761  TTGGGGTATATATATCCAAATGCCTAAAACTATGGGAGGAAACCTTGGCCACCCCAAAAG  5820
18665  3131  TTGGGGTATATATATCCAAATGCCTAAAACTATGGGAGGAAACCTTGGCCACCCCAAAAG  3190

Query  5821  GAAAACTAACATGATTTGTGTCTATGAAGTGCTGGATAATTAGCATGGGATGAGCTCTGG  5880
18665  3191  GAAAACTAACATGATTTGTGTCTATGAAGTGCTGGATAATTAGCATGGGATGAGCTCTGG  3250

Query  5881  GCATGCCATGAAGGAAAGCCACGCTCCCTTCAGAATTCAGAGGCAGGGAGCAATTCCAGT  5940
18665  3251  GCATGCCATGAAGGAAAGCCACGCTCCCTTCAGAATTCAGAGGCAGGGAGCAATTCCAGT  3310

Query  5941  TTCACCTAAGTCTCATAATTTTAGTTCCCTTTTAAAAACCCTGAAAACTACATCACCATG  6000
18665  3311  TTCACCTAAGTCTCATAATTTTAGTTCCCTTTTAAAAACCCTGAAAACTACATCACCATG  3370

Query  6001  GAATGAAAAATATTGTTATACAATACATTGATCTGTCAAACTTCCAGAACCATGGTAGCC  6060
18665  3371  GAATGAAAAATATTGTTATACAATACATTGATCTGTCAAACTTCCAGAACCATGGTAGCC  3430

Query  6061  TTCAGTGAGATTTCCATCTTGGCTGGTCACTCCCTGACTGTAGCTGTAGGTGAAtgtgtt  6120
18665  3431  TTCAGTGAGATTTCCATCTTGGCTGGTCACTCCCTGACTGTAGCTGTAGGTGAATGTGTT  3490

Query  6121  tttgtgtgtgtgtgtCTGGTTTTAGTGTCAGAAGGGAAATAAAAGTGTAAGGAGGACACT  6180
18665  3491  TTTGTGTGTGTGTGTCTGGTTTTAGTGTCAGAAGGGAAATAAAAGTGTAAGGAGGACACT  3550

Query  6181  TTAAACCCTTTGGGTGGAGTTTCGTAATTTCCCAGACTATTTTCAAGCAACCTGGTCCAC  6240
18665  3551  TTAAACCCTTTGGGTGGAGTTTCGTAATTTCCCAGACTATTTTCAAGCAACCTGGTCCAC  3610

Query  6241  CCAGGATTAGTGACCAGGTTTTCAGGAAAGGATTTGCTTCTCTAGAAAATGTCTGAAA  6300
18665  3611  CCAGGATTAGTGACCAGGTTTTCAGGAAAGGATTTGCTTCTCTAGAAAATGTCTGAAA  3670

Query  6301  GGATTTTATTTTCTGATGAAAGGCTGTATGAAAATACCCTCCTCAAATAACTTGCTTAAC  6360
18665  3671  GGATTTTATTTTCTGATGAAAGGCTGTATGAAAATACCCTCCTCAAATAACTTGCTTAAC  3730

Query  6361  TACATATAGATTCAAGTGTGTCAATATTCTATTTTGTATATTAAATGCTATATAATGGGG  6420
18665  3731  TACATATAGATTCAAGTGTGTCAATATTCTATTTTGTATATTAAATGCTATATAATGGGG  3790

Query  6421  ACAAATCTATATTATACTGTGTATGGCATTATTAAGAAGCTTTTTCATTATTTTTTATCA  6480
18665  3791  ACAAATCTATATTATACTGTGTATGGCATTATTAAGAAGCTTTTTCATTATTTTTTATCA  3850

Query  6481  CAGTAATTTTAAAATGTGTAAAAATTAAAACCAGTGACTCCTGTTTAAAAATAAAAGTTG  6540
18665  3851  CAGTAATTTTAAAATGTGTAAAAATTAAAACCAGTGACTCCTGTTTAAAAATAAAAGTTG  3910

Query  6541  TAGTTTTTTATTCATGCTGAATAATAATCTGTAGTTaaaaaaaaaGTGTCTTTTTACCTA  6600
18665  3911  TAGTTTTTTATTCATGCTGAATAATAATCTGTAGTTAAAAAAAAAGTGTCTTTTTACCTA  3970

Query  6601  CGCAGTGAAATGTCAGACTGTAAAACCTTGTGTGGAAATGTTTAACTTTTATTTTTTCAT  6660
18665  3971  CGCAGTGAAATGTCAGACTGTAAAACCTTGTGTGGAAATGTTTAACTTTTATTTTTTCAT  4030

Query  6661  TTAAATTTGCTGTTCTGGTATTACCAAACCACACATTTGTACCGAATTGGCAGTAAATGT  6720
18665  4031  TTAAATTTGCTGTTCTGGTATTACCAAACCACACATTTGTACCGAATTGGCAGTAAATGT  4090

Query  6721  TAGCCATTTACAGCAATGCCAAATATGGAGAAACATCATAATaaaaaaaTCTGCTTTTTC  6780
18665  4091  TAGCCATTTACAGCAATGCCAAATATGGAGAAACATCATAATAAAAAAATCTGCTTTTTC  4150

Query  6781  ATTA  6784
```

FIG. 7E 18665   4151   ATTA   4154

FIG. 7F

METHODS AND COMPOSITIONS RELATED TO GLUCOCORTICOID RECEPTOR ANTAGONISTS AND BREAST CANCER

CROSS-REFERENCES TO RELATED APPLICATIONS

This application is a Continuation of U.S. application Ser. No. 14/296,127, filed Jun. 4, 2014, which is a Continuation of U.S. application Ser. No. 14/172,051, filed Feb. 4, 2014, which is a Continuation of U.S. application Ser. No. 13/071,363, filed Mar. 24, 2011, which claims priority to U.S. Provisional Application No. 61/317,182, filed on Mar. 24, 2010, which is hereby incorporated by reference.

STATEMENT AS TO RIGHTS TO INVENTIONS MADE UNDER FEDERALLY SPONSORED RESEARCH AND DEVELOPMENT

This invention was made with government support under CA089208 awarded by the National Institutes of Health. The government has certain rights in the invention.

REFERENCE TO A "SEQUENCE LISTING," A TABLE, OR A COMPUTER PROGRAM LISTING APPENDIX SUBMITTED ON AN ASCII TEXT FILE

The Sequence Listing written in file "SeqListing096487-1040478.TXT", created on Mar. 2, 2017, 231,303 bytes, machine format IBM-PC, MS-Windows operating system, is hereby incorporated by reference in its entirety for all purposes.

BACKGROUND OF THE INVENTION

I. Field of the Invention

Embodiments of this invention are directed generally to biology and medicine. In certain aspects methods involve determining the prognosis for a breast cancer patient. In other embodiments, there are methods and compositions for treating a breast cancer patient with a glucocorticoid antagonist.

II. Background

There are over 1 million cases of breast cancer per year on a global basis, of which around 0.5 million are in the US, 40,000 are in the UK and nearly 2,000 in Ireland. It is the leading cause of cancer deaths among women (Keen and Davidson, 2003). Although the overall incidence of the disease is increasing within the western world, wider screening and improved treatments have led to a gradual decline in the fatality rate of about 1% per year since 1991. Inheritance of susceptibility genes, such as BRCA1 and BRCA2, account for only 5% of breast cancer cases and the factors responsible for the other 95% remain obscure (Grover and Martin, 2002). In the absence of a strategy to reduce causative agents of breast cancer, early detection remains the best approach to reducing the mortality rate of this disease. It is widely held that breast cancer initiates as the pre-malignant stage of atypical ductal hyperplasia (ADH), progresses into the pre-invasive stage of ductal carcinoma in situ (DCIS), and culminates in the potentially lethal stage of invasive ductal carcinoma (IDC). This linear model of breast cancer progression has been the rationale for the use of detection methods such as mammography in the hope of diagnosing and treating breast cancer at earlier clinical stages (Ma et al., 2003).

As more molecular information is being collated, diseases such as breast cancer are being sub-divided according to genetic signatures linked to patient outcome, providing valuable information for the clinician. Emerging novel technologies in molecular medicine have already demonstrated their power in discriminating between disease sub-types that are not recognizable by traditional pathological criteria (Sorlie et al., 2001) and in identifying specific genetic events involved in cancer progression (Srinivas et al., 2002).

Endocrine therapy is a popular mode of treatment for all stages of breast cancer. A majority of breast cancers belong to the type in which growth is stimulated by the female sex hormones, estrogens and progesterone. Therefore some of the therapies are based on depriving the tumor of the hormone-induced growth stimulus. Some of the current modes of endocrine treatments include blockade of the estrogen receptor with an antiestrogen, e.g. tamoxifen; hormonal ablation by surgery (oophorectomy, adrenalectomy or hypophysectomy), radiotherapy or medically by administration of a luteinizing hormone-releasing hormone analogue (LH-RHa), e.g., goserelin; suppression of estrogen synthesis with aromatase inhibitors, e.g., anastrozole; pharmacological doses of estrogens and progestagens, e.g., megestrol acetate.

Despite recent advances, the challenge of cancer treatment, including breast cancer therapy remains. Progress is limited with respect to the development of specific treatment regimens to clinically distinct tumor types, and to personalize tumor treatment in order to maximize outcome and efficiency. Moreover, a number of patients exhibit chemotherapy resistance.

Mere classification of breast cancers into a few subgroups characterized by low to absent gene expression of the estrogen receptor (ER) alone may not reflect the cellular and molecular heterogeneity of breast cancer, and may not allow the design of treatment strategies maximizing patient response. Once a patient is diagnosed with cancer, such as breast or ovarian cancer, or an individual wants predisposition analysis, there is a strong need for methods that allow the physician to predict the expected course of disease, including the likelihood of cancer recurrence, long-term survival of the patient, and the like, and accordingly select an appropriate treatment option that is effective.

SUMMARY OF THE INVENTION

Embodiments concern methods, compositions, and apparatuses related to assessing, prognosing, and/or treating breast cancer patients. It concerns using information related to glucocorticoid receptor (GR) activity and/or expression in conjunction with information related to estrogen receptor (ER) activity or expression to identify patients with the least favorable prognosis based on current standards of care for breast cancer. Patients with relatively low levels of estrogen receptor expression and relatively high levels of glucocorticoid expression fall into a group of breast cancer patients with the least favorable prognosis (i.e., mortality rate).

Accordingly, methods concern evaluating a patient with breast cancer. Embodiments include evaluating a biological sample from a patient; evaluating breast cancer cells from a patient; evaluating a biological sample from a breast cancer patient; assessing a breast cancer patient; testing a breast cancer sample or biopsy; testing a breast tumor; prognosing a breast cancer patient; treating a breast cancer patient, particularly a patient with a particular profile related to ER and GR; determining a treatment for a breast cancer patient; altering a treatment plan for a breast cancer patient; reporting prognosis of a breast cancer patient; determining a prognosis score for a breast cancer patient; generating a prognosis score for a breast cancer patient; assessing the risk of mortality of a breast cancer patient generally or within a certain time frame, such as 150 months from end of cancer treatment; generating an ER and GR expression profile for a breast cancer patient; comparing a patient's ER and GR expression profile to a standardized profile; and/or, determining a breast cancer patient has a poor prognosis based on the patient's ER and GR status.

Embodiments also cover apparatuses, kits, and computer readable medium and systems for assessing the level or activity of ER and/or GR in a patient's breast cancer sample and determining a prognosis; and/or treating the patient accordingly. It is specifically contemplated that a breast cancer patient is a human. Accordingly, in human patients, ER refers to an estrogen receptor in a human and GR refers to a glucocorticoid receptor in a human.

Some embodiments include generating an expression profile for glucocorticoid receptor, which means obtaining the level of expression of GR directly or indirectly by measuring or assaying activity or expression. Methods include directly measuring or assaying the level of expression or activity refers to measuring or assaying a sample to determine the level of GR expression (protein or transcript) in the cell. Indirectly obtaining the level of expression includes measuring or assaying expression or activity of a gene or protein that correlates with GR expression or activity. In some embodiments, the level of GR expression can be indirectly obtained by measuring or assaying expression of a GR-responsive gene, which refers to a gene whose expression is affected in a dose-dependent manner by GR expression or activity. Expression refers to either protein expression or RNA (transcript) expression. Methods may involve either type of expression and a variety of assays are well known to those of skill in the art. For example, quantitative PCR may be performed to obtain RNA expression levels. The Affymetrix chip used in the Examples also provides information regarding RNA expression levels. Alternatively, reagents to detect protein expression levels may be employed in embodiments. Methods may involve probes, primers, and/or antibodies that are specific to GR or ER in order to assess expression levels.

In some embodiments, the activity level of GR is measured by assaying the level of GR expression. In additional embodiments, GR expression is GR transcript expression. In other embodiments, GR expression is GR protein expression. As discussed above, in some embodiments, the activity level of GR is measured by assaying the expression level of one or more GR-responsive genes. A GR-responsive gene may be one or more of the following: MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, or MAOA.

In some embodiments, there is a step of assaying or measuring the activity level of glucocorticoid receptor (GR) in a biological sample from the patient containing breast cancer cells. As discussed above, the activity level of GR can be obtained directly or indirectly. It is specifically contemplated that levels of glucocorticoid activity or expression refers to activity or expression of GR α, GR β, or both. Unless specifically stated otherwise, the terms "glucocorticoid receptor" or "GR" refer to both forms. Embodiments discussed with respect to glucocorticoid receptor or GR may also be implemented solely with GRα or solely with GRβ.

Methods may also include obtaining a level of estrogen receptor (ER) expression in breast cancer cells from the patient. The level can be obtained by obtaining the results of an assay that measured the level of ER expression. In some embodiments, the level is obtained by measuring or assaying the level of ER expression.

In some embodiments, the level of estrogen receptor expression in breast cancer cells from patient is obtained by measuring the level of estrogen receptor expression from the biological sample from the patient. In other embodiments, the level is obtained by receiving qualitative and/or quantitative data regarding the level.

In some embodiments, methods include identifying the patient as having or not having a risk factor for cancer recurrence based on the levels of ER and GR expression. Methods may involve categorizing the patient as ER+ or ER– based the level of estrogen receptor expression and a predetermined threshold value for ER expression. The term "ER+" refers to a classification of ER expression that indicates the patient expresses estrogen receptor in breast cancer cells at or above a certain level. The term "ER–" refers to a classification of ER expression that indicates the patient expresses estrogen receptor at a relatively low level in breast cancer cells, meaning at or below a certain level. In embodiments of the invention, that certain level or a predetermined threshold value is at, below, or above 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein.

Methods may involve measuring the activity level of glucocorticoid receptor in a biological sample from the patient containing breast cancer cells and measuring the expression level of estrogen receptor in the biological sample.

In certain embodiments, the predetermined threshold value for ER expression identifies a patient as ER+ if the patient's ER expression level is in the $25^{th}$ percentile or greater compared to a normalized sample. This means the patient may be designated as having a level of ER expression that is at or above 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein. It is contemplated that in some cases, a patient may be designated as ER+ if the patient's ER expression level is at or above 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. The patient may also be referred to as having a normal or high ER expression level. The higher the percentile, the higher the relative expression level.

In embodiments, methods may also involve categorizing the patient as GR+ or GR– based on a predetermined threshold value for GR activity. In some cases, a predetermined threshold value for GR activity is dependent on whether the patient is categorized as ER+ or ER–. Embodiments may involve a predetermined threshold value for GR activity that identifies a patient as GR+ if the patient is ER− and GR activity level is in the 65$^{th}$ percentile or greater compared to a normalized sample. It is contemplated that in some cases, a patient may be designated as GR+ if the patient's GR expression level is at or above 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. The threshold value may or may not be dependent on ER expression levels or status. In some embodiments, the threshold value depends on whether the patient is ER− or not. The higher the percentile, the higher the relative expression level.

Methods may involve the use of a normalized sample or control that is based on one or more breast cancer samples that are not from the patient being tested.

In some embodiments, methods involve calculating a prognosis score for the patient based on the levels of ER and/or GR expression. Methods may alternatively or additionally involve reporting a prognosis score or report the levels of ER and/or GR expression. The score or report may contain or reflect raw data regarding expression levels or it may reflect a categorization of the expression levels obtained. A score could indicate the risk factor for mortality, recurrence, and/or both. The score could be a number within a numeric scale in which one end of the scale is most favorable and the other end is the least favorable with respect to a prognosis for breast cancer.

In certain embodiments, methods may involve identifying the patient as having a poor prognosis if the patient is determined to have a glucocorticoid receptor activity level at or above a certain threshold level and a level of estrogen receptor that is at or below a second threshold level. In each case, the threshold levels are specific for each of GR and ER. In certain embodiments, it is contemplated that a GR level in the 65th percentile or above based on breast cancer patients whose are in the 35$^{th}$ percentile or below is indicative of a poor prognosis. In some embodiments, patients with a poor prognosis include a population of breast cancer patients that numbers approximately 10% or less.

Methods also include identifying the patient as having a poor prognosis if the patient is determined to have i) an activity level of glucocorticoid receptor that is higher than the activity level of glucocorticoid receptor in normalized control sample and ii) a expression level of estrogen receptor expression that is lower than the expression level of estrogen receptor in a normalized control sample. Consequently, methods of the invention include prognosing a breast cancer patient. In some cases, a patient is identified as having a relatively good prognosis.

Other embodiments include methods of treating a patient for breast cancer comprising: treating the patient for breast cancer after a biological sample from the patient containing breast cancer cells is analyzed for i) the activity level of glucocorticoid receptor and ii) the expression level of estrogen receptor. A patient may be treated with a different treatment protocol than the patient would have been treated with if the patient's biological sample had not been analyzed. In some embodiments, the patient is categorized as ER− and GR+ based on the activity level of the glucocorticoid receptor and the expression level of estrogen receptor. In some cases, the patient is treated with a more aggressive therapy than the patient would have been treated with if the patient had not been categorized as ER− and GR+. The term "more aggressive" refers to a treatment regimen that may include more drugs or drugs with more severe side effects and/or it may include an increased dosage or increased frequency of drugs. It may also include radiation or a combination of therapies. In some cases, the therapy includes one or more chemotherapeutics and/or biologics. In some embodiments, the patient is treated with a therapy comprising an anti-angiogenic agent. In additional embodiments, the therapy further comprises a chemotherapeutic agent in addition to the anti-angiogenic agent. Embodiments also include administering a glucocorticoid receptor antagonist and/or tyrosine kinase inhibitor.

Embodiments may also include where the patient is treated with more than one type of cancer therapy. This may be after the patient is determined to have a particular prognosis or after the status of the patient's GR and ER expression profile is known. In some embodiments, certain treatments are provided to an ER−/GR+ breast cancer patient who might have otherwise been treated with a less aggressive treatment for breast cancer. In some embodiments, a patient is treated with at least two of the following: radiation, chemotherapy, or a biologic. In particular embodiments, the patient may be treated with a kinase inhibitor and/or anti-angiogenic agent.

Methods may also involve obtaining a biological sample comprising breast cancer cells from the patient and categorizing the patient as i) GR+ or GR− based on the level of glucocorticoid activity assayed in the sample and compared to a predetermined threshold value for GR activity; and ii) ER+ or ER− based on the level of estrogen receptor expression assayed in the sample and compared to a predetermined threshold value for ER expression.

Any method may also include treating the patient for breast cancer, which may include directly administering or providing a cancer therapy. In some embodiments, a practitioner or doctor may prescribe a cancer therapy that the patient administers to herself.

To achieve these methods, a doctor, medical practitioner, or their staff may retrieve a biological sample from a patient for evaluation. The sample may be a biopsy, such as a breast tissue or tumor biopsy. The sample may be analyzed by the practitioner or their staff, or it may be sent to an outside or independent laboratory. The medical practitioner may be cognizant of whether the test is providing information regarding the patient's level of GR and/or ER expression or activity, or the medical practitioner may be aware only that the test indicates directly or indirectly that the test reflects that the patient has a particular prognosis or can be given a particular prognosis score. Furthermore, the practitioner may know the patient's ER or GR status, such as ER+ or ER−, or GR+ or GR−. Alternatively, she may be aware only that the test or assay indicates the patient has a poor prognosis, or the worst prognosis.

Embodiments also concern kits to determine glucocorticoid receptor status in breast cancer cells comprising: (a) one or more reagents for determining expression levels of NR3C1 in a biological sample; and (b) an algorithm and software encoding the algorithm for calculating a risk factor index from the expression of NR3C1 in a sample and the estrogen receptor status of the breast cancer cells to determine a prognosis or a prognosis score. Kits may also include one or more reagents for determining expression levels of ESR1 in the biological sample to provide estrogen receptor status.

Other embodiments include a computer readable medium having software modules for performing a method comprising the acts of: (a) comparing glucocorticoid receptor data obtained from a patient's breast cancer sample with a reference; and (b) providing an assessment of glucocorticoid receptor status to a physician for use in determining an appropriate therapeutic regimen for a patient. In further embodiments, the computer readable medium further comprises a software module for assessing estrogen receptor status of the patient's breast cancer sample.

Computer systems are also included. In some embodiments, they have a processor, memory, external data storage, input/output mechanisms, a display, for assessing glucocorticoid receptor activity, comprising: (a) a database; (b) logic mechanisms in the computer generating for the database a GR-responsive gene expression reference; and (c) a comparing mechanism in the computer for comparing the GR-responsive gene expression reference to expression data from a patient sample using a comparison model to determine a GR gene expression profile of the sample.

Other embodiments include an internet accessible portal for providing biological information constructed and arranged to execute a computer-implemented method for providing: (a) a comparison of gene expression data of one or more GR-responsive genes in a patient sample with a calculated reporter index; and (b) providing an assessment of GR activity or expression to a physician for use in determining an appropriate therapeutic regime for a patient.

In addition to compiling, collecting and or processing data related to GR status, methods, media and systems may also include the same embodiments with respect to data related to ER status. Such aspects may be instead of or in addition to the aspects related to GR status or data.

Embodiments also include methods of killing breast cancer cells comprising administering to a breast cancer patient an effective amount of a combination of anti-cancer compounds, wherein the anticancer compounds comprise a glucocorticoid receptor antagonist and a chemotherapeutic.

In other embodiments, there are methods for treating breast cancer in a patient comprising administering to the patient an effective amount of glucocorticoid receptor antagonist and a chemotherapeutic.

In further embodiments, methods are provided for treating chemotherapy-insensitive breast cancer cells comprising administering to a breast cancer patient an effective amount of a glucocorticoid receptor antagonist followed by chemotherapy.

Other methods include methods for treating breast cancer in a patient comprising: a) administering radiation or at least a first chemotherapeutic to the patient; b) subsequently administering an effective amount of a glucocorticoid receptor antagonist to the patient; and, c) administering radiation again or at least a second chemotherapeutic to the patient after the glucocorticoid receptor antagonist is administered to the patient.

In some embodiments, there are methods for treating breast cancer in a patient comprising: a) administering an effective amount of a glucocorticoid receptor antagonist to the patient, wherein the patient expresses detectable levels of GR prior to administration of the GR antagonist; b) then administering an effective amount of radiation or at least one chemotherapeutic.

It is contemplated that in methods described herein, breast cancer cells may undergo apoptosis following treatment set forth herein. Moreover, in some embodiments, the combination of a glucocorticoid receptor antagonist and an anti-cancer agent or compound induces more apoptosis than treatment with just the anticancer treatment alone. In other methods, it is specifically contemplated to exclude treatment with a synthetic glucocorticoid, such as dexamethasone.

Glucocorticoid receptor antagonists are known to those of skill in the art. It refers to a compound or substance that that does not provoke a biological response itself upon binding to the glucocorticoid receptor, but blocks or dampens agonist-mediated responses. Examples include, but are not limited to, beclometasone, betamethasone, budesonide, ciclesonide, flunisolide, fluticasone, mifepristone, mometasone, and triamcinolone. In additional embodiments, the glucocorticoid receptor antagonist has undetectable level or a lower level of activity as a progesterone receptor antagonist. In certain embodiments, the glucocorticoid receptor antagonist has greater than 10-fold, 50-fold, 100-fold, 200-fold, 300-fold, 400-fold, 500-fold, 1000-fold lower binding activity (or any range derivable therein) for another hormone receptor compared to its binding activity for glucocorticoid receptor. In specific embodiments the hormone receptor is estrogen receptor or progesterone receptor.

In some embodiments, a patient had been previously treated with an anti-cancer therapy, such as radiation, chemotherapy, or immunotherapy (or a combination or multiple therapies thereof). In certain embodiments, a first anti-cancer therapy prior to therapy with glucocorticoid receptor antagonist was last administered more than two weeks prior to the glucocorticoid receptor antagonist or its combination with a second anti-cancer therapy. In certain embodiments, this first anti-cancer therapy that does not include a glucocorticoid receptor antagonist was last administered to the breast cancer patient at least 7, 8, 9, 10, 11, 12, 13, 14 days, and/or 1, 2, 3, 4, or 5 weeks, and/or 1, 2, 3, 4, 5, 6, 7, 8, 9, 10, 11, or 12 months prior to treatment with a glucocorticoid receptor antagonist. Treatment methods may be applied to breast cancer or breast cancer cells that are chemo-resistant or breast cancer cells that are not chemo-sensitive. Moreover, treatment may be applied to breast cancer or to breast cancer cells that were previously administered a first apoptosis inducing agent, but were resistant to apoptosis.

In some embodiments, the breast cancer cells are determined to be resistant to apoptosis. In additional embodiments, the breast cancer or the breast cancer cells are determined not to be chemo-sensitive or are determined to be chemo-resistant. This determination may be based on the results of a genetic test or based on information obtained from an assessment of a tumor or the breast cancer after treatment with a first anti-cancer therapy. In specific embodiments, the first anti-cancer therapy is a chemotherapeutic, Herceptin®, radiation, a combination of chemotherapeutics, or a combination of one or more chemotherapeutic agents and Herceptin®.

In additional embodiments, the breast cancer cells express a detectable level of glucocorticoid receptor or its transcript. In some embodiments, the patient is determined to have breast cancer cells that express a detectable level of glucocorticoid receptor or its transcript. This may be determined directly or indirectly.

It is contemplated that breast cancer cells may be treated with a glucocorticoid receptor antagonist regardless of estrogen receptor status. Therefore, breast cancer cells may be estrogen receptor-negative (ER−) or estrogen receptor-positive (ER+), accordingly to a standardized and industry accepted test for ER status. In certain embodiments, the breast cancer cells do not express any detectable levels of ER; in other embodiments, ER expression is detectable in the breast cancer cells.

It is contemplated that breast cancer cells may be treated with a glucocorticoid receptor antagonist depending on or regardless of progesterone receptor status. Therefore, breast cancer cells may be progesterone receptor-negative (PR−) or progesterone receptor-positive (PR+), accordingly to a standardized and industry accepted test for ER status. In certain embodiments, the breast cancer cells do not express any detectable levels of PR; in other embodiments, PR expression is detectable in the breast cancer cells.

Methods involve treating breast cancer, particularly a chemo-resistant breast cancer, with a combination of therapies that includes a glucocorticoid receptor antagonist and an anticancer therapy that induces apoptosis (together they may be referred to as a combination of anti-cancer agents or compounds), such as a chemotherapeutic. In some embodiments, the chemotherapeutic is capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, or vinorelbin, or a combination of these agents. In other embodiments, therapy with a glucocorticoid receptor antagonist is combined Herceptin®, radiation, chemotherapeutic(s) and radiation, a combination of chemotherapeutics, or a combination of one or more chemotherapeutic agents and Herceptin®.

It is contemplated that in some embodiments of the combination therapy the glucocorticoid receptor antagonist is administered within 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof within administration of at least one or the combination of the anti-cancer agents or compounds. In specific embodiments, the glucocorticoid receptor antagonist is administered within 2 hours, 12 hours or 24 hours of administration of a anticancer agent or compound (or a combination of such agents or compounds).

It is specifically contemplated that treatment may continue or be repeated. In some embodiments, once treated with the combination of a glucocorticoid receptor antagonist and at least one anticancer agent or compound, all or part of the treatment may be repeated alone or in combination with a different anticancer agent or compound.

In certain embodiments, the glucocorticoid receptor antagonist is administered prior to as the other agent or therapy included in the combination therapy. In certain embodiments, the glucocorticoid receptor antagonist is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof prior to administration of at least one or the combination of the anti-cancer agents or compounds. It is specifically contemplated that in some embodiments, the glucocorticoid receptor antagonist is given prior to administration of the anticancer agent or compound but that the glucocorticoid receptor antagonist is also given concurrently with or after administration of the initial or a subsequent dose of the anticancer agent or compound. As discussed throughout, the anticancer agent or compound may be in a combination of such agents or compounds. In certain embodiments, the glucocorticoid receptor antagonist is administered up to three days prior to administering the anticancer agent or compound.

Additionally or alternatively, the glucocorticoid receptor antagonist is administered after administration of the other agent or therapy included in the combination therapy. In certain embodiments, the glucocorticoid receptor antagonist is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof after administration of at least one or the combination of the anti-cancer agents or compounds. It is specifically contemplated that in some embodiments, the glucocorticoid receptor antagonist is given after to administration of the anticancer agent or compound; such administration may be repeated. As discussed throughout, the anticancer agent or compound may be in a combination of such agents or compounds. In certain embodiments, the glucocorticoid receptor antagonist is administered up to three days after administering the anticancer agent or compound.

In certain embodiments, the breast cancer is an unresectable breast cancer. In further embodiments, the breast cancer is inflammatory breast cancer.

It is specifically contemplated that in some methods, dexamethasone has not been administered to the patient within 24 hours of administration of the glucocorticoid receptor antagonist.

Compositions are contemplated to include a glucocorticoid receptor antagonist and any other anticancer compound discussed herein, such a Herceptin or one or more chemotherapeutic compounds. In some embodiments, the composition is in a pharmaceutically acceptable formulation.

Use of the one or more compositions may be employed based on methods described herein. Other embodiments are discussed throughout this application. Any embodiment discussed with respect to one aspect of the invention applies to other aspects of the invention as well and vice versa. The embodiments in the Example section are understood to be embodiments o that are applicable to all aspects of the technology described herein.

"Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, and/or duration of response in a patient or a group of patients susceptible to or diagnosed with a cancer.

In certain aspects, prognosis is an estimation of the likelihood of metastasis free survival of said patient over a predetermined period of time, e.g., over a period of 5 years.

In further aspects, prognosis is an estimation of the likelihood of death of disease of said patient over a predetermined period of time, e.g., over a period of 5 years.

The term "recurrence" refers to the detection of breast cancer in form of metastatic spread of tumor cells, local recurrence, contralateral recurrence or recurrence of breast cancer at any site of the body of the patient after breast cancer had been substantially undetectable or responsive to treatments.

As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, and/or duration of response in a patient or a group of patients susceptible to or diagnosed with a cancer.

By "gene" is meant any polynucleotide sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The polynucleotide sequence may contain a genetic abnormality within exons, introns, initiation or termination regions, promoter sequences, other regulatory sequences or unique adjacent regions to the gene.

As used herein, "treatment" or "therapy" is an approach for obtaining beneficial or desired clinical results. This includes: reduce the number of cancer cells; reduce the tumor size; inhibit (i.e., slow to some extent and/or stop) cancer cell infiltration into peripheral organs; inhibit (i.e., slow to some extent and/or stop) tumor metastasis; inhibit, to some extent, tumor growth; and/or relieve to some extent one or more of the symptoms associated with the disorder, shrinking the size of the tumor, decreasing symptoms resulting from the disease, increasing the quality of life of those suffering from the disease, decreasing the dose of other medications required to treat the disease, delaying the progression of the disease, and/or prolonging survival of patients.

The term "therapeutically effective amount" refers to an amount of the drug that may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "overexpress", "overexpression", "overexpressed", "up-regulate", or "up-regulated" interchangeably refer to a biomarker that is transcribed or translated at a detectably greater level, usually in a cancer cell, in comparison to a non-cancer cell or cancer cell that is not associated with the worst or poorest prognosis. The term includes overexpression due to transcription, post transcriptional processing, translation, post-translational processing, cellular localization, and/or RNA and protein stability, as compared to a non-cancer cell or cancer cell that is not associated with the worst or poorest prognosis. Overexpression can be detected using conventional techniques for detecting mRNA (i.e., RT-PCR, PCR, hybridization) or proteins (i.e., ELISA, immunohistochemical techniques, mass spectroscopy). Overexpression can be 10%, 20%, 30%, 40%, 50%, 60%, 70%, 80%, 90% or more in comparison to a normal cell or cancer cell that is not associated with the worst or poorest prognosis. In certain instances, overexpression is 1-fold, 2-fold, 3-fold, 4-fold 5, 6, 7, 8, 9, 10, or 15-fold or more higher levels of transcription or translation in comparison to a non-cancer cell or cancer cell that is not associated with the worst or poorest prognosis.

"Biological sample" includes sections of tissues such as biopsy and autopsy samples, and frozen sections taken for histologic purposes. Such samples include breast cancer tissues, cultured cells, e.g., primary cultures, explants, and transformed cells. A biological sample is typically obtained from a mammal, such as a primate, e.g., human.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., breast), the size and type of the tumor, among other factors. Representative biopsy techniques include, but are not limited to, excisional biopsy, incisional biopsy, needle biopsy, and surgical biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy", or a "fine-needle aspiration biopsy" which generally obtains a suspension of cells from within a target tissue. Biopsy techniques are discussed, for example, in Harrison's Principles of Internal Medicine, 2005. Obtaining a biopsy includes both direct and indirect methods, including obtaining the biopsy from the patient or obtaining the biopsy sample after it is removed from the patient.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7A-F. Schematic of glucocorticoid receptor (GR) isoforms. GR alpha=SEQ ID NO:47; GR beta=SEQ ID NO:48

DETAILED DESCRIPTION OF THE INVENTION

Figure 1:
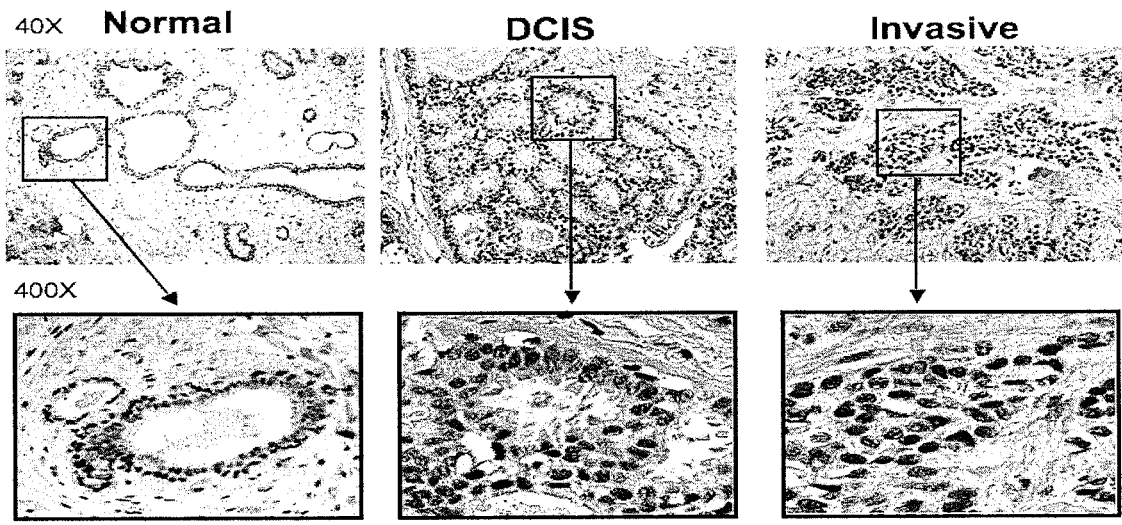
FIG. 1. Primary human breast ductal epithelium, DCIS (60%) in vasive human cancers ('30-40%) exhibit significant glucocorticoid receptor expression.
Figure 2:
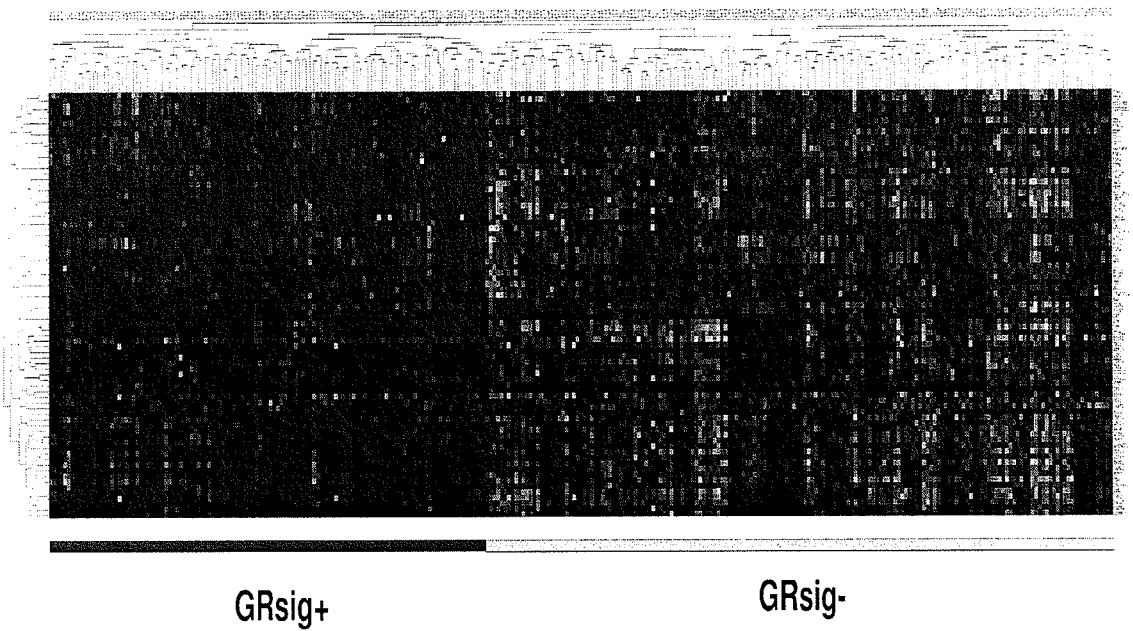
FIG. 2. Unsupervised cluster analysis identifies GR target gene signature (Sig+) vs Sig− tumors (n=68 genes) A GR-regulated gene expression set from MCF10A-Myc (ER−/GR+) cells treated +/− Dex from 30 m-24 h was used to perform a two dimensional unsupervised clustering analysis on the NKI-295 early breast cancer gene expression data set (n=2034 starting genes). GR-regulated genes (n=68) that separate these tumors into two groups (GRsig+=Red and GRsig−=Green) are shown in rows while each column represents a patient. Several EMT genes (e.g. Snail) and known anti-apoptotic genes are included.
Figure 3:
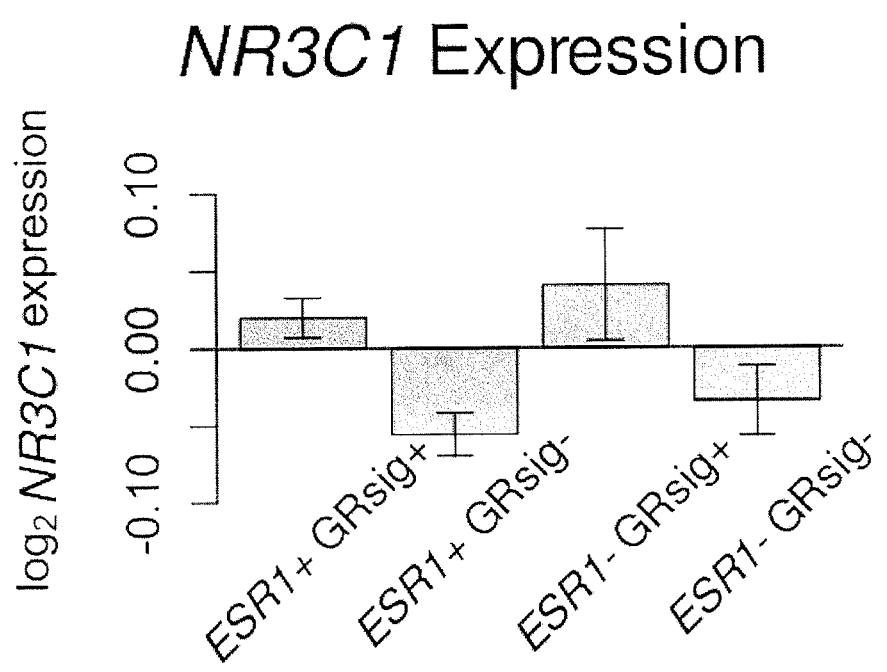
FIG. 3. NR3C1 expression correlates with GR signature gene expression. The GRsig+ vs. GRsig− tumor designations correlate with higher NR3C1 vs. lower expression, respectively. For ESR1+ tumors (orange) the P<0.00001 and for ESR1− tumors (green) p=0.7 (t test). Error bars are +/−SD.
Figure 4:
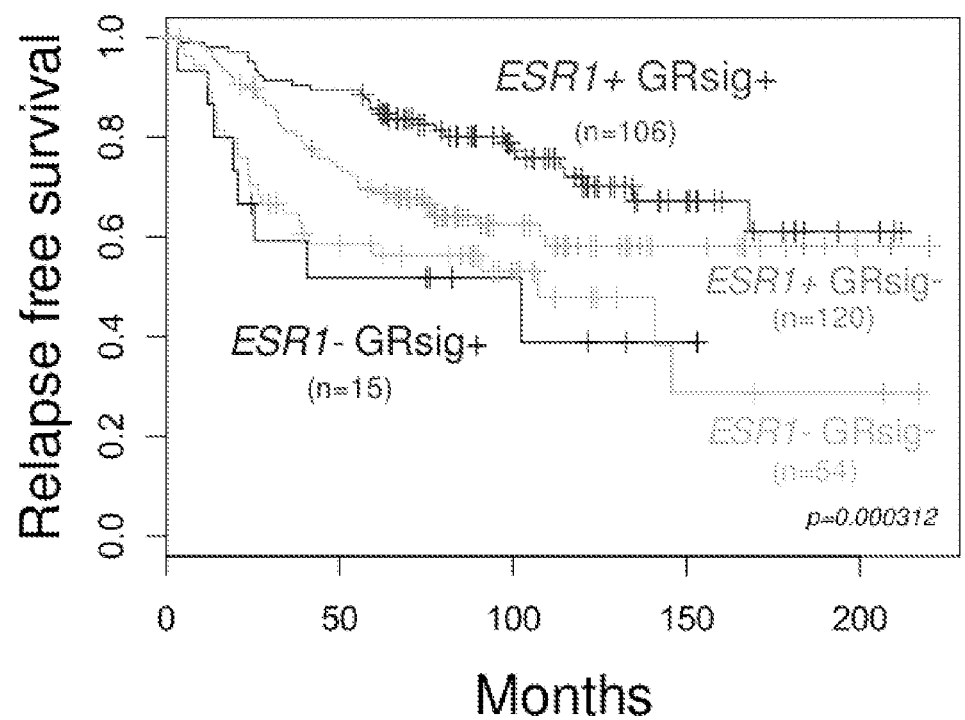
FIG. 4. RFS of GR gene expression signature. The GR signature predicts a differential prognosis for ESR1+ patients and ESR1− pts with respect to GR-signature expression. ESR1−/GR+ signature patients have the worst prognosis.
Figure 5:
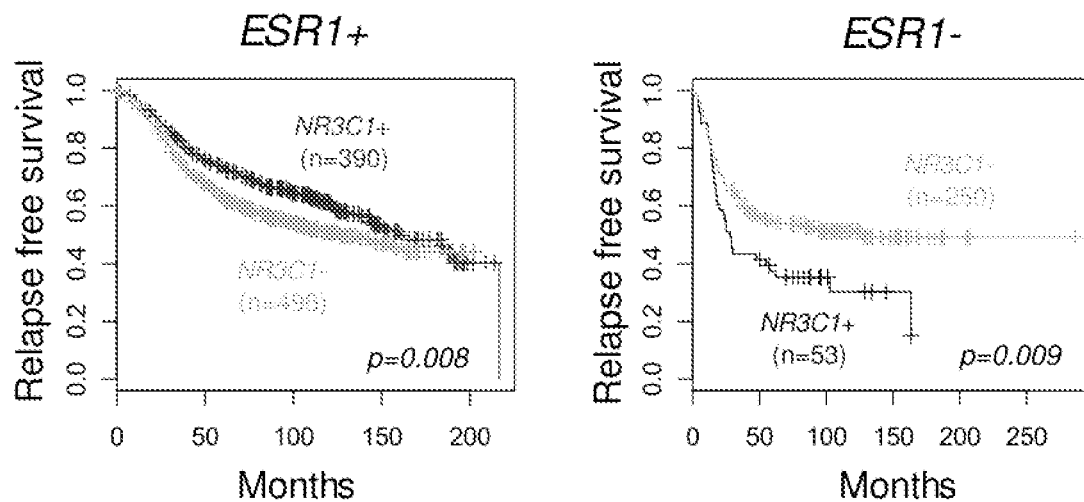
FIG. 5. Meta-analysis of NR3C1 expression and RFS.
Figure 6:
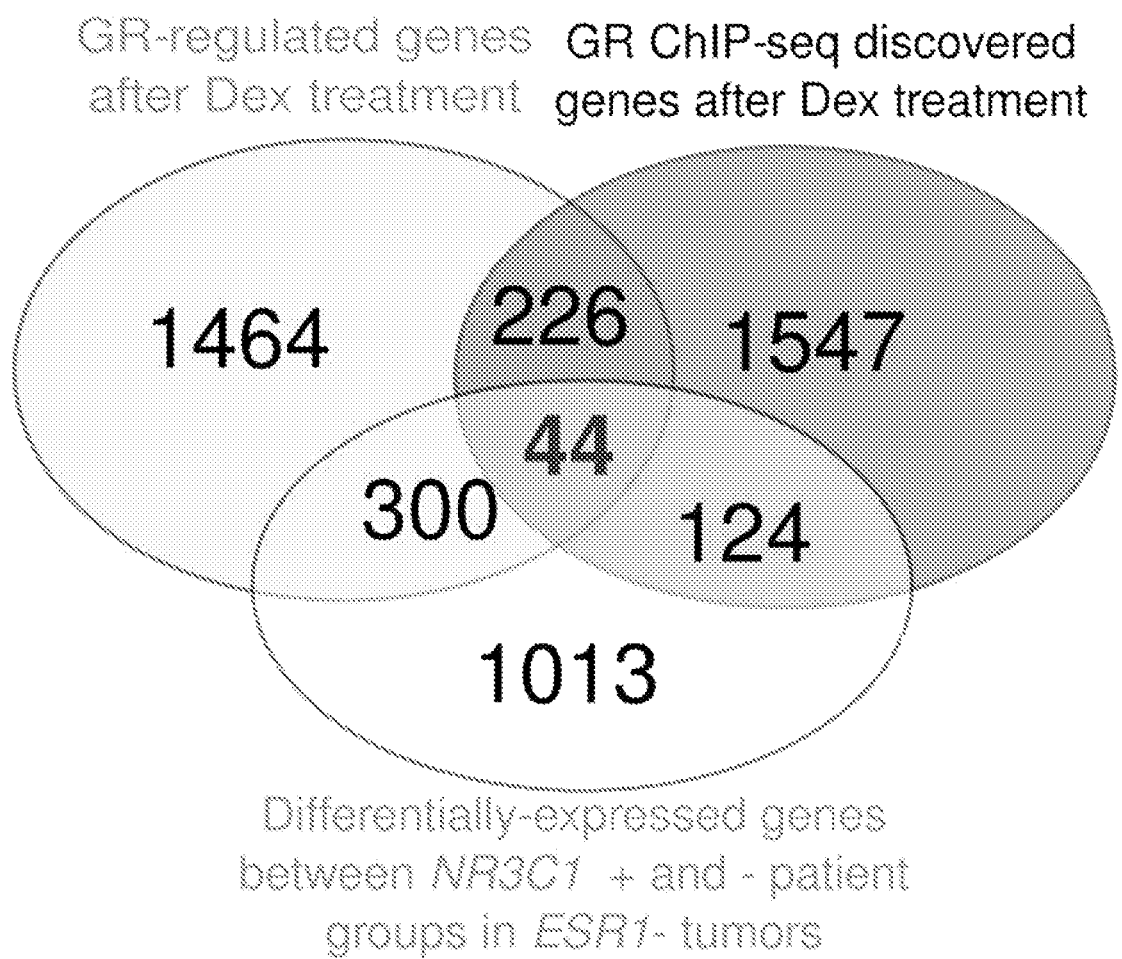
FIG. 6. Common genes differentially expressed in ESR1− and NR3C1+/− tumors, ChIP-seq and gene expression in Dex-treated MCF10A-Myc cells.

Glucocorticoid receptor (GR) activation initiates a potent cell survival signal in ER-breast cancer models. However, GR activity has not been previously examined in primary human breast cancers. Because anti-apoptotic signaling is believed to be an important determinant of breast cancer viability and relapse, the inventors contemplate that early stage primary human breast cancer demonstrates a correlation between high GR (NR3C1) and GR-mediated gene expression and cancer recurrence.

The Dutch NKI 295 data set was examined and the inventors determined that a gene expression signature of 68 GR-regulated genes (based on in vitro data) could cluster patients into different groups with differential outcome. In addition, it was found that GR-mediated gene expression correlated with NR3C1 expression levels. The inventors examined NR3C1 tumor expression in a much larger meta-dataset and again found that ER−/GR (NR3C1)+ patients did the worst. Moreover, key cell survival genes identified as GR gene targets from ChIP-seq experiments were differentially expressed.

I. Hormone Receptor Status of Breast Cancer

Intracellular receptors (IRs) form a class of structurally-related genetic regulators scientists have named "ligand dependent transcription factors" (R. M. Evans, Science, 240:889, 1988). Steroid receptors are a recognized subset of the IRs, including androgen receptor (AR), progesterone receptor (PR), estrogen receptor (ER), glucocorticoid receptor (GR), and mineralocorticoid receptor (MR). Regulation of a gene by such factors requires both the IR itself and a corresponding ligand, which has the ability to selectively bind to the IR in a way that affects gene transcription.

Naturally occurring as well as synthetic steroidal glucocorticoids (e.g., cortisol, cortisone, prednisolone, dexamethasone) have been widely used for over fifty years for the treatment of acute and chronic inflammatory and immune disorders. In particular, glucocorticoids have been prescribed for the treatment of rheumatoid arthritis, osteoarthritis, rheumatic fever, asthma, allergic rhinitis, systemic lupus erythematosus, chronic obstructive pulmonary disease, Crohn's disease, inflammatory bowel disease, and ulcerative colitis. However, the use of glucocorticoids is often associated with severe and sometimes irreversible side effects such as bone loss/osteoporosis, hyperglycemia, diabetes mellitus, hypertension, glaucoma, muscle atrophy, Cushing's syndrome, and psychosis.

Glucocorticoids exert their pharmacological effects by regulating gene transcription after the formation of a complex with the glucocorticoid receptor (GR). GR-glucocorticoid complex affects gene transcription by translocating to the nucleus after binding of the glucocorticoid where it acts as a dimer in binding to DNA glucocorticoid hormone response elements (GREs) in the promoter regions of particular genes. The GR-glucocorticoid/GRE complex then, in turn, activates (transactivation) or inhibits transcription of proximally located genes. Conversely, the GR-glucocorticoid complex may negatively regulate gene transcription by a process that does not involve binding to DNA. In this process, termed transrepression, following binding of the glucocorticoid, the complexed GR enters the nucleus where it acts as a monomer to directly interact (via protein-protein interaction) with other transcription factors, repressing their ability to induce gene transcription and thus protein expression.

Estrogen, mediated through the estrogen receptor (ER), plays a major role in regulating the growth and differentiation of normal breast epithelium (Pike et al. Epidemiologic Reviews (1993) 15(1):17-35; Henderson et al. Cancer Res. (1988) 48:246-253). It stimulates cell proliferation and regulates the expression of other genes, including the progesterone receptor (PgR). PgR then mediates the mitogenic effect of progesterone, further stimulating proliferation (Pike et al., 1993; Henderson et al., 1988). The molecular differences between estrogen receptor ("ER") negative and ER positive tumors are significant in light of clinical observations which indicate that the nature and biological behavior of ER positive and ER negative tumors are distinct even in the absence of hormonal therapy. For example, ER negative cancers tend to recur sooner and show a different rate of recurrence in distant organ sites compared to ER positive tumors. Clinical observations and molecular profiling data suggest that tumors not expressing both ER and PgR represent a different clinical entity in terms of chemotherapy responsiveness. (Colleoni et al., Annals of Oncology 11(8): 1057 (2000)). Thus, ER negative and ER positive breast cancers are two distinct disease entities rather than phenotypic variations of the same disease.

Relatively increased expression of these genes in primary ER-negative human breast tumors is associated with high GR expression and with an earlier relapse in ER-negative breast cancer patients (described herein). Activation of the glucocorticoid receptor (GR) in epithelial cells has been shown to initiate an anti-apoptotic (i.e., cell survival) signaling pathway that prevents breast (Wu et al, 2004) and ovarian cancer (Melhem et al, 2009) cell death in vitro and in vivo (Pang et al, 2006). Blocking or antagonizing GR activation with a GR antagonist such as mifepristone reverses cell survival signaling pathways initiated by the GR (Moran et al., 2000). Other GR antagonists (e.g., dexamethasone oxetanone) also reverse GR-mediated cell survival and potentiate apoptosis in response to cell stressors such as growth factor withdrawal (Mikosz et al, 2001). The mechanism(s) whereby GR activation protects from cell death includes the transcriptional upregulation of genes encoding anti-apoptotic proteins such as SGK1, MKP1, MCL1, and BIRC3. However, experiments with a glucocorticoid receptor antagonist, RU486, in conjunction with dexamethasone did not increase the number of apoptotic cells induced by paclitaxel, compared to paclitaxel alone (Wu et al., 2004).

II. Biomarkers and Evaluating Levels of Biomarkers

Biomarkers for prognosing human breast cancer patients have been identified. They include estrogen receptor (ER) in combination with the activity of the glucocorticoid receptor (GR) activity. It is contemplated that these biomarkers may be evaluated based on their gene products. In some embodiments, the gene product is the RNA transcript. In other embodiments, the gene product is the protein expressed by the RNA transcript. In still another embodiment is the evaluation of surrogate genes or gene targets of ER, GR, or ER and GR.

In certain aspects a meta-analysis of expression or activity can be performed. In statistics, a meta-analysis combines the results of several studies that address a set of related research hypotheses. This is normally done by identification of a common measure of effect size, which is modeled using a form of meta-regression. Generally, three types of models can be distinguished in the literature on meta-analysis: simple regression, fixed effects meta-regression and random effects meta-regression. Resulting overall averages when controlling for study characteristics can be considered meta-effect sizes, which are more powerful estimates of the true effect size than those derived in a single study under a given single set of assumptions and conditions. A meta-gene expression value, in this context, is to be understood as being the median of the normalized expression of a marker gene or activity. Normalization of the expression of a marker gene is preferably achieved by dividing the expression level of the individual marker gene to be normalized by the respective individual median expression of this marker genes, wherein said median expression is preferably calculated from multiple measurements of the respective gene in a sufficiently large cohort of test individuals. The test cohort preferably comprises at least 3, 10, 100, 200, 1000 individuals or more including all values and ranges thereof. Dataset-specific bias can be removed or minimized allowing multiple datasets to be combined for meta-analyses (See Sims et al. BMC Medical Genomics (1:42), 1-14, 2008, which is incorporated herein by reference in its entirety).

The calculation of a meta-gene expression value is performed by: (i) determining the gene expression value of at least two, preferably more genes (ii) "normalizing" the gene expression value of each individual gene by dividing the expression value with a coefficient which is approximately the median expression value of the respective gene in a representative breast cancer cohort (iii) calculating the median of the group of normalized gene expression values.

A gene shall be understood to be specifically expressed in a certain cell type if the expression level of said gene in said cell type is at least 2-fold, 5-fold, 10-fold, 100-fold, 1000-fold, or 10000-fold higher than in a reference cell type, or in a mixture of reference cell types. Reference cell types include non-cancerous breast tissue cells or a heterogenous population of breast cancers.

In certain algorithms a suitable threshold level is first determined for a marker gene. The suitable threshold level can be determined from measurements of the marker gene expression in multiple individuals from a test cohort. The median expression of the marker gene in said multiple expression measurements is taken as the suitable threshold value.

Comparison of multiple marker genes with a threshold level can be performed as follows:

1. The individual marker genes are compared to their respective threshold levels.
2. The number of marker genes, the expression level of which is above their respective threshold level, is determined.
3. If a marker genes is expressed above its respective threshold level, then the expression level of the marker gene is taken to be "above the threshold level".

"A sufficiently large number", in this context, means preferably 30%, 50%, 80%, 90%, or 95% of the marker genes used.

In certain aspects, the determination of expression levels is on a gene chip, such as an Affymetrix™ gene chip.

In another aspect, the determination of expression levels is done by kinetic real time PCR.

In certain aspects, the methods can relate to a system for performing such methods, the system comprising (a) apparatus or device for storing data on the ER or nodal status of the patient; (b) apparatus or device for determining the expression level of at least one marker gene or activity; (c) apparatus or device for comparing the expression level of the first marker gene or activity with a predetermined first threshold value; (d) apparatus or device for determining the expression level of at least one second marker gene or activity; and (e) computing apparatus or device programmed to provide a unfavorable or poor prognosis if the data indicates a negative ER status and an increased or decreased expression level of said first marker gene or activity (e.g., GR expression or activity) with the predetermined first threshold value and, alternatively, the expression level of said second marker gene is above or below a predetermined second threshold level.

The person skilled in the art readily appreciates that an unfavorable or poor prognosis can be given if the expression level of the first marker gene with the predetermined first threshold value indicates a tumor that is likely to recur or not respond well to standard therapies.

The expression patterns can also be compared by using one or more ratios between the expression levels of different breast cancer biomarkers. Other suitable measures or indicators can also be employed for assessing the relationship or difference between different expression patterns.

The GR nucleic acid and protein sequences are provided in GenBank accession number AY436590. The ER nucleic acid and protein sequences are provided in GenBank accession number NG_008493. The content of all of these GenBank Accession numbers is specifically incorporated herein by reference as of the filing date of this application.

The following biomarkers are provided for implementation with embodiments discussed herein. All of them designate nucleic acid sequences for the particular gene identifier. Nucleic acid sequences related to these gene designation can be found in the Genbank sequence databases. Additional biomarkers include the MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, and MAOA genes.

One or more of the biomarkers can be used to prognose a human patient with breast cancer. The expression pattern of these biomarkers in breast cancer cells may be used to evaluate a patient to determine whether they are likely to respond to standard chemotherapy, likely not to respond to standard chemotherapy, or likely to relapse after standard chemotherapy.

The expression levels of breast cancer biomarkers can be compared to reference expression levels using various methods. These reference levels can be determined using expression levels of a reference based on all breast cancer patients or all breast cancer patients determined to be ER+ and/or ER−. Alternatively, it can be based on an internal reference such as a gene that is expressed in all cells. In some embodiments, the reference is a gene expressed in breast cancer cells at a higher level than any biomarker. Any comparison can be performed using the fold change or the absolute difference between the expression levels to be compared. One or more breast cancer biomarkers can be used in the comparison. It is contemplated that 1, 2, 3, 4, 5, 6, 7, 8, and/or 9 biomarkers may be compared to each other and/or to a reference that is internal or external. A person of ordinary skill in the art would know how to do such comparisons.

Comparisons or results from comparisons may reveal or be expressed as x-fold increase or decrease in expression relative to a standard or relative to another biomarker or relative to the same biomarker but in a different class of prognosis. In some embodiments, patients with a poor prognosis have a relatively high level of expression (overexpression) or relatively low level of expression (underexpression) when compared to patients with a better or favorable prognosis, or vice versa.

Fold increases or decreases may be, be at least, or be at most 1-, 2-, 3-, 4-, 5-, 6-, 7-, 8-, 9-, 10-, 11-, 12-, 13-, 14-, 15-, 16-, 17-, 18-, 19-, 20-, 25-, 30-, 35-, 40-, 45-, 50-, 55-, 60-, 65-, 70-, 75-, 80-, 85-, 90-, 95-, 100- or more, or any range derivable therein. Alternatively, differences in expression may be expressed as a percent decrease or increase, such as at least or at most 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 1000% difference, or any range derivable therein.

Other ways to express relative expression levels are by normalized or relative numbers such as 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, or any range derivable therein.

Algorithms, such as the weighted voting programs, can be used to facilitate the evaluation of biomarker levels. In addition, other clinical evidence can be combined with the biomarker-based test to reduce the risk of false evaluations. Other cytogenetic evaluations may be considered in some embodiments of the invention.

Any biological sample from the patient that contains breast cancer cells may be used to evaluate the expression pattern of any biomarker discussed herein. In some embodiments, a biological sample from a breast tumor is used. Evaluation of the sample may involve, though it need not involve, panning (enriching) for cancer cells or isolating the cancer cells.

A. Nucleic Acids

Screening methods based on differentially expressed gene products are well known in the art. In accordance with one aspect of the present invention, the differential expression patterns of breast cancer biomarkers can be determined by measuring the levels of RNA transcripts of these genes, or genes whose expression is modulated by the these genes, in the patient's breast cancer cells. Suitable methods for this purpose include, but are not limited to, RT-PCR, Northern Blot, in situ hybridization, Southern Blot, slot-blotting, nuclease protection assay and oligonucleotide arrays.

In certain aspects, RNA isolated from breast cancer cells can be amplified to cDNA or cRNA before detection and/or quantitation. The isolated RNA can be either total RNA or mRNA. The RNA amplification can be specific or nonspecific. Suitable amplification methods include, but are not limited to, reverse transcriptase PCR, isothermal amplification, ligase chain reaction, and Qbeta replicase. The amplified nucleic acid products can be detected and/or quantitated through hybridization to labeled probes. In some embodiments, detection may involve fluorescence resonance energy transfer (FRET) or some other kind of quantum dots.

Amplification primers or hybridization probes for a breast cancer biomarker can be prepared from the gene sequence or obtained through commercial sources, such as Affymatrix. In certain embodiments the gene sequence is identical or complementary to at least 8 contiguous nucleotides of the coding sequence.

Sequences suitable for making probes/primers for the detection of their corresponding breast cancer biomarkers include those that are identical or complementary to all or part of genes or SEQ ID NOs described herein. These sequences are all nucleic acid sequences of breast cancer biomarkers.

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

In one embodiment, each probe/primer comprises at least 15 nucleotides. For instance, each probe can comprise at least or at most 20, 25, 50, 75, 100, 125, 150, 175, 200, 225, 250, 275, 300, 325, 350, 400 or more nucleotides (or any range derivable therein). They may have these lengths and have a sequence that is identical or complementary to a gene or SEQ ID NO described herein. Preferably, each probe/primer has relatively high sequence complexity and does not have any ambiguous residue (undetermined "n" residues). The probes/primers preferably can hybridize to the target gene, including its RNA transcripts, under stringent or highly stringent conditions. In some embodiments, because each of the biomarkers has more than one human sequence, it is contemplated that probes and primers may be designed for use with each on of these sequences. For example, inosine is a nucleotide frequently used in probes or primers to hybridize to more than one sequence. It is contemplated that probes or primers may have inosine or other design implementations that accommodate recognition of more than one human sequence for a particular biomarker.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In another embodiment, the probes/primers for a gene are selected from regions which significantly diverge from the sequences of other genes. Such regions can be determined by checking the probe/primer sequences against a human genome sequence database, such as the Entrez database at the NCBI. One algorithm suitable for this purpose is the BLAST algorithm. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence to increase the cumulative alignment score. Cumulative scores are calculated using, for nucleotide sequences, the parameters M (reward score for a pair of matching residues; always >0) and N (penalty score for mismatching residues; always <0). The BLAST algorithm parameters W, T, and X determine the sensitivity and speed of the alignment. These parameters can be adjusted for different purposes, as appreciated by one of ordinary skill in the art.

In one embodiment, quantitative RT-PCR (such as Taq-Man, ABI) is used for detecting and comparing the levels of RNA transcripts in breast cancer samples. Quantitative RT-PCR involves reverse transcription (RT) of RNA to cDNA followed by relative quantitative PCR (RT-PCR). The concentration of the target DNA in the linear portion of the PCR process is proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived may be determined for the respective tissues or cells. This direct proportionality between the concentration of the PCR products and the relative mRNA abundances is true in the linear range portion of the PCR reaction. The final concentration of the target DNA in the plateau portion of the curve is determined by the availability of reagents in the reaction mix and is independent of the original concentration of target DNA. Therefore, the sampling and quantifying of the amplified PCR products preferably are carried out when the PCR reactions are in the linear portion of their curves. In addition, relative concentrations of the amplifiable cDNAs preferably are normalized to some independent standard, which may be based on either internally existing RNA species or externally introduced RNA species. The abundance of a particular mRNA species may also be determined relative to the average abundance of all mRNA species in the sample.

In one embodiment, the PCR amplification utilizes one or more internal PCR standards. The internal standard may be an abundant housekeeping gene in the cell or it can specifically be GAPDH, GUSB and β-2 microglobulin. These standards may be used to normalize expression levels so that the expression levels of different gene products can be compared directly. A person of ordinary skill in the art would know how to use an internal standard to normalize expression levels.

A problem inherent in clinical samples is that they are of variable quantity and/or quality. This problem can be overcome if the RT-PCR is performed as a relative quantitative RT-PCR with an internal standard in which the internal standard is an amplifiable cDNA fragment that is similar or larger than the target cDNA fragment and in which the abundance of the mRNA encoding the internal standard is roughly 5-100 fold higher than the mRNA encoding the target. This assay measures relative abundance, not absolute abundance of the respective mRNA species.

In another embodiment, the relative quantitative RT-PCR uses an external standard protocol. Under this protocol, the PCR products are sampled in the linear portion of their amplification curves. The number of PCR cycles that are optimal for sampling can be empirically determined for each target cDNA fragment. In addition, the reverse transcriptase products of each RNA population isolated from the various samples can be normalized for equal concentrations of amplifiable cDNAs.

Nucleic acid arrays can also be used to detect and compare the differential expression patterns of breast cancer biomarkers in breast cancer cells. The probes suitable for detecting the corresponding breast cancer biomarkers can be stably attached to known discrete regions on a solid substrate. As used herein, a probe is "stably attached" to a discrete region if the probe maintains its position relative to the discrete region during the hybridization and the subsequent washes. Construction of nucleic acid arrays is well known in the art. Suitable substrates for making polynucleotide arrays include, but are not limited to, membranes, films, plastics and quartz wafers.

A nucleic acid array of the present invention can comprise at least 1, 2, 3, 4, 5, 6, 7, 8, 9, 10, 15, 20, 25, 30, 35, 40, 45, 50, 60, 70, 80, 90, 100, 150, 200, 250 or more different polynucleotide probes, which may hybridize to different and/or the same biomarkers. Multiple probes for the same gene can be used on a single nucleic acid array. Probes for other disease genes can also be included in the nucleic acid array. The probe density on the array can be in any range. In some embodiments, the density may be 50, 100, 200, 300, 400, 500 or more probes/cm$^2$.

Specifically contemplated by the present inventors are chip-based nucleic acid technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991). It is contemplated that this technology may be used in conjunction with evaluating the expression level of one or more breast cancer biomarkers with respect to diagnostic, prognostic, and treatment methods of the invention.

The present invention may involve the use of arrays or data generated from an array. Data may be readily available. Moreover, an array may be prepared in order to generate data that may then be used in correlation studies.

An array generally refers to ordered macroarrays or microarrays of nucleic acid molecules (probes) that are fully or nearly complementary or identical to a plurality of mRNA molecules or cDNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon. Such arrays may vary in a number of different ways, including average probe length, sequence or types of probes, nature of bond between the probe and the array surface, e.g. covalent or non-covalent, and the like. The labeling and screening methods of the present invention and the arrays are not limited in its utility with respect to any parameter except that the probes detect expression levels; consequently, methods and compositions may be used with a variety of different types of genes.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments. In certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols include information found in WO 9743450; WO 03023058; WO 03022421; WO 03029485; WO 03067217; WO 03066906; WO 03076928; WO 03093810; WO 03100448A1, all of which are specifically incorporated by reference.

In one embodiment, nuclease protection assays are used to quantify RNAs derived from the breast cancer samples. There are many different versions of nuclease protection assays known to those practiced in the art. The common characteristic that these nuclease protection assays have is that they involve hybridization of an antisense nucleic acid with the RNA to be quantified. The resulting hybrid double-stranded molecule is then digested with a nuclease that digests single-stranded nucleic acids more efficiently than double-stranded molecules. The amount of antisense nucleic acid that survives digestion is a measure of the amount of the target RNA species to be quantified. An example of a nuclease protection assay that is commercially available is the RNase protection assay manufactured by Ambion, Inc. (Austin, Tex.).

B. Proteins and Polypeptides

In other embodiments, the differential expression patterns of breast cancer biomarkers can be determined by measuring the levels of polypeptides encoded by these genes in breast cancer cells. Methods suitable for this purpose include, but are not limited to, immunoassays such as ELISA, RIA, FACS, dot blot, Western Blot, immunohistochemistry, and antibody-based radioimaging. Protocols for carrying out these immunoassays are well known in the art. Other methods such as 2-dimensional SDS-polyacrylamide gel electrophoresis can also be used. These procedures may be used to recognize any of the polypeptides encoded by the breast cancer biomarker genes described herein.

One example of a method suitable for detecting the levels of target proteins in peripheral blood samples is ELISA. In an exemplifying ELISA, antibodies capable of binding to the target proteins encoded by one or more breast cancer biomarker genes are immobilized onto a selected surface exhibiting protein affinity, such as wells in a polystyrene or polyvinylchloride microtiter plate. Then, breast cancer cell samples to be tested are added to the wells. After binding and washing to remove non-specifically bound immunocomplexes, the bound antigen(s) can be detected. Detection can be achieved by the addition of a second antibody which is specific for the target proteins and is linked to a detectable label. Detection may also be achieved by the addition of a second antibody, followed by the addition of a third antibody that has binding affinity for the second antibody, with the third antibody being linked to a detectable label. Before being added to the microtiter plate, cells in the peripheral blood samples can be lysed using various methods known in the art. Proper extraction procedures can be used to separate the target proteins from potentially interfering substances.

In another ELISA embodiment, the breast cancer cell samples containing the target proteins are immobilized onto the well surface and then contacted with the antibodies of the invention. After binding and washing to remove non-specifically bound immunocomplexes, the bound antigen is detected. Where the initial antibodies are linked to a detectable label, the immunocomplexes can be detected directly. The immunocomplexes can also be detected using a second antibody that has binding affinity for the first antibody, with the second antibody being linked to a detectable label.

Another typical ELISA involves the use of antibody competition in the detection. In this ELISA, the target proteins are immobilized on the well surface. The labeled antibodies are added to the well, allowed to bind to the target proteins, and detected by means of their labels. The amount of the target proteins in an unknown sample is then determined by mixing the sample with the labeled antibodies before or during incubation with coated wells. The presence of the target proteins in the unknown sample acts to reduce the amount of antibody available for binding to the well and thus reduces the ultimate signal.

Different ELISA formats can have certain features in common, such as coating, incubating or binding, washing to remove non-specifically bound species, and detecting the bound immunocomplexes. For instance, in coating a plate with either antigen or antibody, the wells of the plate can be incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test samples. Examples of these nonspecific proteins include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means can also be used. After binding of a protein or antibody to the well, coating with a non-reactive material to reduce background, and washing to remove unbound material, the immobilizing surface is contacted with the control and/or clinical or biological sample to be tested under conditions effective to allow immunocomplex (antigen/antibody) formation. These conditions may include, for example, diluting the antigens and antibodies with solutions such as BSA, bovine gamma globulin (BGG) and phosphate buffered saline (PBS)/Tween and incubating the antibodies and antigens at room temperature for about 1 to 4 hours or at 49° C. overnight. Detection of the immunocomplex then requires a labeled secondary binding ligand or antibody, or a secondary binding ligand or antibody in conjunction with a labeled tertiary antibody or third binding ligand.

After all of the incubation steps in an ELISA, the contacted surface can be washed so as to remove non-complexed material. For instance, the surface may be washed with a solution such as PBS/Tween, or borate buffer. Following the formation of specific immunocomplexes between the test sample and the originally bound material, and subsequent washing, the occurrence of the amount of immunocomplexes can be determined.

To provide a detecting means, the second or third antibody can have an associated label to allow detection. In one embodiment, the label is an enzyme that generates color development upon incubating with an appropriate chromogenic substrate. Thus, for example, one may contact and incubate the first or second immunocomplex with a urease, glucose oxidase, alkaline phosphatase or hydrogen peroxidase-conjugated antibody for a period of time and under conditions that favor the development of further immunocomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl)-benzhiazoline-6-sulfonic acid (ABTS) and hydrogen peroxide, in the case of peroxidase as the enzyme label. Quantitation can be achieved by measuring the degree of color generation, e.g., using a spectrophotometer.

Another suitable method is RIA (radioimmunoassay). An example of RIA is based on the competition between radiolabeled-polypeptides and unlabeled polypeptides for binding to a limited quantity of antibodies. Suitable radiolabels include, but are not limited to, $I^{125}$. In one embodiment, a fixed concentration of $I^{215}$-labeled polypeptide is incubated with a series of dilution of an antibody specific to the polypeptide. When the unlabeled polypeptide is added to the system, the amount of the $I^{125}$-polypeptide that binds to the antibody is decreased. A standard curve can therefore be constructed to represent the amount of antibody-bound $I^{125}$-polypeptide as a function of the concentration of the unlabeled polypeptide. From this standard curve, the concentration of the polypeptide in unknown samples can be determined. Various protocols for conducting RIA to measure the levels of polypeptides in breast cancer cell samples are well known in the art.

Suitable antibodies for this invention include, but are not limited to, polyclonal antibodies, monoclonal antibodies, chimeric antibodies, humanized antibodies, single chain antibodies, Fab fragments, and fragments produced by a Fab expression library.

Antibodies can be labeled with one or more detectable moieties to allow for detection of antibody-antigen complexes. The detectable moieties can include compositions detectable by spectroscopic, enzymatic, photochemical, biochemical, bioelectronic, immunochemical, electrical, optical or chemical means. The detectable moieties include, but are not limited to, radioisotopes, chemiluminescent compounds, labeled binding proteins, heavy metal atoms, spectroscopic markers such as fluorescent markers and dyes, magnetic labels, linked enzymes, mass spectrometry tags, spin labels, electron transfer donors and acceptors, and the like.

Protein array technology is discussed in detail in Pandey and Mann (2000) and MacBeath and Schreiber (2000), each of which is herein specifically incorporated by reference. These arrays typically contain thousands of different proteins or antibodies spotted onto glass slides or immobilized in tiny wells and allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds. In certain embodiments such technology can be used to quantitate a number of proteins in a sample, such as a breast cancer biomarker proteins.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

The earliest and best-known protein chip is the ProteinChip by Ciphergen Biosystems Inc. (Fremont, Calif.). The ProteinChip is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip system detects proteins ranging from small peptides of less than 1000 Da up to proteins of 300 kDa and calculates the mass based on time-of-flight (TOF).

The ProteinChip biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

In other aspects, the levels of polypeptides in samples can be determined by detecting the biological activities associated with the polypeptides. If a biological function/activity of a polypeptide is known, suitable in vitro bioassays can be designed to evaluate the biological function/activity, thereby determining the amount of the polypeptide in the sample.

III. Breast Cancer Therapy

Certain embodiments are directed to methods of treating breast cancer based on GR status of the breast cancer tissue. In some embodiments, the hormone receptor status is determined based on the expression of a hormone receptor such as the estrogen receptor (ER) in combination with the glucocorticoid receptor (GR).

In certain aspects, the hormone receptor status is high for GR and may also be low for one or more other hormone receptors such as the estrogen receptor. An individual having an elevated GR and low ER is likely to have a poor prognosis. In the event of a poor prognosis the physician may pursue a more aggressive therapy for those patients. In some embodiments, the method comprises identifying a breast cancer patient based on a hormone receptor status of patients having tumor tissue with elevated levels of GR expression.

In certain aspects, there may be provided methods for treating a subject determined to have cancer and with a predetermined expression profile of one or more biomarkers disclosed herein.

In a further aspect, biomarkers and related systems that can establish a prognosis of cancer patients in this invention can be used to identify patients who may get benefit of conventional single or combined modality therapy. In the same way, the invention can identify those patients who do not get much benefit from such conventional single or combined modality therapy and can offer them alternative treatment(s).

In certain aspects of the present invention, conventional cancer therapy may be applied to a subject wherein the subject is identified or reported as having a good prognosis based on the assessment of the biomarkers as disclosed. On the other hand, at least an alternative cancer therapy may be prescribed, as used alone or in combination with conventional cancer therapy, if a poor prognosis is determined by the disclosed methods, systems, or kits.

Embodiments concern a glucocorticoid receptor antagonist. In some embodiments, the glucocorticoid receptor antagonist is a selective glucocorticoid receptor antagonist, as set forth in Clark, 2008, which is hereby incorporated by reference. In other embodiments, the glucocorticoid receptor antagonist is a non-selective glucocorticoid receptor antagonist, such as mifepristone. In certain embodiments, the glucocorticoid receptor antagonist is steroidal. In other embodiments, the glucocorticoid receptor antagonist is non-steroidal. A glucocorticoid receptor antagonist includes those in the following classes of chemical compounds: octahydrophenanthrenes, spirocyclic dihydropyridines, triphenylmethanes and diaryl ethers, chromenes, dibenzyl anilines, dihydroisoquinolines, pyrimidinediones, azadecalins, and aryl pyrazolo azadecalins, and which are described in more detail in Clark, 2008, which is hereby incorporated by reference. Some embodiments of steroidal antagonists from Clark, 2008 are: RU-486, RU-43044, 11-monoaryl and 11,21 bisaryl steroids (including 11β-substituted steroids), 10β-substituted steroids, 11β-aryl conjugates of mifepristone, and phosphorous-containing mifepristone analogs. Further embodiments of nonsteroidal antagonists from Clark, 2008 are: octahydrophenanthrenes, spirocyclic dihydropyridines, triphenylmethanes and diaryl ethers, chromenes, dibenzyl anilines, dihyrdroquinolines, pyrimidinediones, azadecalins, aryl pyrazolo azadecalins (including 8a-benzyl isoquinolones, N-substituted derivatives, bridgehead alcohol and ethers, bridgehead amines). Additional specific examples include, but are not limited to the following specific antagonists: beclometasone, betamethasone, budesonide, ciclesonide, flunisolide, fluticasone, mifepristone, mometasone, and triamcinolone. Other examples include those described and/or depicted in U.S. Patent Application Publication 2010/0135956, which is hereby incorporated by reference. Even further examples include ORG-34517 (Merck), RU-43044, dexamethasone mesylate (Dex-Mes), dexamethasone oxetanone (Dex-Ox), deoxycorticosterone (DOC) (Peeters et al., 2008, which is hereby incorporated by reference in its entirety and Cho et al. 2005, which is hereby incorporated by reference in its entirety). In additional embodiments the glucocorticoid receptor antagonist may be CORT 0113083 or CORT 00112716, which are described in Belanoff et al. (2011), which is hereby incorporated by reference. It is specifically contemplated that one or more of the antagonists discussed herein or in the incorporated references may be excluded in embodiments of the invention. It is also contemplated that in some embodiments, more than one glucocorticoid receptor antagonist is employed, while in other embodiments, only one is employed as part of the therapeutic method (though it may be administered multiple times). It is contemplated that the second one may be administered concurrently with the first one or they may be administered at different times.

Conventional cancer therapies include one or more selected from the group of chemical or radiation based treatments and surgery. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, or any analog or derivative variant of the foregoing.

Suitable therapeutic agents include, for example, vinca alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), serine kinase targeting agents, transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

Certain chemotherapeutics are well known for use against breast cancer. These breast cancer chemotherapeutics are capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, vinorelbine.

In some embodiments, the chemotherapeutic agent is any of (and in some embodiments selected from the group consisting of) adriamycin, colchicine, cyclophosphamide, actinomycin, bleomycin, daunorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), topetecan, vinblastine, vincristine, tamoxifen, piposulfan, nab-5404, nab-5800, nab-5801, Irinotecan, HKP, Ortataxel, gemcitabine, Herceptin®, vinorelbine, capecitabine, Gleevec®, Alimta®, Avastin®, Velcade®, Tarceva®, Neulasta®, Lapatinib, STI-571, ZD1839, Iressa® (gefitinib), SH268, genistein, CEP2563, SU6668, SU11248, EMD121974, and Sorafenib.

In some embodiments, the chemotherapeutic agent is a composition comprising nanoparticles comprising a thiocolchicine derivative and a carrier protein (such as albumin).

In further embodiments a combination of chemotherapeutic agents is administered to breast cancer cells. The chemotherapeutic agents may be administered serially (within minutes, hours, or days of each other) or in parallel; they also may be administered to the patient in a pre-mixed single composition. The composition may or may not contain a glucocorticoid receptor antagonist. Combinations of breast cancer therapeutics include, but are not limited to the following: AT (Adriamycin and Taxotere), AC±T: (Adriamycin and Cytoxan, with or without Taxol or Taxotere), CMF (Cytoxan, methotrexate, and fluorouracil), CEF (Cytoxan, Ellence, and fluorouracil), FAC (fluorouracil, Adriamycin, and Cytoxan), CAF (Cytoxan, Adriamycin, and fluorouracil) (the FAC and CAF regimens use the same medicines but use different doses and frequencies), TAC (Taxotere, Adriamycin, and Cytoxan), and GET (Gemzar, Ellence, and Taxol). In some embodiments trastuzumab (Herceptin®) is administered to a breast cancer patient with a glucocorticoid receptor antagonist, which may be with or without a chemotherapeutic or a combination of chemotherapeutics.

Various combinations with a glucocorticoid receptor antagonist and an anticancer agent or compound (or a combination of such agents and/or compounds) may be employed, for example glucocorticoid receptor antagonist is "A" and the anticancer agent or compound (or a combination of such agents and/or compounds) given as part of an anticancer therapy regime, is "B".

A/B/A B/A/B B/B/A A/A/B A/B/B B/A/A A/B/B/B B/A/B/B B/B/B/A
B/B/A/B A/A/B/B A/B/A/B A/B/B/A B/B/A/A B/A/B/A B/A/A/B
A/A/A/B B/A/A/A A/B/A/A A/A/B/A

Administration of the therapeutic compounds or agents to a patient will follow general protocols for the administration of such compounds, taking into account the toxicity, if any, of the therapy. It is expected that the treatment cycles would be repeated as necessary. It also is contemplated that various standard therapies, as well as surgical intervention, may be applied in combination with the described therapy.

The term "a serine/threonine kinase inhibitor", as used herein, relates to a compound which inhibits serine/threonine kinases. An example of a target of a serine/threonine kinase inhibitor includes, but is not limited to, dsRNA-dependent protein kinase (PKR). Examples of indirect targets of a serine/threonine kinase inhibitor include, but are not limited to, MCP-1, NF-kappaB, eIF2alpha, COX2, RANTES, IL8, CYP2A5, IGF-1, CYP2B1, CYP2B2, CYP2H1, ALAS-1, HIF-1, erythropoietin and/or CYP1A1. An example of a serine/theronin kinase inhibitor includes, but is not limited to, Sorafenib and 2-aminopurine, also known as 1H-purin-2-amine(9CI). Sorafenib is marketed as NEXAVAR.

The term "an angiogenesis inhibitor", as used herein, relates to a compound which targets, decreases or inhibits the production of new blood vessels. Targets of an angiogenesis inhibitor include, but are not limited to, methionine aminopeptidase-2 (MetAP-2), macrophage inflammatory protein-1 (MIP-1a), CCL5, TGF-.beta., lipoxygenase, cyclooxygenase, and topoisomerase. Indirect targets of an angiogenesis inhibitor include, but are not limited to, p21, p53, CDK2 and collagen synthesis. Examples of an angiogenesis inhibitor include, but are not limited to, Fumagillin, which is known as 2,4,6,8-decatetraenedioic acid, mono[3R,4S,5S,6R)-5-methoxy-4-[(2R,3R)-2-methyl-3-(3-methyl-2-butenyl)oxi-ranyl]-1-oxaspiro[2.5]oct-6-yl]ester, (2E,4E,6E,8E)-(9CI); Shikonin, which is also known as 1,4-naphthalenedione, 5,8-dihydroxy-2-[(1R)-1-hydroxy-4-methyl-3-pentenyl]-(9CI); Tranilast, which is also known as benzoic acid, 2-[[3-(3,4-dimethoxyphenyl)-1-oxo-2-propenyl]amino]-(9CI); ursolic acid; suramin; thalidomide and lenalidomide, and marketed as REVLIMID.

Radiation therapy that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Laser therapy is the use of high-intensity light to destroy tumor cells. Laser therapy affects the cells only in the treated area. Laser therapy may be used to destroy cancerous tissue and relieve a blockage in the esophagus when the cancer cannot be removed by surgery. The relief of a blockage can help to reduce symptoms, especially swallowing problems.

Photodynamic therapy (PDT), a type of laser therapy, involves the use of drugs that are absorbed by cancer cells; when exposed to a special light, the drugs become active and destroy the cancer cells. PDT may be used to relieve symptoms of esophageal cancer such as difficulty swallowing.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg (or any range derivable therein). A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg/kg/day (or any range derivable therein).

Alternative cancer therapy include any cancer therapy other than surgery, chemotherapy and radiation therapy in the present invention, such as immunotherapy, gene therapy, hormonal therapy or a combination thereof. Subjects identified with poor prognosis using the present methods may not have favorable response to conventional treatment(s) alone and may be prescribed or administered one or more alternative cancer therapy per se or in combination with one or more conventional treatments.

For example, the alternative cancer therapy may be a targeted therapy. The targeted therapy may be an anti-EGFR treatment. In one embodiment of the method of the invention, the anti-EGFR agent used is a tyrosine kinase inhibitor. Examples of suitable tyrosine kinase inhibitors are the quinazoline derivatives described in WO 96/33980, in particular gefitinib (Iressa). Other examples include quinazoline derivatives described in WO 96/30347, in particular erlotinib (Tarceva), dual EGFR/HER2 tyrosine kinase inhibitors, such as lapatinib, or pan-Erb inhibitors. In a preferred embodiment of the method or use of the invention, the anti-EGFR agent is an antibody capable of binding to EGFR, i.e. an anti-EGFR antibody.

In a further embodiment, the anti-EGFR antibody is an intact antibody, i.e. a full-length antibody rather than a fragment. An anti-EGFR antibody used in the method of the present invention may have any suitable affinity and/or avidity for one or more epitopes contained at least partially in EGFR. Preferably, the antibody used binds to human EGFR with an equilibrium dissociation constant ($K_D$) of $10^{-8}$M or less, more preferably $10^{-10}$ M or less.

Particularly antibodies for use in the present invention include zalutumumab (2F8), cetuximab (Erbitux), nimotuzumab (h-R3), panitumumab (ABX-EGF), and matuzumab (EMD72000), or a variant antibody of any of these, or an antibody which is able to compete with any of these, such as an antibody recognizing the same epitope as any of these. Competition may be determined by any suitable technique. In one embodiment, competition is determined by an ELISA assay. Often competition is marked by a significantly greater relative inhibition than 5% as determined by ELISA analysis.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Gene therapy is the insertion of polynucleotides, including DNA or RNA, into an individual's cells and tissues to treat a disease. Antisense therapy is also a form of gene therapy in the present invention. A therapeutic polynucleotide may be administered before, after, or at the same time of a first cancer therapy. Delivery of a vector encoding a variety of proteins is encompassed within the invention. For example, cellular expression of the exogenous tumor suppressor oncogenes would exert their function to inhibit excessive cellular proliferation, such as p53, p16 and C-CAM.

Additional agents to be used to improve the therapeutic efficacy of treatment include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

II. Kits

Certain aspects of the present invention also encompass kits for performing the diagnostic and prognostic methods of the invention. Such kits can be prepared from readily available materials and reagents. For example, such kits can comprise any one or more of the following materials: enzymes, reaction tubes, buffers, detergent, primers, probes, antibodies. In a preferred embodiment, these kits allow a practitioner to obtain samples of neoplastic cells in blood, tears, semen, saliva, urine, tissue, serum, stool, sputum, cerebrospinal fluid and supernatant from cell lysate. In another preferred embodiment these kits include the needed apparatus for performing RNA extraction, RT-PCR, and gel electrophoresis. Instructions for performing the assays can also be included in the kits.

In a particular aspect, these kits may comprise a plurality of agents for assessing the differential expression of a plurality of biomarkers, for example, GR and/or ER, wherein the kit is housed in a container. The kits may further comprise instructions for using the kit for assessing expression, means for converting the expression data into expression values and/or means for analyzing the expression values to generate prognosis. The agents in the kit for measuring biomarker expression may comprise a plurality of PCR probes and/or primers for qRT-PCR and/or a plurality of antibody or fragments thereof for assessing expression of the biomarkers. In another embodiment, the agents in the kit for measuring biomarker expression may comprise an array of polynucleotides complementary to the mRNAs of the biomarkers of the invention. Possible means for converting the expression data into expression values and for analyzing the expression values to generate scores that predict survival or prognosis may be also included.

Kits may comprise a container with a label. Suitable containers include, for example, bottles, vials, and test tubes. The containers may be formed from a variety of materials such as glass or plastic. The container may hold a composition which includes a probe that is useful for prognostic or non-prognostic applications, such as described above. The label on the container may indicate that the composition is used for a specific prognostic or non-prognostic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Tumor Biomarker Status

A. Results

The glucocorticoid receptor (GR) is highly expressed in the myoepithelium of the normal human breast and in a subset of both ERalpha-positive and negative human breast cancers. In vitro and in vivo experiments suggest that activation of the GR in ER– pre-malignant breast epithelial and cancer cells triggers cell survival pathways under stress conditions (e.g. chemotherapy) that usually induce apoptosis. The inventors examined the association between NR3C1 gene expression and GR target gene expression in human ER– breast cancers and found that ER– breast cancers with high NR3C1 expression also express GR target genes associated with EMT and anti-apoptotic signaling, and that those ER– patients with high NR3C1 gene expression have a significantly worse outcome than NR3C1-low patients. Interestingly, the high NR3C1 gene expression in the ER+ (ESR1-high) subset of patients suggests a slight better outcome, implying a crosstalk between the ER and the GR that is absent in ER– tumors.

Using a global approach of gene expression studies merged with data from GR ChIP-sequencing in ER– pre-malignant breast cells (MCF10A-Myc), the inventors have identified direct GR target genes are significantly associated with cell survival signaling pathways. Interestingly, a meta-analysis of the high NR3C1-expressing ER− tumors reveals that many genes identified by ChIP-sequencing/gene expression analysis are indeed differentially expressed in high versus low NR3C1-primary breast cancers. These results suggest that GR expression may be a functional biomarker in ER− breast cancer.

TABLE 1

Clinical studies used for meta-analysis

| GEO ID | # of pts | Reference |
|---|---|---|
| GSE9195 | 77 | Loi S, et al |
| GSE7390 | 189 | Desmedt C, et al |
| GSE6532 | 212 | Loi S, et al |
| GSE2603 | 73 | Minn A J, et al |
| GSE2990 | 183 | Sotiriou C, et al |
| GSE2034 | 280 | Wang Y X, et al |
| TOTAL | 1206 | |

TABLE 2

Differentially expressed genes with concordant expression by all three methods (33/44 genes)

| Gene expression after Dex-treatment in MCF10A-Myc | Gene expression in NR3C1 + vs. − tumors | GR-binding within distance to TSS after Dex-treatment in MCF10A-Myc | Genes |
|---|---|---|---|
| Up | Up | 10 kb | DUSP1, SGK1, SMARCA2, PTGDS, MCL1 |
| | | 10-100 kb | DPYSL2, STOM, LAPTM5, NNMT, SERPINF1, NRIP1, WIPF1, BIN1, IL1R1, ST3GAL5, SEMA4D, MAP3K5, SMARCA2, DPT, BIRC3, PTGDS, PHF15, MAOA, TFPI, SLC46A3, PIAS1, ACSL5, SESN1, C14orf139, LBH |
| Down | Down | 10 kb | NONE |
| | | 10-100 kb | SFN, SPP1, ERBB2 |
| Overlapping genes with NKI-295 gene signature | | | DUSP1, DPT, NNMT, SERPINF1, IL1R1, FN1, DPYSL2 |

B. Materials and Methods

Cell Culture and Glucocorticoid Treatment:

MCF10A-Myc cells were cultured in a 1:1 mixture of DMEM and Hams/F12 medium supplemented with 10% fetal bovine serum, hydrocortisone (0.5 μg/ml), EGF (10 ng/ml), insulin (5 ng/ml) and 100 U/ml penicillin/streptomycin were also added. The cells were then starved for three days of all growth factors and treated with dexamethasone ($10^{-6}$M) and ethanol of the same volume as a control.

Microarray Gene Expression: MCF10A-Myc Cells:

Time course (0.5 h, 2 h, 4 h and 24 h) microarray data were obtained using Affymetrix gene arrays (HG-U133A) (Wu et al., 2006). Genes that were induced or repressed ≥1.5 fold-change were considered to be regulated.

GR ChIP-Seq Experiment and Analysis for MCF10A-Myc Cells:

Cells were collected for the ChIP assay following 1 hour of Dex ($10^{-6}$M) or EtOH treatment. The ChIP assay was done basically following Millipore's ChIP Assay Kit instructions. The DNA input (1%) was also sequenced using Illumina's Solexa Sequencer. Short-tag reads (36 bp) were mapped to the Human Genome (UCSC, hg18) by using Maq aligner. GR-binding peaks were called by using MACS software. Known SGK1 and GILZ promoter GR binding-regions (GBRs) were used as positive controls to determine the FDR threshold for retrieving significant GBRs.

Human Primary Breast Cancer Analysis:

1) Data Collection: All the clinical data and raw CEL files (all Affymetrix HU-133A and HU-133+2) were obtained from GEO (see Table 1). Low quality arrays were removed by AffyPLM. Arrays were normalized by using RMA and then centered by mean within each study and pooled together. 2) Determination of ESR1 and NR3C1 positivity: Expression data of tumors with known ER IHC status were analyzed using ROC analysis. The Youden Index of the best ESR1 probe's ROC curve was used as the cut-off point to separate ESR1+ and ESR1− tumors. Due to the lack of tumors with both GR IHC and NR3C1 gene expression information, we were unable to use ROC analysis to determine the NR3C1 cutoff. Therefore, based on published and our unpublished GR IHC data, we used the percentiles of NR3C1 gene expression levels that correspond to the observed proportion of GR+ patients. 3) Clustering: Unsupervised clustering was performed by Cluster using Pearson correlation distance and complete-linkage method. Heat-maps were plotted by Treeview. 4) Statistical analysis: Relapse-free survival (RFS) Kaplan-Meier plot and log-rank test were done by using R's "survival" package. Microarray SAM analysis was performed by using R's "siggenes" package.

Tumor Assessment.

pAUC areas were calculated for all the probes on the chip by setting p=0.2 (meaning can separate at least 80% patients) for tumors with known ER status (n=1000). A probe was then selected that has biggest pAUC area, which is the ESR1 probe 205225_at. So, this probe is the best one that can separate ER IHC + versus −. Using the 205225_at probe, the Youden Index of its ROC curve was calculated, that is the max (sensitivity+specificity−1) as the cut-off value for ESR1+ and −. The range of ESR1 expression after normalization was [−5.223868-3.944120]. The Youden Index, i.e. the cut-off is −1.257434. In the n=1000, training set, n=773>−1.257434 (ESR1+), and n=227<=−1.257434. (ESR1−) or i.e. 77.3% quantile This cut-off was applied to the entire dataset, n=898 (ESR+), n=308 (ESR−). In addition to the method, the ACTUAL Log 2 value cutoff is needed for ESR1 positivity in normalized meta-dataset, as well as the range of ESR1 values encountered following batched mean normalization. If in one study, samples are obtained from different hospitals, they are normalized separately. So, to be precisely accurate, the normalization is done within the samples from the same source.

The ESR1 probe ID from Affymetrix is 205225_at.

The NR3C1 probe ID from Affymetrix is 216321_s_at

The range for NR3C1 probe (216321_s_at) is [−3.145456 to 2.158716] for the entire data set. For ESR1+, the range is [−3.009359 2.158716] and for ESR1−, the range is [−3.145456 1.917823] Thus, the cut-off for ESR1+, is 0.172189, 55.98% quantile (or about 44% NR3C1+ percentage) and the cut-off for ESR1−, is 0.47332, 82.51% quantile (or about 17.5% NR3C1+ percentage). All the cut-off are log 2 values.

The cutoffs used are the best cut-off that can separate patients with a p<0.01. If the p-value is loosened to 0.05, the range can be widened.

For ESR1+ patients, NR3C1+ patients can be from about 35% to 60% (about 44% is the best). For ESR1− patients, NR3C1+ patients can be from about 30% to 15% (about 17.5% is the best)

Example 2

Figure 8:
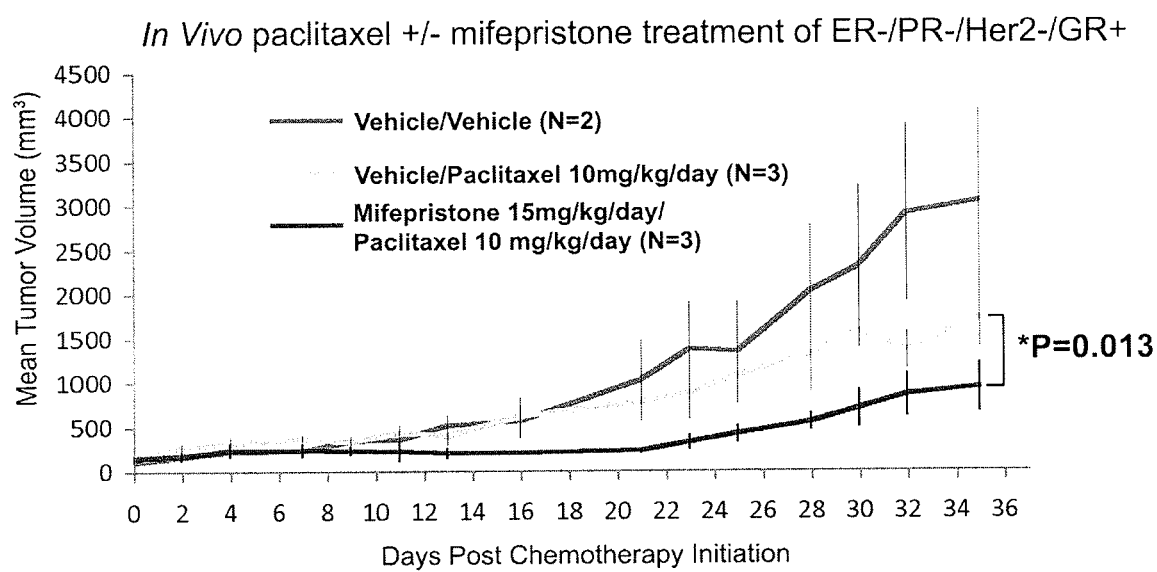
FIG. 8. Administration of mifepristone increases MDA-MB-231 tumor susceptibility to paclitaxel treatment in vivo.

Mifepristone Pretreatment Enhances Paclitaxel Anti-Tumor Effectiveness in Models of Human Breast Cancer Xenografted ER−/PR−/HER2− (GR+) MDA-MB-231 human breast cancer cells ($1 \times 10^7$ cells in 50 µl of PBS) were injected into the mammary fat pad of female Severe Combined Immunodeficient Mice (SCID) mice and allowed to grow until reaching approximately 100 mm$^3$. Mice were then injected intraperitoneally with either both vehicles, paclitaxel (10 mg/kg)+the mifepristone vehicle, or the combination of mifepristone (15 mg/kg) administered two hours prior to paclitaxel (10 mg/kg) for five successive days. The longest (L) and shortest (S) diameters of the tumors were measured bi-weekly with electronic calipers and tumor volume was calculated using the formula for an ellipsoid sphere: volume=S2×L×0.52. Mifepristone pretreatment significantly decreased tumor volume over time (P=0.013) compared to treatment with paclitaxel alone (FIG. 8).

Example 3

Figure 9:
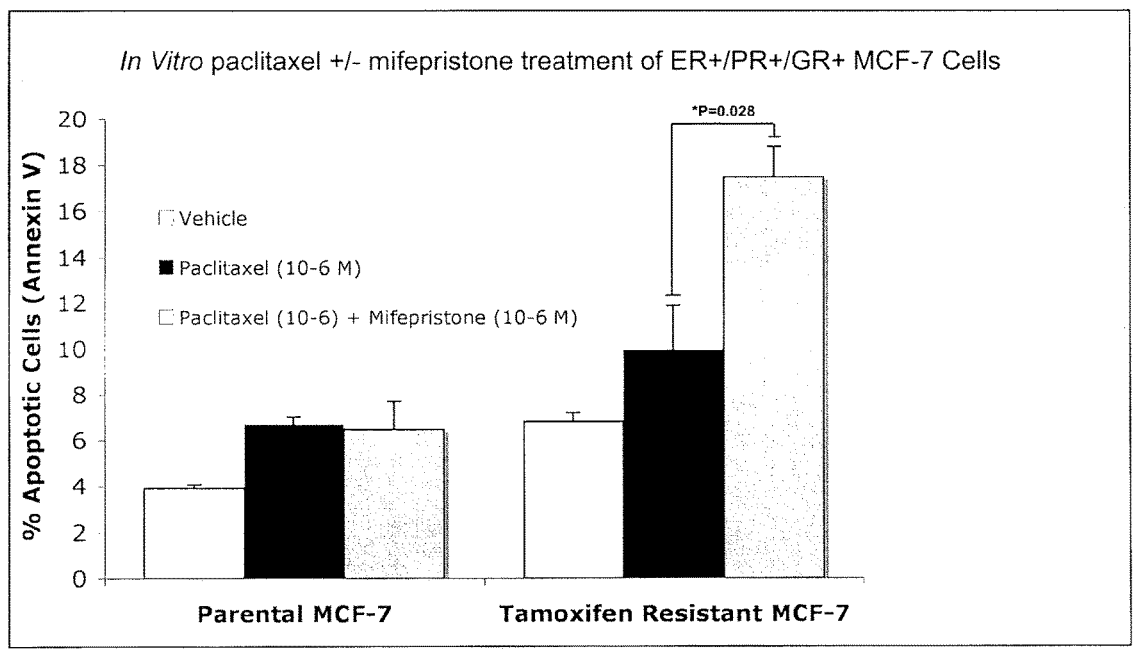
FIG. 9. Mifepristone pretreatment increases tamoxifen-resistant MCF-7 (T-R-MCF-7), but not parental MCF-7 cell susceptibility to paclitaxel in vitro.

Mifepristone Pretreatment Increases Tamoxifen-Resistant MCF-7 (T-R-MCF-7), but not Parental MCF-7 Cell Susceptibility to Paclitaxel In Vitro Parental MCF-7 (ER+/PR+/GR+) and T-R MCF-7 (ER+/PR+/GR+) cells were treated with the appropriate vehicle (ethanol for mifepristone and castor oil/saline for paclitaxel), paclitaxel alone ($10^{-6}$ M), and paclitaxel/mifepristone ($10^{-6}$ M). Apoptosis was measured using FITC conjugated-anti-Annexin V antibody labeling followed FACS analysis to determine the percentage of the total cell population undergoing apoptosis after 20 hours of treatment. Mean+/−SE is shown. Significantly more apoptosis (P=0.028) was observed in the T-R MCF-7 cells when treated with mifepristone/paclitaxel compared to paclitaxel alone (FIG. 9). No difference was seen in the parental MCF-7 cells.

```
Sequence Listing

NR3C1 GenBank AY436590-127687 bp, incorporated herein by reference
ESR1 GenBank NG_008493-419779 bp, incorporated herein by reference NR3C1 mRNA
                                                            SEQ ID NO: 1
TTTTTAGAAAAAAAAATATATTTCCCTCCTGCTCCTTCTGCGTTCACAAGCTAAGTTGTTTATCTCGGC

TGCGGCGGGAACTGCGGACGGTGGCGGGCGAGCGGCTCCTCTGCCAGAGTTGATATTCACTGATGGACTC

CAAAGAATCATTAACTCCTGGTAGAGAAGAAAACCCCAGCAGTGTGCTTGCTCAGGAGAGGGGAGATGTG

ATGGACTTCTATAAAACCCTAAGAGGAGGAGCTACTGTGAAGGTTTCTGCGTCTTCACCCTCACTGGCTG

TCGCTTCTCAATCAGACTCCAAGCAGCGAAGACTTTTGGTTGATTTTCCAAAAGGCTCAGTAAGCAATGC

GCAGCAGCCAGATCTGTCCAAAGCAGTTTCACTCTCAATGGGACTGTATATGGGAGAGACAGAAACAAAA

GTGATGGGAAATGACCTGGGATTCCCACAGCAGGGCCAAATCAGCCTTTCCTCGGGGGAAACAGACTTAA

AGCTTTTGGAAGAAAGCATTGCAAACCTCAATAGGTCGACCAGTGTTCCAGAGAACCCCAAGAGTTCAGC

ATCCACTGCTGTGTCTGCTGCCCCCACAGAGAAGGAGTTTCCAAAAACTCACTCTGATGTATCTTCAGAA

CAGCAACATTTGAAGGGCCAGACTGGCACCAACGGTGGCAATGTGAAATTGTATACCACAGACCAAAGCA

CCTTTGACATTTTGCAGGATTTGGAGTTTTCTTCTGGGTCCCCAGGTAAAGAGACGAATGAGAGTCCTTG

GAGATCAGACCTGTTGATAGATGAAAACTGTTTGCTTTCTCCTCTGGCGGGAGAAGACGATTCATTCCTT

TTGGAAGGAAACTCGAATGAGGACTGCAAGCCTCTCATTTTACCGGACACTAAACCCAAAATTAAGGATA

ATGGAGATCTGGTTTTGTCAAGCCCCAGTAATGTAACACTGCCCCAAGTGAAAACAGAAAAAGAAGATTT

CATCGAACTCTGCACCCCTGGGGTAATTAAGCAAGAGAAACTGGGCACAGTTTACTGTCAGGCAAGCTTT

CCTGGAGCAAATATAATTGGTAATAAAATGTCTGCCATTTCTGTTCATGGTGTGAGTACCTCTGGAGGAC

AGATGTACCACTATGACATGAATACAGCATCCCTTTCTCAACAGCAGGATCAGAAGCCTATTTTTAATGT

CATTCCACCAATTCCCGTTGGTTCCGAAAATTGGAATAGGTGCCAAGGATCTGGAGATGACAACTTGACT
```

```
TCTCTGGGGACTCTGAACTTCCCTGGTCGAACAGTTTTTTCTAATGGCTATTCAAGCCCCAGCATGAGAC
CAGATGTAAGCTCTCCTCCATCCAGCTCCTCAACAGCAACAACAGGACCACCTCCCAAACTCTGCCTGGT
GTGCTCTGATGAAGCTTCAGGATGTCATTATGGAGTCTTAACTTGTGGAAGCTGTAAAGTTTTCTTCAAA
AGAGCAGTGGAAGGACAGCACAATTACCTATGTGCTGGAAGGAATGATTGCATCATCGATAAAATTCGAA
GAAAAAACTGCCCAGCATGCCGCTATCGAAAATGTCTTCAGGCTGGAATGAACCTGGAAGCTCGAAAAAC
AAAGAAAAAATAAAAGGAATTCAGCAGGCCACTACAGGAGTCTCACAAGAAACCTCTGAAAATCCTGGT
AACAAAACAATAGTTCCTGCAACGTTACCACAACTCACCCCTACCCTGGTGTCACTGTTGGAGGTTATTG
AACCTGAAGTGTTATATGCAGGATATGATAGCTCTGTTCCAGACTCAACTTGGAGGATCATGACTACGCT
CAACATGTTAGGAGGGCGGCAAGTGATTGCAGCAGTGAAATGGGCAAAGGCAATACCAGGTTTCAGGAAC
TTACACCTGGATGACCAAATGACCCTACTGCAGTACTCCTGGATGTTTCTTATGGCATTTGCTCTGGGGT
GGAGATCATATAGACAATCAAGTGCAAACCTGCTGTGTTTTGCTCCTGATCTGATTATTAATGAGCAGAG
AATGACTCTACCCTGCATGTACGACCAATGTAAACACATGCTGTATGTTTCCTCTGAGTTACACAGGCTT
CAGGTATCTTATGAAGAGTATCTCTGTATGAAAACCTTACTGCTTCTCTCTTCAGTTCCTAAGGACGGTC
TGAAGAGCCAAGAGCTATTTGATGAAATTAGAATGACCTACATCAAAGAGCTAGGAAAAGCCATTGTCAA
GAGGGAAGGAAACTCCAGCCAGAACTGGCAGCGGTTTTATCAACTGACAAAACTCTTGGATTCTATGCAT
GAAGTGGTTGAAAATCTCCTTAACTATTGCTTCCAAACATTTTTGGATAAGACCATGAGTATTGAATTCC
CCGAGATGTTAGCTGAAATCATCACCAATCAGATACCAAAATATTCAAATGGAAATATCAAAAAACTTCT
GTTTCATCAAAAGTGACTGCCTTAATAAGAATGGTTGCCTTAAAGAAAGTCGAATTAATAGCTTTTATTG
TATAAACTATCAGTTTGTCCTGTAGAGGTTTTGTTGTTTTATTTTTATTGTTTTCATCTGTTGTTTTGT
TTTAAATACGCACTACATGTGGTTTATAGAGGGCCAAGACTTGGCAACAGAAGCAGTTGAGTCGTCATCA
CTTTTCAGTGATGGGAGAGTAGATGGTGAAATTTATTAGTTAATATATCCCAGAAATTAGAAACCTTAAT
ATGTGGACGTAATCTCCACAGTCAAAGAAGGATGGCACCTAAACCACCAGTGCCCAAAGTCTGTGTGATG
AACTTTCTCTTCATACTTTTTTTCACAGTTGGCTGGATGAAATTTTCTAGACTTTCTGTTGGTGTATCCC
CCCCCCTGTATAGTTAGGATAGCATTTTTGATTTATGCATGGAAACCTGAAAAAAAGTTTACAAGTGTAT
ATCAGAAAAGGGAAGTTGTGCCTTTTATAGCTATTACTGTCTGGTTTTAACAATTTCCTTTATATTTAGT
GAACTACGCTTGCTCATTTTTTCTTACATAATTTTTTATTCAAGTTATTGTACAGCTGTTTAAGATGGGC
AGCTAGTTCGTAGCTTTCCCAAATAAACTCTAAACATTAATCAATCATCTGTGTGAAAATGGGTTGGTGC
TTCTAACCTGATGGCACTTAGCTATCAGAAGACCACAAAAATTGACTCAAATCTCCAGTATTCTTGTCAA
AAAAAAAAAAAAAAAGCTCATATTTTGTATATATCTGCTTCAGTGGAGAATTATATAGGTTGTGCAAAT
TAACAGTCCTAACTGGTATAGAGCACCTAGTCCAGTGACCTGCTGGGTAAACTGTGGATGATGGTTGCAA
AAGACTAATTTAAAAAATAACTACCAAGAGGCCCTGTCTGTACCTAACGCCCTATTTTTGCAATGGCTAT
ATGGCAAGAAAGCTGGTAAACTATTTGTCTTTCAGGACCTTTTGAAGTAGTTTGTATAACTTCTTAAAAG
TTGTGATTCCAGATAACCAGCTGTAACACAGCTGAGAGACTTTTAATCAGACAAAGTAATTCCTCTCACT
AAACTTTACCCAAAACTAAATCTCTAATATGGCAAAAATGGCTAGACACCCATTTTCACATTCCCATCT
GTCACCAATTGGTTAATCTTTCCTGATGGTACAGGAAAGCTCAGCTACTGATTTTTGTGATTTAGAACTG
TATGTATGTCAGACATCCATGTTTGTAAAACTACACATCCCTAATGTGTGCCATAGAGTTTAACACAAGT
CCTGTGAATTTCTTCACTGTTGAAAATTATTTTAAACAAAATAGAAGCTGTAGTAGCCCTTTCTGTGTGC
ACCTTACCAACTTTCTGTAAACTCAAAACTTAACATATTTACTAAGCCACAAGAAATTTGATTTCTATTC
AAGGTGGCCAAATTATTTGTGTAATAGAAAACTGAAAATCTAATATTAAAAATATGGAACTTCTAATATA
```

TTTTTATATTTAGTTATAGTTTCAGATATATATCATATTGGTATTCACTAATCTGGGAAGGGAAGGGCTA
CTGCAGCTTTACATGCAATTTATTAAAATGATTGTAAAATAGCTTGTATAGTGTAAAATAAGAATGATTT
TTAGATGAGATTGTTTTATCATGACATGTTATATATTTTTTGTAGGGGTCAAAGAAATGCTGATGGATAA
CCTATATGATTTATAGTTTGTACATGCATTCATACAGGCAGCGATGGTCTCAGAAACCAAACAGTTTGCT
CTAGGGGAAGAGGGAGATGGAGACTGGTCCTGTGTGCAGTGAAGGTTGCTGAGGCTCTGACCCAGTGAGA
TTACAGAGGAAGTTATCCTCTGCCTCCCATTCTGACCACCCTTCTCATTCCAACAGTGAGTCTGTCAGCG
CAGGTTTAGTTTACTCAATCTCCCCTTGCACTAAAGTATGTAAAGTATGTAAACAGGAGACAGGAAGGTG
GTGCTTACATCCTTAAAGGCACCATCTAATAGCGGGTTACTTTCACATACAGCCCTCCCCCAGCAGTTGA
ATGACAACAGAAGCTTCAGAAGTTTGGCAATAGTTTGCATAGAGGTACCAGCAATATGTAAATAGTGCAG
AATCTCATAGGTTGCCAATAATACACTAATTCCTTTCTATCCTACAACAAGAGTTTATTTCCAAATAAAA
TGAGGACATGTTTTGTTTTCTTTGAATGCTTTTTGAATGTTATTTGTTATTTTCAGTATTTTGGAGAAA
TTATTTAATAAAAAAAACAATCATTTGCTTTTTG

ESR1 Mrna (partial)
SEQ ID NO: 2

AGGAGCTGGC GGAGGGCGTT CGTCCTGGGA CTGCACTTGC TCCCGTCGGG TCGCCCGGCT
TCACCGGACC CGCAGGCTCC CGGGGCAGGG CCGGGGCCAG AGCTCGCGTG TCGGCGGGAC
ATGCGCTGCG TCGCCTCTAA CCTCGGGCTG TGCTCTTTTT CCAGGTGGCC CGCCGGTTTC
TGAGCCTTCT GCCCTGCGGG GACACGGTCT GCACCCTGCC CGCGGCCACG GACCATGACC
ATGACCCTCC ACACCAAAGC ATCTGGGATG CCCTACTGC ATCAGATCCA AGGGAACGAG
CTGGAGCCCC TGAACCGTCC GCAGCTCAAG ATCCCCCTGG AGCGGCCCCT GGGCGAGGTG
TACCTGGACA GCAGCAAGCC CGCCGTGTAC AACTACCCCG AGGGCGCCGC CTACGAGTTC
AACGCCGCGG CCGCCGCCAA CGCGCAGGTC TACGGTCAGA CCGGCCTCCC CTACGGCCCC
GGGTCTGAGG CTGCGGCGTT CGGCTCCAAC GGCCTGGGGG GTTTCCCCCC ACTCAACAGC
GTGTCTCCGA GCCCGCTGAT GCTACTGCAC CCGCCGCCGC AGCTGTCGCC TTTCCTGCAG
CCCCACGGCC AGCAGGTGCC CTACTACCTG GAGAACGAGC CCAGCGGCTA CACGGTGCGC
GAGGCCGGCC CGCCGGCATT CTACAGGCCA AATTCAGATA ATCGACGCCA GGGTGGCAGA
GAAAGATTGG CCAGTACCAA TGACAAGGGA AGTATGGCTA TGGAATCTGC CAAGGAGACT
CGCTACTGTG CAGTGTGCAA TGACTATGCT TCAGGCTACC ATTATGGAGT CTGGTCCTGT
GAGGGCTGCA AGGCCTTCTT CAAGAGAAGT ATTCAAGGAC ATAACGACTA TATGTGTCCA
GCCACCAACC AGTGCACCAT TGATAAAAAC AGGAGGAAGA GCTGCCAGGC CTGCCGGCTC
CGCAAATGCT ACGAAGTGGG AATGATGAAA GGTGGGATAC GAAAAGACCG AAGAGGAGGG
AGAATGTTGA ACACAAGCG CCAGAGAGAT GATGGGGAGG GCAGGGGTGA AGTGGGGTCT
GCTGGAGACA TGAGAGCTGC CAACCTTTGG CCAAGCCCGC TCATGATCAA ACGCTCTAAG
AAGAACAGCC TGGCCTTGTC CCTGACGGCC GACCAGATGG TCAGTGCCTT GTTGGATGCT
GAGCCCCCCA TACTCTATTC CGAGTATGAT CCTACCAGAC CCTTCAGTGA AGCTTCGATG
ATGGGCTTAC TGACCAACCT GGCAGACAGG GAGCTGGTTC ACATGATCAA CTGGGCGAAG
AGGGTGCCAG GCTTTGTGGA TTTGACCCTC CATGATCAGG TCCACCTTCT AGAATGTGCC
TGGCTAGAGA TCCTGATGAT TGGTCTCGTC TGGCGCTCCA TGGAGCACCC AGGGAAGCTA
CTGTTTGCTC CTAACTTGCT CTTGGACAGG AACCAGGGAA AATGTGTAGA GGGCATGGTG

Sequence Listing

```
GAGATCTTCG ACATGCTGCT GGCTACATCA TCTCGGTTCC GCATGATGAA TCTGCAGGGA
GAGGAGTTTG TGTGCCTCAA ATCTATTATT TTGCTTAATT CTGGAGTGTA CACATTTCTG
TCCAGCACCC TGAAGTCTCT GGAAGAGAAG GACCATATCC ACCGAGTCCT GGACAAGATC
ACAGACACTT TGATCCACCT GATGGCCAAG GCAGGCCTGA CCCTGCAGCA GCAGCACCAG
CGGCTGGCCC AGCTCCTCCT CATCCTCTCC CACATCAGGC ACATGAGTAA CAAAGGCATG
GAGCATCTGT ACAGCATGAA GTGCAAGAAC GTGGTGCCCC TCTATGACCT GCTGCTGGAG
ATGCTGGACG CCCACCGCCT ACATGCGCCC ACTAGCCGTG GAGGGCATC CGTGGAGGAG
ACGGACCAAA GCCACTTGGC CACTGCGGGC TCTACTTCAT CGCATTCCTT GCAAAAGTAT
TACATCACGG GGGAGGCAGA GGGTTTCCCT GCCACGGTCT GAGAGCTCCC TGGCTCCCAC
ACGGTTCAGA TAATCCCTGC TGCATTTTAC CCTCATCATG CACCACTTTA GCCAAATTCT
GTCTCCTGCA TACACTCCGG CATGCATCCA ACACCAATGG CTTTCTAGAT GAGTGGCCAT
TCATTTGCTT GCTCAGTTCT TAGTGGCACA TCTTCTGTCT TCTGTTGGGA ACAGCCAAAG
GGATTCCAAG GCTAAATCTT TGTAACAGCT CTCTTTCCCC CTTGCTATGT TACTAAGCGT
GAGGATTCCC GTAGCTCTTC ACAGCTGAAC TCAGTCTATG GGTTGGGGCT CAGATAACTC
TGTGCATTTA AGCTACTTGT AGAGACCCAG GCCTGGAGAG TAGACATTTT GCCTCTGATA
AGCACTTTTT AAATGGCTCT AAGAATAAGC CACAGCAAAG AATTTAAAGT GGCTCCTTTA
ATTGGTGACT TGGAGAAAGC TAGGTCAAGG GTTTATTATA GCACCCTCTT GTATTCCTAT
GGCAATGCAT CCTTTTATGA AAGTGGTACA CCTTAAAGCT TTTATATGAC TGTAGCAGAG
TATCTGGTGA TTGTCAATTC ATTCCCCCTA TAGGAATACA AGGGGCACAC AGGGAAGGCA
GATCCCCTAG TTGGCAAGAC TATTTTAACT TGATACACTG CAGATTCAGA TGTGCTGAAA
GCTCTGCCTC TGGCTTTCCG GTCATGGGTT CCAGTTAATT CATGCCTCCC ATGGACCTAT
GGAGAGCAGC AAGTTGATCT TAGTTAAGTC TCCCTATATG AGGGATAAGT TCCTGATTTT
TGTTTTTATT TTTGTGTTAC AAAAGAAAGC CCTCCCTCCC TGAACTTGCA GTAAGGTCAG
CTTCAGGACC TGTTCCAGTG GGCACTGTAC TTGGATCTTC CCGGCGTGTG TGTGCCTTAC
ACAGGGGTGA ACTGTTCACT GTGGTGATGC ATGATGAGGG TAAATGGTAG TTGAAAGGAG
CAGGGGCCCT GGTGTTGCAT TTAGCCCTGG GGCATGGAGC TGAACAGTAC TTGTGCAGGA
TTGTTGTGGC TACTAGAGAA CAAGAGGGAA AGTAGGGCAG AAACTGGATA CAGTTCTGAG
GCACAGCCAG ACTTGCTCAG GGTGGCCCTG CCACAGGCTG CAGCTACCTA GGAACATTCC
TTGCAGACCC CGCATTGCCC TTTGGGGGTG CCCTGGGATC CCTGGGGTAG TCCAGCTCTT
CTTCATTTCC CAGCGTGGCC CTGGTTGGAA GAAGCAGCTG TCACAGCTGC TGTAGACAGC
TGTGTTCCTA CAATTGGCCC AGCACCCTGG GGCACGGGAG AAGGGTGGGG ACCGTTGCTG
TCACTACTCA GGCTGACTGG GGCCTGGTCA GATTACGTAT GCCCTTGGTG GTTTAGAGAT
AATCCAAAAT CAGGGTTTGG TTTGGGGAAG AAAATCCTCC CCCTTCCTCC CCCGCCCCGT
TCCCTACCGC CTCCACTCCT GCCAGCTCAT TTCCTTCAAT TTCCTTTGAC CTATAGGCTA
AAAAAGAAAG GCTCATTCCA GCCACAGGGC AGCCTTCCCT GGGCCTTTGC TTCTCTAGCA
CAATTATGGG TTACTTCCTT TTTCTTAACA AAAAGAATG TTTGATTTCC TCTGGGTGAC
CTTATTGTCT GTAATTGAAA CCCTATTGAG AGGTGATGTC TGTGTTAGCC AATGACCCAG
GTGAGCTGCT CGGGCTTCTC TTGGTATGTC TTGTTTGGAA AAGTGGATTT CATTCATTTC
TGATTGTCCA GTTAAGTGAT CACCAAAGGA CTGAGAATCT GGGAGGGCAA AAAAAAAAA
```

```
AAAGTTTTTA TGTGCACTTA AATTTGGGGA CAATTTTATG TATCTGTGTT AAGGATATGT

TTAAGAACAT AATTCTTTTG TTGCTGTTTG TTTAAGAAGC ACCTTAGTTT GTTTAAGAAG

CACCTTATAT AGTATAATAT ATATTTTTTT GAAATTACAT TGCTTGTTTA TCAGACAATT

GAATGTAGTA ATTCTGTTCT GGATTTAATT TGACTGGGTT AACATGCAAA AACCAAGGAA

AAATATTTAG TTTTTTTTTT TTTTTTTGTA TACTTTTCAA GCTACCTTGT CATGTATACA

GTCATTTATG CCTAAAGCCT GGTGATTATT CATTTAAATG AAGATCACAT TTCATATCAA

CTTTTGTATC CACAGTAGAC AAAATAGCAC TAATCCAGAT GCCTATTGTT GGATACTGAA

TGACAGACAA TCTTATGTAG CAAAGATTAT GCCTGAAAAG GAAAATTATT CAGGGCAGCT

AATTTTGCTT TTACCAAAAT ATCAGTAGTA ATATTTTTGG ACAGTAGCTA ATGGGTCAGT

GGGTTCTTTT TAATGTTTAT ACTTAGATTT TCTTTTAAAA AAATTAAAAT AAAACAAAAA

AAAATTTCTA GGACTAGACG ATGTAATACC AGCTAAAGCC AAACAATTAT ACAGTGGAAG

GTTTTACATT ATTCATCCAA TGTGTTTCTA TTCATGTTAA GATACTACTA CATTTGAAGT

GGGCAGAGAA CATCAGATGA TTGAAATGTT CGCCCAGGGG TCTCCAGCAA CTTTGGAAAT

CTCTTTGTAT TTTTACTTGA AGTGCCACTA ATGGACAGCA GATATTTTCT GGCTGATGTT

GGTATTGGGT GTAGGAACAT GATTTAAAAA AAAACTCTTG CCTCTGCTTT CCCCCACTCT

GAGGCAAGTT AAAATGTAAA AGATGTGATT TATCTGGGGG GCTCAGGTAT GGTGGGGAAG

TGGATTCAGG AATCTGGGGA ATGGCAAATA TATTAAGAAG AGTATTGAAA GTATTTGGAG

GAAAATGGTT AATTCTGGGT GTGCACCAGG GTTCAGTAGA GTCCACTTCT GCCCTGGAGA

CCACAAATCA ACTAGCTCCA TTTACAGCCA TTTCTAAAAT GGCAGCTTCA GTTCTAGAGA

AGAAAGAACA ACATCAGCAG TAAAGTCCAT GGAATAGCTA GTGGTCTGTG TTTCTTTTCG

CCATTGCCTA GCTTGCCGTA ATGATTCTAT AATGCCATCA TGCAGCAATT ATGAGAGGCT

AGGTCATCCA AAGAGAAGAC CCTATCAATG TAGGTTGCAA AATCTAACCC CTAAGGAAGT

GCAGTCTTTG ATTTGATTTC CCTAGTAACC TTGCAGATAT GTTTAACCAA GCCATAGCCC

ATGCCTTTTG AGGGCTGAAC AAATAAGGGA CTTACTGATA ATTTACTTTT GATCACATTA

AGGTGTTCTC ACCTTGAAAT CTTATACACT GAAATGGCCA TTGATTTAGG CCACTGGCTT

AGAGTACTCC TTCCCCTGCA TGACACTGAT TACAAATACT TTCCTATTCA TACTTTCCAA

TTATGAGATG GACTGTGGGT ACTGGGAGTG ATCACTAACA CCATAGTAAT GTCTAATATT

CACAGGCAGA TCTGCTTGGG GAAGCTAGTT ATGTGAAAGG CAAATAGAGT CATACAGTAG

CTCAAAAGGC AACCATAATT CTCTTTGGTG CAGGTCTTGG GAGCGTGATC TAGATTACAC

TGCACCATTC CCAAGTTAAT CCCCTGAAAA CTTACTCTCA ACTGGAGCAA ATGAACTTTG

GTCCCAAATA TCCATCTTTT CAGTAGCGTT AATTATGCTC TGTTTCCAAC TGCATTTCCT

TTCCAATTGA ATTAAAGTGT GGCCTCGTTT TTAGTCATTT AAAATTGTTT TCTAAGTAAT

TGCTGCCTCT ATTATGGCAC TTCAATTTTG CACTGTCTTT TGAGATTCAA GAAAAATTTC

TATTCTTTTT TTTGCATCCA ATTGTGCCTG AACTTTTAAA ATATGTAAAT GCTGCCATGT

TCCAAACCCA TCGTCAGTGT GTGTGTTTAG AGCTGTGCAC CCTAGAAACA ACATATTGTC

CCATGAGCAG GTGCCTGAGA CACAGACCCC TTTGCATTCA CAGAGAGGTC ATTGGTTATA

GAGACTTGAA TTAATAAGTG ACATTATGCC AGTTTCTGTT CTCTCACAGG TGATAAACAA

TGCTTTTTGT GCACTACATA CTCTTCAGTG TAGAGCTCTT GTTTTATGGG AAAAGGCTCA
```

-continued

Sequence Listing

AATGCCAAAT TGTGTTTGAT GGATTAATAT GCCCTTTTGC CGATGCATAC TATTACTGAT

GTGACTCGGT TTTGTCGCAG CTTTGCTTTG TTTAATGAAA CACACTTGTA AACCTCTTTT

GCACTTTGAA AAAGAATCCA GCGGGATGCT CGAGCACCTG TAAACAATTT TCTCAACCTA

SEQ ID NO: 3-46
MCL1, SAP30, DUSP1, SGK1, SMARCA2, PTGDS, TNFRSF9, SFN,
LAPTM5, GPSM2, SORT1, DPT, NRP1, ACSL5, BIRC3, NNMT, IGFBP6,
PLXNC1, SLC46A3, C14orf139, PIAS1, IDH2, SERPINF1, ERBB2,
PECAM1, LBH, ST3GAL5, IL1R1, BIN1, WIPF1, TFPI, FN1, FAM134A,
NRIP1, RAC2, SPP1, PHF15, BTN3A2, SESN1, MAP3K5, DPYSL2, SEMA4D,
STOM, and MAOA gene.

SEQ ID NO: 47
GR alpha.

SEQ ID NO: 48
GR beta.

SEQ ID NO: 49
NRR3C1 mRNA (complete)

REFERENCES

The following references, to the extent that they provide exemplary procedural or other details supplementary to those set forth herein, are specifically incorporated herein by reference.

U.S. Pat. No. 5,143,854
U.S. Pat. No. 5,202,231
U.S. Pat. No. 5,242,974
U.S. Pat. No. 5,288,644
U.S. Pat. No. 5,324,633
U.S. Pat. No. 5,384,261
U.S. Pat. No. 5,405,783
U.S. Pat. No. 5,412,087
U.S. Pat. No. 5,424,186
U.S. Pat. No. 5,429,807
U.S. Pat. No. 5,432,049
U.S. Pat. No. 5,436,327
U.S. Pat. No. 5,445,934
U.S. Pat. No. 5,468,613
U.S. Pat. No. 5,470,710
U.S. Pat. No. 5,472,672
U.S. Pat. No. 5,492,806
U.S. Pat. No. 5,503,980
U.S. Pat. No. 5,510,270
U.S. Pat. No. 5,525,464
U.S. Pat. No. 5,525,464
U.S. Pat. No. 5,527,681
U.S. Pat. No. 5,529,756
U.S. Pat. No. 5,532,128
U.S. Pat. No. 5,545,531
U.S. Pat. No. 5,547,839
U.S. Pat. No. 5,554,501
U.S. Pat. No. 5,556,752
U.S. Pat. No. 5,561,071
U.S. Pat. No. 5,571,639
U.S. Pat. No. 5,580,726
U.S. Pat. No. 5,580,732
U.S. Pat. No. 5,593,839
U.S. Pat. No. 5,599,672
U.S. Pat. No. 5,599,695
U.S. Pat. No. 5,610,287
U.S. Pat. No. 5,624,711
U.S. Pat. No. 5,631,134
U.S. Pat. No. 5,639,603
U.S. Pat. No. 5,654,413
U.S. Pat. No. 5,658,734
U.S. Pat. No. 5,661,028
U.S. Pat. No. 5,665,547
U.S. Pat. No. 5,667,972
U.S. Pat. No. 5,695,940
U.S. Pat. No. 5,700,637
U.S. Pat. No. 5,744,305
U.S. Pat. No. 5,800,992
U.S. Pat. No. 5,807,522
U.S. Pat. No. 5,830,645
U.S. Pat. No. 5,837,196
U.S. Pat. No. 5,847,219
U.S. Pat. No. 5,871,928
U.S. Pat. No. 5,876,932
U.S. Pat. No. 5,919,626
U.S. Pat. No. 6,004,755
U.S. Pat. No. 6,087,102
U.S. Pat. No. 6,368,799
U.S. Pat. No. 6,383,749
U.S. Pat. No. 6,617,112
U.S. Pat. No. 6,638,717
U.S. Pat. No. 6,720,138
U.S. Patent Publn. 2010/0135956
Belanoff et al., *Eur. J. Pharmacol.*, 655(1-3):117-20, 2011.
Cho et al. *Biochemistry*, 44(9):3547-61, 2005.
Clark, *Curr. Top. Med. Chem.* 8(9):813-838, 2008.
Colleoni et al., *Annals of Oncology*, 11(8):1057, 2000.
European Appln. EP 373 203
European Appln. EP 785 280
European Appln. EP 799 897
Evans, *Science*, 240:889, 1988.
Fodor et al., *Science*, 251:767-777, 1991.
Grover and Martin, *Carcinogenesis*, 23(7):1095-102, 2002.
Hacia et al., *Nature Genet.*, 14:441-449, 1996.
Harrison's Principles of Internal Medicine, Kasper et al. (Eds.), 16th Ed., Chapter 70, 2005.
Henderson et al. *Cancer Res.*, 48:246-253, 1988.
Keen and Davidson, *Cancer*, 97(3 Suppl):825-33, 2003.

Ma et al., *J. Immunol.*, 171(2):608-615, 2003.
MacBeath and Schreiber, *Science*, 289(5485):1760-3, 2000.
Melhem et al, *Clin. Cancer Res.*, 15(9):3196-204, 2009.
Mikosz et al., *J. Biol. Chem.*, 276:16649-54, 2001.
Moran et al., *Cancer Res.*, 60:867-872, 2000.
Pandey and Mann, *Nature*, 405(6788):837-46, 2000.
Pang and Conzen, *Cancer Biol. Ther. Cancer Biol. Ther.*, 5(8):933-40, 2006.
PCT Appln. WO 01/68255
PCT Appln. WO 03/020898
PCT Appln. WO 03/022421
PCT Appln. WO 03/023058
PCT Appln. WO 03/029485
PCT Appln. WO 03/040410
PCT Appln. WO 03/053586
PCT Appln. WO 03/066906
PCT Appln. WO 03/067217
PCT Appln. WO 03/076928
PCT Appln. WO 03/087297
PCT Appln. WO 03/091426
PCT Appln. WO 03/093810
PCT Appln. WO 03/100448A1
PCT Appln. WO 04/020085
PCT Appln. WO 04/027093
PCT Appln. WO 09/923256
PCT Appln. WO 09/936760
PCT Appln. WO 93/17126
PCT Appln. WO 95/11995
PCT Appln. WO 95/21265
PCT Appln. WO 95/21944
PCT Appln. WO 95/35505
PCT Appln. WO 96/30347
PCT Appln. WO 96/31622
PCT Appln. WO 96/33980
PCT Appln. WO 97/10365
PCT Appln. WO 97/27317
PCT Appln. WO 9743450
PCT Appln. WO 99/35505
PCT Appln. WO 01/38580
PCT Appln. WO 03/100012
Pease et al., *Proc. Natl. Acad. Sci. USA*, 91:5022-5026, 1994.
Peeters et al., *Ann. NY Acad. Sci.*, 1148:536-41, 2008.
Pike et al., *Epidemiologic Revi.*, 15(1):17-35, 1993.
Shoemaker et al., *Nature Genetics*, 14:450-456, 1996.
Sims et al. *BMC Medical Genomics*, 1(42):1-14, 2008.
Sorlie et al., *Proc. Natl. Acad. Sci. USA*, 98:10869-10874., 2001.
Srinivas et al., *Clin. Chem.*, 48(8):1160-9, 2002.
UK Appln. 8 803 000
Wu et al., *Cancer Res.*, 64:1757-64, 2004.
Wu et al., *J. Clin. Invest.*, 114:560-568, 2004.
Wu et al., *Mol Endocrinol.*, 2006

---

What is claimed is:

1. A method for treating estrogen receptor alpha-negative breast cancer in a patient, the method comprising: determining that the breast cancer does not express detectable levels of estrogen receptor alpha; and a) administering radiation or at least a first chemotherapeutic agent to said patient; then b) administering an effective amount of a glucocorticoid receptor antagonist (GRA) to the patient; then c) administering radiation again or at least a second chemotherapeutic agent to the patient after the glucocorticoid receptor antagonist is administered to the patient, whereby said estrogen receptor alpha-negative breast cancer is treated in the patient.

2. The method of claim 1, wherein the breast cancer comprises cancer cells that are glucocorticoid receptor-positive (GR+).

3. The method of claim 1, wherein the glucocorticoid receptor antagonist (GRA) has an undetectable or a lower level of activity as a progesterone receptor antagonist as compared to its level of activity as a glucocorticoid receptor antagonist.

4. The method of claim 1 wherein the first or the second chemotherapeutic agent is a platinum based agent selected from carboplatin and cisplatin.

5. The method of claim 1 wherein the first or the second chemotherapeutic agent is a taxane.

6. The method of claim 1 wherein the first or the second chemotherapy agent is selected from the group consisting of a serine/threonine kinase inhibitor, a tyrosine kinase inhibitor, an angiogenesis inhibitor, an anti-epidermal growth factor receptor antibody, and trastuzumab.

7. The method of claim 1 wherein the GRA comprises an azadecalin moiety.

8. The method of claim 1 wherein the GRA comprises a pyrimidinedione moiety.

9. The method of claim 1 wherein the GRA comprises a dihydropyridine moiety.

10. The method of claim 1 wherein the GRA comprises an octahydrophenanthrene moiety.

11. The method of claim 1 wherein the GRA is mifepristone.

12. The method of claim 1, wherein said first chemotherapeutic agent, said second chemotherapeutic agent, or both, comprises an apoptosis-inducing agent.

13. The method of claim 12, wherein said apoptosis inducing-agent is radiation, a chemotherapeutic, or an immunotherapy.

14. The method of claim 12 wherein the GRA is in a class of compounds selected from the group of classes of compounds consisting of steroids, octahydrophenanthrenes, pyrimidinediones, dihydropyridines, dihydroisoquinolines and azadecalins.

15. The method of claim 14 wherein the GRA is an aryl pyrazolo azadecalin.

16. The method of claim 12 wherein the GRA is a selective GRA having an undetectable or a lower level of activity as a progesterone receptor antagonist as compared to its level of activity as a glucocorticoid receptor antagonist.

17. The method of claim 12 wherein the GRA is a non-selective GRA.

18. The method of claim 17 wherein the GRA is mifepristone.

19. The method of claim 1 wherein the GRA comprises a dihydroisoquinoline moiety.

20. The method of claim 1 wherein the first or the second chemotherapeutic agent is a camptothecin.

* * * * *

SEQUENCE LISTING

```
<160> NUMBER OF SEQ ID NOS: 49

<210> SEQ ID NO 1
<211> LENGTH: 4794
<212> TYPE: DNA
<213> ORGANISM: Homo sapiens
<220> FEATURE:
<223> OTHER INFORMATION: nuclear receptor subfamily 3, group C, member 1
      (NR3C1), glucocorticoid receptor cDNA

<400> SEQUENCE: 1
tttttagaaa aaaaaatat  atttccctcc tgctccttct gcgttcacaa gctaagttgt      60
ttatctcggc tgcggcggga actgcggacg gtggcgggcg agcggctcct ctgccagagt     120
tgatattcac tgatggactc caaagaatca ttaactcctg gtagagaaga aaacccagc      180 agtgtgcttg ctcaggagag gggagatgtg atggacttct ataaaaccct aagaggagga    240
gctactgtga aggtttctgc gtcttcaccc tcactggctg tcgcttctca atcagactcc    300
aagcagcgaa gactttggt  tgatttttcca aaaggctcag taagcaatgc gcagcagcca    360
gatctgtcca aagcagtttc actctcaatg ggactgtata tgggagagac agaaacaaaa    420
gtgatgggaa atgacctggg attcccacag cagggccaaa tcagcctttc ctcgggggaa    480
acagacttaa agcttttgga agaaagcatt gcaaacctca ataggtcgac cagtgttcca    540
gagaacccca agagttcagc atccactgct gtgtctgctg cccccacaga aaggagttt    600 ccaaaaactc actctgatgt atcttcagaa cagcaacatt tgaagggcca gactggcacc    660
aacggtggca atgtgaaatt gtataccaca gaccaaagca cctttgacat tttgcaggat    720
ttggagtttt cttctgggtc cccaggtaaa gagacgaatg agagtccttg gagatcagac    780
ctgttgatag atgaaaactg tttgctttct cctctggcgg gagaagacga ttcattcctt    840
ttggaaggaa actcgaatga ggactgcaag cctctcattt taccggacac taaaccccaa    900
attaaggata tggagatct  ggttttgtca agccccagta atgtaacact gccccaagtg    960
```

```
aaaacagaaa aagaagattt catcgaactc tgcacccctg ggtaattaa gcaagagaaa    1020 ctgggcacag tttactgtca ggcaagcttt cctggagcaa atataattgg taataaaatg    1080
tctgccattt ctgttcatgg tgtgagtacc tctggaggac agatgtacca ctatgacatg    1140
aatacagcat ccctttctca acagcaggat cagaagccta ttttaatgt cattccacca    1200 attcccgttg gttccgaaaa ttggaatagg tgccaaggat ctggagatga caacttgact    1260
tctctgggga ctctgaactt ccctggtcga acagttttt ctaatggcta ttcaagcccc    1320
agcatgagac cagatgtaag ctctcctcca tccagctcct caacagcaac aacaggacca    1380
cctcccaaac tctgcctggt gtgctctgat gaagcttcag gatgtcatta tggagtctta    1440
acttgtggaa gctgtaaagt tttcttcaaa agagcagtgg aaggacagca caattaccta    1500
tgtgctggaa ggaatgattg catcatcgat aaaattcgaa gaaaaactg cccagcatgc    1560 cgctatcgaa aatgtcttca ggctggaatg aacctggaag ctcgaaaaac aagaaaaaa    1620 ataaaaggaa ttcagcaggc cactacagga gtctcacaag aaacctctga aaatcctggt    1680
aacaaaacaa tagttcctgc aacgttacca caactcaccc ctaccctggt gtcactgttg    1740
gaggttattg aacctgaagt gttatatgca ggatatgata gctctgttcc agactcaact    1800
tggaggatca tgactacgct caacatgtta ggagggcggc aagtgattgc agcagtgaaa    1860
tgggcaaagg caataccagg tttcaggaac ttacacctgg atgaccaaat gaccctactg    1920
cagtactcct ggatgtttct tatggcattt gctctggggt ggagatcata tagacaatca    1980
agtgcaaacc tgctgtgttt tgctcctgat ctgattatta tgagcagag aatgactcta    2040 ccctgcatgt acgaccaatg taaacacatg ctgtatgttt cctctgagtt acacaggctt    2100
caggtatctt atgaagagta tctctgtatg aaaaccttac tgcttctctc ttcagttcct    2160
aaggacggtc tgaagagcca agagctattt gatgaaatta gaatgaccta catcaaagag    2220
ctaggaaaag ccattgtcaa gagggaagga aactccagcc agaactggca gcggttttat    2280
caactgacaa aactcttgga ttctatgcat gaagtggttg aaaatctcct taactattgc    2340
ttccaaacat ttttggataa gaccatgagt attgaattcc ccgagatgtt agctgaaatc    2400
atcaccaatc agataccaaa atattcaaat ggaaatatca aaaaacttct gtttcatcaa    2460
aagtgactgc cttaataaga atggttgcct taaagaaagt cgaattaata gcttttattg    2520
tataaactat cagtttgtcc tgtagaggtt ttgttgtttt attttttatt gttttcatct    2580
gttgttttgt tttaaatacg cactacatgt ggtttataga gggccaagac ttggcaacag    2640
aagcagttga gtcgtcatca cttttcagtg atgggagagt agatggtgaa atttattagt    2700
taatatatcc cagaaattag aaaccttaat atgtggacgt aatctccaca gtcaaagaag    2760
gatggcacct aaaccaccag tgcccaaagt ctgtgtgatg aactttctct tcatactttt    2820
tttcacagtt ggctggatga attttctag actttctgtt ggtgtatccc cccccctgta    2880
tagttaggat agcatttttg atttatgcat ggaaacctga aaaaagttt acaagtgtat    2940 atcagaaaag ggaagttgtg cctttatag ctattactgt ctggttttaa caatttcctt    3000
tatatttagt gaactacgct tgctcatttt ttcttacata atttttattt caagttattg    3060
tacagctgtt aagatgggc agctagttcg tagctttccc aaataaactc taaacattaa    3120
tcaatcatct gtgtgaaaat gggttggtgc ttctaacctg atggcactta gctatcagaa    3180
gaccacaaaa attgactcaa atctccagta ttcttgtcaa aaaaaaaaa aaaaagctc    3240 atattttgta tatatctgct tcagtggaga attatatagg ttgtgcaaat taacagtcct    3300
aactggtata gagcacctag tccagtgacc tgctgggtaa actgtggatg atggttgcaa    3360
```

```
aagactaatt taaaaaataa ctaccaagag gccctgtctg tacctaacgc cctattttg   3420 caatggctat atggcaagaa agctggtaaa ctatttgtct ttcaggacct tttgaagtag   3480
tttgtataac ttcttaaaag ttgtgattcc agataaccag ctgtaacaca gctgagagac   3540
ttttaatcag acaaagtaat tcctctcact aaactttacc caaaaactaa atctctaata   3600
tggcaaaaat ggctagacac ccattttcac attcccatct gtcaccaatt ggttaatctt   3660
tcctgatggt acaggaaagc tcagctactg attttgtga tttagaactg tatgtatgtc   3720
agacatccat gtttgtaaaa ctacacatcc ctaatgtgtg ccatagagtt aacacaagt   3780 cctgtgaatt tcttcactgt tgaaaattat tttaaacaaa atagaagctg tagtagccct   3840
ttctgtgtgc accttaccaa ctttctgtaa actcaaaact taacatattt actaagccac   3900
aagaaatttg atttctattc aaggtggcca aattatttgt gtaatagaaa actgaaaatc   3960
taatattaaa aatatggaac ttctaatata tttttatatt tagttatagt ttcagatata   4020
tatcatattg gtattcacta atctgggaag ggaagggcta ctgcagcttt acatgcaatt   4080
tattaaaatg attgtaaaat agcttgtata gtgtaaaata agaatgattt ttagatgaga   4140
ttgttttatc atgacatgtt atatatttt tgtaggggtc aaagaaatgc tgatggataa   4200
cctatatgat ttatagtttg tacatgcatt catacaggca gcgatggtct cagaaaccaa   4260
acagtttgct ctaggggaag agggagatgg agactggtcc tgtgtgcagt gaaggttgct   4320
gaggctctga cccagtgaga ttacagagga agttatcctc tgcctcccat tctgaccacc   4380
cttctcattc aacagtgag tctgtcagcg caggtttagt ttactcaatc tccccttgca   4440
ctaaagtatg taaagtatgt aaacaggaga caggaaggtg gtgcttacat ccttaaaggc   4500
accatctaat agcgggttac tttcacatac agccctcccc cagcagttga atgcaacag   4560 aagcttcaga agtttggcaa tagtttgcat agaggtacca gcaatatgta aatagtgcag   4620
aatctcatag gttgccaata atacactaat tcctttctat cctacaacaa gagtttattt   4680
ccaaataaaa tgaggacatg tttttgtttt ctttgaatgc ttttgaatg ttatttgtta   4740 ttttcagtat tttggagaaa ttatttaata aaaaaaacaa tcatttgctt tttg          4794
```

<210> SEQ ID NO 2
<211> LENGTH: 6300
<212> TYPE: DNA
<213> ORGANISM: Homo sapiens
<220> FEATURE:
<223> OTHER INFORMATION: nuclear receptor subfamily 3, group A, member
    1, transcript variant 4 (NR3A1), estrogen receptor
    (ESR1, ER, ESR, ESRA, ESRR) cDNA (partial)

<400> SEQUENCE: 2

```
aggagctggc ggagggcgtt cgtcctggga ctgcacttgc tcccgtcggg tcgcccggct    60
tcaccggacc cgcaggctcc cggggcaggg ccggggccag agctcgcgtg tcggcgggac   120
atgcgctgcg tcgcctctaa cctcgggctg tgctcttttt ccaggtggcc cgccggtttc   180
tgagccttct gccctgcggg gacacggtct gcaccctgcc cgcggccacg gaccatgacc   240
atgaccctcc acaccaaagc atctgggatg ccctactgc atcagatcca agggaacgag   300
ctggagcccc tgaaccgtcc gcagctcaag atccccctgg agcggcccct gggcgaggtg   360
tacctggaca gcagcaagcc cgccgtgtac aactacccg agggcgccgc ctacgagttc   420
aacgccgcgg ccgccgccaa cgcgcaggtc tacggtcaga ccggcctccc ctacggcccc   480
gggtctgagg ctgcggcgtt cggctccaac ggcctggggg gtttcccccc actcaacagc   540
```

```
gtgtctccga gcccgctgat gctactgcac ccgccgccgc agctgtcgcc tttcctgcag    600
ccccacggcc agcaggtgcc ctactacctg gagaacgagc ccagcggcta cacggtgcgc    660
gaggccggcc cgccggcatt ctacaggcca aattcagata atcgacgcca gggtggcaga    720
gaaagattgg ccagtaccaa tgacaaggga agtatggcta tggaatctgc caaggagact    780
cgctactgtg cagtgtgcaa tgactatgct tcaggctacc attatggagt ctggtcctgt    840
gagggctgca aggccttctt caagagaagt attcaaggac ataacgacta tatgtgtcca    900
gccaccaacc agtgcaccat tgataaaaac aggaggaaga gctgccaggc ctgccggctc    960
cgcaaatgct acgaagtggg aatgatgaaa ggtgggatac gaaaagaccg aagaggaggg   1020
agaatgttga acacaagcg ccagagagat gatggggagg gcaggggtga agtggggtct   1080
gctggagaca tgagagctgc caacctttgg ccaagcccgc tcatgatcaa cgctctaag   1140 aagaacagcc tggccttgtc cctgacggcc gaccagatgg tcagtgcctt gttggatgct   1200 gagccccca tactctattc cgagtatgat cctaccagac ccttcagtga agcttcgatg   1260
atgggcttac tgaccaacct ggcagacagg gagctggttc acatgatcaa ctgggcgaag   1320
agggtgccag gctttgtgga tttgacccctc catgatcagg tccaccttct agaatgtgcc   1380
tggctagaga tcctgatgat tggtctcgtc tggcgctcca tggagcaccc agggaagcta   1440
ctgtttgctc ctaacttgct cttggacagg aaccagggaa aatgtgtaga gggcatggtg   1500
gagatcttcg acatgctgct ggctacatca tctcggttcc gcatgatgaa tctgcaggga   1560
gaggagtttg tgtgcctcaa atctattatt ttgcttaatt ctggagtgta cacatttctg   1620
tccagcaccc tgaagtctct ggaagagaag gaccatatcc accgagtcct ggacaagatc   1680
acagacactt tgatccacct gatggccaag gcaggcctga ccctgcagca gcagcaccag   1740
cggctggccc agctcctcct catcctctcc cacatcaggc acatgagtaa caaaggcatg   1800
gagcatctgt acagcatgaa gtgcaagaac gtggtgcccc tctatgacct gctgctggag   1860
atgctggacg cccaccgcct acatgcgccc actagccgtg gaggggcatc cgtggaggag   1920
acggaccaaa gccacttggc cactgcgggc tctacttcat cgcattcctt gcaaaagtat   1980
tacatcacgg gggaggcaga gggttttccct gccacggtct gagagctccc tggctcccac   2040
acggttcaga taatccctgc tgcattttac cctcatcatg caccacttta gccaaattct   2100
gtctcctgca tacactccgg catgcatcca acaccaatgg ctttctagat gagtggccat   2160
tcatttgctt gctcagttct tagtggcaca tcttctgtct tctgttggga acagccaaag   2220
ggattccaag gctaaatctt tgtaacagct ctctttcccc cttgctatgt tactaagcgt   2280
gaggattccc gtagctcttc acagctgaac tcagtctatg ggttgggct cagataactc   2340 tgtgcatttta agctacttgt agagacccag gcctggagag tagacatttt gcctctgata   2400
agcacttttt aaatggctct aagaataagc cacagcaaag aatttaaagt ggctccttta   2460
attggtgact tggagaaagc taggtcaagg gtttattata gcaccctctt gtattcctat   2520
ggcaatgcat ccttttatga aagtggtaca ccttaaagct tttatatgac tgtagcagag   2580
tatctggtga ttgtcaattc attcccccta taggaataca aggggcacac agggaaggca   2640
gatcccctag ttggcaagac tatttttaact tgatacactg cagattcaga tgtgctgaaa   2700
gctctgcctc tggctttccg gtcatggggtt ccagttaatt catgcctccc atggacctat   2760
ggagagcagc aagttgatct tagttaagtc tccctatatg agggataagt tcctgatttt   2820 tgttttatt tttgtgttac aaaagaaagc cctccctccc tgaacttgca gtaaggtcag   2880
cttcaggacc tgttccagtg ggcactgtac ttggatcttc ccggcgtgtg tgtgccttac   2940
```

```
acaggggtga actgttcact gtggtgatgc atgatgaggg taaatggtag ttgaaaggag    3000
caggggccct ggtgttgcat ttagccctgg ggcatggagc tgaacagtac ttgtgcagga    3060
ttgttgtggc tactagagaa caagagggaa agtagggcag aaactggata cagttctgag    3120
gcacagccag acttgctcag ggtggccctg ccacaggctg cagctaccta ggaacattcc    3180
ttgcagaccc cgcattgccc tttggggtg ccctgggatc cctggggtag tccagctctt    3240
cttcatttcc cagcgtggcc ctggttggaa gaagcagctg tcacagctgc tgtagacagc    3300
tgtgttccta caattggccc agcaccctgg ggcacgggag aagggtgggg accgttgctg    3360
tcactactca ggctgactgg ggcctggtca gattacgtat gcccttggtg gtttagagat    3420
aatccaaaat cagggtttgg tttggggaag aaaatcctcc cccttcctcc cccgcccgt    3480 tccctaccgc ctccactcct gccagctcat ttccttcaat ttcctttgac ctataggcta    3540
aaaaagaaag gctcattcca gccacagggc agccttccct gggcctttgc ttctctagca    3600
caattatggg ttacttcctt tttcttaaca aaaagaatg tttgatttcc tctgggtgac    3660
cttattgtct gtaattgaaa ccctattgag aggtgatgtc tgtgttagcc aatgacccag    3720
gtgagctgct cgggcttctc ttggtatgtc ttgtttggaa aagtggattt cattcatttc    3780
tgattgtcca gttaagtgat caccaaagga ctgagaatct ggagggcaa aaaaaaaaa    3840 aaagttttta tgtgcactta aatttgggga caatttatg tatctgtgtt aaggatatgt    3900
ttaagaacat aattctttg ttgctgtttg tttaagaagc accttagttt gtttaagaag    3960
caccttatat agtataatat atatttttt gaaattacat tgcttgttta tcagacaatt    4020
gaatgtagta attctgttct ggatttaatt tgactgggtt aacatgcaaa aaccaaggaa    4080
aaatatttag ttttttttt ttttttgta tacttttcaa gctaccttgt catgtataca    4140
gtcatttatg cctaaagcct ggtgattatt catttaaatg aagatcacat tcatatcaa    4200 cttttgtatc cacagtagac aaaatagcac taatccagat gcctattgtt ggatactgaa    4260
tgacagacaa tcttatgtag caaagattat gcctgaaaag gaaaattatt cagggcagct    4320
aattttgctt ttaccaaaat atcagtagta atatttttgg acagtagcta atgggtcagt    4380
gggttctttt taatgtttat acttagattt tcttttaaaa aaattaaaat aaaacaaaaa    4440
aaaatttcta ggactagacg atgtaatacc agctaaagcc aaacaattat acagtggaag    4500
gttttacatt attcatccaa tgtgtttcta ttcatgttaa gatactacta catttgaagt    4560
gggcagagaa catcagatga ttgaaatgtt cgcccagggg tctccagcaa ctttggaaat    4620
ctctttgtat ttttacttga agtgccacta atggacagca gatattttct ggctgatgtt    4680
ggtattgggt gtaggaacat gatttaaaaa aaaactcttg cctctgcttt cccccactct    4740
gaggcaagtt aaaatgtaaa agatgtgatt tatctggggg gctcaggtat ggtggggaag    4800
tggattcagg aatctgggga atggcaaata tattaagaag agtattgaaa gtatttggag    4860
gaaaatggtt aattctgggt gtgcaccagg gttcagtaga gtccacttct gccctggaga    4920
ccacaaatca actagctcca tttacagcca tttctaaaat ggcagcttca gttctagaga    4980
agaaagaaca acatcagcag taaagtccat ggaatagcta gtggtctgtg tttcttttcg    5040
ccattgccta gcttgccgta atgattctat aatgccatca tgcagcaatt atgagaggct    5100
aggtcatcca aagagaagac cctatcaatg taggttgcaa aatctaaccc ctaaggaagt    5160
gcagtctttg atttgatttc cctagtaacc ttgcagatat gtttaaccaa gccatagccc    5220
atgccttttg agggctgaac aaataaggga cttactgata atttactttt gatcacatta    5280
```

```
aggtgttctc accttgaaat cttatacact gaaatggcca ttgatttagg ccactggctt      5340
agagtactcc ttcccctgca tgacactgat tacaaatact ttcctattca tactttccaa      5400
ttatgagatg gactgtgggt actgggagtg atcactaaca ccatagtaat gtctaatatt      5460
cacaggcaga tctgcttggg gaagctagtt atgtgaaagg caaatagagt catacagtag      5520
ctcaaaaggc aaccataatt ctctttggtg caggtcttgg gagcgtgatc tagattacac      5580
tgcaccattc ccaagttaat cccctgaaaa cttactctca actggagcaa atgaactttg      5640
gtcccaaata tccatctttt cagtagcgtt aattatgctc tgtttccaac tgcatttcct      5700
ttccaattga attaaagtgt ggcctcgttt ttagtcattt aaaattgttt tctaagtaat      5760
tgctgcctct attatggcac ttcaattttg cactgtcttt tgagattcaa gaaaaatttc      5820 tattctttt tttgcatcca attgtgcctg aactttaaaa atatgtaaat gctgccatgt       5880
tccaaaccca tcgtcagtgt gtgtgtttag agctgtgcac cctagaaaca acatattgtc      5940
ccatgagcag gtgcctgaga cacagacccc tttgcattca cagagaggtc attggttata      6000
gagacttgaa ttaataagtg acattatgcc agtttctgtt ctctcacagg tgataaacaa      6060 tgcttttgt gcactacata ctcttcagtg tagagctctt gttttatggg aaaaggctca       6120
aatgccaaat tgtgtttgat ggattaatat gccctttgc cgatgcatac tattactgat       6180
gtgactcggt tttgtcgcag ctttgctttg tttaatgaaa cacacttgta aacctctttt      6240
gcactttgaa aaagaatcca gcgggatgct cgagcacctg taaacaattt tctcaaccta     6300
```

<210> SEQ ID NO 3
<211> LENGTH: 4107
<212> TYPE: DNA
<213> ORGANISM: Homo sapiens
<220> FEATURE:
<223> OTHER INFORMATION: MCL1 glucocorticoid receptor-responsive gene

<400> SEQUENCE: 3

```
gcgcaaccct ccggaagctg ccgcccctt ccccttttat gggaatactt ttttttaaaaa      60 aaagagttc gctggcgcca ccccgtagga ctggccgccc taaaaccgtg ataaaggagc      120
tgctcgccac ttctcacttc cgcttccttc cagtaaggag tcggggtctt ccccagtttt      180
ctcagccagg cggcggcggc gactggcaat gtttggcctc aaaagaaacg cggtaatcgg      240
actcaacctc tactgtgggg gggccggctt ggggccggc agcggcggcg ccacccgccc      300
gggagggcga cttttggcta cggagaagga ggcctcggcc cggcgagaga tagggggagg      360
ggaggccggc gcggtgattg gcggaagcgc cggcgcaagc ccccgtcca ccctcacgcc      420 agactcccgg agggtcgcgc ggccgccgcc cattggcgcc gaggtccccg acgtcaccgc      480 gaccccccgcg aggctgcttt tcttcgcgcc caccgccgc gcggcgccgc ttgaggagat      540
ggaagccccg gccgctgacg ccatcatgtc gcccgaagag gagctggacg ggtacgagcc      600
ggagcctctc gggaagcggc cggctgtcct gccgctgctg gagttggtcg gggaatctgg      660
taataacacc agtacggacg ggtcactacc ctcgacgccg ccgccagcag aggaggagga      720
ggacgagttg taccggcagt cgctggagat tatctctcgg taccttcggg agcaggccac      780
cggcgccaag gacacaaagc caatgggcag gtctggggcc accagcagga aggcgctgga      840
gaccttacga cggggttgggg atggcgtgca gcgcaaccac gagacggcct tccaaggcat      900
gcttcggaaa ctggacatca aaaacgaaga cgatgtgaaa tcgttgtctc gagtgatgat      960
ccatgttttc agcgacggcg taacaaactg gggcaggatt gtgactctca tttctttgg      1020 tgcctttgtg gctaaacact tgaagaccat aaaccaagaa agctgcatcg aaccattagc     1080
```

```
agaaagtatc acagacgttc tcgtaaggac aaaacgggac tggctagtta aacaaagagg    1140
ctgggatggg tttgtggagt tcttccatgt agaggaccta gaaggtggca tcaggaatgt    1200
gctgctggct tttgcaggtg ttgctggagt aggagctggt ttggcatatc taataagata    1260
gccttactgt aagtgcaata gttgactttt aaccaaccac caccaccacc aaaaccagtt    1320
tatgcagttg gactccaagc tgtaacttcc tagagttgca ccctagcaac ctagccagaa    1380
aagcaagtgg caagaggatt atggctaaca agaataaata catgggaaga gtgctcccca    1440
ttgattgaag agtcactgtc tgaaagaagc aaagttcagt ttcagcaaca aacaaacttt    1500
gtttgggaag ctatggagga ggacttttag atttagtgaa gatggtaggg tggaaagact    1560
taatttcctt gttgagaaca ggaaagtggc cagtagccag gcaagtcata gaattgatta    1620
cccgccgaat tcattaattt actgtagtgt taagagaagc actaagaatg ccagtgacct    1680
gtgtaaaagt tacaagtaat agaactatga ctgtaagcct cagtactgta caagggaagc    1740
ttttcctctc tctaattagc tttcccagta tacttcttag aaagtccaag tgttcaggac    1800 ttttataccct gttatacttt ggcttggttt ccatgattct tactttatta gcctagttta    1860
tcaccaataa tacttgacgg aaggctcagt aattagttat gaatatggat atcctcaatt    1920
cttaagacag cttgtaaatg tatttgtaaa aattgtatat attttttacag aaagtctatt    1980 tctttgaaac gaaggaagta tcgaatttac attagttttt ttcatacccct tttgaacttt    2040 gcaacttccg taattaggaa cctgtttctt acagctttc tatgctaaac tttgttctgt     2100
tcagttctag agtgtataca gaacgaattg atgtgtaact gtatgcagac tggttgtagt    2160
ggaacaaatc tgataactat gcaggtttaa attttcttat ctgattttgg taagtattcc    2220
ttagataggt ttttctttga aaacctggga ttgagaggtt gatgaatgga aattctttca    2280
cttcattata tgcaagtttt caataattag gtctaagtgg agttttaagg ttactgatga    2340
cttacaaata atgggctctg attgggcaat actcatttga gttccttcca tttgacctaa    2400
tttaactggt gaaatttaaa gtgaattcat gggctcatct ttaaagctttt tactaaaaga    2460 ttttcagctg aatggaactc attagctgtg tgcatataaa aagatcacat caggtggatg    2520
gagagacatt tgatcccttg tttgcttaat aaattataaa atgatggctt ggaaaagcag    2580
gctagtctaa ccatggtgct attattaggc ttgcttgtta cacacacagg tctaagccta    2640
gtatgtcaat aaagcaaata cttactgttt tgtttctatt aatgattccc aaaccttgtt    2700
gcaagttttt gcattggcat ctttggattt cagtcttgat gtttgttcta tcagacttaa    2760 cctttattt cctgtccttc cttgaaattg ctgattgttc tgctccctct acagatattt     2820
atatcaattc ctacagcttt cccctgccat ccctgaactc tttctagccc ttttagattt    2880
tggcactgtg aaaccctgc tggaaacctg agtgaccctc cctccccacc aagagtccac     2940
agacctttca tctttcacga acttgatcct gttagcaggt ggtaatacca tgggtgctgt    3000
gacactaaca gtcattgaga ggtgggagga agtccctttt ccttggactg gtatcttttc    3060
aactattgtt ttatcctgtc tttggggca atgtgtcaaa agtcccctca ggaattttca    3120
gaggaaagaa cattttatga ggctttctct aaagtttcct ttgtatagga gtatgctcac    3180
ttaaatttac agaagaggt gagctgtgtt aaacctcaga gttaaaagc tactgataaa      3240 ctgaagaaag tgtctatatt ggaactaggg tcatttgaaa gcttcagtct cggaacatga    3300
cctttagtct gtggactcca tttaaaaata ggtatgaata agatgactaa gaatgtaatg    3360
gggaagaact gccctgcctg cccatctcag agccataagg tcatctttgc tagagctatt    3420
```

```
tttacctatg tatttatcgt tcttgatcat aagccgctta tttatatcat gtatctctaa    3480
ggacctaaaa gcactttatg tagtttttaa ttaatcttaa gatctggtta cggtaactaa    3540
aaaagcctgt ctgccaaatc cagtggaaac aagtgcatag atgtgaattg gtttttaggg    3600
gccccacttc ccaattcatt aggtatgact gtggaaatac agacaaggat cttagttgat    3660
attttgggct tggggcagtg agggcttagg acaccccaag tggtttggga aaggaggagg    3720
ggagtggtgg gtttataggg ggaggaggag gcaggtggtc taagtgctga ctggctacgt    3780
agttcgggca aatcctccaa aagggaaagg gaggatttgc ttagaaggat ggcgctccca    3840
gtgactactt tttgacttct gtttgtctta cgcttctctc agggaaaaac atgcagtcct    3900
ctagtgtttc atgtacattc tgtgggggt gaacaccttg gttctggtta aacagctgta     3960
cttttgatag ctgtgccagg aagggttagg accaactaca aattaatgtt ggttgtcaaa    4020
tgtagtgtgt ttccctaact ttctgttttt cctgagaaaa aaaataaat cttttattca     4080 aatacaggga aaaaaaaaa aaaaaaa                                         4107

<210> SEQ ID NO 4
<211> LENGTH: 1126
<212> TYPE: DNA
<213> ORGANISM: Homo sapiens
<220> FEATURE:
<223> OTHER INFORMATION: SAP30 glucocorticoid receptor-responsive gene

<400> SEQUENCE: 4
tccccatgtg acagtgagcg gggtccccgc tccaggagac gctcgagtct gcgtcccggc      60
cctcagcact gtccactgtt tcggtgccag cagagaccag caggcccggg acagttggtg     120
tttggccgtg ccgctgtcta acttggtgtg cagagtgaat tgccgctgcc ggagcggaga     180
gaggcggagc ggccaggaga gaggggattt ctgtcagcgc cggcctcggg agctcggaga     240
catgaacggc ttcacgcctg acgagatgag ccgcggcggg gatgcggccg ccgcagtggc     300
cgcagtggtc gctgccgcgg ccgccgccgc ctcggcgggg aacgggaccg gcgcgggcac     360
cggggctgag gtgccgggcg cggggcggt ctcagcggct gggcccccgg gggcggccgg      420
gccgggcccc gggcaactgt gctgcctgcg ggaggatggt gagcggtgcg gccgggcggc     480
aggcaacgcc agcttcagca agaggatcca gaagagcatc tcccagaaga aggtgaagat     540
cgagctggat aagagcgcaa ggcatcttta catatgtgat tatcataaaa acttaattca     600
gagtgttcga aacagaagaa agagaaaagg gagtgatgat gatggaggtg attcacctgt     660
tcaagatatt gatacccag aggttgattt ataccaatta caagtaaata cacttaggag      720
atacaaaaga cacttcaagc taccaaccag accaggactt aataaagcac aacttgttga    780
gatagttggt tgccacttta ggtctattcc agtgaatgaa aaagacacct taacatattt    840
catctactca gtgaagaatg acaagaacaa atcagatctc aaggttgata gtggtgttca    900
ctaggagacg tggaattgag actaataact tggatgttaa cactgtttac tgttttttca    960
catgtagaaa tgttctttgt gtattttttc tacagaggat tttctctgat tttattttct    1020
ttgtttctga ctctaataat tagttggaaa ctcatataaa atgagctttc ctaaattaaa    1080 tctatttaa ataaaggtta ttactattaa aaaaaaaaa aaaaaa                     1126

<210> SEQ ID NO 5
<211> LENGTH: 2040
<212> TYPE: DNA
<213> ORGANISM: Homo sapiens
<220> FEATURE:
<223> OTHER INFORMATION: DUSP1 glucocorticoid receptor-responsive gene
```

<400> SEQUENCE: 5

```
tcgctgcgaa ggacatttgg gctgtgtgtg cgacgcgggt cggaggggca gtcgggggaa        60
ccgcgaagaa gccgaggagc ccggagcccc gcgtgacgct cctctctcag tccaaaagcg       120
gcttttggtt cggcgcagag agacccgggg gtctagcttt tcctcgaaaa gcgccgccct       180
gcccttggcc ccgagaacag acaaagagca ccgcagggcc gatcacgctg ggggcgctga       240
ggccggccat ggtcatggaa gtgggcaccc tggacgctgg aggcctgcgg gcgctgctgg       300
gggagcgagc ggcgcaatgc ctgctgctgg actgccgctc cttcttcgct ttcaacgccg       360
gccacatcgc cggctctgtc aacgtgcgct tcagcaccat cgtgcggcgc cgggccaagg       420
gcgccatggg cctggagcac atcgtgccca cgccgagct ccgcggccgc ctgctggccg        480
gcgcctacca cgccgtggtg ttgctggacg agccagcgc cgccctggac ggcgccaagc        540
gcgacggcac cctggccctg gcggccggcg cgctctgccg cgaggcgcgc gccgcgcaag       600
tcttcttcct caaaggagga tacgaagcgt tttcggcttc ctgcccggag ctgtgcagca       660
aacagtcgac ccccatgggg ctcagccttc ccctgagtac tagcgtccct gacagcgcgg       720
aatctgggtg cagttcctgc agtaccccac tctacgatca gggtggcccg gtggaaatcc       780
tgcccttcct gtacctgggc agtgcgtatc acgcttcccg caaggacatg ctggatgcct       840
tgggcatcac tgccttgatc aacgtctcag ccaattgtcc caaccatttt gagggtcact       900
accagtacaa gagcatccct gtggaggaca accacaaggc agacatcagc tcctggttca       960
acgaggccat tgacttcata gactccatca agaatgctgg aggaagggtg tttgtccact      1020
gccaggcagg catttcccgg tcagccacca tctgccttgc ttaccttatg aggactaatc      1080
gagtcaagct ggacgaggcc tttgagtttg tgaagcagag gcgaagcatc atctctccca      1140
acttcagctt catgggccag ctgctgcagt ttgagtccca ggtgctggct ccgcactgtt      1200
cggcagaggc tgggagcccc gccatggctg tgctcgaccg aggcacctcc accaccaccg      1260
tgttcaactt ccccgtctcc atccctgtcc actccacgaa cagtgcgctg agctaccttc      1320
agagccccat tacgacctct cccagctgct gaaaggccac ggggaggtgag gctcttcaca      1380
tcccattggg actccatgct ccttgagagg agaaatgcaa taactctggg aggggctcga      1440
gagggctggt ccttatttat ttaacttcac ccgagttcct ctgggtttct aagcagttat      1500
ggtgatgact tagcgtcaag acatttgctg aactcagcac attcgggacc aatatatagt      1560
gggtacatca agtccatctg acaaaatggg gcagaagaga aaggactcag tgtgtgatcc      1620
ggtttctttt tgctcgcccc tgttttttgt agaatctctt catgcttgac atacctacca      1680
gtattattcc cgacgacaca tatacatatg agaatatacc ttatttattt ttgtgtaggt      1740
gtctgccttc acaaatgtca ttgtctactc ctagaagaac caaatacctc aattttttgtt     1800
tttgagtact gtactatcct gtaaatatat cttaagcagg tttgttttca gcactgatgg      1860
aaaataccag tgttgggttt ttttttagtt gccaacagtt gtatgtttgc tgattattta      1920
tgacctgaaa taatatattt cttcttctaa gaagacattt tgttacataa ggatgacttt      1980
tttatacaat ggaataaatt atggcatttc tattgaaatt tcaaaaaaaa aaaaaaaaa       2040
```

<210> SEQ ID NO 6
<211> LENGTH: 3208
<212> TYPE: DNA
<213> ORGANISM: Homo sapiens
<220> FEATURE:
<223> OTHER INFORMATION: SGK1 glucocorticoid receptor-responsive gene

```
<400> SEQUENCE: 6
agatattcat gaaccgttgc ttcttccagc ctcgccttct cgctccctct gcctttctgg      60
cgctgttctc cctccctccc tctggcttct gctctttctt actccttctc tcagctgctt     120
aactacagct cccactggaa cttgcacaat caaaaacaac tctcctctct caagccgcct     180
ccaggagcgc atcacctgga gaagagcgac tcgctccccg cgccggccgc ggaagagcag     240
ccaggtagct gggggcgggg aggcgtaccc ttctcccgct cggtaagagc cacagcatct     300
ccccggagat tggccgtatc ccaccgtccg gccccaggg tcctgcagcg gtgatgcata     360
tgtttcggag caatgatgga aggagaaaag ccgctgtcgg tggcaactga aagtggggag     420
aggttgctgc agtagctggt gctgcagaat gcgcgagtga agaactgagc cccgctagat     480
tctccatccc gctcagtctt cattaactgt ctgcaggagg taaaccgggg aaacagatat     540
gcactaacca ggcgggtgcc aacctggatc tataactgtg aattccccac ggtggaaaat     600
ggtaaacaaa gacatgaatg gattcccagt caagaaatgc tcagccttcc aattttttaa     660
gaagcgggta cgaaggtgga tcaagagccc aatggtcagt gtggacaagc atcagagtcc     720
cagcctgaag tacaccggct cctccatggt gcacatccct ccaggggagc cagacttcga     780
gtcttccttg tgtcaaacat gcctgggtga acatgctttc caaagagggg ttctccctca     840
ggagaacgag tcatgttcat gggaaactca atctgggtgt gaagtgagag agccatgtaa     900
tcatgccaac atcctgacca agcccgatcc aagaaccttc tggactaatg atgatccagc     960
tttcatgaag cagaggagga tgggtctgaa cgactttatt cagaagattg ccaataactc    1020 ctatgcatg aaacaccctg aagttcagtc catcttgaag atctcccaac ctcaggagcc    1080
tgagcttatg aatgccaacc cttctcctcc accaagtcct tctcagcaaa tcaaccttgg    1140
cccgtcgtcc aatcctcatg ctaaaccatc tgactttcac ttcttgaaag tgatcggaaa    1200
gggcagtttt ggaaaggttc ttctagcaag acacaaggca gaagaagtgt tctatgcagt    1260
caaagtttta cagaagaaag caatcctgaa aaagaaagag gagaagcata ttatgtcgga    1320
gcggaatgtt ctgttgaaga atgtgaagca ccctttcctg gtgggccttc acttctcttt    1380
ccagactgct gacaaattgt actttgtcct agactacatt aatggtggag agttgttcta    1440
ccatctccag agggaacgct gcttcctgga accacgggct cgtttctatg ctgctgaaat    1500
agccagtgcc ttgggctacc tgcattcact gaacatcgtt tatagagact aaaaccaga    1560 gaatattttg ctagattcac agggacacat tgtccttact gacttcggac tctgcaagga    1620
gaacattgaa cacaacagca caacatccac cttctgtggc acgccggagt atctcgcacc    1680
tgaggtgctt cataagcagc cttatgacag gactgtggac tggtggtgcc tgggagctgt    1740
cttgtatgag atgctgtatg gcctgccgcc tttttatagc cgaaacacag ctgaaatgta    1800
cgacaacatt ctgaacaagc ctctccagct gaaaccaaat attacaaatt ccgcaagaca    1860
cctcctggag ggcctcctgc agaaggacag gacaaagcgg ctcggggcca aggatgactt    1920
catggagatt aagagtcatg tcttcttctc cttaattaac tgggatgatc tcattaataa    1980
gaagattact ccccctttta acccaaatgt gagtgggccc aacgacctac ggcactttga    2040
ccccgagttt accgaagagc ctgtccccaa ctccattggc aagtcccctg acagcgtcct    2100
cgtcacagcc agcgtcaagg aagctgccga ggcttttcta ggcttttcct atgcgcctcc    2160
cacggactct ttcctctgaa ccctgttagg gcttggtttt aaaggatttt atgtgtgttt    2220
ccgaatgttt tagttagcct tttggtggag ccgccagctg acaggacatc ttacaagaga    2280
atttgcacat ctctggaagc ttagcaatct tattgcacac tgttcgctgg aagcttttg     2340
```

-continued

```
aagagcacat tctcctcagt gagctcatga ggttttcatt tttattcttc cttccaacgt    2400
ggtgctatct ctgaaacgag cgttagagtg ccgccttaga cggaggcagg agtttcgtta    2460
gaaagcggac gctgttctaa aaaaggtctc ctgcagatct gtctgggctg tgatgacgaa    2520
tattatgaaa tgtgcctttt ctgaagagat tgtgttagct ccaaagcttt tcctatcgca    2580
gtgtttcagt tctttatttt cccttgtgga tatgctgtgt gaaccgtcgt gtgagtgtgg    2640
tatgcctgat cacagatgga ttttgttata agcatcaatg tgacacttgc aggacactac    2700
aacgtgggac attgtttgtt tcttccatat ttggaagata aatttatgtg tagacttttt    2760
tgtaagatac ggttaataac taaaatttat tgaaatggtc ttgcaatgac tcgtattcag    2820
atgcttaaag aaagcattgc tgctacaaat atttctattt ttagaaaggg ttttatgga    2880 ccaatgcccc agtgtcagt cagagccgtt ggtgttttc attgtttaaa atgtcacctg      2940
taaaatgggc attatttatg tttttttttt tgcattcctg ataattgtat gtattgtata    3000
aagaacgtct gtacattggg ttataacact agtatattta aacttacagg cttatttgta    3060
atgtaaacca ccatttaat gtactgtaat taacatggtt ataatacgta caatccttcc     3120
ctcatcccat cacacaactt tttttgtgtg tgataaactg attttggttt gcaataaaac    3180
cttgaaaaat atttacatat aaaaaaaa                                        3208
```

<210> SEQ ID NO 7  
<211> LENGTH: 5758  
<212> TYPE: DNA  
<213> ORGANISM: Homo sapiens  
<220> FEATURE:  
<223> OTHER INFORMATION: SMARCA2 glucocorticoid receptor-responsive gene

<400> SEQUENCE: 7

```
tttctgtact ctgggtgact cagagaggga agagattcag ccagcacact cctcgcgagc     60
aagcattact ctactgactg gcagagacag gagaggtaga tgtccacgcc cacagaccct    120
ggtgcgatgc cccacccagg gccttcgccg gggcctgggc cttcccctgg gccaattctt    180
gggcctagtc caggaccagg accatcccca ggttccgtcc acagcatgat ggggccaagt    240
cctggacctc caagtgtctc ccatcctatg ccgacgatgg ggtccacaga cttcccacag    300
gaaggcatgc atcaaatgca taagcccatc gatggtatac atgacaaggg gattgtagaa    360
gacatccatt gtggatccat gaagggcact ggtatgcgac cacctcaccc aggcatgggc    420
cctccccaga gtccaatgga tcaacacagc caaggttata tgtcaccaca cccatctcca    480
ttaggagccc cagagcacgt ctccagccct atgtctggag gaggcccaac tccacctcag    540
atgccaccaa gccagccggg ggccctcatc ccaggtgatc cgcaggccat gagccagccc    600
aacagaggtc cctcaccttt cagtcctgtc cagctgcatc agcttcgagc tcagatttta    660
gcttataaaa tgctggcccg aggccagccc ctccccgaaa cgctgcagct tgcagtccag    720
gggaaaagga cgttgcctgg cttgcagcaa caacagcagc agcaacagca gcagcagcag    780
cagcagcagc agcagcagca gcagcaacag cagccgcagc agcagccgcc gcaaccacag    840
acgcagcaac aacagcagcc ggcccttgtt aactacaaca gaccatctgg cccggggccg    900
gagctgagcg gcccgagcac cccgcagaag ctgccggtgc ccgcgcccgg cggcggccc    960 tcgcccgcgc ccccgcagc cgcgcagccc cccgcggccg cagtgcccgg gccctcagtg    1020
ccgcagccgg ccccgggggca gccctcgccc gtcctccagc tgcagcagaa gcagagccgc    1080
atcagcccca tccagaaacc gcaaggcctg gaccccgtgg aaattctgca agagcgggaa    1140
```

```
tacagacttc aggcccgcat agctcatagg atacaagaac tggaaaatct gcctggctct   1200
ttgccaccag atttaagaac caaagcaacc gtggaactaa aagcacttcg gttactcaat   1260
ttccagcgtc agctgagaca ggaggtggtg gcctgcatgc gcagggacac gaccctggag   1320
acggctctca actccaaagc atacaaacgg agcaagcgcc agactctgag agaagctcgc   1380
atgaccgaga agctggagaa gcagcagaag attgagcagg agaggaaacg ccgtcagaaa   1440
caccaggaat acctgaacag tattttgcaa catgcaaaag attttaagga atatcatcgg   1500
tctgtggccg aaagatccaa gaagctctcc aaagcagtgg caacttggca tgccaacact   1560
gaaagagagc agaagaagga gacagagcgg attgaaaagg agagaatgcg gcgactgatg   1620
gctgaagatg aggagggtta tagaaaactg attgatcaaa agaaagacag gcgtttagct   1680
taccttttgc agcagaccga tgagtatgta gccaatctga ccaatctggt ttgggagcac   1740
aagcaagccc aggcagccaa agagaagaag aagaggagga ggaggaagaa gaaggctgag   1800
gagaatgcag agggtgggga gtctgccctg ggaccggatg gagagcccat agatgagagc   1860
agccagatga gtgacctccc tgtcaaagtg actcacacag aaaccggcaa ggttctgttc   1920
ggaccagaag cacccaaagc aagtcagctg gacgcctggc tggaaatgaa tcctggttat   1980
gaagttgccc ctagatctga cagtgaagag agtgattctg attatgagga agaggatgag   2040
gaagaagagt ccagtaggca ggaaaccgaa gagaaaatac tcctggatcc aaatagcgaa   2100
gaagtttctg agaaggatgc taagcagatc attgagacag ctaagcaaga cgtggatgat   2160
gaatacagca tgcagtacag tgccaggggc tcccagtcct actacaccgt ggctcatgcc   2220
atctcggaga gggtggagaa acagtctgcc ctcctaatta tgggaccct aaagcattac   2280 cagctccagg gcctggaatg gatggtttcc ctgtataata acaacttgaa cggaatctta   2340
gccgatgaaa tggggcttgg aaagaccata cagaccattg cactcatcac ttatctgatg   2400
gagcacaaaa gactcaatgg cccctatctc atcattgttc cccttcgac tctatctaac   2460 tggacatatg aatttgacaa atgggctcct tctgtggtga agatttctta caagggtact   2520
cctgccatgc gtcgctccct tgtcccccag ctacggagtg gcaaattcaa tgtcctcttg   2580
actacttatg agtatattat aaaagacaag cacattcttg caaagattcg gtggaaatac   2640
atgatagtgg acgaaggcca ccgaatgaag aatcaccact gcaagctgac tcaggtcttg   2700
aacactcact atgtggcccc cagaaggatc ctcttgactg ggaccccgct gcagaataag   2760
ctccctgaac tctgggccct cctcaacttc ctcctcccaa caattttta gagctgcagc   2820 acatttgaac aatggttcaa tgctccattt gccatgactg tgaaagggt ggacttaaat   2880 gaagaagaaa ctatattgat catcaggcgt ctacataagg tgttaagacc atttttacta   2940
aggagactga agaagaagt tgaatcccag cttcccgaaa agtggaata tgtgatcaag   3000 tgtgacatgt cagctctgca gaagattctg tatcgccata tgcaagccaa ggggatcctt   3060
ctcacagatg gttctgagaa agataagaag gggaaggag gtgctaagac acttatgaac   3120
actattatgc agttgagaaa aatctgcaac cacccatata tgtttcagca cattgaggaa   3180
tcctttgctg aacacctagg ctattcaaat ggggtcatca atggggctga actgtatcgg   3240
gcctcaggga gtttgagct gcttgatcgt attctgccaa aattgagagc gactaatcac   3300
cgagtgctgc tttctgcca gatgacatct ctcatgacca tcatggagga ttattttgct   3360
tttcggaact tccttttacct acgccttgat ggcaccacca agtctgaaga tcgtgctgct   3420
ttgctgaaga aattcaatga acctggatcc cagtatttca ttttcttgct gagcacaaga   3480
gctggtggcc tgggcttaaa tcttcaggca gctgatacag tggtcatctt tgacagcgac   3540
```

```
tggaatcctc atcaggatct gcaggcccaa gaccgagctc accgcatcgg gcagcagaac    3600
gaggtccggg tactgaggct ctgtaccgtg aacagcgtgg aggaaaagat cctcgcggcc    3660
gcaaaataca agctgaacgt ggatcagaaa gtgatccagg cgggcatgtt tgaccaaaag    3720
tcttcaagcc acgagcggag ggcattcctg caggccatct ggagcatga ggaggaaaat    3780
gaggaagaag atgaagtacc ggacgatgag actctgaacc aaatgattgc tcgacgagaa    3840
gaagaatttg accttttat gcggatggac atggaccggc ggaggaaga tgcccggaac     3900
ccgaaacgga agccccgttt aatggaggag gatgagctgc cctcctggat cattaaggat    3960
gacgctgaag tagaaaggct cacctgtgaa gaagaggagg agaaaatatt tgggaggggg    4020
tcccgccagc gccgtgacgt ggactacagt gacgccctca cggagaagca gtggctaagg    4080
gccatcgaag acggcaattt ggaggaaatg aagaggaag tacggcttaa gaagcgaaaa     4140
agacgaagaa atgtggataa agatcctgca aaagaagatg tggaaaaagc taagaagaga    4200
agaggccgcc ctcccgctga gaaactgtca ccaaatcccc ccaaactgac aaagcagatg    4260
aacgctatca tcgatactgt gataaactac aaagataggt gtaacgtgga aaggtgccc    4320
agtaattctc agttggaaat agaaggaaac agttcagggc gacagctcag tgaagtcttc    4380
attcagttac cttcaaggaa agaattacca gaatactatg aattaattag gaagccagtg    4440
gatttcaaaa aaataaagga aaggattcgt aatcataagt accggagcct aggcgacctg    4500
gagaaggatg tcatgcttct ctgtcacaac gctcagacgt tcaacctgga gggatcccag    4560
atctatgaag actccatcgt cttacagtca gtgtttaaga gtgcccggca gaaaattgcc    4620
aaagaggaag agagtgagga tgaaagcaat gaagaggagg aagaggaaga tgaagaagag    4680
tcagagtccg aggcaaaatc agtcaaggtg aaaattaagc tcaataaaaa agatgacaaa    4740
ggccgggaca aagggaaagg caagaaaagg ccaaatcgag gaaaagccaa acctgtagtg    4800
agcgattttg acagcgatga ggagcaggat aacgtgaac agtcagaagg aagtgggacg    4860
gatgatgagt gatcagtatg gacctttttc cttggtagaa ctgaattcct tcctcccctg    4920
tctcatttct acccagtgag ttcatttgtc atataggcac tgggttgttt ctatatcatc    4980
atcgtctata aactagcttt aggatagtgc cagacaaaca tatgatatca tggtgtaaaa    5040
aacacacaca tacacaaata tttgtaacat attgtgacca aatgggcctc aaagattcag    5100
attgaaacaa acaaaaagct tttgatgaa atatgtggg tggatagtat atttctatgg      5160
gtgggtctaa tttggtaacg gtttgattgt gcctggtttt atcacctgtt cagatgagaa    5220
gatttttgtc ttttgtagca ctgataacca ggagaagcca ttaaaagcca ctggttattt    5280
tattttcat caggcaattt tcgaggtttt tatttgttcg gtattgtttt tttacactgt     5340
ggtacatata agcaactta ataggtgata aatgtacagt agttagattt cacctgcata     5400
tacatttttc cattttatgc tctatgatct gaacaaaagc ttttgaatt gtataagatt     5460
tatgtctact gtaaacattg cttaattttt ttgctcttga tttaaaaaaa agttttgttg    5520
aaagcgctat tgaatattgc aatctatata gtgtattgga tggcttcttt tgtcaccctg    5580
atctcctatg ttaccaatgt gtatcgtctc cttctcccta agtgtacttt aatctttgct    5640
ttctttgcac aatgtctttg gttgcaagtc ataagcctga ggcaaataaa attccagtaa    5700
tttcgaagaa tgtggtgttg gtgctttcct aataaagaaa taatttagct tgacaaaa     5758
```

```
<210> SEQ ID NO 8
<211> LENGTH: 837
<212> TYPE: DNA
```

<213> ORGANISM: Homo sapiens
<220> FEATURE:
<223> OTHER INFORMATION: PTGDS glucocorticoid receptor-responsive gene

<400> SEQUENCE: 8

```
gctcctcctg cacacctccc tcgctctccc acaccactgg caccaggccc cggacacccg    60
ctctgctgca ggagaatggc tactcatcac acgctgtgga tgggactggc cctgctgggg   120
gtgctgggcg acctgcaggc agcaccggag gcccaggtct ccgtgcagcc caacttccag   180
caggacaagt tcctggggcg ctggttcagc gcgggcctcg cctccaactc gagctggctc   240
cgggagaaga aggcggcgtt gtccatgtgc aagtctgtgg tggcccctgc cacggatggt   300
ggcctcaacc tgacctccac cttcctcagg aaaaaccagt gtgagacccg aaccatgctg   360
ctgcagcccg cggggtccct cggctcctac agctaccgga gtccccactg ggcagcacc   420
tactccgtgt cagtggtgga gaccgactac gaccagtacg cgctgctgta cagccagggc   480
agcaagggcc ctggcgagga cttccgcatg gccaccctct acagccgaac ccagaccccc   540
agggctgagt taaaggagaa attcaccgcc ttctgcaagg cccagggctt cacagaggat   600
accattgtct tcctgcccca aaccgataag tgcatgacgg aacaatagga ctccccaggg   660
ctgaagctgg gatcccggcc agccaggtga ccccacgct ctggatgtct ctgctctgtt   720
ccttccccga gccctgccc cggctccccg ccaaagcaac cctgcccact caggcttcat   780
cctgcacaat aaactccgga agcaagtcag taaaaaaaaa aaaaaaaaa aaaaaaa      837
```

<210> SEQ ID NO 9
<211> LENGTH: 6001
<212> TYPE: DNA
<213> ORGANISM: Homo sapiens
<220> FEATURE:
<223> OTHER INFORMATION: TNFRSF9 glucocorticoid receptor-responsive gene

<400> SEQUENCE: 9

```
caaggaggga tcccacagat gtcacagggc tgtcacagag ctgtggtggg aatttcccat    60
gagaccccgc ccctggctga gtcaccgcac tcctgtgttt gacctgaagt cctctcgagc   120
tgcagaagcc tgaagaccaa ggagtggaaa gttctccggc agccctgaga tctcaagagt   180
gacatttgtg agaccagcta atttgattaa aattctcttg gaatcagctt tgctagtatc   240
atacctgtgc cagatttcat catgggaaac agctgttaca acatagtagc cactctgttg   300
ctggtcctca actttgagag gacaagatca ttgcaggatc cttgtagtaa ctgcccagct   360
ggtacattct gtgataataa caggaatcag atttgcagtc cctgtcctcc aaatagtttc   420
tccagcgcag gtggacaaag gacctgtgac atatgcaggc agtgtaaagg tgttttcagg   480
accaggaagg agtgttcctc caccagcaat gcagagtgtg actgcactcc agggtttcac   540
tgcctggggg caggatgcag catgtgtgaa caggattgta acaaggtcca gaactgaca   600
aaaaaggtt gtaaagactg ttgctttggg acatttaacg atcagaaacg tggcatctgt   660
cgaccctgga caaactgttc tttggatgga aagtctgtgc ttgtgaatgg gacgaaggag   720
agggacgtgg tctgtggacc atctccagcc gacctctctc cgggagcatc ctctgtgacc   780
ccgcctgccc ctgcgagaga gccaggacac tctccgcaga tcatctcctt ctttcttgcg   840
ctgacgtcga ctgcgttgct cttcctgctg ttcttcctca cgctccgttt ctctgttgtt   900
aaacgggggca gaaagaaact cctgtatata ttcaaacaac catttatgag accagtacaa   960
actactcaag aggaagatgg ctgtagctgc cgatttccag aagaagaaga aggaggatgt  1020
gaactgtgaa atggaagtca atagggctgt tgggactttc ttgaaaagaa gcaaggaaat  1080
```

```
atgagtcatc cgctatcaca gctttcaaaa gcaagaacac catcctacat aatacccagg    1140
attcccccaa cacacgttct tttctaaatg ccaatgagtt ggcctttaaa aatgcaccac    1200 ttttttttt tttttgacag ggtctcactc tgtcacccag gctggagtgc agtggcacca    1260
ccatggctct ctgcagcctt gacctctggg agctcaagtg atcctcctgc ctcagtctcc    1320
tgagtagctg gaactacaag gaagggccac cacacctgac taacttttt gttttttgtt    1380 tggtaaagat ggcatttcac catgttgtac aggctggtct caaactccta ggttcacttt    1440
ggcctcccaa agtgctggga ttacagacat gaactgccag gcccggccaa ataatgcac    1500 cacttttaac agaacagaca gatgaggaca gagctggtga taaaaaaaaa aaaaaaaaag    1560
cattttctag ataccactta acaggtttga gctagttttt ttgaaatcca agaaaatta    1620 tagtttaaat tcaattacat agtccagtgg tccaactata attataatca aaatcaatgc    1680
aggtttgttt tttggtgcta atatgacata tgacaataag ccacgaggtg cagtaagtac    1740
ccgactaaag tttccgtggg ttctgtcatg taacacgaca tgctccaccg tcagggggga    1800
gtatgagcag agtgcctgag tttagggtca aggacaaaaa acctcaggcc tggaggaagt    1860
tttggaaaga gttcaagtgt ctgtatatcc tatggtcttc tccatcctca cccttctgc    1920 ctttgtcctg ctccctttta agccaggtta cattctaaaa attcttaact tttaacataa    1980
tattttatac caaagccaat aaatgaactg catatgatag gtatgaagta cagtgagaaa    2040
attaacacct gtgagctcat tgtcctacca cagcactaga gtgggggccg ccaaactccc    2100
atggccaaac ctggtgcacc atttgccttt gtttgtctgt tggtttgctt gagacagtct    2160
tgctctgttg cccaggctgg aatggagtgg ctattcacag gcacaatcat agcacacttt    2220
agccttaaac tcctgggctc aagtgatcca cccgcctcag tctcccaagt agctgggatt    2280
acaggtgcaa acctggcatg cctgccattg tttggcttat gatctaagga tagctttta    2340 aattttattc atttttattt tttttgagac agtgtctcac tctgtctccc aggctggagt    2400
acagtggtac aatcttggat caccgcctcc cagtttcaag tgatctccct gcctcagcct    2460
cctaagtagc tgggactaca ggtatgtgcc accacgcctg gctaattttt atattttag    2520 tagagacggg gtttcaccat gttgtccagg ctggtctcaa actcctgacc tcaggtgatc    2580
tgcccacctc tgcctcccaa agtgctggga ttacaggcat gagccaccat gcctggccat    2640
ttcttacact tttgtatgac atgcctattg caagcttgcg tgcctctgtc ccatgttatt    2700
ttactctggg atttaggtgg agggagcagc ttctatttgg aacattggcc atcgcatggc    2760
aaatgggtat ctgtcacttc tgctcctatt tagttggttc tactataacc tttagagcaa    2820
atcctgcagc caagccaggc atcaataggg cagaaaagta tattctgtaa ataggggtga    2880
ggagaagata tttctgaaca atagtctact gcagtaccaa attgcttttc aaagtggctg    2940
ttctaatgta ctcccgtcag tcatataagt gtcatgtaag tatcccattg atccacatcc    3000
ttgctaccct ctggtactat caggtgccct taattttgcc aagccagtgg gtatagaatg    3060
agatctcact gtggtcttag tttgcatttg cttggttact gatgagcacc ttgtcaaata    3120
tttatatacc atttgtgttt attttttttaa ataaaatgct tgctcatgct ttttgcccca    3180
tttgcaaaaa aacttggggc cgggtgcagt ggctcatgcc tgtagtccca gctctttggg    3240
aggccaaggt gggcagatcg cttgagccca ggagttcgag accagccttg gcaacatggc    3300
gaaaccctgt ctttacaaaa aatacaaaaa ttagccgggt gtggtggtgt gcacctgaag    3360
tcccagctac tcagtaggtt cgctttgagc ctggaggca gaggttgcag tgagctggga    3420
```

```
ccgcatcact acacttcagc ctgggcaaca gagaaaaacc ttttctcaga aacaaacaaa    3480
cccaaatgtg gttgtttgtc ctgattccta aaaggtcttt atgtattcta gataataatc    3540
tttggtcagt tatatgtgtt aaaaaatatc ttctttgtgg ccaggcacgg tagctcacac    3600
ctgtaatccc agcactttgc ggggctgagg tgggtggatc atctgaggtc aagagttcaa    3660
gatcagcctg gccaacacag tgaaacccca tctctactaa acatgtacaa aacttagctg    3720
ggtatggtgg cgggtgcctg taaccccagc tgctccagag gctgtggcag aagaatcgct    3780
tgaacccagg aggcagaggt tgcagcgagc caagattgtg ccattgcact ccagactggg    3840
tgacaagagt gaaattctgc ctatctatct atctatctat ctatatctat atatatatat    3900
atatatatcc tttgtaattt attttcccct ttttaaaatt ttttataaaa ttctttttta    3960
tttttatttt tagcagaggt gaggtttctg aggtttcatt atgttgccca ggctggtctt    4020
gaactcctga gctcaagtga tcctcccacc tcagccttcc aaagtgctgg aattgcagac    4080
atgagccacc gcgcccctcc tgttttctc taattaatgg tgtctttctt tgtctttctg    4140
gtaataagca aaaagttctt catttgattt ggttaaattt ataactgttt tctcatatgg    4200
ttaacatttt tcttgcctg gctaaagaaa tccttttctg cccaatacta taaagaggtt    4260
tgcccacatt ttattccaaa agttttaagt tttgtctttc atcttgaagt ctaatgtatc    4320
aggaactggc ttttgtgcct gttgggaggt agtgatccaa ttccatgtct tgcatgtagg    4380
taaccactgt ccctgcgcc atgtattcaa tacgtcgtct ttctcctgcg ggtctgcaat    4440
ctcacctacc atccatcaag tttccatagg gccatgggtc tgcttctggg ctccctgttc    4500
tgttccattg tcaatttgtc tatcctgtgc cagtatcaca ctgtgtttat tacaatagct    4560
ttgtaacagc tctcgatatc cggtaggaca tctccctcca ccttcttttt ctacttcaga    4620
agtgtcttag ctaggtcagg cacggtggct cacgcctgta atcccagcac tttgggaggc    4680
cgacgcggat ggatcacctg aggtcaggag ttttgagaca gcctggccaa catggtgaaa    4740
ccccatctct actaaaaaat acaaaaatta gtcaggcatg gtggcatgtg cctgtaatcc    4800
cagctatttg ggaggctgag gccggagaat tgcttgaacc cggggggcgg aggttgcagt    4860
gagccgagat cgtaccattg cactccagcc tgggtgacag agcgaaactc tgtctcagga    4920 aaaaaagaa aagagatgtc ttggttattc ttggttcttt attattcaat ataaatttta    4980
gaagctgaat ttgaaaagat ttggattgga atttcattaa atctacaggt caatttaggg    5040
agagttgata attttacaga attgagtcat ctggtgttcc aataagaata agagaacaat    5100
tattggctgt acaattcttg ccaaatagta ggcaaagcaa agcttaggaa gtatactggt    5160
gccatttcag gaacaaagct aggtgcgaat attttgtct ttctgaatca tgatgctgta    5220
agttctaaag tgatttctcc tcttggcttt ggacacatgg tgtttaatta cctactgctg    5280
actatccaca aacagaaaga gactggtcat gccccacagg gttggggtat ccaagataat    5340
ggagcgaggc tctcatgtgt cctaggttac acaccgaaaa tccacagttt attctgtgaa    5400
gaaaggaggc tatgtttatg atacagactg tgatatttt atcatagcct attctggtat    5460
catgtgcaaa agctataaat gaaaaacaca ggaacttggc atgtgagtca ttgctccccc    5520
taaatgacaa ttaataagga aggaacattg agacagaata aaatgatccc cttctgggtt    5580
taatttagaa agttccataa ttaggtttaa tagaaataaa tgtaaatttc tatgattaaa    5640
aataaattag cacatttagg gatacacaaa ttataaatca ttttctaaat gctaaaaaca    5700
agctcaggtt ttttcagaa gaaagttta atttttttc tttagtggaa gatatcactc    5760
tgacggaaag ttttgatgtg aggggcggat gactataaag tgggcatctt cccccacagg    5820
```

```
aagatgtttc catctgtggg tgagaggtgc ccaccgcagc tagggcaggt tacatgtgcc    5880
ctgtgtgtgg taggacttgg agagtgatct ttatcaacgt ttttatttaa aagactatct    5940
aataaaacac aaaactatga tgttcacagg aaaaaaagaa taagaaaaaa agaaaaaaaa    6000
a                                                                   6001
```

<210> SEQ ID NO 10
<211> LENGTH: 1336
<212> TYPE: DNA
<213> ORGANISM: Homo sapiens
<220> FEATURE:
<223> OTHER INFORMATION: SFN glucocorticoid receptor-responsive gene

<400> SEQUENCE: 10

```
gagagacaca gagtccggca ttggtcccag gcagcagtta gcccgccgcc cgcctgtgtg      60
tccccagagc catggagaga gccagtctga tccagaaggc caagctggca gagcaggccg     120
aacgctatga ggacatggca gccttcatga aggcgccgt ggagaagggc gaggagctct      180
cctgcgaaga gcgaaacctg ctctcagtag cctataagaa cgtggtgggc ggccagaggg     240
ctgcctggag ggtgctgtcc agtattgagc agaaaagcaa cgaggagggc tcggaggaga     300
aggggcccga ggtgcgtgag taccgggaga aggtggagac tgagctccag ggcgtgtgcg     360
acaccgtgct gggcctgctg gacagccacc tcatcaagga ggccggggac gccgagagcc     420
gggtcttcta cctgaagatg aagggtgact actaccgcta cctggccgag gtggccaccg     480
gtgacgacaa gaagcgcatc attgactcag cccggtcagc ctaccaggag gccatggaca     540
tcagcaagaa ggagatgccg cccaccaacc ccatccgcct gggcctggcc ctgaactttt     600
ccgtcttcca ctacgagatc gccaacagcc ccgaggaggc catctctctg gccaagacca     660
cttttgacga ggccatggct gatctgcaca ccctcagcga ggactcctac aaagacagca     720
ccctcatcat gcagctgctg cgagacaacc tgacactgtg gacggccgac aacgccgggg     780 aagaggggg cgaggctccc caggagcccc agagctgagt gttgcccgcc accgccccgc      840 cctgcccct ccagtccccc accctgccga gggactagt atggggtggg aggccccacc       900
cttctcccct aggcgctgtt cttgctccaa agggctccgt ggagagggac tggcagagct     960
gaggccacct ggggctgggg atcccactct tcttgcagct gttgagcgca cctaaccact    1020
ggtcatgccc ccaccctgc tctccgcacc cgcttcctcc cgaccccagg accaggctac     1080 ttctccctc ctcttgcctc cctcctgccc ctgctgcctc tgatcgtagg aattgaggag     1140
tgtcccgcct tgtggctgag aactggacag tggcagggc tggagatggg tgtgtgtgtg    1200
tgtgtgtgtg tgtgtgtgtg tgtgcgcgcg cgccagtgca agaccgagat tgagggaaag    1260
catgtctgct gggtgtgacc atgtttcctc tcaataaagt tcccctgtga cactcaaaaa    1320
aaaaaaaaaa aaaaaa                                                   1336
```

<210> SEQ ID NO 11
<211> LENGTH: 2240
<212> TYPE: DNA
<213> ORGANISM: Homo sapiens
<220> FEATURE:
<223> OTHER INFORMATION: LAPTM5 glucocorticoid receptor-responsive gene

<400> SEQUENCE: 11

```
ggagggcagc cagcagcttc cccttctctg ccctgctcca ggcaccaggc tctttcccct      60
tcagtgtctc agaggagggg acggcagcac catggacccc cgcttgtcca ctgtccgcca    120
```

```
gacctgctgc tgcttcaatg tccgcatcgc aaccaccgcc ctggccatct accatgtgat    180
catgagcgtc ttgttgttca tcgagcactc agtagaggtg gcccatggca aggcgtcctg    240
caagctctcc cagatgggct acctcaggat cgctgacctg atctccagct tcctgctcat    300
caccatgctc ttcatcatca gcctgagcct actgatcggc gtagtcaaga accgggagaa    360
gtacctgctg cccttcctgt ccctgcaaat catggactat ctcctgtgcc tgctcaccct    420
gctgggctcc tacattgagc tgcccgccta cctcaagttg gcctcccgga gccgtgctag    480
ctcctccaag ttcccctga tgacgctgca gctgctggac ttctgcctga gcatcctgac    540
cctctgcagc tcctacatgg aagtgcccac ctatctcaac ttcaagtcca tgaaccacat    600
gaattacctc cccagccagg aggatatgcc tcataaccag ttcatcaaga tgatgatcat    660
cttttccatc gccttcatca ctgtccttat cttcaaggtc tacatgttca agtgcgtgtg    720
gcggtgctac agattgatca agtgcatgaa ctcggtggag gagaagagaa actccaagat    780
gctccagaag gtggtcctgc cgtcctacga ggaagccctg tctttgccat cgaagacccc    840
agagggggc ccagcaccac ccccatactc agaggtgtga ccctcgccag gccccagccc    900
cagtgctggg agggtggag ctgcctcata atctgctttt ttgctttggt ggcccctgtg    960
gcctgggtgg gccctcccgc ccctccctgg caggacaatc tgcttgtgtc tccctcgctg   1020
gcctgctcct cctgcagggc ctgtgagctg ctcacaactg ggtcaacgct ttaggctgag   1080
tcactcctcg ggtctctcca taattcagcc caacaatgct tggtttattt caatcagctc   1140
tgacacttgt ttagacgatt ggccattcta aagttggtga gtttgtcaag caactatcga   1200
cttgatcagt tcagccaagc aactgacaaa tcaaaaccc acttgtcagt tcagtaaat    1260
aatttggtca acaacagtc tattgcattg atttataaat agttgtcagt tcacatagca   1320
atttaatcaa gtaatcatta attagttacc ccctatatat aaatatatgt aatcaatttc   1380
ttcaaatagc ttgcttacat gataatcaat tagccaacca tgagtcattt agaatagtga   1440
taaatagaat acacagaata gtgatgaaat tcaatttaaa aaatcacgtt agcctccaaa   1500
ccatttaatt caaatgaacc catcaactgg atgccaactc tggcgaatgt aggacctctg   1560
agtggctgta taattgttaa ttcaaatgaa attcatttaa acagttgaca aactgtcatt   1620
caacaattag ctccaggaaa taacagttat ttcatcataa aacagtccct tcaaacacac   1680
aattgttctg ctgaagagtt gtcatcaaca atccaatgct cacctattca gttgctctgt   1740
ggtcagtgtg gctgcataac agtggattcc atgaaaggag tcattttagt gatgagctgc   1800
cagtccattc ccaggccagg ctgtcgctgg ccatccattc agtcgattca gtcataggcg   1860
aatctgttct gcccgaggct tgtggtcaag caaaaattca gccctgaaat caggcacatc   1920
tgttcgttgg actaaaccca caggttagtt cagtcaaagc aggcaacccc cttgtgggca   1980
ctgaccctgc cactggggtc atggcggttg tggcagctgg ggaggtttgg ccccaacagc   2040
cctcctgtgc ctgcttccct gtgtgtcggg gtcctccagg gagctgaccc agaggtggag   2100
gccacggagg cagggtctct ggggactgtc gggggtaca gagggagaag gctctgcaag   2160
agctccctgg caataccccc ttgtgtaatt gctttgtgtg cgacagggag gaagtttcaa   2220
taaagcagca acaagcttct                                             2240
```

<210> SEQ ID NO 12
<211> LENGTH: 3039
<212> TYPE: DNA
<213> ORGANISM: Homo sapiens
<220> FEATURE:
<223> OTHER INFORMATION: GPSM2 glucocorticoid receptor-responsive gene

<400> SEQUENCE: 12

```
aggcgcagag gagggcggtg ttgagaccgg cggagcggcg ggacccctag gtggcggagg      60
gacgctccgg gaaagcgagg ggcgctacga gctctggccc acgtgacctg ccggggggcgg    120
gagcaggggg cgcgccggcc tcctgcggtg cccctgcctt ggggaggggc cgtgaccacc     180
cgtctgtcgc ccgaggcggc cgccgctgca ccttcaccgc gtacccggga cccgcccgcc    240
cgcgggagaa atgttgctga agtgctgctg aaagggccag agatgcaagg atttgggata    300
cattttgaac ctttaagctg tctgacattg acctcctttc attattaata aagaagaatc    360
aggagcttag gatgtattaa caccaactca ttaatatact aaccggacaa tgttctacaa    420
acaattctac attgtaaagg actggattgg cacaaaataa ataattttta ttttattcag    480
cttataatat gactcgatgg aggaaaattt gataagcatg agagaagacc attcttttca    540
tgttcgttac agaatggaag cttcttgcct agagctggcc ttggaagggg aacgtctatg    600
taaatcagga gactgccgcg ctggcgtgtc attctttgaa gctgcagttc aagttggaac    660
tgaagaccta aaaacactta gcgctattta cagccagttg ggcaatgctt atttctattt    720
gcatgattat gccaaagcat tagaatatca ccatcatgat ttaacccttg caaggactat    780
tggagaccag ctgggggaag cgaaagctag tggtaatctg ggaaacacct taaaagttct    840
tgggaatttt gacgaagcca tagtttgttg tcagcgacac ctagatattt ccagagagct    900
taatgacaag gtgggagaag caagagcact ttacaatctt gggaatgtgt atcatgccaa    960
agggaaaagt tttggttgcc ctggtcccca ggatgtagga gaatttccag aagaagtgag   1020
agatgctctg caggcagccg tggattttta tgaggaaaac ctatcattag tgactgcttt   1080
gggtgaccga gcggcacaag gacgtgcctt tggaaatctt ggaaacacac attacctcct   1140
tggcaacttc agggatgcag ttatagctca tgagcagcgt ctccttattg caaaagaatt   1200
tggagataaa gcagctgaaa gaagagcata tagcaacctt ggaaatgcat atatatttct   1260
tggtgaattt gaaactgcct cggaatacta caagaagaca ctactgttgg cccgacagct   1320
taaagaccga gctgtagaag cacagtcttg ttacagtctt ggaaatacat atactttact   1380
tcaagactat gaaaaggcca ttgattatca tctgaagcac ttagcaattg ctcaagagct   1440
gaatgataga attggtgaag gaagagcatg ttggagctta ggaaatgcat acacagcact   1500
aggaaatcat gatcaagcaa tgcattttgc tgaaaagcac ttggaaattt caagagaggt   1560
tgggggataaa agtggtgaac taacagcacg acttaatctc tcagaccttc aaatggttct   1620
tggtctgagc tacagcacaa ataactccat aatgtctgaa atactgaaa ttgatagcag   1680
tttgaatggt gtacgcccca agttgggacg ccggcatagt atggaaaata tggaacttat   1740
gaagttaaca ccagaaaagg tacagaactg gaacagtgaa attcttgcta agcaaaaacc   1800
tcttattgcc aaaccttctg caaagctact ctttgtcaac agactgaagg ggaaaaaata   1860
caaaacgaat tcctccacta aagttctcca agatgccagt aattctattg accaccgaat   1920
tccaaattct cagaggaaaa tcagtgcaga tactattgga gatgaagggt tctttgactt   1980
attaagccga tttcaaagca ataggatgga tgatcagaga tgttgcttac aagaaaagaa   2040
ctgccataca gcttcaacaa caacttcttc cactccccct aaaatgatgc taaaaacatc   2100
atctgttcct gtggtatccc ccaacacgga tgagttttta gatcttcttg ccagctcaca   2160
gagtcgccgt ctgatgacc agagggctag tttcagtaat ttgccagggc ttcgtctaac   2220
acaaaacagc cagtcggtac ttagccacct gatgactaat gacaacaaag aggctgatga   2280
```

```
agatttctttt gacatccttg taaaatgtca aggatccaga ttagatgatc aaagatgtgc    2340
tccaccacct gctaccacaa agggtccgac agtaccagat gaagacttttt tcagccttat    2400 tttacggtcc cagggaaaga gaatggatga acagagagtt cttttacaaa gagatcaaaa    2460
cagagacact gactttgggc taaaggactt tttgcaaaat aatgctttgt tggagtttaa    2520
aaattcaggg aaaaaatcgg cagaccatta gttactatgg atttattttt tttcctttca    2580
aacacggtaa ggaaacaatc tattactttt ttccttaaaa ggagaattta tagcactgta    2640
atacagctta aaatattttt agaatgatgt aaatagttaa ccttcagtag tctattaagg    2700
cattaatact tctctggaca tgcgcgtttg agggtggagg ggtcctgtaa ggtgcttcat    2760
cgtctgtgat tactgcttgg gatgtgttct ttggcagctt gtgagattac tttacctagt    2820
gtttataaag taggaagtta agtgaatcat agattagaat ttaatactct tatgaaaata    2880
attttttaac atcttaattg acaatggcgt ttttttatac ataaccatgg atgtagtggg    2940
aaacaatgtt gtttggtaaa aataatgtac ttgatcaatg taaaaaagta tataaaatag    3000
tcttactaaa aatctaggtt ttttttttcct ccaaaaaaa                           3039

<210> SEQ ID NO 13
<211> LENGTH: 7018
<212> TYPE: DNA
<213> ORGANISM: Homo sapiens
<220> FEATURE:
<223> OTHER INFORMATION: SORT1 glucocorticoid receptor-responsive gene

<400> SEQUENCE: 13
ggcgggcgcg ccgggcggca ggtgtcggcg tcggcggcat tcggcggcga tggagcggcc      60
ctggggagct gcggacggcc tctcgcgctg gccccatggc ctcggcctcc tcctcctcct     120
gcagctgctg ccgccgtcga ccctcagcca ggaccggctg gacgcgccgc cgccgccgc     180 tgcgccgctg ccgcgctggt ctggccccat cggggtgagc tgggggctgc gggcggccgc    240 agccggggc gcgtttcccc gcggcggccg ttggcgtcgc agcgcgccgg gcgaggacga     300
ggagtgcggc cgggtccggg acttcgtcgc caagctggcc aacaacacgc accagcatgt    360
gtttgatgat ctcagaggct cagtatcctt gtcctgggtt ggagatagca ctggggtcat    420
tctagtcttg actaccttcc atgtaccact ggtaattatg acttttggac agtccaagct    480
atatcgaagt gaggattatg ggaagaactt taaggatatt acagatctca tcaataacac    540
ctttattcgg actgaatttg gcatggctat tggtcctgag aactctggaa aggtggtgtt    600
aacagcagag gtgtctggag gaagtcgtgg aggaagaatc ttcagatcat cagatttgc     660 gaagaatttt gtgcaaacag atctcccttt tcatcctctc actcagatga tgtatagccc    720
tcagaattct gattatcttt tagctctcag cactgaaaat ggcctgtggg tgtccaagaa    780
ttttggggga aaatgggaag aaatccacaa agcagtatgt ttggccaaat ggggatcaga    840
caacaccatc ttctttacaa cctatgcaaa tggctcctgc aaagctgacc ttggggctct    900
ggaattatgg agaacttcag acttgggaaa aagcttcaaa actattggtg tgaaaatcta    960 ctcatttgt cttgggggac gtttccttttt tgcctctgtg atggctgata aggataccac    1020
aagaaggatc cacgtttcaa cagatcaagg ggacacatgg agcatggccc agctccctc     1080 cgtgggacag gaacagttct attctattct ggcagcaaat gatgacatgg tattcatgca    1140
tgtagatgaa cctggagaca ctgggttttgg cacaatcttt acctcagatg atcgaggcat    1200
tgtctattcc aagtctttgg accgacatct ctacactacc acaggcgagg agacggactt    1260
taccaacgtg acctccctcc gcggcgtcta cataacaagc gtgctctccg aagataattc    1320
```

```
tatccagacc atgatcactt ttgaccaagg aggaaggtgg acgcacctga ggaagcctga    1380
aaacagtgaa tgtgatgcta cagcaaaaaa caagaatgag tgcagccttc atattcatgc    1440
ttcctacagc atctcccaga aactgaatgt tccaatggcc ccactctcag agccgaatgc    1500
cgtaggcatt gtcattgctc atggtagcgt gggggatgcc atctcagtga tggttccaga    1560
tgtgtacatc tcagatgatg ggggttactc ctggacaaag atgctggaag acccccacta    1620
ttacaccatc ctggattctg gaggcatcat tgtggccatt gagcacagca gccgtcctat    1680
caatgtgatt aagttctcca cagacgaagg tcaatgctgg caaacctaca cgttcaccag    1740 ggacccatc tatttcactg gcctagcttc agaacctgga gctaggtcca tgaatatcag    1800
catttggggc ttcacagaat cttccctgac cagccagtgg gtctcctaca ccattgattt    1860
taaagatatc cttgaaagga actgtgaaga aaggactat accatatggc tggcacactc    1920
cacagaccct gaagattatg aagatggctg catttgggc tacaaagaac agtttctgcg    1980
gctacgcaag tcatccgtgt gtcagaatgg tcgagactat gttgtgacca agcagccctc    2040
catctgcctc tgttccctgg aggactttct ctgtgatttt ggctactacc gtccagaaaa    2100
tgactccaag tgtgtggaac agccagaact gaagggccac gacctggagt tttgtctgta    2160
cggaagagaa gaacacctaa caacaaatgg gtaccggaaa attccagggg acaaatgcca    2220
gggtggggta aatccagttc gagaagtaaa agacttgaaa aagaaatgca caagcaactt    2280
tttgagtccg gaaaaacaga attccaagtc aaattctgtt ccaattatcc tggccatcgt    2340
gggattgatg ctggtcacag tcgtagcagg agtgctcatt gtgaagaaat atgtctgtgg    2400
gggaaggttc ctggtgcatc gatactctgt gctgcagcag catgcagagg ccaatggtgt    2460
ggatggtgtg gatgctttgg acacagcctc ccacactaat aaaagtggtt atcatgatga    2520
ctcagatgag gacctcttgg aatagctctt cagaggagct ggacccagca tggatggtgg    2580
aaccacagta cctcttacac tccctgtggc tccaacttca ggaaataaat ttcccattgc    2640
gagggaccca gctctgtttc tgctgcttcc atcaaagcca aaaggaccta cactaaagaa    2700
atgcagggtg ggggtgggga accctgagca cttttttaca attggctctg agaaaaaggg    2760
agacatttta aattctttaa cttcttattt ctcgtcctgt ctctttgcaa agtatgggct    2820
tttttgtttt tgtttttaa gggaaacgaa atggaattcg aagggacctt ttcactaacc    2880
ccacttctgt gtgttctgca tggcgcctgc cccagggcat ctgccaactc cagtatcagc    2940
tctcacagtg tacttggtac catccctggg ctctgctggc gagacgaaac agctgtagag    3000
atgaaaacag gctgcagagg ctggcacagc ctggccggct tttctccatc tggggacagt    3060
cctactccaa gaacactgca caccagctcc tcacacagat cccacttact ctttttttt    3120 ttttcagaga ccacagacca cagtgatttt tcttttccct tgtttaatta ggcaataccc    3180
ttgttaattg cccttttggca actaacttaa ccatgtgctt cccacacagt acatcaggaa    3240
aacttacagg gcaatatttt taacttgggg caggaagaag ggagcagcag agaattgact    3300
agatatagca cctattaaaa gagaactctt gcttcttctg agattttca agctgtgctt    3360 tgtgtgtgtg ccagtagact tacgcaagga cagggtacaa acttagctgg aagtctgccc    3420
aggctgaatg atctcttccc tagagttgat tgtcgggtac acagtgtgaa cccccgaaga    3480
cggaacctca cagtcttcca tgttcccttc ttaactgtcg tgtggctcgt tgctaaatca    3540
tgacaatggc tgcctatctg ctgcttctta ggttgctgtt gtacatggaa ccaggactag    3600
agattttttc agatttatag acttaaaaaa ttagaatttt attaccaggc tttccttctc    3660
```

```
acccctttttt tctgactttg ccaagtaatt tgttgacacg aaaattttgg aggaaccaat    3720
tgaaaacaca cttccagtct agatgatgct ttgtgtgata cattaagttc ttattttgga    3780
ttaaaagaag ttttccattt gatacttctc taaattaaat aaattataga atgtagttgg    3840
gtggattttg gggtggccat atagtaatgg aaagctgcaa taattagttt taatacagct    3900
tgaatatttg ctatatagaa atatagtatg gaaagttttt ggtcttaatg tagctactgt    3960
gcgggtcaca gtttctccca atgattatga ctgggacatt cttggtagaa taccatttgc    4020
tactagttta ttttgtggct agaaagtcag ttttgtgtgt ttttttttt ttttatttga     4080 agtgccaaat taactttagt cagaatgtga gcagatggct aagttctctc ctccccagaa    4140
tggattaaca gctgcgtgga aagtggggga gagagtggat ggagactttt agagatgtta    4200
aaactgcagt agaatgaaat gagtcaggga gcttcagtta gaaaataaag ttgaggcagt    4260
ttttgtgaag ataatatggt tagggctgga gtgcactagt ctttttgctt attcattttg    4320
catggtttta aaattaaaaa taattccgaa gatacaccag ctcacaaatg aaaacgtcag    4380
cctctgcccc accctccctc ctgcccaaag tgaatttggt actcagaaaa gaactgttta    4440
taccactcac ctttctccca gcatgtactc actgtgggca gatgcaccaa tacatggtaa    4500
tcctcttact catttaaga cgtaggaaac tcaatattct tctctaacca tatacgatag     4560
ggctcttcgc ttttaatgat atctgggatt tctgtggaac ttggcaaatt ttcagagcac    4620
cttcactcac ataatgtcat ttgaacctca caatgttctt gggatggagt cagttgttca    4680
gggtccccgt gtgtgtgata agcagtgctg gctggctgtc ttcagaactc ttggaaatct    4740
ttacacatgc gagtgctaac cactttgagc aaggctgcct tcttgtagat gacttgctgt    4800
tctttatgac agggatcagt ggcatttgtt tcctagcagt atttagcacc tttttgccac    4860
cttggtgaac agaaaattgt attttcctgt ctttcatggc tgaaaacaaa gtaatggga     4920 atttttaaata cgtttgcaga aactgccccct ccctcattg agggtcactg ctcaagagtg    4980
caggagtgga ctctccactg atgggtctcc ctccccatcc tggtttccac cccgggctgg    5040
ctagctctgt tggtttgaag actgacagcc agcctggctc attctcatta ttggctagtt    5100
agctttcttt atcaacctgc tcactcacaa atgtgtgccc tcagccagag agtaagaaag    5160
cccaaatctg ttacagcttc taaaaaaata gatttctaat ttgtcctact catgttagga    5220
gcattatctt tgaaggtaaa acatagtgta tcattgtgta aactcccagg cttgatgtag    5280
cagaagagat catttctgga ggcttcagca atggaattta gcattataag agagattgga    5340
caaaccagtc caaagtggtc cgagttctta aatccaggta gggaactcac tcttcttcct    5400
tctctggacc taattgggca ttgggcttta gtgagaccac agaccaggcc cgtctctcct    5460
gtaggctttt aattcaatgg caactctatt tcaaagaata aaagcctttg gagagttgcg    5520
gcagttctgg gggcgggctc aggagagtcc atagatcagc cgtaactgga acgtagaatc    5580
tacgtctgcc tctgaatgga cttcccacct cctctctctt gctctgatgc ttgcctctgg    5640
gcctctccat gcccaaggtg gtctttcatc cttgacaggt tggtaatgtg ctggccacct    5700
ccagctcctg catcgagtct gtaaaccaga gctggttctc atggccttcg tcacgatacc    5760
aggatacgga ggggagccca gggccatcca tacccacccc agggtaacgg ggctggcctg    5820
gcattagtca ttatttagtt tccaggccaa ccatccagat agagattccc tctttccttt    5880
gagcagtgct ctcaagagct ccgtgcctgt ccacaatgac ctagagtgca tcctgctcat    5940
tgtcagtgta gcccctcgcc cctatattca tccaggatac ttggaagtgc taaaatagga    6000
agggattcgg ctttcaactt tgctaccatc ttccctgaag caggaaaatg aacatggact    6060
```

```
taaatgttct tgaaaaaac caaagtttta agatttgctg tgtgatgaag tgacagggag    6120
ggccggagtc agcaggtgcc agactttctg ttctgtctgc catgggtttg tccagctcag    6180
gtagctctag gagcaccatc ctgccctagc agagcccagg ccttgccctc atgaagcatc    6240
attgaaatag caggagcatg ttgatttctt ggttaggttg cattataata acaagagtca    6300
gaacattaat tcgaaacaac ttgcagtatg catttcttca caccagtaca ttcttaagtg    6360
tacttgttta taaggaataa cataaactaa tctgtacctt tatatatatg tgtgtgtaca    6420
tatatacata tataaactgt atagtgtaca tggtaatgat ttattgctat gccccagatc    6480
cttaatgtag ttctcatcct ccgcatgccc tcagccacaa gcgggtgact gactgttccc    6540
tgatgatttg gcccacctcc tgtgtttgga cctctaggga ggagggtttt ggtcatactc    6600
tccttatcct cgtgcacaga aatgctcagg gtccccatgt gcctgttgtt cagccctctc    6660
tcttgttccc tttctgagca tgtggtcctt ccccaggctg tgggacagct gccttcccac    6720
gaaagtgtaa agcagtatta agatcattac tgcatgtgcc ctaaaaaccc aagttttcta    6780
ttcccttagg acagaaaatt gcatgtgagg tgggataatc gagtttcagt gacccacgtc    6840
agttacacat taaagccaga ccccatgata aaattccaca aaatggaaat aaaactcaaa    6900
tttctttagc attgtgtaaa taaatctgaa tgtgtttaac tttgtactgg taattttctg    6960
tatatttgga atatttgggt taaaaataaa acagactgga ctttgttacc tgacctac     7018

<210> SEQ ID NO 14
<211> LENGTH: 1749
<212> TYPE: DNA
<213> ORGANISM: Homo sapiens
<220> FEATURE:
<223> OTHER INFORMATION: DPT glucocorticoid receptor-responsive gene

<400> SEQUENCE: 14
gtgacattgt ttgccaaaat cccaggcagc atggacctca gtcttctctg ggtacttctg      60
cccctagtca ccatggcctg gggccagtat ggcgattatg atacccata ccagcagtat     120 catgactaca gcgatgatgg gtgggtgaat ttgaaccggc aaggcttcag ctaccagtgt     180
ccccaggggc aggtgatagt ggccgtgagg agcatcttca gcaagaagga aggttctgac     240
agacaatgga actacgcctg catgcccacg ccacagagcc tcgggaaacc cacggagtgc     300
tggtgggagg agatcaacag ggctggcatg aatggtacc agacgtgctc caacaatggg     360
ctggtggcag gattccagag ccgctacttc gagtcagtgc tggatcggga gtggcagttt     420
tactgttgtc gctacagcaa gaggtgccca tattcctgct ggctaacaac agaatatcca     480
ggtcactatg gtgaggaaat ggacatgatt cctacaatt atgattacta tatccgagga     540
gcaacaacca ctttctctgc agtggaaagg atcgccagt ggaagttcat aatgtgccgg     600
atgactgaat acgactgtga atttgcaaat gtttagattt gccacatacc aaatctgggt     660
gaaaggaaag gggccgggga caggagggtg tccacatatg ttaacatcag ttggatctcc     720
tatagaagtt tctgctgctc tctttccttc tccctgagct ggtaactgca atgccaactt     780
cctgggcctt tctgactagt atcacacttc taataaaatc cacaattaaa ccatgtttct     840
cacttttcac atgtttcata gcaactgctt tatatgactg atgatggctt ccttgcacac     900
cacatataca gtgcgcatgc ttacagccgg gcttctggag caccagctgc agcctggcta     960
ctgcttttta ctgcagaatg aactgcaagt tcagcatagt ggaggggaga ggcagaactg    1020
gaggagaggt gcagtgaagg ttctctacag ctaagcctgt ttgaatgata cgtaggttcc    1080
```

```
ccaccaaaag caggctttct gccctgaggg acatcttccc actcccctgc tccacatgag    1140
ccatgcatgc ttagcaatcc aagtgcagag ctctttgctc caggagtgag gagactggga    1200
ggtgaaatgg ggaaatggaa gggtttggag gcagagctga aaacagggtt ggaaggattt    1260
cctgaattag aagacaaacg ttagcatacc cagtaaggaa aatgagtgca ggggccaggg    1320
gaacccgtga ggatcactct caaatgagat taaaaacaag gaagcagaga atggtcagag    1380
aatgggattc agattgggaa cttgtgggga tgagagtgac caggttgaac tgggaagtgg    1440
aaaaaggagt ttgagtcact ggcacctaga agcctgccca cgattcctag gaaggctggc    1500
agacaccctg gaaccctggg gagctactgg caaactctcc tggattgggc ctgattttt     1560 tggtgggaaa ggctgccctg gggatcaact ttccttctgt gtgtggctca ggagttcttc    1620
tgcagagatg gcgctatctt tcctcctcct gtgatgtcct gctcccaacc atttgtactc    1680
ttcattacaa aagaaataaa aatattaacg ttcactatgc tgaaaataaa aaaaaaaaa     1740 aaaaaaaaa                                                            1749

<210> SEQ ID NO 15
<211> LENGTH: 2478
<212> TYPE: DNA
<213> ORGANISM: Homo sapiens
<220> FEATURE:
<223> OTHER INFORMATION: NRP1 glucocorticoid receptor-responsive gene

<400> SEQUENCE: 15
gcagttggtg aaactcctct gtctcccgct catcttttca ttgctcgttc ccctccttcc      60
cgcagacacc cggaccctcc ctgggcgcca gctccgcggc tccaacgggt ccagaaacaa     120
gccggatttt tttttttct tcctggaaat tggctttggt gtgtgttgcc ctacctccct      180 cctcccctc ccacccacag ccccccccg gcctttttt ttttttttt ttttttgag          240 acatggcccg ggcagtggct cctggaagag gaacaagtgt gggaaaaggg agaggaagcc     300
ggagctaaat gacaggatgc aggcgacttg agacacaaaa agagaagcgt tcctctcgga     360
tccaggcatt gcctcgctgc tttctttcct ccaagacggg ctgaggattg tacagctcta     420
ggcggagttg ggctcttcg gatcgcttag attctcctct ttgctgcatt tccccccacg      480
tcctcgttct cccgcgtctg cctgcggacc cggagaaggg agaatggaga gggggctgcc     540
gctcctctgc gccgtgctcg ccctcgtcct cgccccggcc ggcgcttttc gcaacgataa     600
atgtggcgat actataaaaa ttgaaagccc cgggtacctt acatctcctg gttatcctca     660
ttcttatcac ccaagtgaaa aatgcgaatg gctgattcag gctccggacc cataccagag     720
aattatgatc aacttcaacc ctcacttcga tttggaggac agagactgca agtatgacta     780
cgtggaagtc ttcgatggag aaaatgaaaa tggacatttt aggggaaagt tctgtggaaa     840
gatagcccct cctcctgttg tgtcttcagg gccatttctt tttatcaaat ttgtctctga     900
ctacgaaaca catggtgcag gattttccat acgttatgaa attttcaaga gaggtcctga     960
atgttcccag aactacacaa cacctagtgg agtgataaag tcccccggat tccctgaaaa    1020
atatcccaac agccttgaat gcacttatat tgtctttgcg ccaaagatgt cagagattat    1080
cctgaatttt gaaagctttg acctggagcc tgactcaaat cctccagggg gatgttctg     1140 tcgctacgac cggctagaaa tctgggatgg attccctgat gttggccctc acattgggcg    1200
ttactgtgga cagaaaacac caggtcgaat ccgatcctca tcgggcattc tctccatggt    1260 ttttttacacc gacagcgcga tagcaaaaga aggtttctca gcaaaactaca gtgtcttgca    1320 gagcagtgtc tcagaagatt tcaaatgtat ggaagctctg ggcatggaat caggagaaat    1380
```

```
tcattctgac cagatcacag cttcttccca gtatagcacc aactggtctg cagagcgctc    1440
ccgcctgaac taccctgaga atgggtggac tcccggagag gattcctacc gagagtggat    1500
acaggtagac ttgggccttc tgcgctttgt cacggctgtc gggacacagg gcgccatttc    1560
aaaagaaacc aagaagaaat attatgtcaa gacttacaag atcgacgtta gctccaacgg    1620
ggaagactgg atcaccataa agaaggaaa caaacctgtt ctctttcagg aaacaccaa    1680 ccccacagat gttgtggttg cagtattccc caaaccactg ataactcgat ttgtccgaat    1740
caagcctgca acttgggaaa ctggcatatc tatgagattt gaagtatacg gttgcaagat    1800
aacagattat ccttgctctg gaatgttggg tatggtgtct ggacttattt ctgactccca    1860
gatcacatca tccaaccaag gggacagaaa ctggatgcct gaaaacatcc gcctggtaac    1920
cagtcgctct ggctgggcac ttccacccgc acctcattcc tacatcaatg agtggctcca    1980
aatagacctg ggggaggaga agatcgtgag gggcatcatc attcagggtg ggaagcaccg    2040 agaaacaag gtgttcatga ggaagttcaa gatcgggtac agcaacaacg gctcggactg    2100
gaagatgatc atggatgaca gcaaacgcaa ggcgaagtct tttgagggca caacaacta    2160 tgatacacct gagctgcgga cttttccagc tctctccacg cgattcatca ggatctaccc    2220
cgagagagcc actcatggcg gactgggggct cagaatggag ctgctgggct gtgaagtgga    2280 agccctaca gctggaccga ccactcccaa cgggaacttg gtggatgaat gtgatgacga    2340
ccaggccaac tgccacagtg aacaggtga tgacttccag ctcacaggtg gcaccactgt    2400
gctggccaca gaaaagccca cggtcataga cagcaccata caatcaggta tcaaataaaa    2460
tacgaaatgt gacagatt                                                 2478

<210> SEQ ID NO 16
<211> LENGTH: 3372
<212> TYPE: DNA
<213> ORGANISM: Homo sapiens
<220> FEATURE:
<223> OTHER INFORMATION: ACSL5 glucocorticoid receptor-responsive gene

<400> SEQUENCE: 16
taaaaccagg aagtgaagtc cccgagcacg ttagaaagcc tgacatggcc tgactcggga      60
cagctcagag cagggcagaa ctggggacac tctgggccgg ccttctgcct gcatggacgc     120
tctgaagcca ccctgtctct ggaggaacca cgagcgaggg aagaaggaca gggactcgtg     180
tggcaggaag aactcagagc cgggaagccc ccattcacta gaagcactga gagatgcggc     240
cccctcgcag ggtctgaatt tcctgctgct gttcacaaag atgcttttta tctttaactt     300
tttgttttcc ccacttccga ccccggcgtt gatctgcatc ctgacatttg gagctgccat     360
cttcttgtgg ctgatcacca gacctcaacc cgtcttacct cttcttgacc tgaacaatca     420
gtctgtggga attgagggag gagcacggaa ggggtttcc cagaagaaca atgacctaac     480
aagttgctgc ttctcagatg ccaagactat gtatgaggtt ttccaaagag gactcgctgt     540
gtctgacaat gggccctgct tgggatatag aaaaccaaac cagccctaca gatggctatc     600
ttacaaacag gtgtctgata gagcagagta cctgggttcc tgtctcttgc ataaaggtta     660
taaatcatca ccagaccagt ttgtcggcat ctttgctcag aataggccag agtggatcat     720
ctccgaattg gcttgttaca cgtactctat ggtagctgta cctctgtatg acaccttggg     780
accagaagcc atcgtacata ttgtcaacaa ggctgatatc gccatggtga tctgtgacac     840
accccaaaag gcattggtgc tgataggga tgtagagaaa ggcttcaccc cgagcctgaa     900
```

```
ggtgatcatc cttatggacc cctttgatga tgacctgaag caaagagggg agaagagtgg      960
aattgagatc ttatccctat atgatgctga gaacctaggc aaagagcact tcagaaaacc     1020
tgtgcctcct agcccagaag acctgagcgt catctgcttc accagtggga ccacaggtga     1080
ccccaaagga gccatgataa cccatcaaaa tattgtttca aatgctgctg cctttctcaa     1140
atgtgtggag catgcttatg agcccactcc tgatgatgtg gccatatcct acctccctct     1200
ggctcatatg tttgagagga ttgtacaggc tgttgtgtac agctgtggag ccagagttgg     1260
attcttccaa ggggatattc ggttgctggc tgacgacatg aagactttga agcccacatt     1320
gtttcccgcg gtgcctcgac tccttaacag gatctacgat aaggtacaaa atgaggccaa     1380
gacacccttg aagaagttct tgttgaagct ggctgtttcc agtaaattca aagagcttca     1440
aaagggtatc atcaggcatg atagtttctg ggacaagctc atctttgcaa agatccagga     1500
cagcctgggc ggaagggttc gtgtaattgt cactggagct gcccccatgt ccacttcagt     1560
catgacattc ttccgggcag caatgggatg tcaggtgtat gaagcttatg gtcaaacaga     1620
atgcacaggt ggctgtacat ttacattacc tggggactgg acatcaggtc acgttggggt     1680
gcccctggct tgcaattacg tgaagctgga agatgtggct gacatgaact actttacagt     1740
gaataatgaa ggagaggtct gcatcaaggg tacaaacgtg ttcaaaggat acctgaagga     1800
ccctgagaag acacaggaag ccctggacag tgatggctgg cttcacacag gagacattgg     1860
tcgctggctc ccgaatggaa ctctgaagat catcgaccgt aaaaagaaca ttttcaagct     1920
ggcccaagga gaatacattg caccagagaa gatagaaaat atctacaaca ggagtcaacc     1980
agtgttacaa attttgtac acggggagag cttacggtca tccttagtag gagtggtggt     2040
tcctgacaca gatgtacttc cctcatttgc agccaagctt ggggtgaagg gctccttga     2100
ggaactgtgc caaaaccaag ttgtaaggga agccatttta aagacttgc agaaaattgg     2160
gaaagaaagt ggccttaaaa cttttgaaca ggtcaaagcc attttttcttc atccagagcc     2220
attttccatt gaaaatgggc tcttgacacc aacattgaaa gcaaagcgag gagagctttc     2280
caaatacttt cggacccaaa ttgacagcct gtatgagcac atccaggatt aggataaggt     2340
acttaagtac ctgccggccc actgtgcact gcttgtgaga aaatggatta aaaactattc     2400
ttacatttgt tttgcctttc ctcctatttt tttttaacct gttaaactct aaagccatag     2460
cttttgtttt atattgagac atataatgtg taaacttagt tcccaaataa atcaatcctg     2520
tctttcccat cttcgatgtt gctaatatta aggcttcagg gctacttta tcaacatgcc     2580
tgtcttcaag atcccagttt atgttctgtg tccttcctca tgatttccaa ccttaatact     2640
attagtaacc acaagttcaa gggtcaaagg gaccctctgt gccttcttct ttgttttgtg     2700
ataaacataa cttgccaaca gtctctatgc ttatttacat cttctactgt tcaaactaag     2760
agatttttaa attctgaaaa actgcttaca attcatgttt tctagccact ccacaaacca     2820
ctaaaatttt agttttagcc tatcactcat gtcaatcata tctatgagac aaatgtctcc     2880
gatgctcttc tgcgtaaatt aaattgtgta ctgaagggaa aagtttgatc ataccaaaca     2940
tttcctaaac tctctagtta gatatctgac ttgggagtat aaaaattgg gtctatgaca     3000
tattgtccaa aaggaatgct gttcttaaag cattatttac agtaggaact ggggagtaaa     3060
tctgttccct acagtttgct gctgagctgg aagctgtggg ggaaggagtt gacaggtggg     3120
cccagtgaac ttttccagta aatgaagcaa gcactgaata aaaacctcct gaactgggaa     3180
caaagatcta caggcaagca agatgccaca acaacaggct tattttctgt gaaggaacca     3240
actgatctcc cccacccttg gattagagtt cctgctctac cttacccaca gataacacat     3300
```

```
gttgtttcta cttgtaaatg taaagtcttt aaaataaact attacagata cttaaaaaaa    3360
aaaaaaaaaa aa                                                         3372

<210> SEQ ID NO 17
<211> LENGTH: 5243
<212> TYPE: DNA
<213> ORGANISM: Homo sapiens
<220> FEATURE:
<223> OTHER INFORMATION: BICR3 glucocorticoid receptor-responsive gene

<400> SEQUENCE: 17
agcgtgagac tcgcgccctc cggcacggaa aaggccaggc gacaggtgtc gcttgaaaag      60
actgggcttg tccttgctgg tgcatgcgtc gtcggcctct gggcagcagg tttacaaagg     120
aggaaaacga cttcttctag attttttttt cagtttcttc tataaatcaa acatctcaa      180 aatggagacc taaatccttt aaagggactt agtctaatct cgggaggtag ttttgtgcat     240
gggtaaacaa attaagtatt aactggtgtt ttactatcca agaatgcta attttataaa      300 catgatcgag ttatataagg tataccataa tgagtttgat tttgaatttg atttgtggaa     360
ataaaggaaa agtgattcta gctggggcat attgttaaag cattttttc agagttggcc      420 aggcagtctc ctactggcac attctcccat tatgtagaat agaaatagta cctgtgtttg     480
ggaaagattt taaatgagt gacagttatt tggaacaaag agctaataat caatccactg      540
caaattaaag aaacatgcag atgaaagttt tgacacatta aaatacttct acagtgacaa     600
agaaaaatca agaacaaagc tttttgatat gtgcaacaaa tttagaggaa gtaaaaagat    660
aaatgtgatg attggtcaag aaattatcca gttatttaca aggccactga tatttttaaac    720 gtccaaaagt ttgtttaaat gggctgttac cgctgagaat gatgaggatg agaatgatgg     780
ttgaaggtta catttttagga aatgaagaaa cttagaaaat taatataaag acagtgatga    840
atacaaagaa gattttttata acaatgtgta aaattttttgg ccaggaaaag gaatattgaa    900
gttagataca attacttacc tttgagggaa ataattgttg gtaatgagat gtgatgtttc      960
tcctgccacc tggaaacaaa gcattgaagt ctgcagttga aaagcccaac gtctgtgaga    1020
tccaggaaac catgcttgca aaccactggt aaaaaaaaaa aaaaaaaaaa aaaaaagcca    1080
cagtgacttg cttattggtc attgctagta ttatcgactc agaacctctt tactaatggc    1140
tagtaaatca taattgagaa attctgaatt ttgacaaggt ctctgctgtt gaaatggtaa    1200
atttattatt ttttttgtca tgataaattc tggttcaagg tatgctatcc atgaaataat    1260
ttctgaccaa aactaaattg atgcaatttg attatccatc ttagcctaca gatggcatct    1320
ggtaactttt gactgttta aaaaataaat ccactatcag agtagatttg atgttggctt    1380
cagaaacatt tagaaaaaca aaagttcaaa aatgttttca ggaggtgata agttaataa    1440 ctctacaatg ttagttcttt gagggggaca aaaaatttaa aatctttgaa aggtcttatt    1500
ttacagccat atctaaatta tcttaagaaa attttttaaca aagggaatga aatatatatc    1560
atgattctgt tttttccaaaa gtaacctgaa tatagcaatg aagttcagtt ttgttattgg    1620
tagtttgggc agagtctctt tttgcagcac ctgttgtcta ccataattac agaggacatt    1680
tccatgttct agccaagtat actattagaa taaaaaaact taacattgag ttgcttcaac    1740
agcatgaaac tgagtccaaa agaccaaatg aacaaacaca ttaatctctg attattatt    1800 ttaaatagaa tatttaattg tgtaagatct aatagtatca ttatacttaa gcaatcatat    1860
tcctgatgat ctatgggaaa taactattat ttaattaata ttgaaaccag gttttaagat    1920
```

```
gtgttagcca gtcctgttac tagtaaatct ctttatttgg agagaaattt tagattgttt    1980
tgttctcctt attagaagga ttgtagaaag aaaaaaatga ctaattggag aaaaattggg    2040
gatatatcat atttcactga attcaaaatg tcttcagttg taaatcttac cattatttta    2100
cgtacctcta agaaataaaa gtgcttctaa ttaaaatatg atgtcattaa ttatgaaata    2160
cttcttgata acagaagttt taaaatagcc atcttagaat cagtgaaata tggtaatgta    2220 ttatttttcct cctttgagtt aggtcttgtg cttttttttc ctggccacta aatttcacaa    2280
tttccaaaaa gcaaaataaa catattctga atattttgc tgtgaaacac ttgacagcag    2340
agctttccac catgaaaaga agcttcatga gtcacacatt acatctttgg gttgattgaa    2400
tgccactgaa acattctagt agcctggaga agttgaccta cctgtggaga tgcctgccat    2460
taaatggcat cctgatggct taatacacat cactcttctg tgaagggttt taattttcaa    2520
cacagcttac tctgtagcat catgtttaca ttgtatgtat aaagattata caaggtgca    2580 attgtgtatt tcttccttaa aatgtatcag tataggattt agaatctcca tgttgaaact    2640
ctaaatgcat agaaataaaa ataataaaaa attttcatt ttggctttc agcctagtat     2700 taaaactgat aaaagcaaag ccatgcacaa aactacctcc ctagagaaag gctagtccct    2760
tttcttcccc attcatttca ttatgaacat agtagaaaac agcatattct tatcaaattt    2820
gatgaaaagc gccaacacgt ttgaactgaa atacgacttg tcatgtgaac tgtaccgaat    2880
gtctacgtat tccacttttc ctgctggggt tcctgtctca gaaggagtc ttgctcgtgc     2940 tggtttctat tacactggtg tgaatgacaa ggtcaaatgc ttctgttgtg gcctgatgct    3000
ggataactgg aaaagaggag acagtcctac tgaaaagcat aaaaagttgt atcctagctg    3060
cagattcgtt cagagtctaa attccgttaa caacttggaa gctacctctc agcctacttt    3120
tccttcttca gtaacaaatt ccacacactc attacttccg ggtacagaaa acagtggata    3180
tttccgtggc tcttattcaa actctccatc aaatcctgta aactccagag caaatcaaga    3240
tttttctgcc ttgatgagaa gttcctacca ctgtgcaatg aataacgaaa atgccagatt    3300
acttactttt cagacatggc cattgacttt tctgtcgcca acagatctgg caaaagcagg    3360
cttttactac ataggacctg gagacagagt ggcttgcttt gcctgtggtg gaaaattgag    3420
caattgggaa ccgaaggata atgctatgtc agaacacctg agacattttc ccaaatgccc    3480
atttatagaa aatcagcttc aagacacttc aagatacaca gtttctaatc tgagcatgca    3540
gacacatgca gcccgcttta aaacattctt taactggccc tctagtgttc tagttaatcc    3600
tgagcagctt gcaagtgcgg ttttttatta tgtgggtaac agtgatgatg tcaaatgctt    3660
ttgctgtgat ggtggactca ggtgttggga atctggagat gatccatggg ttcaacatgc    3720
caagtggttt ccaaggtgtg agtacttgat aagaattaaa ggacaggagt tcatccgtca    3780
agttcaagcc agttaccctc atctacttga acagctgcta tccacatcag acagcccagg    3840
agatgaaaat gcagagtcat caattatcca ttttgaacct ggagaagacc attcagaaga    3900
tgcaatcatg atgaatactc ctgtgattaa tgctgccgtg gaaatgggct ttagtagaag    3960
cctggtaaaa cagacagttc agagaaaaat cctagcaact ggagagaatt atagactagt    4020
caatgatctt tgttagact tactcaatgc agaagatgaa ataagggaag aggagagaga     4080
aagagcaact gaggaaaaag aatcaaatga tttattatta atccggaaga atagaatggc    4140 acttttttcaa catttgactt tgtgtaattcc aatcctggat agtctactaa ctgccggaat    4200
tattaatgaa caagaacatg atgttattaa acagaagaca cagacgtctt tacaagcaag    4260
agaactgatt gatacgattt tagtaaaagg aaatattgca gccactgtat tcagaaactc    4320
```

```
tctgcaagaa gctgaagctg tgttatatga gcatttattt gtgcaacagg acataaaata    4380
tattcccaca gaagatgttt cagatctacc agtggaagaa caattgcgga gactacaaga    4440
agaaagaaca tgtaaagtgt gtatggacaa agaagtgtcc atagtgttta ttccttgtgg    4500
tcatctagta gtatgcaaag attgtgctcc ttctttaaga aagtgtccta tttgtaggag    4560
tacaatcaag ggtacagttc gtacatttct ttcatgaaga agaaccaaaa catcgtctaa    4620
actttagaat taatttatta aatgtattat aactttaact tttatcctaa tttggttttcc   4680 ttaaaatttt tatttattta caactcaaaa acattgtttt tgtgtaacat atttatatat    4740
gtatctaaac catatgaaca tatatttttt agaaactaag agaatgatag gcttttgttc    4800
ttatgaacga aaaagaggta gcactacaaa cacaatattc aatcaaaatt tcagcattat    4860
tgaaattgta agtgaagtaa aacttaagat atttgagtta acctttaaga attttaaata    4920
ttttggcatt gtactaatac cgggaacatg aagccaggtg tggtggtatg tgcctgtagt    4980
cccaggctga ggcaagagaa ttacttgagc ccaggagttt gaatccatcc tgggcagcat    5040
actgagaccc tgcctttaaa aacaaacaga acaaaaacaa aacaccaggg acacatttct    5100
ctgtcttttt tgatcagtgt cctatacatc gaaggtgtgc atatatgttg aatgacattt    5160
tagggacatg gtgtttttat aaagaattct gtgagaaaaa atttaataaa gcaacaaaaa    5220
ttactcttaa aaaaaaaaaa aaa                                            5243

<210> SEQ ID NO 18
<211> LENGTH: 1579
<212> TYPE: DNA
<213> ORGANISM: Homo sapiens
<220> FEATURE:
<223> OTHER INFORMATION: NNMT glucocorticoid receptor-responsive gene

<400> SEQUENCE: 18
gaggaggtgc ttgccagaca ctgggtcatg gcagtggtcg gtgaagctgc agttgcctag      60
ggcagggatg gagagagagt ctgggcatga ggagagggtc tcgggatgtt tggctggact     120
agattttaca gaaagcctta tccaggcttt taaaattact ctttccagac ttcatctgag     180
actccttctt cagccaacat tccttagccc tgaatacatt tcctatcctc atctttccct     240 tcttttttt cctttctttt acatgtttaa atttaaacca ttcttcgtga cccctttctc     300
tgggagattc atggcaagaa cgagaagaat gatggtgctt gttaggggat gtcctgtctc     360
tctgaacttt ggggtcctat gcattaaata attttcctga cgagctcaag tgctccctct     420
ggtctacaat ccctggcggc tggccttcat cccttgggca agcattgcat acagctcatg     480
gccctccctc taccataccc tccaccccg ttcgcctaag ctcccttctc cgggaatttc      540
atcatttcct agaacagcca gaacattgt ggtctatttc tctgttagtg tttaaccaac     600
catctgttct aaaagaaggg ctgaactgat ggaaggaatg ctgttagcct gagactcagg     660
aagacaactt ctgcagggtc actccctggc ttctggagga aagagaagga gggcagtgct     720
ccagtggtac agaagtgaga cataatggaa tcaggcttca cctccaagga cacctatcta     780
agccatttta accctcggga ttacctagaa aaatattaca agtttggttc taggcactct     840
gcagaaagcc agattcttaa gcaccttctg aaaaatcttt tcaagatatt ctgcctagac     900
ggtgtgaagg gagacctgct gattgacatc ggctctggcc ccactatcta tcagctcctc     960
tctgcttgtg aatcctttaa ggagatcgtg gtcactgact actcagacca gaacctgcag    1020
gagctggaga agtggctgaa gaaagagcca gaggcctttg actggtcccc agtggtgacc    1080
```

| | |
|---|---|
| tatgtgtgtg atcttgaagg gaacagagtc aagggtccag agaaggagga gaagttgaga | 1140 |
| caggcggtca agcaggtgct gaagtgtgat gtgactcaga gccagccact gggggccgtc | 1200 |
| cccttacccc cggctgactg cgtgctcagc acactgtgtc tggatgccgc ctgcccagac | 1260 |
| ctccccacct actgcagggc gctcaggaac ctcggcagcc tactgaagcc aggggcttc | 1320 |
| ctggtgatca tggatgcgct caagagcagc tactacatga ttggtgagca gaagttctcc | 1380 |
| agcctccccc tgggccggga ggcagtagag gctgctgtga agaggctggg ctacacaatc | 1440 |
| gaatggtttg aggtgatctc gcaaagttat tcttccacca tggccaacaa cgaaggactt | 1500 |
| ttctccctgg tggcgaggaa gctgagcaga cccctgtgat gcctgtgacc tcaattaaag | 1560 |
| caattccttt gacctgtca | 1579 |

<210> SEQ ID NO 19
<211> LENGTH: 980
<212> TYPE: DNA
<213> ORGANISM: Homo sapiens
<220> FEATURE:
<223> OTHER INFORMATION: IGFBP6 glucocorticoid receptor-responsive gene

<400> SEQUENCE: 19

| | |
|---|---|
| gcggcggcgg gcagcagctg cgctgcgact gctctggaag gagaggacgg ggcacaaacc | 60 |
| ctgaccatga cccccacag gctgctgcca ccgctgctgc tgctgctagc tctgctgctc | 120 |
| gctgccagcc caggaggcgc cttggcgcgg tgcccaggct gcgggcaagg ggtgcaggcg | 180 |
| ggttgtccag ggggctgcgt ggaggaggag gatggggggt cgccagccga gggctgcgcg | 240 |
| gaagctgagg gctgtctcag gagggagggg caggagtgcg gggtctacac ccctaactgc | 300 |
| gccccaggac tgcagtgcca tccgcccaag gacgacgagg cgcctttgcg ggcgctgctg | 360 |
| ctcggccgag gccgctgcct tccggcccgc gcgcctgctg ttgcagagga gaatcctaag | 420 |
| gagagtaaac cccaagcagg cactgcccgc ccacaggatg tgaaccgcag agaccaacag | 480 |
| aggaatccag gcacctctac cacgcccctcc cagcccaatt ctgcgggtgt ccaagacact | 540 |
| gagatgggcc catgccgtag acatctggac tcagtgctgc agcaactcca gactgaggtc | 600 |
| taccgagggg ctcaaacact ctacgtgccc aattgtgacc atcgaggctt ctaccggaag | 660 |
| cggcagtgcc gctcctccca ggggcagcgc cgaggtccct gctggtgtgt ggatcggatg | 720 |
| ggcaagtccc tgccagggtc tccagatggc aatggaagct cctcctgccc cactgggagt | 780 |
| agcggctaaa gctgggggat agaggggctg cagggccact ggaaggaaca tggagctgtc | 840 |
| atcactcaac aaaaaaccga ggccctcaat ccaccttcag gccccgcccc atgggcccct | 900 |
| caccgctggt tggaaagagt gttggtgttg gctggggtgt caataaagct gtgcttgggg | 960 |
| tcgctgaaaa aaaaaaaaa | 980 |

<210> SEQ ID NO 20
<211> LENGTH: 7346
<212> TYPE: DNA
<213> ORGANISM: Homo sapiens
<220> FEATURE:
<223> OTHER INFORMATION: PLXNC1 glucocorticoid receptor-responsive gene

<400> SEQUENCE: 20

| | |
|---|---|
| gcgaggagga aacggtgccg gagcgcgcag ggcttgctgc cgccaccgcc gctgcacagg | 60 |
| ctgccggagc gagcctgccg cgcgccgccc tcccgctct ccttcctggg cgagctgcgg | 120 |
| ggatggggcg gccgcgggag cccgagcgcg cgcaggaacc gccgccgccg ccgcccgcgt | 180 |
| ctccgttgcc gcgcgcctga gccgccgtcg ccgccgcgcg ccctgcccgg gggcggcccc | 240 |

```
cccagcccca tggaggtctc ccggaggaag gcgccgccgc gcccccgcg ccccgcagcg      300 ccactgcccc tgctcgccta tctgctggca ctggcggctc ccggccgggg cgcggacgag      360
cccgtgtggc ggtcggagca agccatcgga gccatcgcgg cgagccagga ggacggcgtg      420
tttgtggcga gcggcagctg cctggaccag ctggactaca gcctggagca cagcctctcg      480
cgcctgtacc gggaccaagc gggcaactgc acagagccgg tctcgctggc gcccccgcg       540 cggcccggc ccgggagcag cttcagcaag ctgctgctgc cctaccgcga ggggcggcc        600 ggcctcgggg ggctgctgct caccggctgg accttcgacc ggggcgcctg cgaggtgcgg      660
cccctgggca acctgagccg caactccctg cgcaacggca ccgaggtggt gtcgtgccac      720
ccgcagggct cgacggccgg cgtggtgtac cgcgcgggcc ggaacaaccg ctggtacctg      780
gcggtggccg ccacctacgt gctgcctgag ccggagacgg cgagccgctg caaccccgcg      840
gcatccgacc acgacacggc catcgcgctc aaggacacgg aggggcgcag cctggccacg      900
caggagctgg ggcgcctcaa gctgtgcgag ggcgcgggca gcctgcactt cgtgacgcc        960 tttctctgga acggcagcat ctacttcccc tactacccct acaactacac gagcggcgct     1020
gccaccggct ggcccagcat ggcgcgcatc gcgcagagca ccgaggtgct gttccagggc     1080
caggcatccc tcgactgcgg ccacggccac cccgacggcc gccgcctgct cctctcctcc     1140
agcctagtgg aggccctgga cgtctgggcg ggagtgttca gcgcggccgc tggagagggc     1200
caggagcggc gctcccccac caccacggcg ctctgcctct tcagaatgag tgagatccag     1260
gcgcgcgcca agagggtcag ctgggacttc aagacggccg agagccactg caaagaaggg     1320
gatcaacctg aaagagtcca accaatcgca tcatctacct tgatccattc cgacctgaca     1380
tccgtttatg gcaccgtggt aatgaacagg actgttttat tcttggggac tggagatggc     1440
cagttactta aggttattct tggtgagaat ttgacttcaa attgtccaga ggttatctat     1500
gaaattaaag aagagacacc tgttttctac aaactcgttc ctgatcctgt gaagaatatc     1560
tacatttatc taacagctgg gaaagaggtg aggagaattc gtgttgcaaa ctgcaataaa     1620
cataaatcct gttcggagtg tttaacagcc acagaccctc actgcggttg gtgccattcg     1680
ctacaaaggt gcactttca aggagattgt gtacattcag agaacttaga aaactggctg      1740
gatatttcgt ctggagcaaa aaagtgccct aaaattcaga taattcgaag cagtaaagaa     1800
aagactacag tgactatggt gggaagcttc tctccaagac actcaaagtg catggtgaag     1860
aatgtggact ctagcaggga gctctgccag aataaaagtc agcccaaccg gacctgcacc     1920
tgtagcatcc caaccagagc aacctacaaa gatgtttcag ttgtcaacgt gatgttctcc     1980
ttcggttctt ggaatttatc agacagattc aactttacca actgctcatc attaaaagaa     2040
tgcccagcat gcgtagaaac tggctgcgcg tggtgtaaaa gtgcaagaag gtgtatccac     2100
cccttcacag cttgcgaccc ttctgattat gagagaaacc aggaacagtg tccagtggct     2160
gtcgagaaga catcaggagg aggaagaccc aaggagaaca aggggaacag aaccaaccag     2220
gctttacagg tcttctacat taagtccatt gagccacaga agtatcgac attagggaaa      2280 agcaacgtga tagtaacggg agcaaacttt acccgggcat cgaacatcac aatgatcctg     2340
aaaggaacca gtacctgtga taggatgtg atacaggtta gccatgtgct aaatgacacc      2400
cacatgaaat tctctcttcc atcaagccgg aaagaaatga aggatgtgtg tatccagttt     2460
gatggtggga actgctcttc tgtgggatcc ttatcctaca ttgctctgcc acattgttcc     2520
cttatatttc ctgctaccac ctggatcagt ggtggtcaaa atataaccat gatgggcaga     2580
```

```
aattttgatg taattgacaa cttaatcatt tcacatgaat taaaaggaaa cataaatgtc   2640
tctgaatatt gtgtggcgac ttactgcggg ttttttagccc ccagtttaaa gagttcaaaa   2700
gtgcgcacga atgtcactgt gaagctgaga gtacaagaca cctacttgga ttgtggaacc   2760
ctgcagtatc gggaggaccc cagattcacg gggtatcggg tggaatccga ggtggacaca   2820
gaactggaag tgaaaattca aaaagaaaat gacaacttca acatttccaa aaaagacatt   2880
gaaattactc tcttccatgg ggaaaatggg caattaaatt gcagttttga aaatattact   2940
agaaatcaag atcttaccac catcctttgc aaaattaaag gcatcaagac tgcaagcacc   3000
attgccaact cttctaagaa agttcgggtc aagctgggaa acctggagct ctacgtcgag   3060
caggagtcag ttccttccac atggtatttt ctgattgtgc tccctgtctt gctagtgatt   3120
gtcatttttg cggccgtggg ggtgaccagg cacaaatcga aggagctgag tcgcaaacag   3180
agtcaacaac tagaattgct ggaaagcgag ctccggaaag agatacgtga cggctttgct   3240
gagctgcaga tggataaatt ggatgtggtt gatagtttg gaactgttcc cttccttgac   3300
tacaaacatt ttgctctgag aactttcttc cctgagtcag gtggcttcac ccacatcttc   3360
actgaagata tgcataacag agacgccaac gacaagaatg aaagtctcac agctttggat   3420
gccctaatct gtaataaaag ctttcttgtt actgtcatcc acacccttga aaagcagaag   3480 aactttctg tgaaggacag gtgtctgttt gcctccttcc taaccattgc actgcaaacc   3540
aagctggtct acctgaccag catcctagag gtgctgacca gggacttgat ggaacagtgt   3600
agtaacatgc agccgaaact catgctgaga cgcacggagt ccgtcgtcga aaaactcctc   3660
acaaactgga tgtccgtctg cctttctgga tttctccggg agactgtcgg agagcccttc   3720
tatttgctgg tgacgactct gaaccagaaa attaacaagg gtcccgtgga tgtaatcact   3780
tgcaaagccc tgtacacact taatgaagac tggctgttgt ggcaggttcc ggaattcagt   3840
actgtggcat taaacgtcgt cttttgaaaaa atcccggaaa acgagagtgc agatgtctgt   3900 cggaatatt cagtcaatgt tctcgactgt gacaccattg gccaagccaa agaaaagatt   3960
ttccaagcat tcttaagcaa aaatggctct ccttatggac ttcagcttaa tgaaattggt   4020
cttgagcttc aaatgggcac acgacagaaa gaacttctgg acatcgacag ttcctccgtg   4080
attcttgaag atggaatcac caagctaaac accattggcc actatgagat atcaaatgga   4140
tccactataa aagtctttaa gaagatagca aattttactt cagatgtgga gtactcggat   4200
gaccactgcc atttgatttt accagattcg gaagcattcc aagatgtgca aggaaagaga   4260
catcgaggga agcacaagtt caaagtaaaa gaaatgtatc tgacaaagct gctgtcgacc   4320
aaggtggcaa ttcattctgt gcttgaaaaa cttttttagaa gcatttggag tttacccaac   4380
agcagagctc catttgctat aaaatacttt tttgactttt tggacgccca ggctgaaaac   4440
aaaaaaatca cagatcctga cgtcgtacat atttggaaaa caaacagcct tcctcttcgc   4500
ttctgggtaa acatcctgaa gaaccctcag tttgtctttg acattaagaa gacaccacat   4560
atagacggct gtttgtcagt gattgcccag gcattcatgg atgcattttc tctcacagag   4620
cagcaactag ggaaggaagc accaactaat aagcttctct atgccaagga tatcccaacc   4680
tacaaagaag aagtaaaatc ttattacaaa gcaatcaggg atttgcctcc attgtcatcc   4740
tcagaaatgg aagaattttt aactcaggaa tctaagaaac atgaaaatga atttaatgaa   4800
gaagtggcct tgacagaaat ttacaaatac atcgtaaaat attttgatga gattctaaat   4860
aaactagaaa gagaacgagg gctggaagaa gctcagaaac aactcttgca tgtaaaagtc   4920
ttatttgatg aaaagaagaa atgcaagtgg atgtaagcac tctgggcct ggcttaatct   4980
```

```
ggcaaagttc ttcagacgac ttgggagcaa aatggctgct tgagctactc tgtgtcgtta    5040
atttgttgtt tgcacatagg ttccactttg ggcactgtct ttttaagaga ccaaggcaca    5100
tgcacagctt ttagaaagca taccaaccct tgtgcctgtg tgtataccgt gggaaccctt    5160
ctgtaaatag agttgaagtg gttgttgcaa acagcctcct tgtttacaga aatacaagg     5220 ccagtaagcg aatgtcagta ttgtaactac agtctccact taagcacaat gatataagtg    5280
gttttgtttg aaaactacag ctatgtagca cttgtgctac actgcacctc tgcattgtaa    5340
agggatactg ccagtgctca aaacaaaatg tgaaatgagt catttggaaa caaggtgggg    5400
gtgttagggc aacctcgagg atttgcagca ttgaaacttt ccccagtagt tcttggaaaa    5460
gctgaccgca gaatttggta gtgtacactt agcatttgtg agtgtgtgtg tgtgtttaaa    5520
ccaaaaacta acagtgttgc aacattgttg aaagggctcg tgttttttcag tggtcatcaa   5580 ctgcactcca tcaaactcac ctccatttca ccaaggagct ctaaagtaag gagagtgggc    5640
tttatttaaa tgaacagcat tttaaccaga tactttgtcc taatgtatgt tcctttctt    5700 catctgtttt ttcatactaa atgtatttga tagtggacat gttggatatt atacaaaaaa    5760
atcattaatt catttctgtt ccaaaacctt tgatcagaac gatctgtgga agagtaactc    5820
catttctata tgagtgagtg tctccttgct ttagatttct ggtgaaccct gtggttatga    5880
atacttgtgt gtgatttaaa aaaaaaaga tacattttac atttcatcga attgctgttc     5940
acactggagt attatatata aatatatata tttgaggccc aaggcctgaa aaatattagt    6000
atacaacttg gtatcttagt cttactatgt actttttgaa agtattcctc gcaggagaaa    6060
gaatttaaaa tacccatttt attcatgcct ttcttttttaa agaattctct atccagttat   6120
actgtagtct ttttagtgct gattttttaa ttcctgaatt tttgctgctc atgaccagtt    6180
ttaataccac tgtgttttcc ttctattaaa ccagaagaag taaacagcat aattggcaac    6240
tcttgagctt ttcttgtggc aggcaccttt taccccttggt gctccaaatc ccccatctag   6300
gaaagaaaat ttttttcaagt caaataacat tgatcacata ttccttgaaa tcatttacca   6360
acactgtatg gagcattagg atttaaatat gaatttgtct taaaggcaat tcctttttgc    6420
ttctgtatta tctggaaaag catgagagag gtgacacctc aacaaactga tcagagaaaa    6480
taagcagtta ctaccctgat aggcaccttc ccaatcctgt tgcttttgac cattgtctgt    6540
ccaacggaca cacctcaaac aaacaaaact accaaataga tgacagatca gaataaaggt    6600
gagaggtctg gtccccattg aaggctgcta cagtcttcaa agaggtgaag gagttcataa    6660
gagaacaaca gtaggaaagt tgagagccaa gggtaggaga gttgcccaaa agacttcccc    6720
tactacttta gggtactgaa aactcaaagg atcagctaca gctttatcta agtatttact    6780
aaatgctaca tgagggtgtc cctgtccagc tttctggcac atgagtcctg tgtggagagt    6840
tacctcctct tccagggact gtgctgttgg gaactttggg caagtcactt acctctttgt    6900
gcctcaattt ctgtataata tttctaagct acctcactga ggtggtatga agattcacta    6960
atgtatgtag cgtgtttgtc aatcctccag tgaaaagcac tatctagatc acattttgga   7020
tcacattagc caaatgcagt aaatggccaa attagatgtg tgctgaagac aatcagtcac    7080
tgggtctata ttaaacagca accagagcaa caaatggcaa acaatttcta ttttcaagtt    7140
tctttgcata tttttttggt gcaaaaccat ttataaactt ttttttctaa cactagtgtc    7200
tacagcagca ttcaaaaaaa ttctgttacc ttttctgtat taggatttaa agtctatttc    7260
ttattgtata cctgattgaa gctgttcttg gagatgaatg ttttaaatgt ctatatccaa    7320
```

```
aaaataaaca ttttgatgta actgtg                                    7346
```

<210> SEQ ID NO 21
<211> LENGTH: 2828
<212> TYPE: DNA
<213> ORGANISM: Homo sapiens
<220> FEATURE:
<223> OTHER INFORMATION: SLC46A3 glucocorticoid receptor-responsive gene

<400> SEQUENCE: 21

```
agaacagtga cagcgccgcg gcagccgacc ccgcctcctc ggcggacagc gatgctcagc    60
tggctgcggc cgagtcatcg cctagcgctg cagggccgc tgaccgaccg acggaggcgc   120
cgattggccg attgtccact gcgcagaagg agcagctgct ccgcgccccg ccgcgccgcg   180
ctgaggccga ggtccgcagg gccgcgggga agccgagggc tgccggagaa ccctgcaggt   240
gtcactcggg acgcggaagt gcgcttgccg aggtttgctt tacaatacgc ttgagactcc   300
ccgacaagcg taatttggtc gagttcgacg ggaaagtact ctccccaccc cagcgccggc   360
cgcgtagtcc gaggttactg tccccggcgc gtcctctgtt gccccagtcc agaggctgcc   420
cttgaacccg ggcgcgcacg agcgcagggc atccgaggcg acagcccctg cacggcccg   480
acctgtaccc agcctggcag gaagactgta atcgtgggaa tacagctacc tacccaggca   540
atatgaagat tttatttgta gaacctgcca ttttccttag tgcatttgct atgactttga   600
ccggtccact gacaacgcaa tatgtttatc ggagaatatg ggaagaaact ggcaactaca   660
cttttttcatc tgatagcaat atttctgagt gtgaaaaaaa caaaagcagc ccaattttg   720
cattccagga ggaagttcag aaaaaagtgt cacgttttaa tctgcagatg gacataagtg   780
gattaattcc tggtctagtg tctacattca tacttttgtc tattagtgat cactacggac   840
gaaaattccc tatgattttg tcttccgttg gtgctcttgc aaccagcgtt tggctctgtt   900
tgctttgcta ttttgccttt ccattccagc ttttgattgc atctaccttc attggtgcat   960
tttgtggcaa ttataccaca ttttggggag cttgctttgc ctatatagtt gatcagtgta  1020
aagaacacaa acaaaaaaca attcgaatag ctatcattga cttctactt ggacttgtta  1080
ctggactaac aggactgtca tctggctatt ttattagaga gctaggttt gagtggtcgt  1140
ttctaattat tgctgtgtct cttgctgtta atttgatcta tattttattt tttctcggag  1200
atccagtgaa agagtgttca tctcagaatg ttactatgtc atgtagtgaa ggcttcaaaa  1260
acctatttta ccgaacttac atgctttta agaatgcttc tggtaagaga cgattttgc  1320
tctgtttgtt acttttaca gtaatcactt attttttgt ggtaattggc attgccccaa  1380
ttttatcct ttatgaattg gattcaccac tctgctggaa tgaagttttt ataggttatg  1440
gatcagcttt gggtagtgcc tcttttttga ctagtttcct aggaatatgg cttttttctt  1500
attgtatgga agatattcat atggccttca ttgggatttt taccacgatg acaggaatgg  1560
ctatgaccgc gtttgccagt acaacactga tgatgttttt agccagggtg ccgttcctt  1620
tcactattgt gccattctct gttctacggt ccatgttgtc aaaagtggtt cgttcgactg  1680
aacaaggtac cctgtttgct tgtattgctt cttagaaac acttggagga gtcactgcag  1740
tttctacttt taatggaatt tactcagcca ctgttgcttg gtaccctggc ttcactttcc  1800
tgctgtctgc tggtctgtta ctacttccag ccatcagtct atgtgttgtc aagtgtacca  1860
gctggaatga gggaagctat gaacttctta tacaagaaga atccagtgaa gatgcttcag  1920
acagagcctg ttaagctgct attgatagtc ggagcttata tactgtgact tctgaagact  1980
atacatgaat tccacaatca gtgctttgtt gatacaaaat ccttaaaagg gaggcacttt  2040
```

```
aaagaatatg tattttttcac ttttcttaat atgtttcatc ggtgacaggc atgataatat    2100
ttctatatgt aatgggtaat tgggaaaaaa tagatgataa ataaaattgc tctaaagaag    2160
ttaaaaaact gaatgaacag ctaatactgg tataaagtaa ctaatgtttg gagccaacat    2220
ttgttccttg tgtcagcaaa aggatattca cattccatga tccctggctg agaattctgc    2280
ctctagtctt tcttacccag ctgttgtcta tccttgttca attataaata ctgctaaggg    2340
catttttaaa atacgatctt gtactcctta aatttgaatc cgtcagcacg gtcactcata    2400
ggaaaatgat caaacaagca agccagtcat gatttgactc cttcccatct catttcttac    2460
tgccttacgc tcatcctgag gtccaccttg gtctctaaaa acaccatgtg ttctcatgcc    2520
tccatgtctt ttcacacact gttccatttg ctcttcctcc cacattacat tgaaactttc    2580
aagcctcagt cgaaacattg cttcttctgg atagcagcct tcttgacatc cctcctcact    2640
ccccagtccc tacagggctt ccatagctct ttgtgtgcac ttcgatccca gcattttcca    2700
tcgacttgta attgtttctg ctacctgaca atcatcgcct tgagtactgg gacaaccttt    2760
gattactcat tatatcctca ataaatattt gttgaactaa aaaaaaaaaa aaaaaaaaa    2820 aaaaaaaa                                                             2828
```

<210> SEQ ID NO 22
<211> LENGTH: 2840
<212> TYPE: DNA
<213> ORGANISM: Homo sapiens
<220> FEATURE:
<223> OTHER INFORMATION: C14orf139 glucocorticoid receptor-responsive
      gene

<400> SEQUENCE: 22

```
gttttttgtgc aggaacagcc cctcccgtct ttgtcctggc ggtgagcacc cagggctaag      60
cttttgaaca ctttctttgt gtttggattc agcccaggca atgcatattt gctttcattt     120
cttcttgagc ttgaggagct cctgggtgca aatcttggaa aatgaggatc tctgagcctt     180
tccaggccag ctctttgttt tgtagcagac aattgaggct ttgaaaagga agtgggtgg      240 gggcacccca caggtggccc tcatcaccca attgccagtg cctgcaggct gcttcagcag     300
aggcccagag tcaaagagga cttaaaacca gctgtcgttt ctcccttagc ttctgtgtat     360
gagagaaacg acttctgttt ttcaaagtaa gaacaaggag gaatttgttt ctaaaagaac     420
attaaaacac aggctcgtgg tctaaaagca aatggttcag caggatgttc agggccttaa     480
agcacagtca gcaggactca gcatctccca gcacctgctc tccggttgtc atggtaacat     540
catccccaac ccaaccacct tgtccagccg agagacagca atcataagga gggacctcgg     600
tttcccccga ggatcctggg cttcctttct gaaacgcttg cttctgagct cagcaaccag     660
gaacaccagg ccagcccatc cccagcacct ctgtggagat gagggacaaa gtcctacagt     720
ccctcttcct gttctgatga gaaagggagg gaagaaaaca taccccgagc gcctgcaata     780
tggtcatgac actttcaaaa agcctgtgct atggagtcat gatcagaaac cagagtgtgg     840
agagggtcag cagcctgcct cagagcagcc agctaggcgg ggagtggtaa atttgggact     900
tgtacccagg catgactggc tccgagccca gtgctccact ctatggaatg ttccctgggc     960
ctcagttgct ttccttttcct ttgcaggccg cgggctgctg ccactctggc agctggtgag    1020
ttagctggag ggcaacattc caaagcaggg gcagcatgct gctttcctcc tgtgcccact    1080
cctgcgggga agtccgttga ctcccaccgc tgaagggagc tggcaacacc aggatgaggt    1140
cccaggggac gggagcaggt acccactgtc tgtctacctt cccactggaa aagcacggac    1200
```

```
aggccagccc ttgcgggggc aggcagagga cagagttggc tttgcgcggt ctctgcctgc    1260
tgagcagttc caattcctct catgggagaa acaaggaggc agtcgcttgt gcatgttcca    1320
gaagttttac tggggaggag gaagcggaca gaggaagctg tgtgtgcatg tgaaggggtg    1380
ggcagggtgg gagggatgca cgcgtatgtg agcatagcat gtgtgagtac tacacacatc    1440
tccatgcaga agcacaactg gcagccctg gcttccagct ctgggcttca gcacaacaga    1500
caccagcctg tggtctctca gaagccaggg agaccacatc gggctcagga cgttttaccc    1560
aaagtccaga gttttttatgc ctctccctgg cattctccat aaagaaggga aggtcagatg    1620
accccttaga tctgtgtcat ctgggaattt ccttgggctg gtttagacac gatgccctct    1680
ttttctcagg atagcagata acctgctttg aaagagggct taattctgtg ggtcctaaat    1740
tttctccttt ctctctctct ttctgtgtgt gtgtgttggg aaaatggcaa gtttccaata    1800
ccagctttgg aggaacgatt acgttttccc tccaatttca agtccgaaag accagagccc    1860
tcattccaaa gccccccacc cagatggatt ttttcgtttc atttgtcatc cgtcccatgg    1920
gagggcccca tgtctcctca gaacccatcc tggaggcagc aggtcgggta gagtgagttt    1980
ggcctgctca tgacctccac ccctgagatt gtgaacaagg atgtctgggg cgatgctgag    2040
aatgtttttg aagctgctcc cagatgacgc tgatgatcac accagattga gtgctgcgat    2100
cgccttgagt ccaacctctg cataaacgag gttctcataa acaagttcac tctaccctaa    2160
gctaagtcta tgtgagcaaa cccacttcat cctttgtacc tggagacctg gttacactaa    2220
cctgatactg acctgttcat gtagctggaa tggtgtgttt catgcagtgt ggaccaagca    2280
atggcatggg gtgtgtgtgt gtgtgtgtgt gtgtctgtgt gtgtgtgttt gtgtatgcgt    2340
tcacacttgt gtgtgtatat gtgcatgtag atgctgcata aatgattttt gatgtcaaag    2400
acaaacacat tccattgttt taaatattct attatgtaaa caatacgcag agggaccata    2460
tctactcttg tcatattatt tgtgatggta aacatgcat ttgcaataaa ttaagctttc    2520
tgggaaggca agcagtattg gagccaaacg actgtctcgg aacatgtgtg tgttatctcg    2580
gttcatatca agtccaaagc taatggagcc ttccccgcca tccagggagg aacaccagga    2640
ccccggagtt tcttcttagt gctatatttt aaagttgcat tgacgttttc ctccccttcc    2700
ttttgtgcaa gttggaagta gcagtgttct aaaagatggt ttgacgtttt tgctgttgtt    2760
ttatgttttt aaaaatgtat ctgctttgtg tttggaaata aaaatctcta ttttggtcta    2820
tgaaaaaaaa aaaaaaaaa                                                 2840
```

<210> SEQ ID NO 23
<211> LENGTH: 2309
<212> TYPE: DNA
<213> ORGANISM: Homo sapiens
<220> FEATURE:
<223> OTHER INFORMATION: PIAS1 glucocorticoid receptor-responsive gene

<400> SEQUENCE: 23

```
gcgggggcgg gccggggcgg ggccaggccg gctagagggg cgggtctagc ggcggccccc     60
ggcgaagttc actgcgcttg cgctgacaga cgcaagatgg cggacagtgc ggaactaaag    120
caaatggtta tgagccttag agtttctgaa ctccaagtac tgttgggcta cgccgggaga    180
aacaagcacg gacgcaaaca cgaacttctc acaaaagccc tgcatttgct aaaggctggc    240
tgtagtcctg ctgtgcaaat gaaaattaag gaactctata gcggcgggtt cccacagaaa    300
atcatgacgc ctgcagactt gtccatcccc aacgtacatt caagtcctat gccagcaact    360
```

```
ttgtctccat ctaccattcc acaactcact tacgatggtc accctgcatc atcgccatta    420
ctccctgttt ctcttctggg acctaaacat gaactggaac tcccacatct tacatcagct    480
cttcacccag tccatccgga tataaaactt caaaaattac cattttatga tttactggat    540
gaactgataa aacccaccag tctagcatca gacaacagtc agcgctttcg agaaacctgt    600
tttgcatttg ccttgacacc acaacaagtg cagcaaatca gtagttccat ggatatttct    660
gggaccaaat gtgacttcac agtacaggtc cagttaaggt tttgtttatc agaaaccagt    720
tgtccacaag aagatcactt cccacccaat ctttgtgtga aagtgaatac aaaaccttgc    780
agccttccag gttaccttcc acctacaaaa aatggcgtgg aaccaaagcg acccagccga    840
ccaattaata tcacctcact tgtccgactg tccacaacag taccaaacac gattgttgtt    900
tcttggactg cagaaattgg aagaaactat tccatggcag tatatcttgt aaaacagttg    960
tcctcaacag ttcttcttca gaggttacga gcaaagggaa taaggaatcc ggatcattct   1020
agagctttaa ttaaagagaa gttgactgcg gatccagaca gtgaaatagc tacaaccagc   1080
ctaagggttt ctctactatg tccacttggt aaaatgcggc tgacaattcc gtgtcgggcc   1140
cttacatgtt ctcatctaca atgttttgac gcaactcttt acattcagat gaatgagaaa   1200
aaaccaacct gggtttgtcc tgtctgtgat aagaaggctc catatgaaca ccttattatt   1260
gatggcttgt ttatggaaat cctaaagtac tgtacagact gtgatgaaat acaatttaag   1320
gaggatggca cttgggcacc gatgagatca aaaaaggaag tacaggaagt ttctgcctct   1380
tacaatggag tcgatggatg cttgagctcc acattggagc atcaggtagc gtctcaccac   1440
cagtcctcaa ataaaaacaa gaaagtagaa gtgattgacc taaccataga cagttcatct   1500
gatgaagagg aagaagagcc atctgccaag aggacctgtc cttccctatc tcccacatca   1560
ccactaaata ataaaggcat tttaagtctt ccacatcaag catctccagt atcccgcacc   1620
ccaagccttc ctgctgtaga cacaagctac attaatacct ccctcatcca agactatagg   1680 catccttttcc acatgacacc catgccttac gacttacaag gattagattt ctttcctttc   1740
ttatcaggag acaatcagca ttacaacacc tccttgcttg ccgctgcagc agcagcagtt   1800
tcagatgatc aagacctcct acactcgtct cggttttttcc cgtataccte ctcacagatg   1860 tttcttgatc agttaagtgc aggaggcagt acttctctgc caaccaccaa tggaagcagt   1920
agtggcagta acagcagcct ggtttcttcc aacagcctaa gggaaagcca tagccacacc   1980
gtcacaaaca ggagcagcac ggacacggca tccatctttg gcatcatacc agacattatt   2040
tcattggact gattcccagg ccctgctgct cccatcccca ccccagatcg aatgaacttg   2100
gcagaaagaa gagaactttg tgctctgttt taccttactc tgtttagaaa agtatacaag   2160
cgtgtttttt ttcctttttt tagggaaaaa attaaaagaa atgtacagag aacaaaacta   2220
tattttcagt tttactttttg tatataaatc taagactgcc tgtgtgataa aacacttgtt   2280
taaaaaaaaa aaaaaaaaaa aaaaaaaa                                      2309
```

<210> SEQ ID NO 24
<211> LENGTH: 1740
<212> TYPE: DNA
<213> ORGANISM: Homo sapiens
<220> FEATURE:
<223> OTHER INFORMATION: IDH2 glucocorticoid receptor-responsive gene

<400> SEQUENCE: 24

```
ccagcgttag cccgcggcca ggcagccggg aggagcggcg cgcgctcgga cctctcccgc     60
cctgctcgtt cgctctccag cttgggatgg ccggctacct gcgggtcgtg cgctcgctct    120
```

```
gcagagcctc aggctcgcgg ccggcctggg cgccggcggc cctgacagcc cccacctcgc    180
aagagcagcc gcggcgccac tatgccgaca aaggatcaa ggtggcgaag cccgtggtgg    240
agatggatgg tgatgagatg acccgtatta tctggcagtt catcaaggag aagctcatcc    300
tgccccacgt ggacatccag ctaaagtatt ttgacctcgg gctcccaaac cgtgaccaga    360
ctgatgacca ggtcaccatt gactctgcac tggccaccca gaagtacagt gtggctgtca    420
agtgtgccac catcaccccct gatgaggccc gtgtggaaga gttcaagctg aagaagatgt    480
ggaaaagtcc caatggaact atccggaaca tcctgggggg gactgtcttc cgggagccca    540
tcatctgcaa aaacatccca cgcctagtcc ctggctggac caagcccatc accattggca    600
ggcacgccca tggcgaccag tacaaggcca cagactttgt ggcagaccgg gccggcactt    660
tcaaaatggt cttcaccccca aaagatggca gtggtgtcaa ggagtgggaa gtgtacaact    720
tccccgcagg cggcgtgggc atgggcatgt acaacaccga cgagtccatc tcaggttttg    780
cgcacagctg cttccagtat gccatccaga gaaatggcc gctgtacatg agcaccaaga    840
acaccatact gaaagcctac gatgggcgtt tcaaggacat cttccaggag atctttgaca    900
agcactataa gaccgacttc gacaagaata agatctggta tgagcaccgg ctcattgatg    960
acatggtggc tcaggtcctc aagtcttcgg gtggctttgt gtgggcctgc aagaactatg   1020
acggagatgt gcagtcagac atcctggccc agggctttgg ctcccttggc ctgatgacgt   1080
ccgtcctggt ctgccctgat gggaagacga ttgaggctga ggccgctcat gggaccgtca   1140
cccgccacta tcgggagcac cagaagggcc ggcccaccag caccaacccc atcgccagca   1200
tctttgcctg gacacgtggc ctggagcacc ggggaagct ggatgggaac caagacctca   1260
tcaggtttgc ccagatgctg gagaaggtgt gcgtggagac ggtggagagt ggagccatga   1320
ccaaggacct ggcgggctgc attcacggcc tcagcaatgt gaagctgaac gagcacttcc   1380
tgaacaccac ggacttcctc gacaccatca gagcaacct ggacagagcc ctgggcaggc   1440
agtaggggga ggcgccaccc atggctgcag tggaggggcc agggctgagc cggcgggtcc   1500
tcctgagcgc ggcagagggt gagcctcaca gcccctctct ggaggccttt ctaggggatg   1560 ttttttata agccagatgt ttttaaaagc atatgtgtgt ttcccctcat ggtgacgtga   1620
ggcaggagca gtgcgtttta cctcagccag tcagtatgtt ttgcatactg taatttatat   1680
tgcccttgga acacatggtg ccatatttag ctactaaaaa gctcttcaca aaaaaaaaa   1740
```

<210> SEQ ID NO 25
<211> LENGTH: 1552
<212> TYPE: DNA
<213> ORGANISM: Homo sapiens
<220> FEATURE:
<223> OTHER INFORMATION: SERPINF1 glucocorticoid receptor-responsive gene

<400> SEQUENCE: 25

```
ggtcgcttta agaaaggagt agctgtaatc tgaagcctgc tggacgctgg attagaaggc     60
agcaaaaaaa gctctgtgct ggctggagcc ccctcagtgt gcaggcttag agggactagg    120
ctgggtgtgg agctgcagcg tatccacagg ccccaggatg caggccctgg tgctactcct    180
ctgcattgga gccctcctcg gcacagcag ctgccagaac cctgccagcc ccccggagga    240
gggctcccca gaccccgaca gcacaggggc gctggtggag gaggaggatc ctttcttcaa    300
agtccccgtg aacaagctgg cagcggctgt ctccaacttc ggctatgacc tgtaccgggt    360
gcgatccagc acgagcccca cgaccaacgt gctcctgtct cctctcagtg tggccacggc    420
```

```
cctctcggcc ctctcgctgg gagcggagca gcgaacagaa tccatcattc accgggctct    480
ctactatgac ttgatcagca gcccagacat ccatggtacc tataaggagc tccttgacac    540
ggtcactgcc ccccagaaga acctcaagag tgcctcccgg atcgtctttg agaagaagct    600
gcgcataaaa tccagctttg tggcacctct ggaaaagtca tatgggacca ggcccagagt    660
cctgacgggc aaccctcgct tggacctgca agagatcaac aactgggtgc aggcgcagat    720
gaaagggaag ctcgccaggt ccacaaagga aattcccgat gagatcagca ttctccttct    780
cggtgtggcg cacttcaagg ggcagtgggt aacaaagttt gactccagaa agacttccct    840
cgaggatttc tacttggatg aagagaggac cgtgagggtc cccatgatgt cggaccctaa    900
ggctgtttta cgctatggct tggattcaga tctcagctgc aagattgccc agctgccctt    960
gaccggaagc atgagtatca tcttcttcct gcccctgaaa gtgacccaga atttgacctt   1020
gatagaggag agcctcacct ccgagttcat tcatgacata gaccgagaac tgaagaccgt   1080
gcaggcggtc ctcactgtcc ccaagctgaa gctgagttat gaaggcgaag tcaccaagtc   1140
cctgcaggag atgaagctgc aatccttgtt tgattcacca gactttagca agatcacagg   1200
caaacccatc aagctgactc aggtggaaca ccgggctggc tttgagtgga cagaggatgg   1260
ggcgggaacc accccagcc cagggctgca gcctgcccac ctcaccttcc cgctggacta   1320
tcaccttaac cagccttca tcttcgtact gagggacaca gacacagggg cccttctctt   1380
cattggcaag attctggacc ccaggggccc ctaatatccc agtttaatat tccaataccc   1440
tagaagaaaa cccagggac agcagattcc acaggcacg aaggctgccc ctgtaaggtt   1500
tcaatgcata caataaaaga ctttatccc taaaaaaaaa aaaaaaaaaa aa             1552
```

<210> SEQ ID NO 26
<211> LENGTH: 4816
<212> TYPE: DNA
<213> ORGANISM: Homo sapiens
<220> FEATURE:
<223> OTHER INFORMATION: ERBB2 glucocorticoid receptor-responsive gene

<400> SEQUENCE: 26

```
gttcccggat ttttgtgggc gcctgccccg ccctcgtcc cctgctgtg tccatatatc     60 gaggcgatag ggttaaggga aggcggacgc ctgatgggtt aatgagcaaa ctgaagtgtt    120
ttccatgatc ttttttgagt cgcaattgaa gtaccactc ccgagggtga ttgcttcccc    180
atgcggggta gaacctttgc tgtcctgttc accactctac ctccagcaca gaatttggct    240
tatgcctact caatgtgaag atgatgagga tgaaaacctt tgtgatgatc cacttccact    300
taatgaatgg tggcaaagca aagctatatt caagaccaca tgcaaagcta ctccctgagc    360
aaagagtcac agataaaacg ggggcaccag tagaatggcc aggacaaacg cagtgcagca    420
cagagactca gaccctggca gccatgcctg cgcaggcagt gatgagagtg acatgtactg    480
ttgtggacat gcacaaaagt gagtgtgcac cggcacagac atgaagctgc ggctccctgc    540
cagtcccgag acccacctgg acatgctccg ccacctctac cagggctgcc aggtggtgca    600
gggaaacctg gaactcacct acctgcccac caatgccagc ctgtcctcc tgcaggatat    660 ccaggaggtg cagggctacg tgctcatcgc tcacaaccaa gtgaggcagg tcccactgca    720
gaggctgcgg attgtgcgag gcacccagct ctttgaggac aactatgccc tggccgtgct    780
agacaatgga gacccgctga caataccac ccctgtcaca ggggcctccc caggaggcct    840
gcgggagctg cagcttcgaa gcctcacaga gatcttgaaa ggaggggtct tgatccagcg    900
```

```
gaaccccag ctctgctacc aggacacgat tttgtggaag acatcttcc acaagaacaa      960
ccagctggct ctcacactga tagacaccaa ccgctctcgg gcctgccacc cctgttctcc   1020
gatgtgtaag ggctcccgct gctggggaga gagttctgag gattgtcaga gcctgacgcg   1080
cactgtctgt gccggtggct gtgcccgctg caaggggcca ctgcccactg actgctgcca   1140
tgagcagtgt gctgccggct gcacgggccc caagcactct gactgcctgg cctgcctcca   1200
cttcaaccac agtggcatct gtgagctgca ctgcccagcc ctggtcacct acaacacaga   1260
cacgtttgag tccatgccca atcccgaggg ccggtataca ttcggcgcca gctgtgtgac   1320
tgcctgtccc tacaactacc tttctacgga cgtgggatcc tgcaccctcg tctgccccct   1380
gcacaaccaa gaggtgacag cagaggatgg aacacagcgg tgtgagaagt gcagcaagcc   1440
ctgtgcccga gtgtgctatg gtctgggcat ggagcacttg cgagaggtga gggcagttac   1500
cagtgccaat atccaggagt ttgctggctg caagaagatc tttgggagcc tggcatttct   1560
gccggagagc tttgatgggg acccagcctc caacactgcc ccgctccagc cagagcagct   1620
ccaagtgttt gagactctgg aagagatcac aggttaccta tacatctcag catggccgga   1680
cagcctgcct gacctcagcg tcttccagaa cctgcaagta atccggggac gaattctgca   1740
caatggcgcc tactcgctga ccctgcaagg gctgggcatc agctggctgg ggctgcgctc   1800
actgagggaa ctgggcagtg gactggccct catccaccat aacacccacc tctgcttcgt   1860
gcacacggtg ccctgggacc agctctttcg gaacccgcac caagctctgc tccacactgc   1920
caaccggcca gaggacgagt gtgtgggcga gggcctggcc tgccaccagc tgtgcgcccg   1980
agggcactgc tggggtccag ggcccaccca gtgtgtcaac tgcagccagt ccttcgggg    2040
ccaggagtgc gtggaggaat gccgagtact gcagggctc cccagggagt atgtgaatgc    2100
caggcactgt ttgccgtgcc accctgagtg tcagccccag aatggctcag tgacctgttt   2160
tggaccggag gctgaccagt gtgtggcctg tgcccactat aaggaccctc ccttctgcgt   2220
ggcccgctgc cccagcggtg tgaaacctga cctctcctac atgcccatct ggaagtttcc   2280
agatgaggag ggcgcatgcc agccttgccc catcaactgc acccactcct gtgtggacct   2340
ggatgacaag ggctgccccg ccgagcagag agccagccct ctgacgtcca tcatctctgc   2400
ggtggttggc attctgctgg tcgtggtctt gggggtggtc tttgggatcc tcatcaagcg   2460
acggcagcag aagatccgga agtacacgat gcggagactg ctgcaggaaa cggagctggt   2520
ggagccgctg acacctagcg gagcgatgcc caaccaggcg cagatgcgga tcctgaaaga   2580
gacggagctg aggaaggtga ggtgcttgga atctggcgct tttggcacag tctacaaggg   2640
catctggatc cctgatgggg agaatgtgaa aattccagtg gccatcaaag tgttgaggga   2700
aaacacatcc cccaaagcca caaagaaat cttagacgaa gcatacgtga tggctggtgt   2760
gggctcccca tatgtctccc gccttctggg catctgcctg acatccacgg tgcagctggt   2820
gacacagctt atgccctatg gctgcctctt agaccatgtc cgggaaaacc gcggacgcct   2880
gggctcccag gacctgctga actggtgtat gcagattgcc aaggggatga gctacctgga   2940
ggatgtgcgg ctcgtacaca gggacttggc cgctcggaac gtgctggtca gagtcccaa    3000
ccatgtcaaa attacagact cgggctggc tcggctgctg gacattgacg agacagta     3060
ccatgcagat gggggcaagg tgcccatcaa gtggatggcg ctggagtcca ttctccgccg   3120
gcggttcacc caccagagtg atgtgtggag ttatggtgtg actgtgtggg agctgatgac   3180
ttttgggggcc aaaccttacg atgggatccc agcccgggag atcctgacc tgctggaaaa   3240
gggggagcgg ctgccccagc cccccatctg caccattgat gtctacatga tcatggtcaa   3300
```

```
atgttggatg attgactctg aatgtcggcc aagattccgg gagttggtgt ctgaattctc    3360
ccgcatggcc agggaccccc agcgctttgt ggtcatccag aatgaggact tgggcccagc    3420
cagtcccttg gacagcacct tctaccgctc actgctggag gacgatgaca tgggggacct    3480
ggtggatgct gaggagtatc tggtacccca gcagggcttc ttctgtccag accctgcccc    3540
gggcgctggg ggcatggtcc accacaggca ccgcagctca tctaccagga gtggcggtgg    3600
ggacctgaca ctagggctgg agccctctga agaggaggcc cccaggtctc cactggcacc    3660
ctccgaaggg gctggctccg atgtatttga tggtgacctg gaatgggggg cagccaaggg    3720
gctgcaaagc ctccccacac atgacccag ccctctacag cggtacagtg aggaccccac    3780
agtacccctg ccctctgaga ctgatggcta cgttgccccc ctgacctgca gccccagcc     3840
tgaatatgtg aaccagccag atgttcggcc ccagccccct tcgccccgag agggccctct    3900
gcctgctgcc cgacctgctg gtgccactct ggaaaggccc aagactctct ccccagggaa    3960
gaatgggtc gtcaaagacg tttttgcctt tgggggtgcc gtggagaacc ccagtactt      4020
gacacccag ggaggagctg ccctcagcc ccaccctcct cctgccttca gcccagcctt      4080
cgacaacctc tattactggg accaggaccc accagagcgg ggggctccac ccagcacctt    4140
caaagggaca cctacggcag agaacccaga gtacctgggt ctggacgtgc cagtgtgaac    4200
cagaaggcca gtccgcaga agccctgatg tgtcctcagg gagcagggaa ggcctgactt     4260
ctgctggcat caagaggtgg gagggccctc cgaccacttc caggggaacc tgccatgcca    4320
ggaacctgtc ctaaggaacc ttccttcctg cttgagttcc cagatggctg aaggggtcc     4380
agcctcgttg gaagaggaac agcactgggg agtctttgtg gattctgagg ccctgcccaa    4440
tgagactcta gggtccagtg gatgccacag cccagcttgg ccctttcctt ccagatcctg    4500
ggtactgaaa gccttaggga agctggcctg agaggggaag cggccctaag ggagtgtcta    4560
agaacaaaag cgacccattc agagactgtc cctgaaacct agtactgccc cccatgagga    4620
aggaacagca atggtgtcag tatccaggct ttgtacagag tgcttttctg tttagttttt    4680
acttttttg ttttgttttt ttaaagatga aataaagacc caggggagga atgggtgttg     4740
tatggggagg caagtgtggg gggtccttct ccacacccac tttgtccatt tgcaaatata    4800
ttttggaaaa cagcta                                                   4816
```

<210> SEQ ID NO 27
<211> LENGTH: 6831
<212> TYPE: DNA
<213> ORGANISM: Homo sapiens
<220> FEATURE:
<223> OTHER INFORMATION: PECAM1 glucocorticoid receptor-responsive gene

<400> SEQUENCE: 27

```
ccaggcccca ttgttcccgg tttccagcca tggctgccat tacctgacca gcgccacagc      60
cggtctctct gcaggcgccg ggagaagtga ccagagcaat ttctgctttt cacagggcgg     120
gtttctcaac ggtgacttgt gggcagtgcc ttctgctgag cgagtcatgg cccgaaggca    180
gaactaactg tgcctgcagt cttcactctc aggatgcagc cgaggtgggc caagggggcc    240
acgatgtggc ttggagtcct gctgaccctt ctgctctgtt caagccttga gggtcaagaa    300
aactctttca caatcaacag tgttgacatg aagagcctgc cggactggac ggtgcaaaat    360
gggaagaacc tgaccctgca gtgcttcgcg gatgtcagca ccacctctca cgtcaagcct    420
cagcaccaga tgctgttcta taaggatgac gtgctgtttt acaacatctc ctccatgaag    480
```

```
agcacagaga gttattttat tcctgaagtc cggatctatg actcagggac atataaatgt    540
actgtgattg tgaacaacaa agagaaaacc actgcagagt accaggtgtt ggtggaagga    600
gtgcccagtc ccagggtgac actggacaag aaagaggcca tccaaggtgg gatcgtgagg    660
gtcaactgtt ctgtcccaga ggaaaaggcc ccaatacact tcacaattga aaaacttgaa    720
ctaaatgaaa aaatggtcaa gctgaaaaga gagaagaatt ctcgagacca gaattttgtg    780
atactggaat tccccgttga ggaacaggac cgcgttttat ccttccgatg tcaagctagg    840
atcatttctg ggatccatat gcagacctca gaatctacca agagtgaact ggtcaccgtg    900
acggaatcct tctctacacc caagttccac atcagcccca ccggaatgat catggaagga    960
gctcagctcc acattaagtg caccattcaa gtgactcacc tggcccagga gtttccagaa   1020
atcataattc agaaggacaa ggcgattgtg cccacaaca gacatggcaa caaggctgtg   1080
tactcagtca tggccatggt ggagcacagt ggcaactaca cgtgcaaagt ggagtccagc   1140
cgcatatcca aggtcagcag catcgtggtc aacataacag aactattttc caagcccgaa   1200
ctggaatctt ccttcacaca tctggaccaa ggtgaaagac tgaacctgtc ctgctccatc   1260
ccaggagcac ctccagccaa cttcaccatc cagaaggaag atacgattgt gtcacagact   1320
caagatttca ccaagatagc ctcaaagtcg acagtggga cgtatatctg cactgcaggt   1380
attgacaaag tggtcaagaa aagcaacaca gtccagatag tcgtatgtga aatgctctcc   1440
cagcccagga tttcttatga tgcccagttt gaggtcataa aaggacagac catcgaagtc   1500
cgttgcgaat cgatcagtgg aactttgcct atttcttacc aactttaaa aacaagtaaa   1560 gttttggaga atagtaccaa gaactcaaat gatcctgcgg tattcaaaga caaccccact   1620
gaagacgtcg ataccagtg tgttgcagat aattgccatt cccatgccaa atgttaagt   1680 gaggttctga gggtgaaggt gatagccccg gtggatgagg tccagatttc tatcctgtca   1740
agtaaggtgg tggagtctgg agaggacatt gtgctgcaat gtgctgtgaa tgaaggatct   1800
ggtcccatca cctataagtt ttacagagaa aaagagggca aacccttcta tcaaatgacc   1860
tcaaatgcca cccaggcatt tggaccaag cagaaggcta gcaaggaaca ggagggagag   1920
tattactgca cagccttcaa cagagccaac cacgcctcca gtgtcccag aagcaaaata   1980 ctgacagtca gagtcattct tgccccatgg aagaaggac ttattgcagt ggttatcatc   2040
ggagtgatca ttgctctctt gatcattgcg gccaaatgtt atttctgag gaaagccaag   2100 gccaagcaga tgccagtgga atgtccagg ccagcagtac cacttctgaa ctccaacaac   2160
gagaaaatgt cagatcccaa tatggaagct aacagtcatt acggtcacaa tgacgatgtc   2220
agaaaccatg caatgaaacc aataaatgat aataaagagc ctctgaactc agacgtgcag   2280 tacacgaag ttcaagtgtc ctcagctgag tctcacaaag atctaggaaa gaaggacaca   2340
gagacagtgt acagtgaagt ccggaaagct gtccctgatg ccgtggaaag cagatactct   2400 agaacgaag gctcccttga tggaacttag acagcaaggc cagatgcaca tccctggaag   2460
gacatccatg ttccgagaag aacagataat ccctgtattt caagacctct gtgcacttat   2520
ttatgaacct gccctgctcc cacagaacac agcaattcct caggctaagc tgccggttct   2580
taaatccatc ctgctaagtt aatgttgggt agaaagagat acagagggc tgttgaattt   2640 cccacatacc ctccttccac caagttggaa catccttgga aattggaaga gcacaagagg   2700
agatccaggg caaggccatt gggatattct gaaacttgaa tattttgttt tgtgcagaga   2760
taaagacctt ttccatgcac cctcatacac agaaaccaat tttctttttt atactcaatc   2820
atttctagcg catggcctgg ttagaggctg gtttttctc ttttccttg gtccttcaaa   2880
```

```
ggcttgtagt tttggctagt ccttgttctt tggaaataca cagtgctgac cagacagcct     2940 cccctgtcc cctctatgac ctcgccctcc acaaatggga aaaccagact acttgggagc      3000
accgcctgtg aaataccaac ctgaagacac cgttcattca ggcaacgcac aaaacagaaa     3060
atgaaggtgg aacaagcaca gatgttcttc aactgttttt gtctacactc tttctctttt    3120
cctctaccat gctgaaggct gaaagacagg aagatggtgc catcagcaaa tattattctt    3180
aattgaaaac ttgaaatgtg tatgtttctt actaattttt aaaaatgtat tccttgccag    3240
ggcaggcaag gtggctcacg cctgtaatcc cagcacttca ggaggctgag gtgggcggat    3300
cacctgaggt caggagtttg agaccagcct gatgaaaccc tgtctctact aaaaatacaa    3360
gaattagccg ggcgtggtgg cgcatgcctg tagtatcagc tactcaagag gctgaggtga    3420
gattatcgct tgaacccagg aaacggaggt tgtagtgagc cgagatcgcg ccactgcact    3480
ccagcctgag tgacagagtg agaatccatc tcaaaaaaaa caaaaaacaa aattgcttgc    3540
taaagaagtg gtctcctgag gtcttaagac attcctgaca gtgtcttgag tgggtgggag    3600
agaggctgct gtcattgcgc tgtggaattt cacagatgag aaccacgcct agccaaaatc    3660
acttttcctg tttgcctcag tgacacagct gcagggaccc tcgtggatgt tgtattaaat    3720
aaatttgacc tttgctcttt gcagatctgt gaaatgttgt cttctgaggg gccacatgca    3780
tctatagtgc tgaggactcc ttgggcctct gaagtcacag agagaaccga gcaggtctat    3840 gttttttgttt tgttgttttg agacggagat tcgctcttgt tgcccgggct ggactgcagc    3900
ggcgcaacct ctgctcactg caacctccgc ctcctgggtt caagcagttc tcctgtctca    3960
gcctcccgag tagctgggat tacaggcaca tgtcaccacg cctggctaat ttttgtattt    4020
ttagtagaga tggggtttca ccacgttggc caggctgatc tcgaatgcct gacctttggt    4080
gatctgcccg ccttgtcctc atgtgtgctc cacaggcctt tgggttggga ttgcaggcgt    4140
gagccaccat gcccagccta gactcttttg acaatatgat gaaagctgtt ggttcctttc    4200
cccaacacac acacaccgag ttgtatcacg aaaatgtcat acaatttcca ggttttctga    4260
gtggtgggct cagattgagg tcaaaggatc agacgacctc taacgacctt catgtctctg    4320
ttgatgatct ggggacagcc agatcccctg tgtccaggga gttccttagt cccttgccac    4380
caccagagaa gggcaattgc cacgggagct gcaaagaccc tattcctact cctggtgcct    4440
tacttatgca gcacgactga attttttgtt ttgttttgtt ttgttgagac agggcttgc    4500 tctgttgccc aggctggagt gcagtggcac aacaatggct caccgcagcc tcgaacccct    4560
gggctcaagc gatcctccca tctcagcttc ctgggtagct gggaccagag gcgtgagccg    4620
ccatagctgg ctaatttttta atttttttttt tgcagagatg aggtttcacc atggtgccca    4680
ggctggtctc gaacttctgg gctcaagtga tcctccctcc ttggcctcgc aaagtgctgg    4740
gattgcaggc atgagccacc gcccccggcc tgtggagcac acatgagttt aaaattactt    4800
tcccttctgc ctatatttcc gaggaggaaa cttcatgcgc agggatcttt cttagtggat    4860
ttaatggcta aaaggtctgt ctgaatccag gacgctggct ttagccttcc tcggcagctg    4920 ccgtaaccc ggtgtctaaa cctgaagcat cccaggagca cccactccag gagttttctc     4980
ggccgcggaa ctcattagtt agagcgccct cttgtgttct catgtggtaa tcggtcactg    5040
aaggacttaa aatggtcctt agccaacaca cagtaaaact tttccctctt ctgaccccaa    5100
gaggtcagcc acccatttca tgagcatata ctggtcgccc catcagcgtt ctctgattgg    5160
ctaactgaac ccactccccg acctagactc aagacaggcg aagtgacgct taggtcaaca    5220
```

```
ttcactcact aaagcaacga ctgtcgggcg attttgtctc ccgctggttt tggaatggtg    5280
tctggagaca tttttggttg tcacagctgg gtgggtgtgc tcccggcatc tggtgggtag    5340
aaaccaagca tgctcctaaa catcctacag gcacagaacc gtctcccacg accaagcatg    5400
atcaagtccc aaatgccaat aatggccagg ttgagaaact ctgcacagaa gcatccagtt    5460
atttgtctgt ttgctcaaca agcttgtgct catcatgctc tgtgttcctg acgctgtgct    5520
gggtgttggc ggtgggaaga ttacaagagt cacatggcag ctgtcctcct ggaaggtaca    5580
acccagtaga gatgcagact aacagagagc caattacaaa gcagtgtgac aagcgtcatg    5640
gtggaaaatt aaaagctcaa acaagggcac atgggagggg cttccaacac agactttggg    5700
ggatccagga aggtctaaga ggaaagtggg tctcaccaaa gccttgacca taggcagagg    5760
gtaccagtgg aaaaggtggg gtgaagaaca ttgaggacaa aaggaagaag tgcaggaagg    5820
ccctgaggca agggagtggg gggtgccctg gagggatggc agcagggcag tctgtcagac    5880
ccaagtggcc tccagcccta gaagccaatt agtcctcctc aaaaagctgt cactgtcccc    5940
taagaattgc tgccaggctc ccactggcct gactcagtct ttgagagtct taaggaggag    6000
gtctctgaaa ggtacacacc aagaactctc cccagcacag ctgtttttaa gactctccac    6060
cagcgtcatt ggcgtgttgg gaagaaaccc tctgccacag aggccagctt cagcctttgc    6120
ctaacaccgc aagggcaaat ggaaaggtaa acgggaagga gatgtctccc cagcaggcta    6180
tttgaggaca gtcttccctg cagaagatct caacctgggg tccacagagt ggaaatgtta    6240
gagtagggag ctaggcaaac atgagcagga caggtgaggg cccccacagg aatgtcaggc    6300
taccatcagg tgatggtcag gtggttgtta aactgtctct gtaaataat aattggttgc    6360 agccagctcc aagcaaggac agtctctcaa tagatacaaa acaccctgat ctggtgatca    6420
gccgcttccc gataagatct caggagctgg gcaagcagcc tggagcatgc gcaccaagag    6480
gcaaaatggc ggaatttaac cagtatatga cctaccttcc tctgggaacg cacgactggt    6540
aaggggaaaa atgcctcaag tgagcatgcg cgcaacttca gtaatcacac tgtgcatgcg    6600
accccttcca agtgctggca ggtcaccaca tacgcggaca gcctgctgca agggaagaat    6660
caggggagat gagacgtaaa tcccagaact atgccaaata cataaaaccc caagttaagg    6720
gtcaggcagg gcacttagat ctctcaagtt gcctgcctga cccaagtgta gtgtacttcc    6780
ttttgttcct gctctaaaac tttttaataa actctcactc ctgctctaaa a             6831
```

<210> SEQ ID NO 28
<211> LENGTH: 2956
<212> TYPE: DNA
<213> ORGANISM: Homo sapiens
<220> FEATURE:
<223> OTHER INFORMATION: LBH glucocorticoid receptor-responsive gene

<400> SEQUENCE: 28

```
ggggctgagt gctcagtgga gagcggggag ttgtgtccac cttgccgacg tcgctagccg      60
tggggctgtc ctgggaaggc ggacggcgag cgcccggtgt ccgcactcgg ccgcctgccg     120
tgcccgtctg cgcccgtgtc atcctcactc gggacgcagg gaccgttttt aaatcacagg     180
ggcgtgtgtc agcctgccct aggacttcat gtctatatat ttccccattc actgccccga     240
ctatctgaga tcggccaaga tgactgaggt gatgatgaac acccagccca tggaggagat     300
cggcctcagc ccccgcaagg atggcctttc ctaccagatc ttcccagacc cgtcagattt     360
tgaccgctgc tgcaaactga aggaccgtct gccctccata gtggtggaac ccacagaagg     420
ggaggtggag agcggggagc tccggtggcc ccctgaggag ttcctggtcc aggaggatga     480
```

```
gcaagataac tgcgaagaga cagcgaaaga aaataaagag cagtagagtc cctgtggact    540
cccatgggtc ataccagcca gcatctgttc ctgaactgtg tttttcccat catgacggaa    600
gaagagagtg agccgcaatt gttctgaaaa tgtcaaacga ggcttctgtt ttgcacctgc    660
agatcaccga gttggttttc ttttcttttc ttgccttttt tttttttttga aatttgccga   720 gcagtggagc cctctgacaa tttgcaaggc cctctgagaa aggaagctgc ttagagccag    780 gggggttagtg ggtgagggga gcgagtgctg tttttgagat cattatctga actcaggcag   840
cctagtagag gcagtggtgg gattccaatg ggtcttggtg ggtgggaggt ggggcatgtg    900
caaagcaagc aaggaacatt tggggtaaga aaacaaacat gaggcaaaag aaaaaataca    960 tgttttttaag aaaacattga gcagagaact gcagccagga tgcgctcagc agacattcac  1020
tctggctgct gggacatcag aaaacaaagt cttcatctct ctctccagtt tcacccaccc   1080
caccctttgc tttcatttca ggtgtgttgg tctatatgac agggaggaga gtaaaggaga   1140
gcaggagcaa ttggctgcct gcaaagccag ctggaggtga agtgcaggaa aggaaaggtc   1200
accccattct actccatggc ctctctgctc ccagctgtgg taggctcaca tagccagtgt   1260
gatcggtttt taagaggcag tgcttttcag cttttctccc tgatatatcc attttgcttc   1320
ccagcacttt ttaggagtag tgagagcact tcctgcccct gttggaagcc ccagggtgga   1380
cactcagcac gaaggtctct cccttaactg ctgcccttcc aagacttgct cccgagatgg   1440
agtgggcgtg gtcttccagg ctggcccttc cttctcctca ccgccacctt ccctgcccca   1500
gccccagcag ccatgggtac atgggtcccc agctcaccta tggattcccg ccagtctgcc   1560
cagctgcagt actcacgccc catgggggat cttggtctgt tttcttgtg ggagcctagt    1620 ggagagcaga cgtggctttt tatgtgtctt gttggggagg tgacttgcat ggtggggaca   1680
aggctgtcgt ggcaaccttg ggatcgagtt tgagactaaa ggatgtcatg agatccctgg   1740
cttctcccca tgttgttccc ggacaagggc agaagggagg catggcaagg gacctctgct   1800
gtccttactc aacagtggtc ctcatccctc cccacctccc actgcttcct gcaagggcac   1860
cagttgtatg agaaagttgg cctttggact taggatttct tattgtagct aagagccatc   1920
tgaagcagca ggttgcagga caaatgcttc agtccgccga gagcagtacc gtgtggccaa   1980
gaggtggact cagagccttc cttgagctaa actcggccaa ccaaggcacg cagcatgtcc   2040
cctcaggtct ccagtcagtc caggttgacc ctcagtctg gacgtgtgta tatagctgta    2100
tttaatacct caaggtcatt gtggctctgg ggatgccggg gcaggaggac gagggtgcgc   2160
tgtggacaca gcagtccgcg gaattccgtt ctgggaagcc aatggtcgcc ggcaccccctt  2220 gcttcctccc tctgttgtct gcctgtgtga cacacatcaa tggcaataac ttcttccaac   2280
tcctcgcaga agtgggagag gccggcagcc tgcaccgaga ggggctttcc tctctcttgc   2340
tccccgcttc gttctgtttt ggctgcagag agtggttcat ccatactctc attccctcgc   2400 ctcccccttgt ggacggggggt cttgcctttt caattcctgt gttttggtgt cttcccttat  2460
ctgctaccct gaatcacctg tcctggtctt gctgtgtgat gggaacatgc ttgtaaactg   2520
cgtaacaaat ctactttgtg tatgtgtctg tttatgggggg tggtttatta ttttgctgg   2580 tccctagacc actttgtatg accgtttgca gtctgagcag gccaggggct gacagctaat   2640
gtcaggaccc tcagcggtgg agcctgctgg ggggacccag ctgctcttgg acaagtggct   2700 gagctccctat ctggcctcct cttttttttt tttcaagta atttgtgtgt atttctaact   2760
gattgtattg aaaaaattcc tagtatttca gtaaaaatgc ctgttgtgag atgaacctcc   2820
```

```
tgtaacttct atctgttctt ttttgaggct cagggagaaa ctagcatttt ttttttttcca    2880 aactacttt tgtcactgtg acagttgtaa ataaagtttg aaaatgcttt ccactctgaa     2940
aaaaaaaaaa aaaaaa                                                    2956

<210> SEQ ID NO 29
<211> LENGTH: 2262
<212> TYPE: DNA
<213> ORGANISM: Homo sapiens
<220> FEATURE:
<223> OTHER INFORMATION: ST3GAL5 glucocorticoid receptor-responsive gene

<400> SEQUENCE: 29
ctggggagta atagcatggg caaccattat cctgtctcgc cgccacccag gacatggctt      60
ctgttccaat gccaagtgag tacacctatg tgaaactgag aagtgattgc tcgaggcctt     120
ccctgcaatg gtacacccga gctcaaagca agatgagaag gcccagcttg ttattaaaag     180
acatcctcaa atgtacattg cttgtgtttg gagtgtggat cctttatatc ctcaagttaa     240
attatactac tgaagaatgt gacatgaaaa aaatgcatta tgtggaccct gaccatgtaa     300
agagagctca gaaatatgct cagcaagtct gcagaagga atgtcgtccc aagtttgcca      360
agacatcaat ggcgctgtta tttgagcaca ggtatagcgt ggacttactc ccttttgtgc     420
agaaggcccc caaagacagt gaagctgagt ccaagtacga tcctcctttt gggttccgga     480
agttctccag taaagtccag accctcttgg aactcttgcc agagcacgac ctccctgaac     540
acttgaaagc caagacctgt cggcgctgtg tggttattgg aagcggagga atactgcacg     600
gattagaact gggccacacc ctgaaccagt tcgatgttgt gataaggtta aacagtgcac     660
cagttgaggg atattcagaa catgttggaa ataaaactac tataaggatg acttatccag     720
agggcgcacc actgtctgac cttgaatatt attccaatga cttatttgtt gctgttttat     780
ttaagagtgt tgatttcaac tggcttcaag caatggtaaa aaaggaaacc ctgccattct     840
gggtacgact cttcttttgg aagcaggtgg cagaaaaaat cccactgcag ccaaaacatt     900
tcaggatttt gaatccagtt atcatcaaag agactgcctt tgacatcctt cagtactcag     960
agcctcagtc aaggttctgg ggccgagata agaacgtccc cacaatcggt gtcattgccg    1020
ttgtcttagc cacacatctg tgcgatgaag tcagtttggc gggttttgga tatgacctca    1080
atcaacccag aacacctttg cactacttcg acagtcaatg catggctgct atgaactttc    1140
agaccatgca taatgtgaca acggaaacca agttcctctt aaagctggtc aaagagggag    1200
tggtgaaaga tctcagtgga ggcattgatc gtgaattttg aacacagaaa acctcagttg    1260
aaaatgcaac tctaactctg agagctgttt ttgacagcct tcttgatgta tttctccatc    1320
ctgcagatac tttgaagtgc agctcatgtt tttaactttt aatttaaaaa cacaaaaaaa    1380 atttagctc ttcccacttt ttttttccta tttatttgag gtcagtgttt gtttttgcac      1440
accattttgt aaatgaaact taagaattga attggaaaga cttctcaaag agaattgtat    1500
gtaacgatgt tgtattgatt tttaagaaag taatttaatt tgtaaaactt ctgctcgttt    1560
acactgcaca ttgaatacag gtaactaatt ggaaggagag gggaggtcac tcttttgatg    1620
gtggccctga acctcattct ggttccctgc tgcgctgctt ggtgtgaccc acggaggatc    1680
cactcccagg atgacgtgct ccgtagctct gctgctgata ctgggtctgc gatgcagcgg    1740
cgtgaggcct gggctggttg gagaaggtca caacccttct ctgttggtct gccttctgct    1800
gaaagactcg agaaccaacc agggaagctg tcctggaggt ccctggtcgg agagggacat    1860
agaatctgtg acctctgaca actgtgaagc caccctgggc tacagaaacc acagtcttcc    1920
```

```
cagcaattat tacaattctt gaattccttg gggattttt actgcccttt caaagcactt    1980
aagtgttaga tctaacgtgt tccagtgtct gtctgaggtg acttaaaaaa tcagaacaaa    2040
acttctatta tccagagtca tgggagagta caccctttcc aggaataatg ttttgggaaa    2100
cactgaaatg aaatcttccc agtattataa attgtgtatt taaaaaaaag aaacttttct    2160
gaatgcctac ctggcggtgt ataccaggca gtgtgccagt ttaaaagat gaaaagaat     2220 aaaaactttt gaggaaaaaa aaaaaaaaaa aaaaaaaaaa aa                      2262
```

<210> SEQ ID NO 30
<211> LENGTH: 4909
<212> TYPE: DNA
<213> ORGANISM: Homo sapiens
<220> FEATURE:
<223> OTHER INFORMATION: IL1R1 glucocorticoid receptor-responsive gene

<400> SEQUENCE: 30

```
tagacgcacc ctctgaagat ggtgactccc tcctgagaag ctggacccct tggtaaaaga     60
caaggccttc tccaagaaga atatgaaagt gttactcaga cttatttgtt tcatagctct    120
actgatttct tctctggagg ctgataaatg caaggaacgt gaagaaaaaa taattttagt    180
gtcatctgca aatgaaattg atgttcgtcc ctgtcctctt aacccaaatg aacacaaagg    240
cactataact tggtataaag atgacagcaa gacacctgta tctacagaac aagcctccag    300
gattcatcaa cacaaagaga aactttggtt tgttcctgct aaggtggagg attcaggaca    360
ttactattgc gtggtaagaa attcatctta ctgcctcaga attaaaataa gtgcaaaatt    420
tgtggagaat gagcctaact tatgttataa tgcacaagcc atatttaagc agaaactacc    480
cgttgcagga gacggaggac ttgtgtgccc ttatatggag ttttttaaaa atgaaaataa    540
tgagttacct aaaattacagt ggtataagga ttgcaaacct ctacttcttg acaatataca    600
ctttagtgga gtcaaagata ggctcatcgt gatgaatgtg gctgaaaagc atagagggaa    660
ctatacttgt catgcatcct acacatactt gggcaagcaa tatcctatta cccgggtaat    720
agaatttatt actctagagg aaaacaaacc cacaaggcct gtgattgtga gcccagctaa    780
tgagacaatg gaagtagact tgggatccca gatacaattg atctgtaatg tcaccggcca    840
gttgagtgac attgcttact ggaagtggaa tgggtcagta attgatgaag atgacccagt    900
gctaggggaa gactattaca gtgtggaaaa tcctgcaaac aaaagaagga gtaccctcat    960
cacagtgctt aatatatcgg aaattgaaag tagatttat aaacatccat ttacctgttt    1020
tgccaagaat acacatggta tagatgcagc atatatccag ttaatatatc cagtcactaa    1080
tttccagaag cacatgattg gtatatgtgt cacgttgaca gtcataattg tgtgttctgt    1140
tttcatctat aaaatcttca agattgacat tgtgctttgg tacagggatt cctgctatga    1200
ttttctccca ataaaagctt cagatggaaa gacctatgac gcatatatac tgtatccaaa    1260
gactgttggg gaagggtcta cctctgactg tgatatttttt gtgttaaag tcttgcctga    1320 ggtcttggaa aaacagtgtg gatataagct gttcattat ggaagggatg actacgttgg    1380
ggaagacatt gttgaggtca ttaatgaaaa cgtaaagaaa agcagaagac tgattatcat    1440
tttagtcaga gaaacatcag gcttcagctg gctgggtggt tcatctgaag agcaaatagc    1500
catgtataat gctcttgttc aggatggaat taaagttgtc ctgcttgagc tggagaaaat    1560
ccaagactat gagaaaatgc cagaatcgat taaattcatt aagcagaaac atgggggctat    1620 ccgctggtca ggggacttta cacagggacc acagtctgca aagacaaggt tctggaagaa    1680
```

```
tgtcaggtac cacatgccag tccagcgacg gtcaccttca tctaaacacc agttactgtc    1740
accagccact aaggagaaac tgcaaagaga ggctcacgtg cctctcgggt agcatggaga    1800
agttgccaag agttctttag gtgcctcctg tcttatggcg ttgcaggcca ggttatgcct    1860
catgctgact tgcagagttc atggaatgta actatatcat cctttatccc tgaggtcacc    1920
tggaatcaga ttattaaggg aataagccat gacgtcaata gcagcccagg gcacttcaga    1980
gtagagggct tgggaagatc ttttaaaaag gcagtaggcc cggtgtggtg gctcacgcct    2040
ataatcccag cactttggga ggctgaagtg ggtggatcac cagaggtcag gagttcgaga    2100
ccagcccagc caacatggca aaaccccatc tctactaaaa atacaaaaat gagctaggca    2160
tggtggcaca cgcctgtaat cccagctaca cctgaggctg aggcaggaga attgcttgaa    2220
ccggggagac ggaggttgca gtgagccgag tttgggccac tgcactctag cctggcaaca    2280
gagcaagact ccgtctcaaa aaagggcaa taaatgccct ctctgaatgt ttgaactgcc    2340
aagaaaaggc atggagacag cgaactagaa gaaagggcaa gaaggaaata gccaccgtct    2400
acagatggct tagttaagtc atccacagcc caagggcggg gctatgcctt gtctggggac    2460
cctgtagagt cactgaccct ggagcggctc tcctgagagg tgctgcaggc aaagtgagac    2520
tgacacctca ctgaggaagg gagacatatt cttggagaac tttccatctg cttgtatttt    2580
ccatacacat ccccagccag aagttagtgt ccgaagaccg aatttttattt tacagagctt    2640 gaaaactcac ttcaatgaac aaagggattc tccaggattc caaagttttg aagtcatctt    2700
agctttccac aggagggaga gaacttaaaa aagcaacagt agcagggaat tgatccactt    2760
cttaatgctt tcctccctgg catgaccatc ctgtcctttg ttattatcct gcattttacg    2820
tctttggagg aacagctccc tagtggcttc ctccgtctgc aatgtccctt gcacagccca    2880
cacatgaacc atccttccca tgatgccgct cttctgtcat cccgctcctg ctgaaacacc    2940
tcccaggggc tccacctgtt caggagctga agcccatgct ttcccaccag catgtcactc    3000
ccagaccacc tccctgccct gtcctccagc ttccctcgc tgtcctgctg tgtgaattcc    3060
caggttggcc tggtggccat gtcgcctgcc cccagcactc ctctgtctct gctcttgcct    3120
cgacccttcc tcctccttg cctaggaggc cttctcgcat tttctctagc tgatcagaat    3180
tttaccaaaa ttcagaacat cctccaattc cacagtctct gggagacttt ccctaagagg    3240
cgacttcctc tccagccttc tctctctggt caggcccact gcagagatgg tggtgagcac    3300
atctgggagg ctggtctccc tccagctgga attgctgctc tctgagggag aggctgtggt    3360
ggctgtctct gtccctcact gccttccagg agcaatttgc acatgtaaca tagatttatg    3420
taatgcttta tgtttaaaaa cattccccaa ttatcttatt taattttttgc aattattcta    3480 attttatata tagagaaagt gacctatttt ttaaaaaaat cacactctaa gttctattga    3540
acctaggact tgagcctcca tttctggctt ctagtctggt gttctgagta cttgatttca    3600
ggtcaataac ggtcccccct cactccacac tggcacgttt gtgagaagaa atgcattttt    3660
gctaggaagt gaccgagtct aggaatgctt ttattcaaga caccaaattc caaacttcta    3720
aatgttggaa ttttcaaaaa ttgtgtttag attttatgaa aaactcttct actttcatct    3780
attctttccc tagaggcaaa catttcttaa aatgttttcat tttcattaaa aatgaaagcc    3840
aaatttatat gccaccgatt gcaggacaca agcacagttt taagagttgt atgaacatgg    3900
agaggacttt tggttttat atttctcgta tttaatatgg gtgaacacca acttttattt    3960
ggaataataa ttttcctcct aaacaaaaac acattgagtt taagtctctg actcttgcct    4020
ttccacctgc tttctcctgg gcccgctttg cctgcttgaa ggaacagtgc tgttctggag    4080
```

```
ctgctgttcc aacagacagg gcctagcttt catttgacac acagactaca gccagaagcc    4140
catggagcag ggatgtcacg tcttgaaaag cctattagat gttttacaaa tttaattttg    4200
cagattattt tagtctgtca tccagaaaat gtgtcagcat gcatagtgct aagaaagcaa    4260
gccaatttgg aaacttaggt tagtgacaaa attggccaga gagtgggggt gatgatgacc    4320
aagaattaca agtagaatgg cagctggaat ttaaggaggg acaagaatca atggataagc    4380
gtgggtggag gaagatccaa acagaaaagt gcaaagttat tccccatctt ccaagggttg    4440
aattctggag gaagaagaca cattcctagt tccccgtgaa cttcctttga cttattgtcc    4500
ccactaaaac aaaacaaaaa acttttaatg ccttccacat taattagatt ttcttgcagt    4560 tttttatgg cattttttta aagatgccct aagtgttgaa gaagagtttg caaatgcaac     4620
aaaatattta attaccggtt gttaaaactg gtttagcaca atttatattt tccctctctt    4680
gcctttctta tttgcaataa aaggtattga gccatttttt aaatgacatt tttgataaat    4740
tatgtttgta ctagttgatg aaggagtttt ttttaacctg tttatataat tttgcagcag    4800
aagccaaatt ttttgtatat taaagcacca aattcatgta cagcatgcat cacggatcaa    4860
tagactgtac ttattttcca ataaaatttt caaactttgt actgttaaa                4909

<210> SEQ ID NO 31
<211> LENGTH: 2210
<212> TYPE: DNA
<213> ORGANISM: Homo sapiens
<220> FEATURE:
<223> OTHER INFORMATION: BIN1 glucocorticoid receptor-responsive gene

<400> SEQUENCE: 31
cgcgcccctc cctcctcgcg gacctggcgg tgccggcgcc cggagtggcc ctttaaaagg      60
cagcttattg tccggagggg gcgggcgggg ggcgccgacc gcggcctgag gcccggcccc     120
tcccctctcc ctccctctgt ccccgcgtcg ctcgctggct agctcgctgg ctcgctcgcc     180
cgtccggcgc acgctccgcc tccgtcagtt ggctccgctg tcgggtgcgc ggcgtggagc     240
ggcagccggt ctggacgcgc ggccggggct ggggctggg agcgcggcgc gcaagatctc      300
cccgcgcgag agcggcccct gccaccgggc gaggcctgcg ccgcgatggc agagatgggc     360
agtaaagggg tgacggcggg aaagatcgcc agcaacgtgc agaagaagct cacccgcgcg     420
caggagaagg ttctccagaa gctggggaag gcagatgaga ccaaggatga gcagtttgag     480
cagtgcgtcc agaatttcaa caagcagctg acggagggca cccggctgca gaaggatctc     540
cggacctacc tggcctccgt caaagccatg cacgaggctt ccaagaagct gaatgagtgt     600
ctgcaggagg tgtatgagcc cgattggccc ggcagggatg aggcaaacaa gatcgcagag     660
aacaacgacc tgctgtggat ggattaccac cagaagctgg tggaccaggc gctgctgacc     720
atggacacgt acctgggcca gttccccgac atcaagtcac gcattgccaa gcgggggcgc     780
aagctggtgg actacgacag tgcccggcac cactacgagt cccttcaaac tgccaaaaag     840
aaggatgaag ccaaaattgc caaggccgag gaggagctca tcaaagccca gaaggtgttt     900
gaggagatga atgtggatct gcaggaggag ctgccgtccc tgtggaacag ccgcgtaggt     960
ttctacgtca acacgttcca gagcatcgcg ggcctggagg aaaacttcca caggagatg    1020 agcaagctca accagaacct caatgatgtg ctggtcggcc tggagaagca cacgggagc    1080 aacaccttca cggtcaaggc ccagcccaga aagaaaagta aactgttttc gcggctgcgc    1140
agaaagaaga caagtgacaa cgcgcctgca aagggaaca agagcccttc gcctccagat    1200
```

```
ggctcccctg ccgccacccc cgagatcaga gtcaaccacg agccagagcc ggccggcggg    1260
gccacgcccg gggccaccct ccccaagtcc ccatctcagc cagcagaggc ctcggaggtg    1320
gcgggtggga cccaacctgc ggctggagcc caggagccag gggagacggc ggcaagtgaa    1380
gcagcctcca gctctcttcc tgctgtcgtg gtggagacct tcccagcaac tgtgaatggc    1440
accgtggagg gcggcagtgg ggccgggcgc ttggacctgc ccccaggttt catgttcaag    1500
gtacaggccc agcacgacta cacgccacct gacacagacg agctgcagct caaggctggt    1560
gatgtggtgc tggtgatccc cttccagaac cctgaagagc aggatgaagg ctggctcatg    1620
ggcgtgaagg agagcgactg gaaccagcac aaggagctgg agaagtgccg tggcgtcttc    1680
cccgagaact tcactgagag ggtcccatga cggcggggcc caggcagcct ccgggcgtgt    1740
gaagaacacc tcctcccgaa aaatgtgtgg ttcttttttt tgttttgttt tcgttttttca   1800 tcttttgaag agcaaaggga aatcaagagg agaccccag gcagaggggc gttctcccaa     1860
agattaggtc gttttccaaa gagccgcgtc ccggcaagtc cggcggaatt caccagtgtt    1920
cctgaagctg ctgtgtcctc tagttgagtt tctggcgccc ctgcctgtgc ccgcatgtgt    1980
gcctggccgc agggcggggc tgggggctgc cgagccacca tgcttgcctg aagcttcggc    2040
cgcgccaccc gggcaagggt cctctttttcc tggcagctgc tgtgggtggg gcccagacac   2100
cagcctagcc tggctctgcc ccgcagacgg tctgtgtgct gtttgaaaat aaatcttagt    2160
gttcaaaaca aaatgaaaca aaaaaaaaat gataaaaact ctcaaaaaaa                2210
```

<210> SEQ ID NO 32
<211> LENGTH: 4664
<212> TYPE: DNA
<213> ORGANISM: Homo sapiens
<220> FEATURE:
<223> OTHER INFORMATION: WIPF1 glucocorticoid receptor-responsive gene

<400> SEQUENCE: 32

```
gcagcctccc ggcgctgagc gcttttcctg cccgcccggc tcagccctgc ggaccccggg     60
agaagtttcc cagaaaaaat gcccagcgcg gcgcggggct gcggagtcgt ccggagccgc    120
tgcgcgattt atcagcaaga ctgttgaacg cataactgcc caagatgcct gtccctcccc    180
ctccagcacc cccgccgccc ccgacgtttg cactggccaa tacagagaag cctaccttga    240
ataagacaga gcaggctggg agaaatgctc tcctttctga tatcagcaaa gggaagaaac    300
taaagaagac ggtcaccaat gacagaagtg caccaatact ggacaaacct aaaggagctg    360
gtgctggagc cggtggtggt ggctttggtg gaggcggcgg atttggcgga ggaggtggtg    420
gcggaggcgg tggaagtttt ggaggggggcg gacctccagg tctgggagga ttgttccagg    480
ctggaatgcc gaagctgaga tccacggcca acagggataa tgattctgga ggaagccgac    540
caccattgtt gccaccggga ggaagatcca catctgcgaa acccttttca cccccaagtg    600
gcccagggag gtttcctgtg ccttctccag gccacagaag tggtccccca gagcctcaga    660
ggaaccgaat gccgccccca aggcccgacg tgggctcaaa gcctgatagc attcctcctc    720
cagtacctag tactccaaga cccattcaat caagtccgca caaccggggg tccccaccag    780
tgcccggagg cccaggcag cccagccccg ggcccactcc tccccctttc cctgaaaacc     840
gcggcactgc tttgggagga ggctcaatac gtcagtcccc cttgagctcc tcctcgccct    900
tctccaaccg gcctcccctg ccgcctaccc ccagcagggc cttggatgac aaacccctc     960 caccacctcc tccagtgggc aacaggccct ccatccacag ggaagcggtt ccccctcctc   1020
ctcctcagaa caacaagcct ccagtgcctt ccactccgcg gccttcggcc tcctcacagg   1080
```

```
ccccacctcc gccgccacct cccagcaggc ccgggccgcc tcctctgcct ccaagttcca    1140
gcggcaatga cgaaacccca agactcccac agcggaatct gtccctcagt tcgtccacgc    1200
ccccgttacc ttcgccagga cgttcaggtc ctcttcctcc cccgcccagt gagagacccc    1260
cacctccagt gagggacccg ccaggccgat caggccccct cccaccacct cctccagtaa    1320
gcagaaacgg cagcacatct cgggccctgc ctgctacccc tcagttgcca tccaggagtg    1380
gagtagacag tcccaggagt ggacccaggc ctccccttcc tcctgatagg cccagtgctg    1440
gggcacctcc cccacctcca ccatcaacat ctattagaaa tggcttccaa gactctccat    1500
gtgaagatga gtgggaaagc agattctact tccatccgat ttccgatttg ccacctccag    1560
agccatatgt acaaacgacc aaaagttatc ccagcaaact ggcaagaaac gaaagccgga    1620
gtggatccaa ccgaagagaa aggggtgctc caccactccc tcccatcccg aggtgatctt    1680
tgcctgctct tctctaccca agctcaagag ctgcttctgt tgctatctaa gaactgcata    1740
ccctcctccc tgcttcttcc cttgtgcctc atgtatgggc aggaggaaag gtgggagggg    1800
gagtgggaat atgcgtgtgt gggtgggaat cggtaagaaa tgcacctagc ttttcatatt    1860
gtgtttattc tccaggctat tgcttgcttc agctgcagcc tgcctgtgct ggctgctggg    1920
gtcgataggc ttttgtcgta ataggcagag atgacttgca tcccagcttt ccaccaacca    1980
aattcaaaca ttcactgctt atttgttaca gactgtaatt attaaagtcc ctgagagctg    2040
ttttctcccg ttccttttc gcatgcttgg cctcctctct gtttctatga accacagacc    2100
acctaagcaa gctgctgagt aagggctcac tggaaacttg cagtcacagg atgtccaatc    2160
tttggcagtc cgagcttggc tctaggacag agctgtccaa tagaaatata atgtgagccc    2220
catatacaat ttttcacattt ctaatatatt ttaaacaagt gaagttaata tgcatccaaa    2280
atatttcaac ctgtaatcaa cataaaattt taatgagata ttttatatta tttttggta    2340 ctgaatcttc aaaatccaga gtgtatttta cacttaccgc acatctccat tcagactagt    2400 cacatttta agtgctcagt agccacatgt ggctggtggc tactggatta gacagcacga    2460
gtctggaaga tggaagctag tgcagaaacc tcttgtttaa aaacaaaaa aggcaagatg    2520 ggcttgagcg attcaagagg caactaaaaa taaaattagg acccagcacc ttgtttgaca    2580
cacagtttga ccttcgattt tcctccctta acttccctct tcccttaata tctgtataca    2640
agtgttgctt caaagtacca aggtcagaaa ttgattcagt acggtttact aaagtcatgt    2700
ggaataaagc cattggaaac aaatggaaag cctgtcggga cttctgggct cagaaccagc    2760
tggctcacgc actccacttg tcagctggac ttctgccttg tgaaatggaa gcagcctttg    2820
ttcctttctg gctgagcaag ctcctgaggc tgggagagac taggaaggct tggtaggagg    2880 ggaaaaagt caggaaaaga tatcaaatca gaaacatgga agaagaaggg aaccgatttg    2940
agttggtggg caaaactcta aaaatctaaa tctgatgctt atgtaagggt tgagcgaatt    3000
agggagattg ctagtggaaa ttggagggaa tttgttttgc atcatttgtc taggatctat    3060
gcaaatatag ctccactaaa ggaccatagg gaagagccag ccttgccttt tcttatatga    3120
ttttgtttac aaaattttac tgggactttt aaatctagct atagagttgg gaaaaaatat    3180
ttccacttag atattttaca tggttttgtt taaaattacc attacttgtt ttttaaaaac    3240
acatgaccac atatgtatat gtatatctac ctaaacattg tatcatggtt tcagtatgtt    3300
attcatgtat tactgggaga tgctaccaag aaaccaaccc aaagaaaatt ctgaaaaata    3360
catttctatt tatagaataa atgtttcatt tatataaaag caaagaact tagagttcta    3420
```

```
ataaatggga tgtctaataa attatgaagt tactgatttg aatatattat attttttataa   3480 cttccttgcc aaagtcctga tttagtacat tagagaacct gtgtttcctc tctcctctac   3540
cattcatctc tcttccatac agtcatttgg gcttttttact caaagagaat caagaaataa   3600
taaggtataa caagcttggc aaagtgttgg cttttttaaaa aaaaattttt ttaatctcta   3660
gcagtttggt aatttagcag catcattttat ttgggattct tttatctgat ttcaacagtg   3720
aaaaacatcc ctatgataaa gcctaatgac ccatttcaca aaagatggaa tttgcccttc   3780
ctagaaaata tgacggagaa aagtctgact cagagaaagt gagtctgaat tttataaggg   3840
gtagtaagaa ttggacaatt cctttgcata tctgaacttg gcaggtaccg ttctaaatct   3900
gaaacagggt gatagctcaa agttgccatt catccagaat agattgtttt agaatgtagt   3960
gtttaagtga ctgtttcatt aatacaccta caccctttct ttgaaagttt gcaacctaat   4020
tgcatctaaa actatgaata agttctgtgg taaaatctta aactatggaa aattacaaaa   4080 atgaatttttt cttccctgaa atcagagctt acatgtgtgt ttttttataa cattttcaga   4140
taaatgtatt caacatgtaa tacagtattt taacattcac ctcttatttt atattgaaat   4200
gtattacagt attaaaactc agtgttcagt atttatttca ctatgcattt tatttagtaa   4260
aagccaggag aaatgtttaa tccaatggtg ccttactttg tgatttaaaa gaaatcaact   4320 ttttttttatg tctaagtagt agattatttg catatttgta aaaactgtta ggtctttata   4380
ttttaaagtg taataccagt tttgttattt tagtagcaga aatgggatga ttgttaaagt   4440
tccccaaaaa tgttggcatg aaattaattt ttccctcctt atagtcaagg accgtagagg   4500
aagaaaaact ttttttttcat accatgcact atgtaaacag acacattttg ctatctgtgt   4560
catcaggata gtgtaagtgg tagggtagag actaccctag acatctgcat ctttgtaagt   4620
tagccagaca ataagaaaa gcagaatgaa aaaaaaaaa aaaa                      4664
```

<210> SEQ ID NO 33
<211> LENGTH: 1166
<212> TYPE: DNA
<213> ORGANISM: Homo sapiens
<220> FEATURE:
<223> OTHER INFORMATION: TFPI glucocorticoid receptor-responsive gene

<400> SEQUENCE: 33

```
attcccaact gccagtgatc tctgaagccg actctgaggc tccctctttg ctctaacaga    60
cagcagcgac tttaggctgg ataatagtca aattcttacc tcgctctttc actgctagta   120
agatcagatt gcgtttcttt cagttactct tcaatcgcca gtttcttgat ctgcttctaa   180
aagaagaagt agagaagata atcctgtctc tcaatacctg gaaggaaaaa caaaataacc   240
tcaactccgt tttgaaaaaa acattccaag aactttcatc agagatttta cttagatgat   300
ttacacaatg aagaaagtac atgcactttg ggcttctgta tgcctgctgc ttaatcttgc   360
ccctgcccct cttaatgctg attctgagga agatgaagaa cacacaatta tcacagatac   420
ggagttgcca ccactgaaac ttatgcattc attttgtgca ttcaaggcgg atgatggccc   480
atgtaaagca atcatgaaaa gattttttctt caatattttc actcgacagt gcgaagaatt   540
tatatatggg ggatgtgaag gaaatcagaa tcgatttgaa agtctggaag agtgcaaaaa   600
aatgtgtaca agagataatg caaacaggat tataaagaca cattgcaac aagaaaagcc   660 agatttctgc ttttttggaag aagatcctgg aatatgtcga ggttatatta ccaggtattt   720
ttataacaat cagacaaaac agtgtgaacg tttcaagtat ggtggatgcc tgggcaatat   780
gaacaatttt gagacactgg aagaatgcaa gaacatttgt gaagatggtc cgaatggttt   840
```

```
ccaggtggat aattatggaa cccagctcaa tgctgtgaat aactccctga ctccgcaatc      900
aaccaaggtt cccagccttt ttgttacaaa agaaggaaca aatgatggtt ggaagaatgc      960
ggctcatatt taccaagtct ttctgaacgc cttctgcatt catgcatcca tgttctttct     1020
aggattggat agcatttcat gcctatgtta atatttgtgc ttttggcatt tccttaatat     1080
ttatatgtat acgtgatgcc tttgatagca tactgctaat aaagttttaa tatttacatg     1140
catagtaaaa aaaaaaaaaa aaaaaa                                          1166

<210> SEQ ID NO 34
<211> LENGTH: 8449
<212> TYPE: DNA
<213> ORGANISM: Homo sapiens
<220> FEATURE:
<223> OTHER INFORMATION: FN1 glucocorticoid receptor-responsive gene

<400> SEQUENCE: 34
gcccgcgccg gctgtgctgc acaggggagg gagagggaac cccaggcgcg agcgggaaga       60
ggggacctgc agccacaact tctctggtcc tctgcatccc ttctgtccct ccacccgtcc      120
ccttccccac cctctggccc ccaccttctt ggaggcgaca accccgggga ggcattagaa      180
gggatttttc ccgcaggttg cgaagggaag caaacttggt ggcaacttgc ctcccggtgc      240
gggcgtctct cccccaccgt ctcaacatgc ttagggtcc ggggcccggg ctgctgctgc      300
tggccgtcca gtgcctgggg acagcggtgc cctccacggg agcctcgaag agcaagaggc      360
aggctcagca aatggttcag ccccagtccc cggtggctgt cagtcaaagc aagcccggtt      420
gttatgacaa tggaaaacac tatcagataa atcaacagtg ggagcggacc tacctaggca      480
atgcgttggt ttgtacttgt tatggaggaa gccgaggttt taactgcgag agtaaacctg      540
aagctgaaga gacttgcttt gacaagtaca ctgggaacac ttaccgagtg ggtgacactt      600
atgagcgtcc taaagactcc atgatctggg actgtacctg catcgggct gggcgaggga      660 gaataagctg taccatcgca aaccgctgcc atgaaggggg tcagtcctac aagattggtg      720
acacctggag agaccacat gagactggtg gttacatgtt agagtgtgtg tgtcttggta      780
atggaaaagg agaatggacc tgcaagccca gctgagaa gtgttttgat catgctgctg      840
ggacttccta tgtggtcgga gaaacgtggg agaagcccta ccaaggctgg atgatggtag      900
attgtacttg cctgggagaa ggcagcggac gcatcacttg cacttctaga aatagatgca      960
acgatcagga cacaaggaca tcctatagaa ttggagacac ctggagcaag aaggataatc     1020
gaggaaacct gctccagtgc atctgcacag gcaacgccg aggagagtgg aagtgtgaga     1080
ggcacacctc tgtgcagacc acatcgagcg gatctggccc cttcaccgat gttcgtgcag     1140
ctgtttacca accgcagcct cacccccagc ctcctcccta tggccactgt gtcacagaca     1200
gtggtgtggt ctactctgtg gggatgcagt ggctgaagac acaaggaaat aagcaaatgc     1260
tttgcacgtg cctgggcaac ggagtcagct gccaagagac agctgtaacc cagacttacg     1320
gtggcaactc aaatggagag ccatgtgtct taccattcac ctacaatggc aggacgttct     1380
actcctgcac cacagaaggg cgacaggacg gacatctttg tgcagcaca acttcgaatt     1440 atgagcagga ccagaaatac tctttctgca gagaccacac tgtttggtt cagactcgag     1500 gaggaaattc caatggtgcc ttgtgccact tccccttcct atacaacaac cacaattaca     1560
ctgattgcac ttctgagggc agaagagaca acatgaagtg gtgtgggacc acacagaact     1620
atgatgccga ccagaagttt gggttctgcc ccatggctgc cacgaggaa atctgcacaa     1680
```

-continued

```
ccaatgaagg ggtcatgtac cgcattggag atcagtggga taagcagcat gacatgggtc      1740
acatgatgag gtgcacgtgt gttgggaatg gtcgtgggga atggacatgc attgcctact      1800
cgcagcttcg agatcagtgc attgttgatg acatcactta caatgtgaac gacacattcc      1860
acaagcgtca tgaagagggg cacatgctga actgtacatg cttcggtcag ggtcggggca      1920
ggtggaagtg tgatcccgtc gaccaatgcc aggattcaga gactgggacg ttttatcaaa      1980
ttggagattc atgggagaag tatgtgcatg gtgtcagata ccagtgctac tgctatggcc      2040
gtggcattgg ggagtggcat tgccaacctt tacagaccta tccaagctca gtggtcctg       2100 tcgaagtatt tatcactgag actccgagtc agcccaactc ccaccccatc cagtggaatg      2160
caccacagcc atctcacatt tccaagtaca ttctcaggtg gagacctaaa aattctgtag      2220
gccgttggaa ggaagctacc ataccaggcc acttaaactc ctacaccatc aaaggcctga      2280
agcctggtgt ggtatacgag ggccagctca tcagcatcca gcagtacggc caccaagaag      2340
tgactcgctt tgacttcacc accaccagca ccagcacacc tgtgaccagc aacaccgtga      2400
caggagagac gactcccttt tctcctcttg tggccacttc tgaatctgtg accgaaatca      2460
cagccagtag ctttgtggtc tcctgggtct cagcttccga caccgtgtcg ggattccggg      2520
tggaatatga gctgagtgag gagggagatg agccacagta cctggatctt ccaagcacag      2580
ccacttctgt gaacatccct gacctgcttc ctggccgaaa atacattgta aatgtctatc      2640
agatatctga ggatgggggag cagagtttga tcctgtctac ttcacaaaca cagcgcctg      2700 atgcccctcc tgacccgact gtggaccaag ttgatgacac ctcaattgtt gttcgctgga      2760 gcagaccca ggctcccatc acagggtaca gaatagtcta ttcgccatca gtagaaggta      2820
gcagcacaga actcaacctt cctgaaactg caaactccgt caccctcagt gacttgcaac      2880
ctggtgttca gtataacatc actatctatg ctgtggaaga aaatcaagaa agtacacctg      2940
ttgtcattca acaagaaacc actggcaccc cacgctcaga tacagtgccc tctcccaggg      3000
acctgcagtt tgtggaagtg acagacgtga aggtcaccat catgtggaca ccgcctgaga      3060
gtgcagtgac cggctaccgt gtggatgtga tccccgtcaa cctgcctggc gagcacgggc      3120
agaggctgcc catcagcagg aacaccttg cagaagtcac cggctgtcc cctgggtca       3180 cctattactt caaagtcttt gcagtgagcc atggagggga gagcaagcct ctgactgctc      3240
aacagacaac caaactggat gctcccacta acctccagtt tgtcaatgaa actgattcta      3300
ctgtcctggt gagatggact ccacctcggg cccagataac aggataccga ctgaccgtgg      3360
gccttacccg aagaggacag cccaggcagt acaatgtggg tccctctgtc tccaagtacc      3420
cactgaggaa tctgcagcct gcatctgagt acaccgtatc cctcgtggcc ataaagggca      3480
accaagagag ccccaaagcc actggagtct ttaccacact gcagcctggg agctctattc      3540
caccttacaa caccgaggtg actgagacca ccattgtgat cacatggacg cctgctccaa      3600
gaattggttt taagctgggt gtacgaccaa gccaggagg agaggcacca cgagaagtga      3660
cttcagactc aggaagcatc gttgtgtccg gcttgactcc aggagtagaa tacgtctaca      3720
ccatccaagt cctgagagat ggacaggaaa gagatgcgcc aattgtaaac aaagtggtga      3780
caccattgtc tccaccaaca aacttgcatc tggaggcaaa ccctgacact ggagtgctca      3840
cagtctcctg ggagaggagc accaccccag acattactgg ttatagaatt accacaaccc      3900
ctacaaacgg ccagcaggga aattctttgg aagaagtggt ccatgctgat cagagctcct      3960
gcacttttga taacctgagt cccggcctgg agtacaatgt cagtgtttac actgtcaagg      4020
atgacaagga aagtgtccct atctctgata ccatcatccc agctgttcct cctcccactg      4080
```

```
acctgcgatt caccaacatt ggtccagaca ccatgcgtgt cacctgggct ccaccccat   4140 ccattgattt aaccaacttc ctggtgcgtt actcacctgt gaaaaatgag gaagatgttg   4200
cagagttgtc aatttctcct tcagacaatg cagtggtctt aacaaatctc ctgcctggta   4260
cagaatatgt agtgagtgtc tccagtgtct acgaacaaca tgagagcaca cctcttagag   4320
gaagacagaa aacaggtctt gattccccaa ctggcattga cttttctgat attactgcca   4380
actcttttac tgtgcactgg attgctcctc gagccaccat cactggctac aggatccgcc   4440
atcatcccga gcacttcagt gggagacctc gagaagatcg ggtgccccac tctcggaatt   4500
ccatcaccct caccaacctc actccaggca cagagtatgt ggtcagcatc gttgctctta   4560
atggcagaga ggaaagtccc ttattgattg ccaacaatc aacagtttct gatgttccga   4620
gggacctgga agttgttgct gcgaccccca ccagcctact gatcagctgg gatgctcctg   4680
ctgtcacagt gagatattac aggatcactt acggagagac aggaggaaat agccctgtcc   4740
aggagttcac tgtgcctggg agcaagtcta cagctaccat cagcggcctt aaacctggag   4800
ttgattatac catcactgtg tatgctgtca ctggccgtgg agacagcccc gcaagcagca   4860
agccaatttc cattaattac cgaacagaaa ttgacaaacc atcccagatg caagtgaccg   4920
atgttcagga caacagcatt agtgtcaagt ggctgccttc aagttcccct gttactggtt   4980
acagagtaac caccactccc aaaaatggac caggaccaac aaaaactaaa actgcaggtc   5040
cagatcaaac agaaatgact attgaaggct gcagcccac agtggagtat gtggttagtg   5100
tctatgctca gaatccaagc ggagagagtc agcctctggt tcagactgca gtaaccaaca   5160
ttgatcgccc taaaggactg gcattcactg atgtggatgt cgattccatc aaaattgctt   5220
gggaaagccc acaggggcaa gtttccaggt acagggtgac ctactcgagc cctgaggatg   5280
gaatccatga gctattccct gcacctgatg gtgaagaaga cactgcagag ctgcaaggcc   5340
tcagaccggg ttctgagtac acagtcagtg tggttgcctt gcacgatgat atggagagcc   5400 agccctgat tggaacccag tccacagcta ttcctgcacc aactgacctg aagttcactc   5460
aggtcacacc cacaagcctg agcgcccagt ggacaccacc caatgttcag ctcactggat   5520
atcgagtgcg ggtgaccccc aaggagaaga ccggaccaat gaaagaaatc aaccttgctc   5580
ctgacagctc atccgtggtt gtatcaggac ttatggtggc caccaaatat gaagtgagtg   5640
tctatgctct taaggacact ttgacaagca gaccagctca gggagttgtc accactctgg   5700
agaatgtcag cccaccaaga agggctcgtg tgacagatgc tactgagacc accatcacca   5760
ttagctggag aaccaagact gagacgatca ctggcttcca agttgatgcc gttccagcca   5820
atggccagac tccaatccag agaaccatca gccagatgt cagaagctac accatcacag   5880
gtttacaacc aggcactgac tacaagatct acctgtacac cttgaatgac aatgctcgga   5940
gctcccctgt ggtcatcgac gcctccactg ccattgatgc accatccaac ctgcgtttcc   6000
tggccaccac acccaattcc ttgctggtat catggcagcc gccacgtgcc aggattaccg   6060
gctacatcat caagtatgag aagcctgggt ctcctccag agaagtggtc cctcggcccc   6120
gccctggtgt cacagaggct actattactg gcctggaacc gggaaccgaa tatacaattt   6180
atgtcattgc cctgaagaat aatcagaaga gcgagcccct gattggaagg aaaaagacag   6240
acgagcttcc ccaactggta acccttccac accccaatct tcatggacca gagatcttgg   6300
atgttccttc cacagttcaa aagacccctt tcgtcaccca ccctgggtat gacactggaa   6360
atggtattca gcttcctggc acttctggtc agcaacccag tgttgggcaa caaatgatct   6420
```

```
ttgaggaaca tggtttagg cggaccacac cgcccacaac ggccaccccc ataaggcata      6480
ggccaagacc ataccgccg aatgtaggac aagaagctct ctctcagaca accatctcat      6540
gggcccatt ccaggacact tctgagtaca tcatttcatg tcatcctgtt ggcactgatg      6600
aagaacctt acagttcagg gttcctggaa cttctaccag tgccactctg acaggcctca      6660
ccagaggtgc cacctacaac atcatagtgg aggcactgaa agaccagcag aggcataagg      6720
ttcgggaaga ggttgttacc gtgggcaact ctgtcaacga aggcttgaac caacctacgg      6780
atgactcgtg ctttgacccc tacacagttt cccattatgc cgttggagat gagtgggaac      6840
gaatgtctga atcaggcttt aaactgttgt gccagtgctt aggctttgga agtggtcatt      6900
tcagatgtga ttcatctaga tggtgccatg acaatggtgt gaactacaag attggagaga      6960
agtgggaccg tcaggagaa aatggccaga tgatgagctg cacatgtctt gggaacggaa      7020
aaggagaatt caagtgtgac cctcatgagg caacgtgtta tgatgatggg aagacatacc      7080
acgtaggaga acagtggcag aaggaatatc tcggtgccat ttgctcctgc acatgctttg      7140
gaggccagcg gggctggcgc tgtgacaact gccgcagacc tgggggtgaa cccagtcccg      7200
aaggcactac tggccagtcc tacaaccagt attctcagag ataccatcag agaacaaaca      7260
ctaatgttaa ttgcccaatt gagtgcttca tgcctttaga tgtacaggct gacagagaag      7320
attcccgaga gtaaatcatc tttccaatcc agaggaacaa gcatgtctct ctgccaagat      7380
ccatctaaac tggagtgatg ttagcagacc cagcttagag ttcttctttc tttcttaagc      7440
cctttgctct ggaggaagtt ctccagcttc agctcaactc acagcttctc caagcatcac      7500
cctgggagtt tcctgagggt ttctcataa atgagggctg cacattgcct gttctgcttc      7560
gaagtattca ataccgctca gtattttaaa tgaagtgatt ctaagatttg gtttgggatc      7620
aataggaaag catatgcagc caaccaagat gcaaatgttt tgaaatgata tgaccaaaat      7680
tttaagtagg aaagtcaccc aaacacttct gctttcactt aagtgtctgg cccgcaatac      7740
tgtaggaaca agcatgatct tgttactgtg atatttaaa tatccacagt actcactttt      7800
tccaaatgat cctagtaatt gcctagaaat atctttctct tacctgttat ttatcaattt      7860
ttcccagtat ttttatacgg aaaaaattgt attgaaaaca cttagtatgc agttgataag      7920
aggaatttgg tataattatg gtgggtgatt atttttata ctgtatgtgc caaagcttta      7980
ctactgtgga aagacaactg ttttaataaa agatttacat tccacaactt gaagttcatc      8040
tatttgatat aagcacacctt cgggggaaat aattcctgtg aatattcttt ttcaattcag      8100
caaacatttg aaaatctatg atgtgcaagt ctaattgttg atttcagtac aagattttct      8160
aaatcagttg ctacaaaac tgattggttt ttgtcacttc atctcttcac taatggagat      8220
agctttacac tttctgcttt aatagattta agtggacccc aatatttatt aaaattgcta      8280
gtttaccgtt cagaagtata atagaaataa tctttagttg ctcttttcta accattgtaa      8340
ttcttcccctt cttccctcca cctttccttc attgaataaa cctctgttca aagagattgc      8400
ctgcaaggga aataaaaatg actaagatat taaaaaaaaa aaaaaaaa                   8449
```

<210> SEQ ID NO 35
<211> LENGTH: 4625
<212> TYPE: DNA
<213> ORGANISM: Homo sapiens
<220> FEATURE:
<223> OTHER INFORMATION: FAM134A glucocorticoid receptor-responsive gene

<400> SEQUENCE: 35

```
agcgctccgc agtcacgtga cgctcgtccg caacctctgc tgtcctccgc ggcgcccct       60
```

-continued

```
tccgcctgac gcgccccgg cggcggccgc gcagccctgg ctcctcgcgg gctcgggcgg    120
cggctgcggc ggggctatgg cgagcggcgg tggcggggt aacactggcg cgggtggggg     180
gccggggatg ggcctgagcc tgggcctggg tctgggtctg agcctaggca tgagtgaggc    240
caccagtgag gcagaggagg aggcggccac ggccgaggcg gtgggacgcc tggccacgac    300
gctgtggctg cggctccgcg gctgggaggc ggtgctggcg gcggcgcagc ggttgctggt    360
gtgggagaag ccgctgcaca gcctggtcac ggcggccgcg ctcaacggcc tcttctggtt    420
gctgtcttcc tcgtccctcc ggcccttctt cctactcagc gtctcacttt tggcctattt    480
tctgctggat ctctggcagc ctcgctttct ccctgacgtt tcagcatcat ccccagagga    540
gccacactct gacagtgagg gtgcggggtc aggcgcccgg ccgcacctgc tgagtgtgcc    600
cgagttgtgc agatacctgg ctgagagctg gctcaccttc cagattcacc tgcaggagct    660
gctgcagtac aagaggcaga atccagctca gttctgcgtt cgagtctgct ctggctgtgc    720
tgtgttggct gtgttgggac actatgttcc agggattatg atttcctaca ttgtcttgtt    780
gagtatcctg ctgtggcccc tggtggttta tcatgagctg atccagagga tgtacactcg    840
cctggagccc ctgctcatgc agctggacta cagcatgaag gcagaagcca atgccctgca    900
tcacaaacac gacaagagga agcgtcaggg gaagaatgca ccccaggag gtgatgagcc     960 actggcagag acagagagtg aaagcgaggc agagctggct ggcttctccc cagtggtgga   1020
tgtgaagaaa acagcattgg ccttggccat tacagactca gagctgtcag atgaggaggc   1080
ttctatcttg gagagtggtg gcttctccgt atcccgggcc acaactccgc agctgactga   1140
tgtctccgag gatttggacc agcagagcct gccaagtgaa ccagaggaga ccctaagccg   1200
ggacctaggg gagggagagg agggagagct ggcccctccc gaagacctac taggccgtcc   1260
tcaagctctg tcaaggcaag ccctggactc ggaggaagag gaagaggatg tggcagctaa   1320
ggaaaccttg ttgcggctct catcccccct ccactttgtg aacacgcact tcaatggggc   1380
agggtccccc ccagatggag tgaaatgctc ccctggagga ccagtggaga cactgagccc   1440
cgagacagtg agtggtggcc tcactgctct gcccggcacc ctgtcacctc cactttgcct   1500
tgttggaagt gacccagccc cctccccttc cattctccca cctgttcccc aggactcacc   1560
ccagcccctg cctgcccctg aggaagaaga ggcactcacc actgaggact ttgagttgct   1620
ggatcagggg gagctggagc agctgaatgc agagctgggc ttggagccag agacaccgcc   1680
aaaaccccct gatgctccac ccctgggggcc cgacatccat tctctggtac agtcagacca   1740
agaagctcag gccgtggcag agccatgagc cagccgttga ggaaggagct gcaggcacag   1800
tagggcttcc tggctaggag tgttgctgtt tcctcctttg cctaccactc tggggtgggg   1860
cagtgtgtgg ggaagctggc tgtcggatgg tagctattcc accctctgcc tgcctgcctg   1920
cctgctgtcc tgggcatggt gcagtacctg tgcctaggat tggttttaaa tttgtaaata   1980
attttccatt tgggttagtg gatgtgaaca gggctaggga agtccttccc acagcctgcg   2040
cttgcctccc tgcctcatct ctattctcat tccactatgc cccaagccct ggtggtctgg   2100
cccttctttt ttcctcctat cctcagggac ctgtgctgct ctgccctcat gtcccacttg   2160
gttgtttagt tgaggcactt tataattttt ctcttgtctt gtgttccttt ctgctttatt   2220
tccctgctgt gtcctgtcct tagcagctca accccatcct ttgccagctc ctcctatccc   2280
gtgggcactg gccaagcttt agggaggctc ctggtctggg aagtaaagag taaacctggg   2340
gcagtgggtc aggccagtag ttacactctt aggtcactgt agtctgtgta accttcactg   2400
```

```
catccttgcc ccattcagcc cggcctttca tgatgcagga gagcagggat cccgcagtac    2460
atggcgccag cactggagtt ggtgagcatg tgctctctct tgagattagg agcttcctta    2520
ctgctcctct gggtgatcca agtgtagtgg accccctac tagggtcagg aagtggacac     2580
taacatctgt gcaggtgttg acttgaaaaa taaagtgttg attggctaga actgctgcct    2640
ccctgactgt gagctgcctt ccacaccctg cactgcactg tgttctctcc tcacccttaa    2700
cctgcttcac tccagtctgt tctggctgtt tattaccttg ttgcaaaaca gggccgaagc    2760
aaggattacc ttgacaaccc tagcttctcc ttagccatct tccttgacag tgtgatctgt    2820
ttagtgagat ttagcatgtg tgaataaagt atatgcagga ggaaattgct ttgtcttccc    2880
aatcggtaga aattcgggac cataaaaatt gtgttttacc atgtggccta caaccttaac    2940
actgctttct taagaagtct tcacccatct acatgctaac aactcactca gcctggattt    3000
atctttactg gggaagccaa acaagcaata gaggaccttt acctgtgtta gaaatgagtt    3060
ggagccaagg aacactgaag aaatagtatc ttaacagtta ctgagtccat tgtatgtgct    3120
tggctctgct ctgagtgatt tatatgtatt aagatttttc ctcacaggtc agatatatac    3180
tgttactaac ttcattttat agacaggtta agcttcctga aggccacagg tcccagtaaa    3240
ttgtggagcc agaaccccaa cccaagaagt tttggcttca gcaaatgcat cagacagccc    3300
ctgtccatta atagggcaca ggtaggaaga tgcacaagga tgtgggaact atagagaacc    3360
aatctgatgc cttggcttaa caaagagtgg acatggcaag ccttcctctt tggggaagaa    3420
aagcccagaa ctgagcagat ggcctccttt atgagttcat gtcctccgcc ttcagctgga    3480
ggtaccatat ggcgatgcta cctgtctttc tgctggaggt accatatggt aatgctgcct    3540
ggctgtctgc tggaggtacc atatggtaat gctgcctgtc tttctgaggt tgacttttat    3600
gccatgtctt tcctaagtgt gtaagaattt ttctgtttgc ttcacatttg actgagaatc    3660
attctagggt ttgattgagc ccctgtcctg tgccactaaa ggaactcgaa cttttcatca    3720
cttagagatt tcaggggga atggaaaaac agttctaatc aataagcaag caattcaaga    3780
aaaatagaat taatcaggca atgactgcaa catgtcctat ctttaatcta ttttcttatt    3840
aagcttggac attgacaata gaaccagaag cttgtagctg gatcaaaata ttctccatag    3900
gcctggagtt tcatgagggt ctattctttt gttgttgttg ttttggtttt tgttttttg     3960 tgggtttttt ttttttttt tttgagacgg agtcttgttc tgttgcccag gctggagtgc     4020
aatggtgcag tcttggttca ctgcaacctc tgcctcccag gttcaaacaa ttctcctgcc    4080
tcagccgtcc aagtagctgg gattacaggt gcatgccacg atgcctggct atttttgta    4140 ttttagtag aggtggggtt tcaccatgtt ggccaggctg gtctcgaact cctgacctca    4200
ggtgattcac ccacctcggc ctcccaaagt gctgggatta caggtgtgag ccacggcgcc    4260
cagcctcatg agggtctatt ctttacattc accatggtct gatggttgct acatgtttgt    4320
ctatgatttt tttttctat tatcaggtgt cttggccggt tcatgcccca cgatgaaagg     4380
gccagaggtt ttcatatgag taaaagaaaa aagcagaaat gtgaaaccta caattaggct    4440
aaacaaaaat caactggaaa agtacaggct gaggggagaa gagttggcta catgtttatg    4500
ttaggggagg agggagtaca ttttagctat gtattcaaac agctaatagt ttaatgttgc    4560
tgcttataaa cttaatttta ggctgcatta ataaagtgt agtctccaaa acaaaaaaaa    4620
aaaaa                                                               4625
```

<210> SEQ ID NO 36
<211> LENGTH: 7556

<212> TYPE: DNA
<213> ORGANISM: Homo sapiens
<220> FEATURE:
<223> OTHER INFORMATION: NRIP1 glucocorticoid receptor-responsive gene

<400> SEQUENCE: 36

```
gcaggcgcct tcgcggaccg agcctgacgg agccggaggc tgggagccgc ggcggcctgg      60
ggaagtgttt ggattgtgag ctatttcaga actgttctca ggactcatta ttttaacatt     120
tgggagaaac acagccagaa gatgcacact tgactgaagg aggacaggga atctgaagac     180
tccggatgac atcagagcta cttttcaaca gccttctcaa ttttctttct cagaaagcag     240
aggctcagag cttggagaca gacgaacact gatatttgca tttaatgggg aacaaaagat     300
gaagaaggaa aaggaatata ttcactaagg attctatctg cttactgcta cagacctatg     360
tgttaaggaa ttcttctcct cctccttgcg tagaagttga tcagcactgt ggtcagactg     420
catttatctt gtcattgcca gaagaaatct tggacagaat gtaacagtac gtctctctct     480
gattgcgatg gaaggtgata aactgatact cctttattaa agttacatcg cactcaccac     540
agaaaaccat tctttaaagt gaatagaaac caagcccttg tgaacacttc tattgaacat     600
gactcatgga gaagagcttg gctctgatgt gcaccaggat tctattgttt taacttacct     660
agaaggatta ctaatgcatc aggcagcagg gggatcaggt actgccgttg acaaaaagtc     720
tgctgggcat aatgaagagg atcagaactt taacatttct ggcagtgcat ttcccacctg     780
tcaaagtaat ggtccagttc tcaatacaca tacatatcag gggtctggca tgctgcacct     840
caaaaaagcc agactgttgc agtcttctga ggactggaat gcagcaaagc ggaagaggct     900
gtctgattct atcatgaatt taaacgtaaa gaaggaagct ttgctagctg gcatggttga     960
cagtgtgcct aaaggcaaac aggatagcac attactggcc tctttgcttc agtcattcag    1020
ctctaggctg cagactgttg ctctgtcaca acaaatcagg cagagcctca aggagcaagg    1080
atatgccctc agtcatgatt ctttaaaagt ggagaaggat ttaaggtgct atggtgttgc    1140
atcaagtcac ttaaaaactt tgttgaagaa aagtaaagtt aaagatcaaa agcctgatac    1200
gaatcttcct gatgtgacta aaaacctcat cagagatagg tttgcagagt ctcctcatca    1260
tgttggacaa agtggaacaa aggtcatgag tgaaccgttg tcatgtgctg caagattaca    1320
ggctgttgca agcatggtgg aaaaaagggc tagtcctgcc acctcaccta aacctagtgt    1380
tgcttgtagc cagttagcat tacttctgtc aagcgaagcc catttgcagc agtattctcg    1440
agaacacgct ttaaaaacgc aaaatgcaaa tcaagcagca agtgaaagac ttgctgctat    1500
ggccagattg caagaaaatg gccagaagga tgttggcagt taccagctcc caaaaggaat    1560
gtcaagccat cttaatggtc aggcaagaac atcatcaagc aaactgatgg ctagcaaaag    1620
tagtgctaca gtgtttcaaa atccaatggg tatcattcct tcttccccta aaaatgcagg    1680
ttataagaac tcactggaaa gaaacaatat aaaacaagct gctaacaata gtttgctttt    1740
acatcttctt aaaagccaga ctatacctaa gccaatgaat ggcacagtc acagtgagag     1800
aggaagcatt tttgaggaaa gtagtacacc tacaactatt gatgaatatt cagataacaa    1860
tcctagtttt acagatgaca gcagtggtga tgaaagttct tattccaact gtgttcccat    1920
agacttgtct tgcaaacacc gaactgaaaa atcagaatct gaccaacctg tttccctgga    1980
taacttcact caatccttgc taaacacttg ggatccaaaa gtcccagatg tagatatcaa    2040
agaagatcaa gatacctcaa agaattctaa gctaaactca caccagaaag taacacttct    2100
tcaattgcta cttggccata agaatgaaga aaatgtagaa aaaaacacca gccctcaggg    2160
```

```
agtacacaat gatgtgagca agttcaatac acaaaattat gcaaggactt ctgtgataga    2220
aagccccagt acaaatcgga ctactccagt gagcactcca cctttactta catcaagcaa    2280
agcagggtct cccatcaatc tctctcaaca ctctctggtc atcaaatgga attccccacc    2340
atatgtctgc agtactcagt ctgaaaagct aacaaatact gcatctaacc actcaatgga    2400
ccttacaaaa agcaaagacc caccaggaga gaaaccagcc caaaatgaag gtgcacagaa    2460
ctctgcaacg tttagtgcca gtaagctgtt acaaaattta gcacaatgtg aatgcagtc    2520
atccatgtca gtggaagagc agagacccag caaacagctg ttaactggaa acacagataa    2580
accgataggt atgattgata gattaaatag ccctttgctc tcaaataaaa caaatgcagt    2640
tgaagaaaat aaagcattta gtagtcaacc aacaggtcct gaaccagggc tttctggttc    2700
tgaaatagaa aatctgcttg aaagacgtac tgtcctccag ttgctcctgg ggaaccccaa    2760
caaagggaag agtgaaaaaa aagagaaaac tcccttaaga gatgaaagta ctcaggaaca    2820
ctcagagaga gctttaagtg aacaaatact gatggtgaaa ataaaatctg agccttgtga    2880
tgacttacaa attcctaaca caaatgtgca cttgagccat gatgctaaga gtgccccatt    2940
cttgggtatg gctcctgctg tgcagagaag cgcacctgcc ttaccagtgt ccgaagactt    3000
taaatcggag cctgtttcac ctcaggattt ttctttctcc aagaatggtc tgctaagtcg    3060
attgctaaga caaatcaag atagttacct ggcagatgat tcagacagga gtcacagaaa    3120
taatgaaatg gcacttctag aatcaaagaa tctttgcatg gtccctaaga aaaggaagct    3180
ttatactgag ccattagaaa atccatttaa aaagatgaaa acaacattg ttgatgctgc    3240
aaacaatcac agtgccccag aagtactgta tgggtccttg cttaaccagg aagagctgaa    3300
atttagcaga aatgatcttg aatttaaata tcctgctggt catggctcag ccagcgaaag    3360
tgaacacagg agttgggcca gagagagcaa aagctttaat gttctgaaac agctgcttct    3420
ctcagaaaac tgtgtgcgag atttgtcccc gcacagaagt aactctgtgg ctgacagtaa    3480
aaagaaagga cacaaaaata atgtgaccaa cagcaaacct gaatttagca tttcttcttt    3540
aaatggactg atgtacagtt ccactcagcc cagcagttgc atggataaca ggacattttc    3600
atacccaggt gtagtaaaaa ctcctgtgag tcctactttc cctgagcact gggctgtgc    3660
agggtctaga ccagaatctg ggcttttgaa tgggtgttcc atgcccagtg agaaaggacc    3720
cattaagtgg gttatcactg atgcggagaa gaatgagtat gaaaaagact ctccaagatt    3780
gaccaaaaacc aacccaatac tatattacat gcttcaaaaa ggaggcaatt ctgttaccag    3840
tcgagaaaca caagacaagg acatttggag ggaggcttca tctgctgaaa gtgtctcaca    3900
ggtcacagcc aaagaagagt tacttcctac tgcagaaacg aaagcttctt tctttaattt    3960
aagaagccct tacaatagcc atatgggaaa taatgcttct cgcccacaca gcgcaaatgg    4020
agaagtttat ggacttctgg gaagcgtgct aacgataaag aaagaatcag aataaaatgt    4080
acctgccatc cagtttttgga tcttttttaaa actaatgagt atgaacttga gatctgtata    4140
aataagagca tgatttgaaa aaaagcatgg tataattgaa actttttttca tttttgaaaag    4200
tattggttac tggtgatgtt gaaatatgca tactaatttt tgcttaacat tagatgtcat    4260
gaggaaaacta ctgaactagc aattggttgt ttaacacttc tgtatgcatc agataacaac    4320
tgtgagtagc ctatgaatga aattctttta taaatattag gcataaatta aaatgtaaaa    4380
ctccattcat agtggattaa tgcattttgc tgcctttatt agggtacttt attttgcttt    4440
tcagaagtca gcctacataa cacattttta aagtctaaac tgttaaacaa ctctttaaag    4500
gataattatc caataaaaaa aaacctagtg ctgattcaca gcttattatc caattcaaaa    4560
```

```
ataaattaga aaaatatatg cttacatttt tcacttttgc taaaaagaaa aaaaaaaggt  4620 gtttatttt  aactcttgga agaggttttg tggttcccaa tgtgtctgtc ccaccctgat  4680 cctttcaat  atatatttct ttaaaccttg tgctacttag taaaaattga ttacaattga  4740
gggaagtttg atagatcctt taaaaaaaag gcagatttcc attttttgta ttttaactac  4800
tttactaaat taatactcct ccttttacag aattagaaaa gttaacattt atctttaggt  4860
ggtttcctga aaagttgaat atttaagaaa ttgttttaa  cagaagcaaa atggctttc   4920 tttggacagt tttcaccatc tcttgtaaaa gttaattctc accattcctg tggtacctgc  4980
gagtgttatc accaggattc cttaaacctg aactcagacc acttgcatta gaaccatctg  5040
gagcacttgt tttaaaatgc agattcatag gcagcatctc agatctacag aacaagaatc  5100
tctgctaagt ggacctggaa tcttccatct gcatcttaac atgctctcta ggtgtttctt  5160
gtgtttgaga accatgactt atgactttcc tcagaacatg agactgtaaa acaaaaacaa  5220
aaaactatgt gatgcctcta ttttccccaa tacagtcaca catcagctca aaatttgcaa  5280
tattgtagtt catatattac cgttatgtct ttggaaatcg ggttcagaac acttttatg   5340 acaaaaattg ggtggagggg ataactttca tatctggctc aacatctcag gaaaatctgt  5400
gattatttgt gtgttctaat gagtaacatc tacttagtta gccttaggga tggaaaaaca  5460
gggccactta ccaaactcag gtgattccag gatggtttgg aaacttctcc tgaatgcatc  5520 cttaacctt  attaaaacca ttgtcctaag aacaatgcca acaaagctta caacatttag  5580
tttaaaccca agaagggcac taaactcaga ttgactaaat aaaaagtaca aagggcacat  5640
atacgtgaca gaattgtaca caatcactcc attggatctt ttactttaaa gtagtgatga  5700
aaagtacatg ttgatactgt cttagaagaa attaatatat tagtgaagcc acatggggtt  5760
tcagttgcga aacaggtctg tttttatgtt cagtttgtac aatccacaat tcattcacca  5820
gatattttgt tcttaattgt gaaccaggtt agcaaatgac ctatcaaaaa ttattctata  5880
atcactacta gttaggatat tgatttaaaa ttgttctact tgaagtggtt tctaagattt  5940
ttatattaaa aataggtgtg atttcctaat atgatctaaa accctaaatg gttattttc   6000 ctcagaatga tttgtaaata gctactggaa atattataca gtaataggag tgggtattat  6060
gcaacatcat ggagaagtga aggcataggc ttattctgac ataaaattcc actggccagt  6120
tgaatatatt ctattccatg tccatactat gacaatctta ttgtcaacac tatataaata  6180
agcttttaaa caagtcattt ttcttgatcg ttgtggaagg tttggagcct tagaggtatg  6240
tcagaaaaaa tatgttggta ttctcccttg ggtagggga  aatgaccttt ttacaagaga  6300
gtgaaattta ggtcagggaa aagaccaagg gccagcattg ctacttttgt gtgtgtgtgt  6360
gtgggttttg ttttgtttt  ttggttggct ggttgttttc gttgttgtta acaaaggaat  6420
gagaatatgt aatacttaaa taaacatgac cacgaagaat gctgttctga tttactagag  6480
aatgttccca atttgaattt agggtgattt taaagaacag tgagaaaggg catacatcca  6540
cagattcact ttgtttatgc atatgtagat acaaggatgc acatatacac attttcaagg  6600
actattttag atatctagac aatttcttct aataaagtca tttgtgaaag ggtactacag  6660
cttattgaca tcagtaaggt agcattcatt acctgtttat tctctgctgc atcttacaga  6720
agagtaaact ggtgagagta tatttttat  atatatatat atatatatat atataatatg  6780
tatatatata tatattgact tgttacatga agatgttaaa atcggttttt aaaggtgatg  6840
taaatagtga tttccttaat gaaaaataca tattttgtat tgttctaatg caacagaaaa  6900
```

```
gccttttaat ctctttggtt cctgtatatt ccatgtataa gtgtaaatat aatcagacag    6960
gtttaaaagt tgtgcatgta tgtatacagt tgcaagtctg acaaatgta tagaataaac      7020 cttttattta agttgtgatt acctgctgca tgaaaagtgc atgggggacc ctgtgcatct    7080
gtgcatttgg caaaatgtct taacaaatca gatcagatgt tcatcctaac atgacagtat    7140
tccatttctg acatgacgt ctgtggttta agctttgtga aagaatgtgc tttgattcga     7200
agggtcttaa agaattttt taatcgtcaa ccacttttaa acataaagaa ttcacacaac     7260
tactttcatg aatttttaa tcccattgca aacattattc caagagtatc ccagtattag     7320
caatactgga ataggcac attaccattc atagtaagaa ttctggtgtt tacacaacca     7380
aatttgatgc gatctgctca gtaatataat ttgccatttt tattagaaat ttaatttctt    7440
catgtgatgt catgaaactg tacatactgc agtgtgaatt tttttgtttt gtttttttaat   7500 cttttagtgt ttacttcctg cagtgaattt gaataaatga gaaaaaatgc attgtc         7556

<210> SEQ ID NO 37
<211> LENGTH: 1516
<212> TYPE: DNA
<213> ORGANISM: Homo sapiens
<220> FEATURE:
<223> OTHER INFORMATION: RAC2 glucocorticoid receptor-responsive gene

<400> SEQUENCE: 37
tgccccacca ccgctgctcc tcagcaggcg cctcaccagc ctccacaccc cttgcgcccg    60
cagaaacgcg cctggccctg agctgtcacc accgacactc tccaggctcc ggacacgatg   120
caggccatca agtgtgtggt ggtgggagat ggggccgtgg gcaagacctg ccttctcatc   180
agctacacca ccaacgcctt tcccggagag tacatcccca ccgtgtttga caactattca   240
gccaatgtga tggtggacag caagccagtg aacctggggc tgtgggacac tgctgggcag   300
gaggactacg accgtctccg gccgctctcc tatccacaga cggacgtctt cctcatctgc   360 ttctcccctcg tcagcccagc ctcttatgag aacgtccgcg ccaagtggtt cccagaagtg   420
cggcaccact gccccagcac acccatcatc ctggtgggca ccaagctgga cctgcgggac   480
gacaaggaca ccatcgagaa actgaaggag aagaagctgg ctcccatcac ctacccgcag   540
ggcctggcac tggccaagga gattgactcg gtgaaatacc tggagtgctc agctctcacc   600
cagagaggcc tgaaaaccgt gttcgacgag gccatccggg ccgtgctgtg ccctcagccc   660
acgcggcagc agaagcgcgc ctgcagcctc ctctaggggt tgcaccccag cgctcccacc   720
tagatgggtc tgatcctcca ggatccccac ccaaagcctg atggcacccc ggctggccat   780
gctgtcccct ccctgtggcg tttcttagca gatggctgca gagcttcgtt gatggtcttt    840
tctgtactgg aggcctcctg aggccaggaa cgtgcaaatt tgcaggtgct gcatcccaag    900
cccctcatgc tcctgccttc ctgagggcca gagggagcc ccaggaccca ttaagccacc    960
cccgtgttcc tgccgtcagt gccaactgcc gcatgtggaa gcatctaccc gttcactcca   1020
gtcccacccc acgcctgact ccctctgga aactgcaggc cagatggttg ctgccacaac   1080
ttgtgtacct tcaggatgg ggctcttact ccctcctgag gccagctgct ctaatatcga   1140
tggtcctgct tgccagagag ttcctctacc cagcaaaaat gagtgtctca gaagtgtgct   1200
cctctggcct cagttctcct cttttggaac aacataaaac aaatttaatt ttctacgcct    1260
ctggggatat ctgctcagcc aatggaaaat ctgggttcaa ccagcccctg ccatttctta   1320
agactttctg ctgcactcac aggatcctga gctgcactta cctgtgagag tcttcaaact   1380
tttaaacctt gccagtcagg acttttgcta ttgcaaatag aaaacccaac tcaacctgct   1440
```

```
taagcagaaa ataaatttat tgattcaaaa aaaaaaaaaa aaaaaaaaaa aaaaaaaaaa    1500
aaaaaaaaaa aaaaaa                                                    1516

<210> SEQ ID NO 38
<211> LENGTH: 1641
<212> TYPE: DNA
<213> ORGANISM: Homo sapiens
<220> FEATURE:
<223> OTHER INFORMATION: SPP1 glucocorticoid receptor-responsive gene

<400> SEQUENCE: 38
ctccctgtgt tggtggagga tgtctgcagc agcatttaaa ttctgggagg gcttggttgt      60
cagcagcagc aggaggaggc agagcacagc atcgtcggga ccagactcgt ctcaggccag     120
ttgcagcctt tcagccaaa cgccgaccaa ggaaaactca ctaccatgag aattgcagtg      180
atttgctttt gcctcctagg catcacctgt gccataccag ttaaacaggc tgattctgga     240
agttctgagg aaaagcagct ttacaacaaa tacccagatg ctgtggccac atggctaaac     300
cctgacccat ctcagaagca gaatctccta gccccacaga atgctgtgtc ctctgaagaa     360
accaatgact ttaaacaaga gacccttcca agtaagtcca acgaaagcca tgaccacatg     420
gatgatatgg atgatgaaga tgatgatgac catgtggaca gccaggactc cattgactcg     480
aacgactctg atgatgtaga tgacactgat gattctcacc agtctgatga gtctcaccat     540
tctgatgaat ctgatgaact ggtcactgat tttcccacgg acctgccagc aaccgaagtt     600
ttcactccag ttgtccccac agtagacaca tatgatggcc gaggtgatag tgtggtttat     660
ggactgaggt caaaatctaa gaagtttcgc agacctgaca tccagtaccc tgatgctaca     720
gacgaggaca tcacctcaca catggaaagc gaggagttga atggtgcata caggccatc      780 cccgttgccc aggacctgaa cgcgccttct gattgggaca gccgtgggaa ggacagttat     840
gaaacgagtc agctggatga ccagagtgct gaaaccccaca gccacaagca gtccagatta     900
tataagcgga aagccaatga tgagagcaat gagcattccg atgtgattga tagtcaggaa     960 cttttccaaag tcagccgtga attccacagc catgaatttc acagccatga agatatgctg    1020
gttgtagacc ccaaaagtaa ggaagaagat aaacacctga atttcgtat ttctcatgaa     1080 ttagatagtg catcttctga ggtcaattaa aaggagaaaa aatacaattt ctcactttgc    1140
atttagtcaa aagaaaaaat gctttatagc aaatgaaag agaacatgaa atgcttcttt    1200
ctcagtttat tggttgaatg tgtatctatt tgagtctgga ataactaat gtgtttgata     1260 attagtttag tttgtggctt catggaaact ccctgtaaac taaaagcttc agggttatgt    1320
ctatgttcat tctatagaag aaatgcaaac tatcactgta ttttaatatt tgttattctc    1380
tcatgaatag aaatttatgt agaagcaaac aaaatacttt tacccactta aaagagaat     1440 ataacatttt atgtcactat aatcttttgt tttttaagtt agtgtatatt ttgttgtgat    1500 tatcttttg tggtgtgaat aaatcttta tcttgaatgt aataagaatt tggtggtgtc      1560
aattgcttat ttgttttccc acggttgtcc agcaattaat aaaacataac cttttttact    1620
gcctaaaaaa aaaaaaaaaa a                                              1641

<210> SEQ ID NO 39
<211> LENGTH: 6463
<212> TYPE: DNA
<213> ORGANISM: Homo sapiens
<220> FEATURE:
<223> OTHER INFORMATION: PHF15 glucocorticoid receptor-responsive gene
```

<400> SEQUENCE: 39

```
ctctcttgct cgctcgctcc ctctctctcc tgctggctgc ctgttctagg aagccagcgc    60
ggagagggggg gggatgcaca gcacagggga gagagattgc gcatgttggt cagtcgtgtt   120
ttaaagagta cagtgcgggg aggctgagag gggcgcatgc aacaacaact tttggaagga   180
tggaagagaa gaggcgaaaa tactccatca gcagtgacaa ctctgacacc actgacagtc   240
atgcgacatc tacatccgca tcaagatgct ccaaactgcc cagcagcacc aagtcgggct   300
ggccccgaca gaacgaaaag aagccctccg aggttttccg gacagacttg atcacagcca   360
tgaagatccc ggactcatac cagctcagcc cggatgacta ctacatcctg gcagacccat   420
ggcgacagga atgggagaaa ggtgtgcagg tgcctgccgg ggcagaggcc atcccagagc   480
ccgtggtgag gatcctccca ccactggaag gccccctgc ccaggcatcc ccgagcagca   540
ccatgcttgg tgagggctcc cagcctgatt ggccagggggg cagccgctat gacttggacg   600
agattgatgc ctactggctg gagctcatca actcggagct taaggagatg gagaggccgg   660
agctggacga gctgacatta gagcgtgtgc tggaggagct ggagaccctg tgccaccaga   720
atatggccag ggccattgag acgcaggagg ggctgggcat cgagtacgac gaggatgttg   780
tctgcgacgt gtgtcgctct cctgagggcg aggatggcaa cgagatggtc ttctgtgaca   840
agtgcaacgt ctgtgtgcat caggcatgct acgggatcct caaggtgccc acgggcagct   900
ggctgtgccg gacgtgtgcc ctgggtgtcc agccaaagtg cctgctctgc cccaagcgag   960
gaggagcctt gaagcccact agaagtggga ccaagtgggt gcatgtcagc tgtgccctat  1020
ggattcctga ggtcagcatc ggctgcccag agaagatgga gcccatcacc aagatctcgc  1080
atatcccagc cagccgctgg gctctgtcct gcagcctctg caaggaatgc acaggcacct  1140
gcatccagtg ttcatgcct tcctgcgtca cagcgttcca tgtcacatgc gcctttgacc  1200
acggcctgga aatgcggact atattagcag acaacgatga ggtcaagttc aagtcattct  1260
gccaggagca cagtgacggg ggcccacgta atgagcccac atctgagccc acggaaccca  1320
gccaggctgg cgaggacctg gaaaaggtga ccctgcgcaa gcagcggctg cagcagctag  1380
aggaggactt ctacgagctg gtggagccgg ctgaggtggc tgagcggctg gacctggctg  1440
aggcactggt cgacttcatc taccagtact ggaagctgaa gaggaaagcc aatgccaacc  1500
agccgctgct gacccccaag accgacgagg tggacaacct ggcccagcag gagcaggacg  1560
tcctctaccg ccgcctgaag ctcttcaccc atctgcggca ggacctagag agggttagaa  1620
atctgtgcta catggtgaca aggcgcgaga gaacgaaaca cgccatctgc aaactccagg  1680
agcagatatt ccacctgcag atgaaactta ttgaacagga tctgtgtcga ggcctgtcca  1740
cctcattccc catcgatggc accttcttca acagctggct ggcacagtcg gtgcagatca  1800
cagcagagaa catggccatg agcgagtggc cactgaacaa tgggcaccgc gaggaccctg  1860
ctccagggct gctgtcagag gaactgctgc aggacgagga cactgctc agcttcatgc  1920
gggacccctc gctgcgacct ggtgaccctg ctaggaaggc ccgaggccgc acccgcctgc  1980
ctgccaagaa gaaaccacca ccaccaccac cgcaggacgg gcctggttca cggacgactc  2040
cagacaaagc cccaagaag acctgggccc aggatgcagg cagtggcaag gggggtcaag  2100
ggccacctac caggaagcca ccacgtcgga catcttctca cttgccgtcc agccctgcag  2160
ccggggactg tcccatccta gccacccctg aaagccccccc gccactggcc ctgagaccc  2220
cggacgaggc agcctcagta gctgctgact cagatgtcca agtgcctggc cctgcagcaa  2280
gccctaagcc tttgggccgg ctccggccac cccgcgagag caaggtaacc cggagagttgc  2340
```

```
cgggtgccag gcctgatgct gggatgggac caccttcagc tgtggctgag aggcccaagg    2400
tcagcctgca tttttgacact gagactgatg gctacttctc tgatggggag atgagcgact   2460
cagatgtaga ggccgaggac ggtggggtgc agcggggtcc ccgggaggca ggggcagagg    2520
aggtggtccg catgggcgta ctggcctcct aactcacccc cttccctgtc ccaggccctg    2580
ccctggtccc cccacaaggc ctcagcccag tcacaactgc catttccagt ctctgctgag    2640
tgtcccagac cctcgaggct gccactccgt cgtggtttta ttttaatat agagagagtt    2700 ttgaattcta cactgttgtc tttcctctgt gctggcctag acattagga ttccttccac     2760 ggctccggcc gctaggaccc tgccaggtcc cgcgcaccat ccctgccctg cccacgtggt    2820
attgctgggc tcctggctag atgcaagcaa ggtggacaag agctcaggac tccagcccac    2880
tgccactggg tgacacagac tgtcgtttgg gcattatttc atggcagatg ggccagtcca    2940
gggcctaccc cgccttgccc ccagatccca ctggggtcca tttgggggt cctgctacac     3000 tccaccgatc cccaaggaag tataataaac gatacccagc cagagtctac tcactgtcac    3060
aagcacaacg agtttatatg agaaagcact gagggggtgc agagggcccg ctagttccag    3120
gggaactgaa agctgttcct gatcagcccg tatcatctga ggcctgcctg cccaccctgc    3180
caccctcccc tcccttgctg ctctgcccct gccagtgccc agcccagcgg ctctgggaag    3240
gggttcccag aatccctcct gagctgtgcc atttactcag gggactccca acagccagc    3300 tgccagtgca ggtggagggc tgtaggggag ggccagtgcc cagacagggt catgggctc    3360 agaccagccc actgtagaga atcactctga ggctccaact tccttccttc cttcggggcc    3420
agtctcggcc gaagtctggt cacgctcaga cagagctgac cagaccagac cgtttgcctt    3480
ttcaagtttc ctagtcctgc tacaagatga gcttcttccg tggtttcctt ttggaaactc    3540
ctccttccaa caagcagtgg gatcccgggg cccagggcgg gccggtgttg gccgctgggg    3600
ctgttgtaag tcttgctgga tgttcccctg ttcctgagcc ttaacccctc gcacagccat    3660
cccccccccc gtcctgccat ccccccccgc cgtcctgcct tccccacccc acccttaggt    3720
cccaggtagt tgctctgaag agtttcagta gagtggcccc aggtgatag ctcagggaac     3780 aacaaaaaag gaattccgtg aaaacatttt tttttctttg atgaattact cctgggtcac    3840
ttccaccact ggtaaagcca gaacttctcc aaaaagaacc ttgcaaaaag tccagtgaat    3900
cagtcgaatc attctgtgga tgccaaagaa tattttgacc ataatacagc acagcctgga    3960
cctgacaact tgtcatttgg acttttttttt aaatggagtt ctttagcaac aaagtataga   4020
aacatgttca ttgcacacac ccaaggagaa gagctcaagc gcttggaaga ggatgctttg    4080
ctgctgctga agtgtacctg ggtgttagat ttcagatcct gggctgagcc cactgtgagc    4140
tttcctaaac tgtgagactc acagagggga aagatactga cggtgaaacc agcatggaaa    4200
acgtctttac catgtggttc cctcctcccc aaatacataa agcaaataag caggatgggg    4260
aacagcttga ccttcatcca cccctaactc caaaactatc aaggtacgac agtggcattg    4320
tcatcgacac tcaatttcat gtgaatttta gcaaacagg aaacaaagat aatgactcag     4380
ttcagaggat cggacaaatg tgtctagtcc gggtggactc ggagggagtg gggtgggctt    4440
caaggattct gggcgttggg atggcatgag ctaccctgta gagtttagtc tgcctgcccg    4500
ccttggtagt agtgaccagt cagtgtcagc atcagtgtcc caaccccagt ctctgtttac    4560
tgcctttgaa cagaacttct tccttcccca tgctttgggt cacctcgggc tgcaaccctg    4620
tctgtgccag attgcccggt ctgaccctgc aggaagcaaa gaggtgagct taaagaacaa    4680
```

```
ccaaactctg ccaggggtcc cagaaagccc agggtccagc agtctcagca cttggcccct      4740
tgccccttca caccatcctg gggcaggggc tgggcctccc tggtggcagg ggtgggtgga      4800
gaattaggga gagggtgcaa cgagtctggc cccttgcctc gggctggctg tgttcttcc       4860 aagagcctct gctcacattg ttggcctctg gattctggcc cttcttcatt ggctgttgct      4920
ttggactgga ctgttgctga gcctgtgtcc tgcagaaccc agatgtctgt taggctggct      4980
ggctgctgcg aggggagggg ggtggccttt catttgggt gccctttcac tcccaggcca       5040
agccctggag caatcttctt caggcagctg tctccacctc caggatgtcc agcaggctgc      5100
aaggagaagg atgccagcca cccatcctcc cccagttccc agcctttccc ctgttggtca      5160
cagccgcttc tgtcttttc cggtctactg tccccagtgt agagggcttt gctgtccctg       5220
agactgaggc aggttccttt tccaggtcag aggtggaggt agatcttct ctcaaccaca       5280 tctgcctcca cacacagctc ctccgcaggg aaggagaagc tgctctgtaa ctcattctgg      5340
ctatcgtccc ccttctcact gacctgaccg cccaccacct ccttccccct catcacatga      5400
caaaggataa tgtgcaagaa aagtatttt atgtatcata aatgtatttt gaaacaaatg       5460
agaagaagaa aggtagaagg gtttattta ttaaatgagc ctgacttagt gacagtgtgt       5520
gagcatttgc aatgtaaggg cctcagcttc cttggagaag ccaccccagg tttccagaca      5580
tagatgttga attgtttgtg ggggtgtgc caggccacgt ctcgtgtgtc cgtatgcagg       5640
catgcctgtg tatactgtgt atgggcacac tgggactagc tgggacaatt cctagagatt      5700
caactgccca attctaacca acattggcag cggctgaact tggcatttcc ttgctaactg      5760
ccagatgtgg ccaaccttg tccatatgca aaccactgaa aaatgatctg gatttctata      5820
gcaaggccct tggggagggc actctcccat gcccttggcc tcgctggcca cattggccaa      5880
tgagccaggc ctggagtctg agcctttgg ttgttcttta aggcacctcc tgccactttc       5940
tccctcagag gcacaaacac tttgtgttcc acgtcagttt gagggacgg tgggggatg        6000 atatgaatgt cacaggagga gacaccttct gtctttgttt caaagaaagt gatgtgccat      6060
ttgttaatat acaagagaaa tattgaaaat atattgaaaa gagcaatttt aaattatttt      6120
tggcttatgt tgcaatattt attttcttgt attagaaaag attcctttgt agagaaaaaa      6180
tgtatttttc attaacgcaa agacctattt ctccttttg tacattgtcc atgtgcgcaa       6240
cccttaacga gcaatagaat gtatggtcac ctgggtgtgg ccagtgcccg ctgtgccctg      6300
catgattctg tgttgccgct gctgcatagt tcccagcccc atcctgtcct gctcactcat      6360
gggggcttcc agaccccggc cccaccaggg cttgtgtcat agggagccct ttgcactcct      6420
cgtgtgttgg caaacgcagt taataaagca gtgttttctg tgc                       6463
```

<210> SEQ ID NO 40
<211> LENGTH: 2828
<212> TYPE: DNA
<213> ORGANISM: Homo sapiens
<220> FEATURE:
<223> OTHER INFORMATION: BTN3A2 glucocorticoid receptor-responsive gene

<400> SEQUENCE: 40

```
catagatgaa aatggcaagt tccctggctt tccttctgct caactttcat gtctccctcc        60
tcttggtcca gctgctcact ccttgctcag ctcagttttc tgtgcttgga ccctctgggc       120
ccatcctggc catggtgggt gaagacgctg atctgccctg tcacctgttc ccgaccatga       180
gtgcagagac catggagctg aagtgggtaa gttccagcct aaggcaggtg gtgaacgtgt       240
atgcagatgg aaaggaagtg gaagacaggc agagtgcacc gtatcgaggg agaacttcga       300
```

```
ttctgcggga tggcatcact gcagggaagg ctgctctccg aatacacaac gtcacagcct    360
ctgacagtgg aaagtacttg tgttatttcc aagatggtga cttctatgaa aaagccctgg    420
tggagctgaa ggttgcagca ctgggttcta atcttcacgt cgaagtgaag ggttatgagg    480
atggagggat ccatctggag tgcaggtcca ccggctggta cccccaaccc caaatacagt    540
ggagcaacgc caagggagag aacatcccag ctgtggaagc acctgtggtt gcagatggag    600
tgggcctata tgaagtagca gcatctgtga tcatgagagg cggctccggg gagggtgtat    660
cctgcatcat cagaaattcc ctcctcggcc tggaaaagac agccagcatt tccatcgcag    720
acccttctt caggagcgcc cagccctgga tcgcagccct ggcagggacc ctgcctatct    780
tgctgctgct tctcgccgga gccagttact tcttgtggag acaacagaag gaaataactg    840
ctctgtccag tgagatagaa agtgagcaag agatgaaaga atgggatat gctgcaacag    900
agcgggaaat aagcctaaga gagagcctcc aggaggaact caagaggaaa aaaatccagt    960
acttgactcg tggagaggag tcttcgtccg ataccaataa gtcagcctga tgctctaatg   1020
gaaaaatggc cctcttcaag cctggaaaaa tggctgaccc catggacacc tcctcaaact   1080
ctctgcagca gatgtaattc tgtatccaga catggcaaat gccatcctcc ttgtttctga   1140
ggaccagagg agtgtacagc gtgctgagga gccccatgac ctaccagaca accctgagag   1200
atttgaatgg cgttactgtg tgcttggctg tgaaagcttc atgtcagaga gacactactg   1260
ggaggtggaa gtggggggaca gaaaagagtg gcatattggg gtatgtagta agaacgtgga   1320
gaggaaaaaa gtttgggtca aaatgacacc ggagaacgga tactggacta tgggcctgac   1380
tgatgggaat aagtatcggg ctctcactga gcccagaacc aacctgaaac ttcctgagcc   1440
tcctaggaaa gtggggtca tcctggacta tgagactgga catatctcgt tctacaatgc   1500
cacggatgga tctcatatct acacatttct gcacgcctct tcctctgagc tctgtatcc   1560
tgtattcaga attttgacct ggagcccac tgccctgacc gtttgcccaa taccaaaagt   1620
agagagttcc cccgatcccg acctagtgcc tgatcattcc ctggagatac cactgacccc   1680
aggcttagct aatgaaagtg gggagcctca ggctgaagta acatctctgc ttctccctgc   1740
ccagcctgga gctaagggtc tcaccctcca caacagccag tcagaaccat aaagctacag   1800
gcacacactg aagcacttta ctgatattca ttcaattatt ccataggaca gttgtttgag   1860
tttggtgcca ccttattggc ccctttatac agataaggaa actggggtgt agaaaagtgt   1920
attgacttta caaagcagac aggaatagtg aacaacagag ctgggatctg aacaacaatg   1980
actaacatta tggagaatt taaaacgttc tgagtgctgt gttatgagct ttggtgggtg   2040
tcactccttt aatcctcaca acaccctgtc aggtagtctc atttggcaag tatggaagca   2100
gaggcagggc aacattaagt agcttacata actcacacgg taatttgtgc agttgggaga   2160
tgttcagctt cagtccctgg ccaattgccc gttcttttcc agcctgattt ttcctgcatg   2220
ggaagagccc acatgtagcc ctgaggttcc cttcccagga cagctccagg atcgagatca   2280
ctgtgagtgg ttgtggagtt aagaccccta tggactcctt cccagctgat tatcagagcc   2340
ttagacccag cactccttgg attggctctg cagagtgtct tggttgagag aataacgttg   2400
cagttcccac agggcatgtg actttgaaag agactagagg ccacactcag ttaataatgg   2460
ggcacagatg tgttcccacc caacaaatgt gataagtgat cgtgcagcca gagccagcct   2520
tccttcagtc aaggtttcca ggcagagcaa atacccctaga gattctctgt aatattggta   2580
atttggatga aggaagctag aagaattaca gggatgtttt taatcccact atggactcag   2640
```

```
tctcctggaa aaggatctgt ccactcctgg tcattggtgg atgttaaacc catattcctt    2700
tcaactgctg cctgctaggg aaaactgctc ctcattatca tcactattat tgctcaccac    2760
tgtatcccct ctactgggca agtgcttgtc aagttctagt tgttcaataa atttgttaat    2820
aatgctga                                                             2828
```

<210> SEQ ID NO 41
<211> LENGTH: 2698
<212> TYPE: DNA
<213> ORGANISM: Homo sapiens
<220> FEATURE:
<223> OTHER INFORMATION: SESN1 glucocorticoid receptor-responsive gene

<400> SEQUENCE: 41

```
gccgtccgtg ctgactgagg cgctgcagcc aggagccgcg gccggctgcc cagcgctcgc      60
cgcctccgcg cgtccgcagc cgtccccgcg ccgacatgcg cttggccgcc gccgcgaacg     120
aggcgtacac ggccccttg gcggtctcgg ggctgctggg ctgcaagcag tgcggcgggg     180
gccgcgacca ggacgaggaa cttggcatta gaattcctcg accactagga cagggaccaa     240
gcagattcat cccagaaaag gagatcctcc aagtggggag tgaagacgca cagatgcatg     300
ctttatttgc agattctttt gctgctttgg gccgtttgga taacattacg ttagtgatgg     360
ttttccaccc acaatattta gaaagtttct taaaaactca gcactatcta ctgcaaatgg     420
atgggccgtt acccctacat tatcgtcact acattggaat aatggctgcg gcaagacatc     480
agtgctccta cttagtgaac ctgcatgtaa atgatttcct tcatgttggt ggggacccca     540
agtggctcaa tggtttagag aatgctcctc aaaaactaca gaatttagga gaacttaaca     600
aagtgttagc ccatagacct tggcttatta ccaaagaaca cattgaggga cttttaaaag     660
ctgaagagca cagctggtcc cttgcggaat tggtacatgc agtagtttta ctcacacact     720
atcattctct tgcctcattc acattcggct gtggaatcag tccagaaatt cattgtgatg     780
gtggccacac attcagacct ccttctgtta gcaactactg catctgtgac attacaaatg     840
gcaatcacag tgtggatgag atgccggtca actcagcaga aaatgtttct gtaagtgatt     900
ctttctttga ggttgaagcc tcatggaaa agatgaggca gttacaggaa tgtcgagatg     960
aagaagaggc aagtcaggaa gagatggctt cacgttttga aatagaaaaa agagagagta    1020
tgtttgtctt ctcttcagat gatgaagaag ttacaccagc aagagctgta tctcgtcatt    1080
ttgaggatac tagttatggc tataaagatt tctctagaca tgggatgcat gttccaacat    1140
tcgtgtccca ggactattgc tgggaagatc atggttattc tttggtaaat cgcctttatc    1200
cagatgtggg acagttgatt gatgaaaaat ttcacattgc ttacaatctt acttataata    1260
caatggcaat gcacaaagat gttgatacct caatgcttag acgggcaatt tggaactata    1320
ttcactgcat gtttggaata agatatgatg attatgacta tggtgaaatt aaccagctat    1380
tggatcgtag ctttaaagtt tatatcaaaa ctgttgtttg cactcctgaa aaggttacca    1440
aaagaatgta tgatagcttc tggaggcagt tcaagcactc tgagaaggtt catgttaatc    1500
tgcttcttat agaagctagg atgcaagcag aactccttta tgctctgaga gccattaccc    1560
gctatatgac ctgatgcctt tccttcatta aagatgattc tggaatgatc agcagatata    1620
gtctacaagg gggaaggtac taagccccag gaccaatggt agacaaaata attcagaaat    1680
ccattgtgcc atgattcctt tagtttctgc tattttctg tggaaaacca ctgctggcac    1740
aagcagtgac tgtttggcag cttcaagttt agagctgtga agacaggctg ccattccacg    1800
tattttgctt tttgacagta caagatgctg tgtaactgtt ttaatacagc aaatagtaac    1860
```

```
tctccaaatc ctgttgcttt tatgttaaat aagataacaa gaattggagc atgcaaagaa      1920
tgggacttgg ataatgactt aagctttata tgtaaagaat tttagaagat cttggtgctg      1980
ctattcctgc tggaggaatg aatagatggc tgtttcagtt aagctattag taataaaagt      2040
gaacattgct actatctgag cctacataca taacttgtgt gatttcaaat taaacttgca      2100
ttatgtgtta attttcttgc atctaaaaaa gcatagaatt cctactcaca cagctcagca      2160
acaaccattt tgatggtaac agttaatttc tttcattagt ttttttaaatt cagggttctg     2220 gatattaaat taaaatggca ttcttaaaga ttttcttcaa aaagcaatcc taaatgaaag      2280
tgtgtaaatt ataagaagct ggcgatcttt tgatatgctg tttcacagga tcctgacact      2340
ggagggcagc tgtcttgtgc attacttgtg tttccagcac caaagttgtg ggacatgttg      2400
ctgtagactg ctgcgcagtc ctgggtgcat tcagtctctc tgcctctgcc tgcctcctgg      2460
tccccacttt aaaggctgtg cagctcctta aataataaag ctggaaaata ttttagtcg       2520 ggttatcaaa tttgatttac aaaaacgcta actttgtttg aaatgcaaac aggttttgaaa    2580 atatgtatta agtactttgt attctggaag cgtgaattgc ttttgaagtc tgtcagtatt     2640
actggtattt ttaaataaag aagaattttt ctccaatttt aaaaaaaaaa aaaaaaaa       2698
```

<210> SEQ ID NO 42
<211> LENGTH: 5215
<212> TYPE: DNA
<213> ORGANISM: Homo sapiens
<220> FEATURE:
<223> OTHER INFORMATION: MAP3K5 glucocorticoid receptor-responsive gene

<400> SEQUENCE: 42

```
cgagcgcggc gcccttgagc tgcaccgcgg cgcaggtttg cgagccgact tgtcagccgg       60
ccaagaaaag gaagctccgt cccttcccgc tcacccggct tccccacccc ttgtactcta      120
aactctgcag agggcgagcg cgcgcggccac ggaggcgccg aggaggagcg agccgccgcc    180
gggcagcggc gtgccctcgg gggagagggc gccggagagg aggcggcggc gcggcggcga      240
gggcgcggcg cgcgatggca gctgcttagc ccggcgggcg cggagcagcc ccgagctgtg      300
gctggccagg cggtgcggct gggcggggga cgccgccgcc gttgctgccc ggcccggaga      360
gatgagcacg gaggcggacg agggcatcac tttctctgtg ccaccccttcg cccccctcggg   420 cttctgcacc atccccgagg gcggcatctg caggagggga ggagcggcgg cggtgggcga      480
gggcgaggag caccagctgc caccgccgcc gccgggcagc ttctggaacg tggagagcgc      540
cgctgcccct ggcatcggtt gtccggcggc cacctcctcg agcagtgcca cccgaggccg      600 ggcagctct gttggcgggg gcagccgacg gaccacggtg gcatatgtga tcaacgaagc       660
gagccaaggg caactggtgg tggccgagag cgaggccctg cagagcttgc gggaggcgtg      720
cgagacagtg ggcgccaccc tggaaaccct gcattttggg aaactcgact ttggagaaac      780
caccgtgctg gaccgctttt acaatgcaga tattgcggtg gtggagatga gcgatgcctt      840
ccggcagccg tccttgtttt accaccttgg ggtgagagaa agtttcagca tggccaacaa      900
catcatcctc tactgtgata ctaactcgga ctctctgcag tcactgaagg aaataaatttg     960 ccagaagaat actatgtgca ctgggaacta caccctttgtt ccttacatga taactccaca    1020
taacaaagtc tactgctgtg acagcagctt catgaagggg ttgacagagc tcatgcaacc     1080
gaacttcgag ctgcttcttg gacccatctg cttacctctt gtggatcgtt ttattcaact     1140
tttgaaggtg gcacaagcaa gttctagcca gtacttccgg gaatctatac tcaatgacat     1200
```

```
caggaaagct cgtaatttat acactggtaa agaattggca gctgagttgg caagaattcg     1260
gcagcgagta gataatatcg aagtcttgac agcagatatt gtcataaatc tgttactttc     1320
ctacagagat atccaggact atgattctat tgtgaagctg gtagagactt tagaaaaact     1380
gccaaccttt gatttggcct cccatcacca tgtgaagttt cattatgcat ttgcactgaa     1440
taggagaaat ctccctggtg acagagcaaa agctcttgat attatgattc ccatggtgca     1500
aagcgaagga caagttgctt cagatatgta ttgcctagtt ggtcgaatct acaaagatat     1560
gttttttggac tctaatttca cggacactga aagcagagac catggagctt cttggttcaa     1620
aaaggcatttt gaatctgagc caacactaca gtcaggaatt aattatgcgg tcctcctcct     1680
ggcagctgga caccagtttg aatcttcctt tgagctccgg aaagttgggg tgaagctaag     1740
tagtcttctt ggtaaaaagg gaaacttgga aaaactccag agctactggg aagttggatt     1800
ttttctgggg gccagcgtcc tagccaatga ccacatgaga gtcattcaag catctgaaaa     1860
gcttttaaa ctgaagacac cagcatggta cctcaagtct attgtagaga caattttaat     1920
atataagcat tttgtgaaac tgaccacaga acagcctgtg ccaagcaag aacttgtgga     1980
cttttggatg gatttcctgg tcgaggccac aaagacagat gttactgtgg ttaggttttcc    2040
agtattaata ttagaaccaa ccaaaatcta tcaaccttct tatttgtcta tcaacaatga     2100
agttgaggaa aagacaatct ctatttggca cgtgcttcct gatgacaaga aggtataca     2160
tgagtggaat tttagtgcct cttctgtcag gggagtgagt atttctaaat ttgaagaaag     2220
atgctgcttt ctttatgtgc ttcacaattc tgatgatttc caaatctatt tctgtacaga     2280
acttcattgt aaaaagtttt ttgagatggt gaacaccatt accgaagaga aggggagaag     2340
cacagaggaa ggagactgtg aaagtgactt gctggagtat gactatgaat atgatgaaaa     2400
tggtgacaga gtcgttttag gaaaaggcac ttatgggata gtctacgcag gtcgggactt     2460
gagcaaccaa gtcagaattg ctattaagga aatcccagag agagacagca gatactctca     2520
gcccctgcat gaagaaatag cattgcataa acacctgaag cacaaaaata ttgtccagta     2580
tctgggctct ttcagtgaga atggttttcat taaaatcttc atggagcagg tccctggagg     2640
aagtctttct gctctccttc gttccaaatg gggtccatta aaagacaatg agcaaacaat     2700
tggcttttat acaaagcaaa tactggaagg attaaaatat ctccatgaca atcagatagt     2760
tcaccgggac ataaagggtg acaatgtgtt gattaatacc tacagtggtg ttctcaagat     2820
ctctgacttc ggaacatcaa agaggcttgc tggcataaac ccctgtactg aaacttttac     2880
tggtacccctc cagtatatgg caccagaaat aatagataaa ggaccaagag gctacggaaa     2940
agcagcagac atctggtctc tgggctgtac aatcattgaa atggccacag aaaaccccc      3000
atttatgaa ctgggagaac cacaagcagc tatgttcaag gtgggaatgt taaagtcca      3060
ccctgagatc ccagagtcca tgtctgcaga ggccaaggca ttcatactga atgtttttga     3120
accagatcct gacaagagag cctgtgctaa cgacttgctt gttgatgagt ttttaaaagt     3180
ttcaagcaaa aagaaaaaga cacaacctaa gctttcagct ctttcagctg gatcaaatga     3240
atatctcagg agtatatcct tgccggtacc tgtgctggtg gaggacacca gcagcagcag     3300
tgagtacggc tcagttttcac ccgacacgga gttgaaagtg gacccccttct ctttcaaaac     3360
aagagccaag tcctgcggag aaagagatgt caagggaatt cggacactct ttttgggcat     3420
tccagtgagg aattttgaag atcacagtgc tcctccttcc cctgaagaaa agattctgg      3480
attcttcatg ctgaggaagg acagtgagag gcgagctacc cttcacagga tcctgacgga     3540
agaccaagac aaaattgtga gaaacctaat ggaatcttta gctcagggg ctgaagaacc     3600
```

```
gaaactaaaa tgggaacaca tcacaaccct cattgcaagc ctcagagaat ttgtgagatc    3660
cactgaccga aaaatcatag ccaccacact gtcaaagctg aaactggagc tggacttcga    3720
cagccatggc attagccaag tccaggtggt actctttggt tttcaagatg ctgtcaataa    3780
agttcttcgg aatcataaca tcaagccgca ctggatgttt gccttagaca gtatcattcg    3840
gaaggcggta cagacagcca ttaccatcct ggttccagaa ctaaggccac atttcagcct    3900
tgcatctgag agtgatactg ctgatcaaga agacttggat gtagaagatg accatgagga    3960
acagccttca aatcaaactg tccgaagacc tcaggctgtc attgaagatg ctgtggctac    4020
ctcaggcgtg agcacgctca gttctactgt gtctcatgat tcccagagtg ctcaccggtc    4080
actgaatgta cagcttggaa ggatgaaaat agaaccaat agattactgg aagaattggt    4140
tcggaaagag aaagaattac aagcactcct tcatcgagct attgaagaaa agaccaaga    4200 aattaaacac ctgaagctta gtcccaacc catagaaatt cctgaattgc ctgtatttca    4260
tctaaattct tctggcacaa atactgaaga ttctgaactt accgactggc tgagagtgaa    4320
tggagctgat gaagacacta taagccggtt tttggctgaa gattatacac tattggatgt    4380
tctctactat gttacacgtg atgacttaaa atgcttgaga ctaaggggag ggatgctgtg    4440
cacactgtgg aaggctatca ttgactttcg aaacaaacag acttgactgt tgctcaatct    4500
aatcttcgat ggaaattcta aaattaata cagagctgat cttcttgggg gtgggaaaat    4560
cgaagggaga ggagaaaggc gctgcacttt aaatccagta tttgtttact catgttaaaa    4620
aaaaaaaaaa cagacaaaac acactgaaat ttcctaacta catctatttc tataatttt    4680 aaggactctt cataaggact cttaaaataa tcctgaacat tagaacccta atgttcagga    4740 agatttaat ctaagcattt ttatggaaat attttttaatg cagcagctat tgcacttcag    4800
ccaaatgttt atttcacaca aaacggatgt aacatttcat gtgatcgtgc accactggaa    4860
caaaaccaaa atgtgaccat aactgtttag gcttctgtgt gtttgtaata tgctctaata    4920
atctgagtag aaatgcgtaa tttcaattac tgtataaagt ttatgttttt ttaagtgtgc    4980
agaatctgag agcaatggtt tttacttctc tgtgttaatt gtaatattga ctctattttg    5040
taacttaagt ttctgacctg tcgtacattt gtttgagtcg tttatgtact actgaactgt    5100
accagttgca catgcttgaa ctgtagtaat gttagcttgt tctaaagcta tccattgtgt    5160
catatttact ctaaaaatta aagagactct caacaaaaaa aaaaaaaaaa aaaaa          5215
```

<210> SEQ ID NO 43
<211> LENGTH: 4655
<212> TYPE: DNA
<213> ORGANISM: Homo sapiens
<220> FEATURE:
<223> OTHER INFORMATION: DPYSL2 glucocorticoid receptor-responsive gene

<400> SEQUENCE: 43

```
tctgtgcacc ttgcggtggg cggcgaacgg cagccgcggc agcagctagg gggcttgtgc      60
acacagcgag ggagacttag ggactggcag acggacggac ggacggcgag gaccctaccc     120
gagcccccga gccatggccg agagaaagca atccgggaag gcggcagagg acgaagaggt     180
ccctgctttt tttaaaaacc tgggctccgg cagccccaag ccccggcaga aattctgtgg     240
catgttctgc ccggtggaag ggtcctcgga gaacaagacc atcgacttcg actcgctgtc     300
ggtgggccgg ggctcggggc aggtggtggc tcagcagcgg gacgtcgccc acttgggccc     360
ggacccgcag ccgccgtact cgcggcaggg ccggcgcgcc ggcggagagc catctgttga     420
```

```
atcgggccgg aaggtggaga tccggagggc ctcgggcaaa gaagccctgc agaacatcaa    480
cgaccagagc gatcgtcttc tgatcaaagg aggtaaaatt gttaatgatg accagtcgtt    540
ctatgcagac atatacatgg aagatggggtt gatcaagcaa ataggagaaa atctgattgt    600
gccaggagga gtgaagacca tcgaggccca ctcccggatg gtgatcccg gaggaattga    660
cgtccacact cgtttccaga tgcctgatca gggaatgacg tctgctgatg atttcttcca    720
aggaaccaag gcggccctgg ctgggggaac cactatgatc attgaccacg ttgttcctga    780
gcctgggaca agcctgctcg ctgcctttga ccagtggagg gaatgggccg acagcaagtc    840
ctgctgtgac tactctctgc atgtggacat cagcgagtgg cataagggca tccaggagga    900
gatggaagcg cttgtgaagg atcacggggt aaattccttc ctcgtgtaca tggctttcaa    960
agatcgcttc cagctaacgg attgccagat ttatgaagta ctgagtgtga tccgggatat   1020
tggcgccata gcccaagtcc acgcagaaaa tggcgacatc attgcagagg agcagcagag   1080
gatcctggat ctgggcatca cgggcccga gggacatgtg ctgagccgac ctgaggaggt   1140
cgaggccgaa gccgtgaatc gtgccatcac catcgccaac cagaccaact gcccgctgta   1200
tatcaccaag gtgatgagca aaagctctgc tgaggtcatc gcccaggcac ggaagaaggg   1260
aactgtggtg tatggcgagc ccatcactgc cagcttggga acggacggct cccattactg   1320
gagcaagaac tgggccaagg ctgctgcctt tgtcacctcc ccaccccttga gccctgatcc   1380
aaccactcca gactttctca actccttgct gtcctgtgga gacctccagg tcacgggcag   1440
tgcccattgc acgtttaaca ctgcccagaa ggctgtagga aaggacaact tcaccctgat   1500
tccggagggc accaatggca ctgaggagcg gatgtccgtc atctgggaca aggctgtggt   1560
cactgggaag atggatgaga accagtttgt ggctgtgacc agcaccaatg cagccaaagt   1620
cttcaacctt taccccggga aaggccgcat tgctgtggga tccgatgccg acctggtcat   1680
ctgggacccc gacagcgtta aaaccatctc tgccaagaca cacaacagct ctctcgagta   1740
caacatcttt gaaggcatgg agtgccgcgg ctccccactg gtggtcatca gccaggggaa   1800
gattgtcctg gaggacggca ccctgcatgt caccgaaggc tctggacgct acattccccg   1860
gaagcccttc cctgattttg tttacaagcg tatcaaggca aggagcaggc tggctgagct   1920
gagagggggtt cctcgtggcc tgtatgacgg acctgtgtgt gaagtgtctg tgacgcccaa   1980
gacagtcact ccagcctcct cggccaagac gtctcctgcc aagcagcagg ccccaccctgt   2040
ccggaacctg caccagtctg gattcagttt gtctggtgct cagattgatg acaacattcc   2100
ccgccgcacc cccagcgta tcgtggccgc ccccggtggc cgtgccaaca tcaccagcct   2160
gggctagagc tcctgggctg tgccgtccac tggggactgg ggatgggaca cctgaggaca   2220
ttctgagact tctttcttcc ttcctttttt ttttttttgtt ttttttttta agagcctgtg   2280
atagttactg tggagcagcc agttcatggg gtcccccttg ggccccaca ccccgtctct   2340
caccaagagt tactgatttt gctcatccac ttccctacac atctatgggt atcacaccca   2400
agactaccca ccaagctcat acagggaacc acacccaaca cttagacatg cgaacaagca   2460
gcccccagcg agggtctcct tcgccttcaa cctcctagtg tctgttagca tcttcctttt   2520
catgggggga gggaagataa agtgaattgc ccagagctgc cttttctctt tcttttttaaa   2580
aattttaaga agttttcttt gtggggctgg ggaggggccg gggtcaggga gagtcttttt   2640
tttttttttt tttaaatact aaattggaac atttaattcc atattaatac aaggggtttg   2700
aactggacat cctaatgatg caattacgtc atcacccagc tgattccggg tggttggcaa   2760
actcatcgtg tctgtcctga gaggctccac aatgcccacc cgcatcgcca ttctgtagtc   2820
```

```
ttcagggtca gctgttgata aaggggcagg cttgcgttat tggcctagat tttgctgcag    2880
attaaatcct ttgaggattc tcttctcttt taccattttt ctgcgtgctc tcactctctc    2940
tttctctctc tagcttttta attcatgaat attttcgtgt ctgtctctct ctctctctgt    3000
gtttcctcca gcccttgtct cggagacggt gttttcctcc cttgcccat tatcttttca     3060 cctcccaggt ctaccatttc atggtggtcg ttgggtccgc ctaaaggatt tgagcgtttg    3120
ccattgcaag catagtgctg tgtcatcctg gtccatgtag gactggtgct aaccacctgc    3180
catcatgagg atgtgtgcta gagtgtggga ccctggccaa gtgcaggaat gggccatgcc    3240
gtctcaccca cagtatcaca cgtggaaccg cagacagggc ccagaagctt tagaggtatg    3300
aggctgcaga accggagaga ttttcctctg tgcagtgctc tctggctaaa gtcacggtca    3360
aacctaaaca ccgagcctca ttaacccaag tgaaccaacc aaagtcacca gttcagaagt    3420
gctaagctaa taggagtctg acccgagggc ctgctgcttc ctggttaagt atcttttgag    3480
attctagaac acatgggagc ttttatttt cggggaaaaa ccgtattttt tcttgtcca     3540 attatttcta aagacacact acatagaaag aggccctata aactcaaaaa gtcattggga    3600
aacttaaagt ctattctact ttgcaagagg agaaatgtgt tttatgaacg atagatcaca    3660
tcagaactcc tgtggggagg aaaccttata aattaaacac atggcccct tagagaccac     3720 aggtgatgtc tgtctccatc cttccctctc cttttctgtc acctttcccc ctagctggct    3780
cctttggacc taccctgtc cttgctgact tgtgttgcat tgtattccaa acgtgtttac     3840
aggttctctt aagcaatgtt gtatttgcag gcttttctga ataccaaatc tgcttttgt     3900 aaagcgtaaa aacatcacaa agtaggtcat tccatcacca cccttgtctc tctacacatt    3960 ttgccttttgg ggatctggtt gggqttttgg gttttttgtt gttgttgttt atttgttatt   4020
ttaaaggtaa attgcacttt taaaaaaata attggttgac ttaatatatt tgcttttttt    4080
ctcacctgca cttagaggaa atttgaacaa gttggaaaaa acaatttt gtttcaattc      4140 taagaaacac ttgcagctct agtattcact tgagtcttcc tgttttcct gtaccgggtc     4200 atggtaattt ttggttgttt tggttgtttt cttaaaaaac aagttaaaac ctgacgattt    4260
ctgcaggctg tgtaagcatg tttacctgtt ggcttgcttt gtgtgtctgt taaatgaatg    4320
tcatatgtaa atgctaaaat aaatcgacag tgtctcagaa ctgaataact gcagtgactt    4380
gatgctctaa aacagtgtag gatttaagaa tagatggttt ttaatcctgg aaattgtgat    4440
tgtgacccat gagtggagga actttcagtt ctaaagctga taaagtgtgt agccagaaga    4500 gtacttttt ttttgtaacc actgtcttga tggcaaaata attatggtaa aaacaagtc      4560 tcgtgtttat tattccttaa gaactctgtg ttatattacc atggaacgcc taataaagca    4620
aaatgtggtt gtttcaggaa aaaaaaaaa aaaaa                                4655
```

<210> SEQ ID NO 44  
<211> LENGTH: 4417  
<212> TYPE: DNA  
<213> ORGANISM: Homo sapiens  
<220> FEATURE:  
<223> OTHER INFORMATION: SEMA4D glucocorticoid receptor-responsive gene

<400> SEQUENCE: 44

```
gctgtaacac tcaccgtgaa ggtctgcagc ttcactcccg agccagcgag accacgaacc     60
caccagaagg aagaaactct gaacacatct gaacatcaga agggacagac tccagacgcg    120
ccaccactct gctaacacca gatagtggaa agaaaccatg tgctgaaatg tttgacgaca    180
```

```
ctgatggttt gactctgcta actggaatgg cttattgtgc aagaaagtac acctggtcgg    240
gtcctggggc tcatctctag caccagcaaa gatttctgaa gacgtctttc tagaaatgac    300
tggaaagttt caagaggcat aagatacagc atttcttctg aggccctgaa gaagtatcaa    360
gtgggctttg acattgcggt ggtgagagcg acccctcctc acctggagaa ctgggaaatg    420
tggattctca gggaccgcgc tgttcacgag ctccaggctg tgctgctggc cctggtcctg    480
gggcgctgag ccgcatctgc aatagcacac ttgcccggcc acctgctgcc gtgagccttt    540
gctgctgaag cccctggggt cgcctctacc tgatgaggat gtgcaccccc attagggggc    600
tgctcatggc ccttgcagtg atgtttggga cagcgatggc atttgcaccc ataccccgga    660
tcacctggga gcacagagag gtgcacctgg tgcagtttca tgagccagac atctacaact    720
actcagcctt gctgctgagc gaggacaagg acaccttgta cataggtgcc cgggaggcgg    780
tcttcgctgt gaacgcactc aacatctccg agaagcagca tgaggtgtat tggaaggtct    840
cagaagacaa aaaagcaaaa tgtgcagaaa aggggaaatc aaaacagaca gagtgcctca    900
actacatccg ggtgctgcag ccactcagcg ccacttccct ttacgtgtgt gggaccaacg    960
cattccagcc ggcctgtgac cacctgaact aacatccttt aagtttctg gggaaaaatg    1020 aagatggcaa aggaagatgt ccctttgacc cagcacacag ctacacatcc gtcatggttg    1080
atggagaact ttattcgggg acgtcgtata atttttgggg aagtgaaccc atcatctccc    1140
gaaattcttc ccacagtcct ctgaggacag aatatgcaat cccttggctg aacgagccta    1200
gtttcgtgtt tgctgacgtg atccgaaaaa gcccagacag ccccgacggc gaggatgaca    1260
gggtctactt cttcttcacg gaggtgtctg tggagtatga gtttgtgttc agggtgctga    1320
tcccacggat agcaagagtg tgcaagggggg accagggcgg cctgaggacc ttgcagaaga    1380
aatgaccctc cttcctgaaa gcccgactca tctgctcccg gccagacagc ggcttggtct    1440
tcaatgtgct gcgggatgtc ttcgtgctca ggtccccggg cctgaaggtg cctgtgttct    1500
atgcactctt caccccacag ctgaacaacg tggggctgtc ggcagtgtgc gcctacaacc    1560
tgtccacagc cgaggaggtc ttctcccacg ggaagtacat gcagagcacc acagtggagc    1620
agtcccacac caagtgggtg cgctataatg gcccggtacc caagccgcgg cctggagcgt    1680
gcatcgacag cgaggcacgg gccgccaact acaccagctc cttgaatttg ccagacaaga    1740
cgctgcagtt cgttaaagac cacccttga tggatgactc ggtaacccca atagacaaca    1800
ggcccaggtt aatcaagaaa gatgtgaact acacccagat cgtggtggac cggacccagg    1860
ccctggatgg gactgtctat gatgtcatgt ttgtcagcac agaccgggga gctctgcaca    1920
aagccatcag cctcgagcac gctgttcaca tcatcgagga gacccagctc ttccaggact    1980
ttgagccagt ccagaccctg ctgctgtctt caaagaaggg caacaggttt gtctatgctg    2040
gctctaactc gggcgtggtc caggccccgc tggccttctg tgggaagcac ggcacctgcg    2100
aggactgtgt gctggcgcgg gaccccctact gcgcctggag cccgcccaca gcgacctgcg    2160
tggctctgca ccagaccgag agcccagca gggggtttgat tcaggagatg agcggcgatg    2220
cttctgtgtg cccggcctcg tctcctaagc ccctccctcc tcctggctcc tcttccctgt    2280
cctgtctggg ccatgtgggg gacaggaggc tttcctctcc ctggaccccc tggccagcct    2340
cgggtgcggg gcccgacagc agctcgaggg tctccttgct gccgcccttc ctgagtgacc    2400
aggcacagca cgtgcacgcc ctggggaact tctacctctt ctgccaggcc acaggtcctg    2460
cagacattcg ctttgtctgg gagaagaatg ggcgagctct ggagacctgt gtccctgtgc    2520
agacccatgc actgcccgat ggcagggccc atgcactcag ctggctgcag gacgccatca    2580
```

```
gggaaagcgc tgagtatcgc tgctctgtcc tctcctcagc agggaacaag acttcgaagg    2640
tgcaggttgc tgtgatgaga cctgaagtga cccaccagga gaggtggacc agagagctct    2700
ctgcctggag ggctgtggct ggggagcacg accggatgat gcagagctgg aggaaggcgt    2760
gggaaagctg tagcaaggac accctgtagc caccaggaag gagtccctga caccgacctc    2820
aaccccaaca agaccctgct gccactgacc acagccaccc ccggagaagg cctggtcccc    2880
cacaactgtg aactgtcttg cccaagcctg ctctgaacac agccattggg ccaccacctg    2940
atgggcagag gcgggacagt ggagaagcct ggaacccaag tgggcctgtg acaggaacta    3000
agacttaaaa aattaggtgc ttacctggga cagtaagttc tgtctggcac aagcaggtaa    3060
ccaggatggc taacaggctt tgatagctgc tcgtgaacta aaacagcagg gtgtgtgcag    3120
gttcctcctc tacggtcagg cagcaggctc tgaaggctga tcctacaccg tcccagtgac    3180
tccccttgac agagtgcccc cacccccctaa tagccaacag ggttagcatg ccagcacag    3240 atcgctgctt ttattgatgc aaatcaagcc tgctgcttct cctccctgca gacttagcca    3300
aggaactcca agatgcatga ctgggacaag aaaaggtgag actccacatg gaaatgcctt    3360
gccctaaacc ttgaatgact gtgagatgcg atctgggagt gcatctgtca agtctttgtg    3420
ttttcttcac taacctcaga atactgggct ctattttatc aagcgctgca gtttatgcct    3480
ctgtcccgtc aatgctcagc ttctgcaaca ggacaccaaa cttgatgcag aaagccaaat    3540
aggtcaatta tgcaaatctc ctggtgccat attaaatttc ttgacgatgg aatgagtctc    3600
atgagtgttt tgttctacct gctttcaagt ctctaattat aaagctgta tctctgaaga    3660 ctgtgtcact gtgtgtgtga acttgtccta aagctactca gcctttaatc ttacacacac    3720
gtctcttctt gtctgttgaa tgacagtttt catgtctatc ataaaaccaa agcctctgtt    3780
aaaagtcaag ccgcacccct ctggtgatcc tagcaaatac tgagtgtctt cccagcagtg    3840
tgacaatgac ctgttttgca tcccctcttt ctggagctgg acaaattctc taccagcctt    3900
tgtgtgggat cagcatacat cgcctgctaa ttccttcagg atccatcaca acaggtgtcc    3960
tgaagatgct ggagacaccc tggttgtctc cacacgttcc ccctccgcac cccaagtcga    4020
gaggcccagc tgcctgtgag gtgtgtgctt gcccatccag ccaaggatgc cagtcttgct    4080
cacggaacca tcatactctc ataacctgaa gttttcctgt aaaatatcca tcagctcact    4140
gtggttcttg ctttgggtgt ggcttcaacc actacaaact gatgagtgaa atgctatggg    4200
ctttaggctt atattcttgg tgctgttttc tgtctcttct cctgaagtct ggatttcaag    4260
cactttcaca cttaacaaaa taattacata cttgaagttt tcgtaatgtg gagtgttcta    4320
ctgggaaatg gagttatgag gatgaatttc tgagtctttc tttgctctgc tggaaaaaat    4380
aaaaatagag ttgtacattg aaaaaaaaaa aaaaaaa                              4417
```

<210> SEQ ID NO 45
<211> LENGTH: 3108
<212> TYPE: DNA
<213> ORGANISM: Homo sapiens
<220> FEATURE:
<223> OTHER INFORMATION: STOM glucocorticoid receptor-responsive gene

<400> SEQUENCE: 45

```
gcctctggct cctcagggca ttcccggcgg ctccgggttt ggcaacgagg acgggggagt      60
gcgactgcgt ctcgggcagc atggccgaga agcggcacac acgggactcc gaagcccagc    120
ggctccccga ctccttcaag gacagcccca gtaagggcct tggaccttgc ggatggattt    180
```

```
tggtggcgtt ctcattctta ttcaccgtta aactttccc aatctcaata tggatgtgca    240
taaagattat aaaagagtat gaaagagcca tcatctttag attgggtcgc attttacaag   300
gaggagccaa aggacctggt tgtttttta ttctgccatg cactgacagc ttcatcaaag   360
tggacatgag aactatttca tttgatattc ctcctcagga gatcctcaca aaggattcag   420
tgacaattag cgtggatggt gtggtctatt accgcgttca gaatgcaacc ctggctgtgg   480
caaatatcac caacgctgac tcagcaaccc gtcttttggc acaaactact ctgaggaatg   540
ttctgggcac caagaatctt tctcagatcc tctctgacag agaagaaatt gcacacaaca   600
tgcagtctac tctggatgat gccactgatg cctggggaat aaaggtggag cgtgtggaaa   660
ttaaggatgt gaaactacct gtgcagctcc agagagctat ggctgcagaa gcagaagcgt   720
cccgcgaggc ccgcgccaag gttattgcag ccgaaggaga atgaatgca tccagggctc   780 tgaaagaagc ctccatggtc atcactgaat ctcctgcagc ccttcagctc cgatacctgc   840
agacactgac caccattgct gctgagaaaa actcaacaat tgtcttccct ctgcccatag   900
atatgctgca aggaatcata ggggcaaaac acagccatct aggctagtgt agagatgagc   960
gctagccttc caagcatgaa gtcggggacc aaattagcct ttaactcata aagagagggt  1020
agggcttttc ttttttccata tgtcaattgt ggtgttccca gaatgtatag cagttataaa  1080
aataggtgaa agaattgtta gcttgtaaat actgagagat tggtgattta tataaggtaa  1140
tctgttagtc ttaaaatagt taaaagtttg tattttaga ttattatgta gtaggttaga   1200
tccctcttgt tttgacttcc actgactcat tctgaacccc ctaagcaccc aggccagagg  1260
caagaacctg ggctgtaact gccacctgac accgctgact ggctaaatgc tttgcagaaa  1320
gtgatgacct tacaccacaa ccagcttctc caggtcatat gtgccttacc tccagagagt  1380
cttttttttt tttttttctga gatggagttt cactcttgtt gcccaggctg gagtgcaata  1440
gcatgatctc ggctcactgc aacctccgcc tcctgggttc aagagattct cctgcctcag  1500
cctccccagt agctgggatt acaggctcat gccaccatgc ccagctaatt tttgtattat  1560
tattattgtt ttttagtaga cggggggttt caccatgttg gccaggctag tcacgaactc  1620
ctaacctcag gtgatccacc cacctctgcc tcccaaagtg ctgggattac aggcatgagc  1680
taccacacct ggtttggaga gtcttaatta aggaaatttc cctaatgttc atttattttc  1740
taaatccaga ccgtgtttca gaataatcct tacttgagag tagccatttt cttgcctgta  1800
cttgtcagaa ctagaggaaa tagccaagac taatgaaaaa gattactcta acccttaaaa  1860
gacttttaaa ttcactacta gagtggtcat tttaaaaata catccatgtt ttaacttatt  1920
tgagccttct ttatgagtaa atgattcctc cttgttctgt ctttcaaacc agctaaatat  1980
ttgtcacaaa agtgcttttt tctcactgtt gcctattttc atatatcagg ttttaaatag  2040
ttttaatttt ttaataaaat tttctctacg ttctatatgc aattgttata tatctatttg  2100
aatagctgaa ggactaaaat actttttaa gagataactt caggaaacca ttatatttta  2160
ctatctgcat gctgttaact gtggtacact gtgaaatatg ttgattacaa acccattcat  2220
tacatagtat aaggaattca cagtatattg actatatagt gtctaatgat cttgggcaga  2280
tactgtcaaa cttacaatat ctatatagat gtaggtcttt ttaaatttac ctagtcattc  2340
ttctatcatg tatattgatg ctgaaagagg aactggtcag ctcctctgga caacaaattc  2400
ttagtctata atattaggag acatcttctg ttttgcaaat gtctgtgaat ctgagcaacc  2460
tggcattctg cttactggcc agaaagctgg cgggtgacat ttgtaacatt tcctctttga  2520
gactctgagt tcacctagag aagtctaagc ataacagctt tctttcccag cacgagcctt  2580
```

```
tatagctctc tttagctcaa ccactctgtc catccagcca atggatgtcc cttccctgt    2640 accccaattt caagcttatt ttaggaagcc ttgaactacc atgtatcctg gctcctagct    2700
gagtttatta gaggtatgga gcagtgcaac ttaaactcaa gttgcactta cattttgaat    2760
tttaaaatga tggtttatc tgttgtgtga agtggttcac ccttgaggac caggagcctc    2820
catatcctga ctgaaaacct tttctgagac ttagagtaac agtgcttttg gttccttgag    2880
ttctcctgtc tccagatacc aaatgacctt gactttctg ccttgtgaat tcgtagtcca    2940
atcagctgaa attaaatcac ttgggaggga cgcatagaag gagctctagg aacacagtgc    3000
cagtgcagaa gtttctccag gtggcctccc tttccaacaa tgtacataat aaagtgtatg    3060
cactttcact aataaaaaaa aaaaaaaaa aaaaaaaaa aaaaaaa               3108
```

<210> SEQ ID NO 46
<211> LENGTH: 4090
<212> TYPE: DNA
<213> ORGANISM: Homo sapiens
<220> FEATURE:
<223> OTHER INFORMATION: MAOA glucocorticoid receptor-responsive gene

<400> SEQUENCE: 46

```
gggcgctccc ggagtatcag caaaagggtt cgccccgccc acagtgcccg gctcccccg     60 ggtatcaaaa gaaggatcgg ctccgccccc gggctcccg ggggagttga tagaagggtc    120
cttcccaccc tttgccgtcc ccactcctgt gcctacgacc caggagcgtg tcagccaaag   180
catggagaat caagagaagg cgagtatcgc gggccacatg ttcgacgtag tcgtgatcgg   240
aggtggcatt tcaggactat ctgctgccaa actcttgact gaatatggcg ttagtgtttt   300
ggttttagaa gctcgggaca gggttggagg aagaacatat actataagga atgagcatgt   360
tgattacgta gatgttggtg agcttatgt gggaccaacc caaaacagaa tcttacgctt   420
gtctaaggag ctgggcatag agacttacaa agtgaatgtc agtgagcgtc tcgttcaata   480
tgtcaagggg aaaacatatc catttcgggg cgcctttcca ccagtatgga atcccattgc   540
atatttggat tacaataatc tgtggaggac aatagataac atggggaagg agattccaac   600
tgatgcaccc tgggaggctc aacatgctga caaatgggac aaaatgacca tgaaagagct   660
cattgacaaa atctgctgga caaagactgc taggcggttt gcttatcttt ttgtgaatat   720
caatgtgacc tctgagcctc acgaagtgtc tgccctgtgg ttcttgtggt atgtgaagca   780
gtgcgggggc accactcgga tattctctgt caccaatggt ggccaggaac ggaagtttgt   840
aggtggatct ggtcaagtga gcgaacggat aatggacctc ctcggagacc aagtgaagct   900
gaaccatcct gtcactcacg ttgaccagtc aagtgacaac atcatcatag agacgctgaa   960
ccatgaacat tatgagtgca atacgtaat taatgcgatc cctccgacct tgactgccaa    1020
gattcacttc agaccagagc ttccagcaga gagaaaccag ttaattcagc ggcttccaat    1080
gggagctgtc attaagtgca tgatgtatta caaggaggcc ttctggaaga gaaggatta    1140 ctgtggctgc atgatcattg aagatgaaga tgctccaatt tcaataacct ggatgacac    1200 caagccagat gggtcactgc ctgccatcat gggcttcatt cttgccggga agctgatcg    1260 acttgctaag ctacataagg aaataaggaa gaagaaaatc tgtgagctct atgccaaagt    1320
gctgggatcc caagaagctt tacatccagt gcattatgaa gagaagaact ggtgtgagga    1380
gcagtactct gggggctgct acacggccta cttccctcct gggatcatga ctcaatatgg    1440
aagggtgatt cgtcaacccg tgggcaggat tttctttgcg ggcacagaga ctgccacaaa    1500
```

-continued

```
gtggagcggc tacatggaag gggcagttga ggctggagaa cgagcagcta gggaggtctt    1560
aaatggtctc gggaaggtga ccgagaaaga tatctgggta caagaacctg aatcaaagga    1620
cgttccagcg gtagaaatca cccacacctt ctgggaaagg aacctgccct ctgtttctgg    1680
cctgctgaag atcattggat tttccacatc agtaactgcc ctggggtttg tgctgtacaa    1740
atacaagctc ctgccacggt cttgaagttc tgttcttatg ctctctgctc actggttttc    1800
aataccacca agaggaaaat attgacaagt ttaaaggctg tgtcattggg ccatgtttaa    1860
gtgtactgga tttaactacc tttggcttaa ttccaatcat tgttaaagta aaacaattc     1920 aaagaatcac ctaattaatt tcagtaagat caagctccat cttatttgtc agtgtagatc    1980
aactcatgtt aattgataga ataaagcctt gtgatcactt tctgaaattc acaaagttaa    2040
acgtgatgtg ctcatcagaa acaatttctg tgtcctgttt ttattccctt caatgcaaaa    2100
tacatgatga tttcagaaac aaagcatttg actttctgtc tgtggaggtg gagtaggtga    2160
aggcccagcc tgtaactgtc ctttttcttc ccttaggcaa tggtgaactg tcattacaga    2220
gcctagaggc tcacagcctc ctggaggaag cagcctccac tttggatcag gaaatagtaa    2280
aggaaagcag tgttgggggt agcggcatgc agaccctcag accagaatgg ggacatcttg    2340
tggtctgctg cctcaggaat ctcctgacca cttgtagtcc ctccgacttc tctagacatc    2400
tagtctcagt gctagcttat ttgtattttt cctctttcac ttcttatgga ggagagtgtt    2460
taactgagtt agaatgttga aactgacttg ctgtgactta tgtgcagctt ccagttgag     2520 cagaggaaaa tagtggcagg actgtccccc aggaggactc cctgcttagc tctgtgggag    2580
accaactacg actggcatct tctcttcccc ctggaaggca gctagacacc aatggatcct    2640
tgtcagttgt aacattctat ttcaacttca ggaaagcagc agttttcttt taatttttcc    2700
tatgaccata aaattagaca tacctctcaa cttacatatg tcttcaacat ggttacctct    2760
gcataaatat tagcaaagca tgccaatttc tcttaagtac tgaaatacat atgataaatt    2820
tgactgttat ttgttgagac tatcaaacag aaaagaaatt agggctctaa tttcttaaa    2880 gcaagctcac ttgctttagt tgttaagttt tataaaagac atgaaattga gtcatttat    2940 atatgaaaac taagttctct atcttaggag taatgtcggc ccacaagggt gcccacctct    3000 tgтттттcccc ttttaaaaac tcagattttt aaaagccctt tccaaaggtt tcaactgtaa    3060
aatacttctt tttacaatgt atcaacatat tttatttaa ggggaattaa caattgccag    3120
ggaaaccagc caacccaagt ttattatatc attaacctta tcataaattc aaacctaagt    3180
tgctggaccc tggtgtgagg acataaatct tccaaagttt tgcctatcct aagagctgca    3240

ттттт ctact gctcttt acc tt gcatttta gctaatt tag gagtttt gag aatgtatt gg    3300 atacgctcca gtacataagg agttgccgca tattatatca gactgctttg agaaatctca    3360
tccctagtct attgcagtt g tttctatt ag ctt actgatt aactcagtcc т gacacacct    3420

тт т gggaaat gctgatttaa actt cttaac т ggcaacagt т ggaacagta atcagtttgc    3480 taacatattt aaagtcttga atgttgaaga actcatgtga tttacccttt tcaacttttt    3540
ggaaaacgat ttaatttatt ctaattagat taaccctatt aatctatgga ttgggtatca    3600
aaatgaatgc cagtccagat gtgcctgaca cgaaattgg agctgaggac tctcacgata    3660

tgcaagttca tccaacgtga agataccata agcttttt tct ctgaaccaga gaaatgaaag    3720

tcagtttaag aggctgatag atcttggccc tgtt aaggca tccactt cac agttctgaag    3780 gctgagtcag cccактcca cagttaggcc aagaatt aga tttt aaaact т catctgtct    3840 gtcccagtta actgttaaat aaggcctcat cctccactga agagtatgga ttgaaggatt    3900
```

-continued

```
gtgaactatg tttagtgtga ttgtgaactt ggtgcctaat gttccatgtc tgaagtttgc    3960
cccagtgcta cacgttggag tatacctatg tgtgtgcttt gccactgaag taagattttg    4020
cctgtatggt actgttttgt ttgttaataa agtgcactgc cacccccaat gcaaaaaaaa    4080
aaaaaaaaaa                                                            4090
```

<210> SEQ ID NO 47
<211> LENGTH: 6784
<212> TYPE: DNA
<213> ORGANISM: Homo sapiens
<220> FEATURE:
<223> OTHER INFORMATION: glucocorticoid receptor (GR) alpha

<400> SEQUENCE: 47

```
ggcgccgcct ccacccgctc cccgctcggt cccgctcgct cgcccaggcc gggctgccct      60
ttcgcgtgtc cgcgctctct tccctccgcc gccgcctcct ccattttgcg agctcgtgtc     120
tgtgacggga gcccgagtca ccgcctgccc gtcggggacg gattctgtgg gtggaaggag     180
acgccgcagc cggagcggcc gaagcagctg ggaccgggac ggggcacgcg cgcccggaac     240
ctcgacccgc ggagcccggc gcggggcgga gggctggctt gtcagctggg caatgggaga     300 cttctcttaaa taggggctct cccccaccc atggagaaag gggcggctgt ttacttcctt     360 ttttttagaaa aaaaaatat atttccctcc tgctccttct gcgttcacaa gctaagttgt     420
ttatctcggc tgcggcggga actgcggacg gtggcgggcg agcggctcct ctgccagagt     480
tgatattcac tgatggactc caaagaatca ttaactcctg gtagagaaga aaaccccagc     540
agtgtgcttg ctcaggagag gggagatgtg atggacttct ataaaaccct aagaggagga     600
gctactgtga aggtttctgc gtcttcaccc tcactggctg tcgcttctca atcagactcc     660
aagcagcgaa gacttttggt tgattttcca aaaggctcag taagcaatgc gcagcagcca     720
gatctgtcca aagcagtttc actctcaatg ggactgtata tgggagagac agaaacaaaa     780
gtgatgggaa atgacctggg attcccacag cagggccaaa tcagcctttc ctcggggaa     840 acagacttaa agcttttgga gaaaagcatt gcaaacctca ataggtcgac cagtgttcca     900
gagaacccca agagttcagc atccactgct gtgtctgctg cccccacaga aaggagttt     960 ccaaaaactc actctgatgt atcttcagaa cagcaacatt tgaagggcca gactggcacc    1020
aacggtggca atgtgaaatt gtataccaca gaccaaagca cctttgacat tttgcaggat    1080
ttggagtttt cttctgggtc cccaggtaaa gagacgaatg agagtccttg gagatcagac    1140
ctgttgatag atgaaaactg tttgctttct cctctggcgg gagaagacga ttcattcctt    1200
ttggaaggaa actcgaatga ggactgcaag cctctcattt taccggacac taaacccaaa    1260
attaaggata tgagatct ggttttgtca agccccagta atgtaacact gccccaagtg    1320
aaaacagaaa agaagatt catcgaactc tgcacccctg ggtaattaa gcaagagaaa    1380 ctgggcacag tttactgtca ggcaagcttt cctggagcaa atataattgg taataaaatg    1440
tctgccattt ctgttcatgg tgtgagtacc tctggaggac agatgtacca ctatgacatg    1500
aatacagcat cccttttctca acagcaggat cagaagccta ttttaatgt cattccacca    1560 attcccgttg gttccgaaaa ttggaatagg tgccaaggat ctggagatga acttgact    1620 tctctgggga ctctgaactt ccctggtcga acagttttt ctaatggcta ttcaagcccc    1680
agcatgagac cagatgtaag ctctcctcca tccagctcct caacagcaac aacaggacca    1740
cctcccaaac tctgcctggt gtgctctgat gaagcttcag gatgtcatta tggagtctta    1800
```

```
acttgtggaa gctgtaaagt tttcttcaaa agagcagtgg aaggacagca caattaccta   1860
tgtgctggaa ggaatgattg catcatcgat aaaattcgaa gaaaaaactg cccagcatgc   1920
cgctatcgaa aatgtcttca ggctggaatg aacctggaag ctcgaaaaac aaagaaaaaa   1980
ataaaaggaa ttcagcaggc cactacagga gtctcacaag aaacctctga aaatcctggt   2040
aacaaaacaa tagttcctgc aacgttacca caactcaccc ctaccctggt gtcactgttg   2100
gaggttattg aacctgaagt gttatatgca ggatatgata gctctgttcc agactcaact   2160
tggaggatca tgactacgct caacatgtta ggagggcggc aagtgattgc agcagtgaaa   2220
tgggcaaagg caataccagg tttcaggaac ttacacctgg atgaccaaat gaccctactg   2280
cagtactcct ggatgtttct tatggcattt gctctggggt ggagatcata tagacaatca   2340
agtgcaaacc tgctgtgttt tgctcctgat ctgattatta atgagcagag aatgactcta   2400
ccctgcatgt acgaccaatg taaacacatg ctgtatgttt cctctgagtt acacaggctt   2460
caggtatctt atgaagagta tctctgtatg aaaaccttac tgcttctctc ttcagttcct   2520
aaggacggtc tgaagagcca agagctattt gatgaaatta gaatgaccta catcaaagag   2580
ctaggaaaag ccattgtcaa gagggaagga aactccagcc agaactggca gcggttttat   2640
caactgacaa aactcttgga ttctatgcat gaagtggttg aaaatctcct taactattgc   2700
ttccaaacat ttttggataa gaccatgagt attgaattcc ccgagatgtt agctgaaatc   2760
atcaccaatc agataccaaa atattcaaat ggaaatatca aaaaacttct gtttcatcaa   2820
aagtgactgc cttaataaga atggttgcct taaagaaagt cgaattaata gcttttattg   2880
tataaactat cagtttgtcc tgtagaggtt ttgttgtttt atttttttatt gttttcatct   2940 gttgttttgt tttaaatacg cactacatgt ggtttataga gggccaagac ttggcaacag   3000
aagcagttga gtcgtcatca cttttcagtg atgggagagt agatggtgaa atttattagt   3060
taatatatcc cagaaattag aaaccttaat atgtggacgt aatctccaca gtcaaagaag   3120
gatggcacct aaaccaccag tgcccaaagt ctgtgtgatg aactttctct tcatactttt   3180
tttcacagtt ggctggatga aattttctag actttctgtt ggtgtatccc ccccctgtat   3240
agttaggata gcattttga tttatgcatg gaaacctgaa aaaagtttta caagtgtata   3300
tcagaaaagg gaagttgtgc cttttatagc tattactgtc tggttttaac aatttccttt   3360
atatttagtg aactacgctt gctcattttt tcttacataa ttttttattc aagttattgt   3420
acagctgttt aagatgggca gctagttcgt agctttccca aataaactct aaacattaat   3480
caatcatctg tgtgaaaatg ggttggtgct ctaacctga tggcacttag ctatcagaag   3540
accacaaaaa ttgactcaaa tctccagtat tcttgtcaaa aaaaaaaaaa aaaagctca   3600 tattttgtat atatctgctt cagtggagaa ttatataggt tgtgcaaatt aacagtccta   3660
actggtatag agcacctagt ccagtgacct gctgggtaaa ctgtggatga tggttgcaaa   3720
agactaattt aaaaaataac taccaagagg ccctgtctgt acctaacgcc ctattttgc    3780 aatggctata tggcaagaaa gctggtaaac tatttgtctt tcaggacctt ttgaagtagt   3840
ttgtataact tcttaaaagt tgtgattcca gataaccagc tgtaacacag ctgagagact   3900
tttaatcaga caaagtaatt cctctcacta aactttaccc aaaaactaaa tctctaatat   3960
ggcaaaaatg gctagacacc cattttcaca ttcccatctg tcaccaattg gttaatcttt   4020
cctgatggta caggaaagct cagctactga ttttgtgat ttagaactgt atgtcagaca   4080
tccatgtttg taaaactaca catccctaat gtgtgccata gagtttaaca caagtcctgt   4140
gaatttcttc actgttgaaa attatttttaa acaaaataga agctgtagta gcccttttctg  4200
```

```
tgtgcacctt accaacttc tgtaaactca aaacttaaca tatttactaa gccacaagaa    4260
atttgatttc tattcaaggt ggccaaatta tttgtgtaat agaaaactga aaatctaata    4320
ttaaaaatat ggaacttcta atatattttt atatttagtt atagtttcag atatatatca    4380
tattggtatt cactaatctg ggaagggaag ggctactgca gctttacatg caatttatta    4440
aaatgattgt aaaatagctt gtatagtgta aaataagaat gattttaga tgagattgtt     4500 ttatcatgac atgttatata tttttgtag gggtcaaaga aatgctgatg gataacctat    4560
atgatttata gtttgtacat gcattcatac aggcagcgat ggtctcagaa accaaacagt    4620
ttgctctagg ggaagaggga gatggagact ggtcctgtgt gcagtgaagg ttgctgaggc    4680
tctgacccag tgagattaca gaggaagtta tcctctgcct cccattctga ccacccttct    4740
cattccaaca gtgagtctgt cagcgcaggt ttagtttact caatctcccc ttgcactaaa    4800
gtatgtaaag tatgtaaaca ggagacagga aggtggtgct tacatcctta aaggcaccat    4860
ctaatagcgg gttactttca catacagccc tcccccagca gttgaatgac aacagaagct    4920
tcagaagttt ggcaatagtt tgcatagagg taccagcaat atgtaaatag tgcagaatct    4980
cataggttgc caataataca ctaattcctt tctatcctac aacaagagtt tatttccaaa    5040
taaaatgagg acatgttttt gttttctttg aatgcttttt gaatgttatt tgttattttc    5100 agtatttgg agaaattatt taataaaaaa acaatcattt gcttttgaa tgctctctaa      5160 aagggaatgt aatattttaa gatggtgtgt aacccggctg gataaatttt tggtgcctaa    5220
gaaaactgct tgaatattct tatcaatgac agtgttaagt ttcaaaaaga gcttctaaaa    5280
cgtagattat cattccttta tagaatgtta tgtggttaaa accagaaagc acatctcaca    5340
cattaatctg attttcatcc caacaatctt ggcgctcaaa aaatagaact caatgagaaa    5400
aagaagatta tgtgcacttc gttgtcaata ataagtcaac tgatgctcat cgacaactat    5460
aggaggcttt tcattaaatg ggaaagaag ctgtgcccctt ttaggatacg tgggggaaaa    5520
gaaagtcatc ttaattatgt ttaattgtgg atttaagtgc tatatggtgg tgctgtttga    5580
aagcagattt atttcctatg tatgtgttat ctggccatcc caacccaaac tgttgaagtt    5640
tgtagtaact tcagtgagag ttggttactc acaacaaatc ctgaaaagta tttttagtgt    5700
ttgtaggtat tctgtgggat actatacaag cagaactgag gcacttagga cataacactt    5760
ttggggtata tatatccaaa tgcctaaaac tatgggagga aaccttggcc accccaaaag   5820
gaaaactaac atgatttgtg tctatgaagt gctggataat tagcatggga tgagctctgg    5880
gcatgccatg aaggaaagcc acgctccctt cagaattcag aggcagggag caattccagt    5940
ttcacctaag tctcataatt ttagttccct tttaaaaacc ctgaaaacta catcaccatg    6000
gaatgaaaaa tattgttata caatacattg atctgtcaaa cttccagaac catggtagcc    6060
ttcagtgaga tttccatctt ggctggtcac tccctgactg tagctgtagg tgaatgtgtt    6120
tttgtgtgtg tgtgtctggt tttagtgtca gaagggaaat aaaagtgtaa ggaggacact    6180 ttaaacccctt tgggtggagt ttcgtaattt cccagactat tttcaagcaa cctggtccac   6240
ccaggattag tgaccaggtt ttcaggaaag gatttgcttc tctctagaaa atgtctgaaa    6300
ggattttatt ttctgatgaa aggctgtatg aaaatacccct cctcaaataa cttgcttaac    6360
tacatataga ttcaagtgtg tcaatattct attttgtata ttaaatgcta tataatgggg    6420
acaaatctat attatactgt gtatggcatt attaagaagc tttttcatta ttttttatca    6480
cagtaatttt aaaatgtgta aaaattaaaa ccagtgactc ctgtttaaaa ataaaagttg    6540
```

| | |
|---|---|
| tagttttta ttcatgctga ataataatct gtagttaaaa aaaaagtgtc ttttttaccta | 6600 |
| cgcagtgaaa tgtcagactg taaaaccttg tgtggaaatg tttaactttt attttttcat | 6660 |
| ttaaatttgc tgttctggta ttaccaaacc acacatttgt accgaattgg cagtaaatgt | 6720 |
| tagccattta cagcaatgcc aaatatggag aaacatcata ataaaaaaat ctgcttttc | 6780 |
| atta | 6784 |

<210> SEQ ID NO 48
<211> LENGTH: 4154
<212> TYPE: DNA
<213> ORGANISM: Homo sapiens
<220> FEATURE:
<223> OTHER INFORMATION: glucocorticoid receptor (GR) beta

<400> SEQUENCE: 48

| | |
|---|---|
| ggcgccgcct ccacccgctc cccgctcggt cccgctcgct cgcccaggcc gggctgccct | 60 |
| ttcgcgtgtc cgcgctctct tccctccgcc gccgcctcct ccattttgcg agctcgtgtc | 120 |
| tgtgacggga gcccgagtca ccgcctgccc gtcggggacg gattctgtgg gtggaaggag | 180 |
| acgccgcagc cggagcggcc gaagcagctg ggaccgggac ggggcacgcg cgcccggaac | 240 |
| ctcgacccgc ggagcccggc gcggggcgga gggctggctt gtcagctggg caatgggaga | 300 |
| ctttcttaaa taggggctct ccccccaccc atggagaaag gggcggctgt ttacttcctt | 360 |
| tttttagaaa aaaaaatat atttccctcc tgctccttct gcgttcacaa gctaagttgt | 420 |
| ttatctcggc tgcggcggga actgcggacg gtggcgggcg agcggctcct ctgccagagt | 480 |
| tgatattcac tgatggactc caagaatca ttaactcctg gtagagaaga aaaccccagc | 540 |
| agtgtgcttg ctcaggagag gggagatgtg atggacttct ataaaccct aagaggagga | 600 |
| gctactgtga aggtttctgc gtcttcaccc tcactggctg tcgcttctca atcagactcc | 660 |
| aagcagcgaa gactttggt tgattttcca aaaggctcag taagcaatgc gcagcagcca | 720 |
| gatctgtcca aagcagtttc actctcaatg ggactgtata tgggagagac agaaacaaaa | 780 |
| gtgatgggaa atgacctggg attcccacag cagggccaaa tcagcctttc ctcgggggaa | 840 |
| acagacttaa agcttttgga agaaagcatt gcaaacctca ataggtcgac cagtgttcca | 900 |
| gagaacccca gagttcagc atccactgct gtgtctgctg cccccacaga aaggagtttt | 960 |
| ccaaaaactc actctgatgt atcttcagaa cagcaacatt tgaagggcca gactggcacc | 1020 |
| aacggtggca atgtgaaatt gtataccaca gaccaaagca cctttgacat tttgcaggat | 1080 |
| ttggagtttt cttctgggtc cccaggtaaa gagacgaatg agagtccttg agatcagac | 1140 |
| ctgttgatag atgaaaactg tttgctttct cctctggcgg gagaagacga ttcattcctt | 1200 |
| ttggaaggaa actcgaatga ggactgcaag cctctcattt taccggacac taaacccaaa | 1260 |
| attaaggata atggagatct ggttttgtca agccccagta atgtaacact gccccaagtg | 1320 |
| aaaacagaaa aagaagattt catcgaactc tgcacccctg gggtaattaa gcaagagaaa | 1380 |
| ctgggcacag tttactgtca ggcaagcttt cctggagcaa atataattgg taataaaatg | 1440 |
| tctgccattt ctgttcatgg tgtgagtacc tctggaggac agatgtacca ctatgacatg | 1500 |
| aatacagcat ccctttctca acagcaggat cagaagccta ttttaatgt cattccacca | 1560 |
| attcccgttg gttccgaaaa ttggaatagg tgccaaggat ctggagatga aacttgact | 1620 |
| tctctgggga ctctgaactt ccctggtcga acagttttt ctaatggcta ttcaagcccc | 1680 |
| agcatgagac cagatgtaag ctctcctcca tccagctcct caacagcaac aacaggacca | 1740 |
| cctcccaaac tctgcctggt gtgctctgat gaagcttcag gatgtcatta tggagtctta | 1800 |

```
acttgtggaa gctgtaaagt tttcttcaaa agagcagtgg aaggacagca caattaccta    1860
tgtgctggaa ggaatgattg catcatcgat aaaattcgaa gaaaaaactg cccagcatgc    1920
cgctatcgaa aatgtcttca ggctggaatg aacctggaag ctcgaaaaac aaagaaaaaa    1980
ataaaaggaa ttcagcaggc cactacagga gtctcacaag aaacctctga aaatcctggt    2040
aacaaaacaa tagttcctgc aacgttacca caactcaccc ctaccctggt gtcactgttg    2100
gaggttattg aacctgaagt gttatatgca ggatatgata gctctgttcc agactcaact    2160
tggaggatca tgactacgct caacatgtta ggagggcggc aagtgattgc agcagtgaaa    2220
tgggcaaagg caataccagg tttcaggaac ttacacctgg atgaccaaat gaccctactg    2280
cagtactcct ggatgtttct tatggcattt gctctggggt ggagatcata tagacaatca    2340
agtgcaaacc tgctgtgttt tgctcctgat ctgattatta atgagcagag aatgactcta    2400
ccctgcatgt acgaccaatg taaacacatg ctgtatgttt cctctgagtt acacaggctt    2460
caggtatctt atgaagagta tctctgtatg aaaaccttac tgcttctctc ttcagttcct    2520
aaggacggtc tgaagagcca agagctattt gatgaaatta aatgaccta catcaaagag    2580 ctaggaaaag ccattgtcaa gagggaagga aactccagcc agaactggca gcggttttat    2640
caactgacaa aactcttgga ttctatgcat gaaaatgtta tgtggttaaa accagaaagc    2700
acatctcaca cattaatctg atttcatcc caacaatctt ggcgctcaaa aaatagaact    2760
caatgagaaa aagaagatta tgtgcacttc gttgtcaata ataagtcaac tgatgctcat    2820
cgacaactat aggaggcttt tcattaaatg ggaaagaag ctgtgcccct ttaggatacg     2880 tggggaaaa gaaagtcatc ttaattatgt ttaattgtgg atttaagtgc tatatggtgg     2940
tgctgtttga aagcagattt atttcctatg tatgtgttat ctggccatcc caacccaaac    3000
tgttgaagtt tgtagtaact tcagtgagag ttggttactc acaacaaatc tgaaaagta    3060 tttttagtgt ttgtaggtat tctgtgggat actatacaag cagaactgag gcacttagga    3120
cataacactt tgggtata tatatccaaa tgcctaaaac tatgggagga aaccttggcc     3180
accccaaaag gaaaactaac atgatttgtg tctatgaagt gctggataat tagcatggga    3240
tgagctctgg gcatgccatg aaggaaagcc acgctcccct cagaattcag aggcagggag    3300
caattccagt ttcacctaag tctcataatt ttagttccct tttaaaaacc ctgaaaacta    3360
catcaccatg gaatgaaaaa tattgttata caatacattg atctgtcaaa cttccagaac    3420
catggtagcc ttcagtgaga tttccatctt ggctggtcac tccctgactg tagctgtagg    3480
tgaatgtgtt tttgtgtgtg tgtgtctggt tttagtgtca gaagggaaat aaaagtgtaa    3540
ggaggacact ttaaacccct tgggtggagt ttcgtaattt cccagactat tttcaagcaa    3600
cctggtccac ccaggattag tgaccaggtt tcaggaaag gatttgcttc tctctagaaa     3660
atgtctgaaa ggatttttatt ttctgatgaa aggctgtatg aaaatacccct cctcaaataa    3720 cttgcttaac tacatataga ttcaagtgtg tcaatattct attttgtata ttaaatgcta    3780
tataatgggg acaaatctat attatactgt gtatggcatt attaagaagc ttttcatta    3840 ttttttatca cagtaatttt aaaatgtgta aaaattaaaa ccagtgactc ctgtttaaaa    3900
ataaaagttg tagttttta ttcatgctga ataataatct gtagttaaaa aaaagtgtc    3960 tttttaccta cgcagtgaaa tgtcagactg taaaaccttg tgtggaaatg tttaactttt    4020 atttttcat ttaaatttgc tgttctggta ttaccaaacc acacatttgt accgaattgg    4080
cagtaaatgt tagccatta cagcaatgcc aaatatggag aaacatcata ataaaaaaat    4140
``` ctgcttttc atta                                                              4154

<210> SEQ ID NO 49
<211> LENGTH: 6330
<212> TYPE: DNA
<213> ORGANISM: Homo sapiens
<220> FEATURE:
<223> OTHER INFORMATION: nuclear receptor subfamily 3, group A, member
      1, transcript variant 4 (NR3A1), estrogen receptor
      (ESR1, ER, ESR, ESRA, ESTRR) cDNA (complete)

<400> SEQUENCE: 49
aggagctggc ggagggcgtt cgtcctggga ctgcacttgc tcccgtcggg tcgcccggct    60
tcaccggacc cgcaggctcc cggggcaggg ccggggccag agctcgcgtg tcggcgggac    120
atgcgctgcg tcgcctctaa cctcgggctg tgctcttttt ccaggtggcc cgccggtttc    180
tgagccttct gccctgcggg gacacggtct gcaccctgcc cgcggccacg gaccatgacc    240
atgaccctcc acaccaaagc atctgggatg ccctactgc atcagatcca agggaacgag    300
ctggagcccc tgaaccgtcc gcagctcaag atccccctgg agcggcccct gggcgaggtg    360
tacctggaca gcagcaagcc cgccgtgtac aactaccccg agggcgccgc ctacgagttc    420
aacgccgcgg ccgccgccaa cgcgcaggtc tacggtcaga ccggcctccc ctacggcccc    480
gggtctgagg ctgcggcgtt cggctccaac ggcctggggg gtttcccccc actcaacagc    540
gtgtctccga gccgctgat gctactgcac ccgccgccgc agctgtcgcc tttcctgcag    600
ccccacggcc agcaggtgcc ctactacctg gagaacgagc ccagcggcta cacggtgcgc    660
gaggccggcc cgccggcatt ctacaggcca aattcagata tcgacgcca gggtggcaga    720 gaaagattgg ccagtaccaa tgacaaggga gtatggcta tggaatctgc caaggagact    780
cgctactgtg cagtgtgcaa tgactatgct tcaggctacc attatggagt ctggtcctgt    840
gagggctgca aggccttctt caagagaagt attcaaggac ataacgacta tatgtgtcca    900
gccaccaacc agtgcaccat tgataaaaac aggaggaaga gctgccaggc ctgccggctc    960
cgcaaatgct acgaagtggg aatgatgaaa ggtgggatac gaaaagaccg aagaggaggg    1020
agaatgttga acacaagcg ccagagagat gatgggaggg caggggtga agtgggtct    1080 gctggagaca tgagagctgc caacctttgg ccaagcccgc tcatgatcaa acgctctaag    1140
aagaacagcc tggccttgtc cctgacggcc gaccagatgg tcagtgcctt gttggatgct    1200
gagcccccca tactctattc cgagtatgat cctaccagac ccttcagtga agcttcgatg    1260
atgggcttac tgaccaacct ggcagacagg gagctggttc acatgatcaa ctgggcgaag    1320
agggtgccag gctttgtgga tttgaccctc catgatcagg tccaccttct agaatgtgcc    1380
tggctagaga tcctgatgat tggtctcgtc tggcgctcca tggagcaccc agggaagcta    1440
ctgtttgctc ctaacttgct cttggacagg aaccagggaa atgtgtaga gggcatggtg    1500 gagatcttcg acatgctgct ggctacatca tctcggttcc gcatgatgaa tctgcaggga    1560
gaggagtttg tgtgcctcaa atctattatt ttgcttaatt ctggagtgta cacatttctg    1620
tccagcaccc tgaagtctct ggaagagaag gaccatatcc accgagtcct ggacaagatc    1680
acagacactt tgatccacct gatggccaag gcaggcctga ccctgcagca gcagcaccag    1740
cggctggccc agctcctcct catcctctcc cacatcaggc acatgagtaa caaaggcatg    1800
gagcatctgt acagcatgaa gtgcaagaac gtggtgcccc tctatgacct gctgctggag    1860
atgctggacg cccaccgcct acatgcgccc actagccgtg aggggcatc cgtggaggag    1920 acggaccaaa gccacttggc cactgcgggc tctacttcat cgcattcctt gcaaaagtat    1980

```
tacatcacgg gggaggcaga gggtttccct gccacggtct gagagctccc tggctcccac    2040
acggttcaga taatccctgc tgcattttac cctcatcatg caccacttta gccaaattct    2100
gtctcctgca tacactccgg catgcatcca acaccaatgg ctttctagat gagtggccat    2160
tcatttgctt gctcagttct tagtggcaca tcttctgtct tctgttggga acagccaaag    2220
ggattccaag gctaaatctt tgtaacagct ctctttcccc cttgctatgt tactaagcgt    2280
gaggattccc gtagctcttc acagctgaac tcagtctatg ggttgggct cagataactc    2340 tgtgcattta agctacttgt agagacccag gcctggagag tagacatttt gcctctgata    2400 agcactttt aaatggctct aagaataagc cacagcaaag aatttaaagt ggctccttta    2460
attggtgact tggagaaagc taggtcaagg gttattata gcaccctctt gtattcctat    2520
ggcaatgcat cctttatga aagtggtaca ccttaaagct tttatatgac tgtagcagag    2580
tatctggtga ttgtcaattc attccccta taggaataca aggggcacac agggaaggca    2640
gatcccctag ttggcaagac tattttaact tgatacactg cagattcaga tgtgctgaaa    2700
gctctgcctc tggctttccg gtcatgggtt ccagttaatt catgcctccc atggacctat    2760
ggagagcagc aagttgatct tagttaagtc tccctatatg agggataagt tcctgatttt    2820 tgttttatt tttgtgttac aaaagaaagc cctccctccc tgaacttgca gtaaggtcag    2880
cttcaggacc tgttccagtg ggcactgtac ttggatcttc ccggcgtgtg tgtgccttac    2940 acagggtga actgttcact gtggtgatgc atgatgaggg taaatggtag ttgaaaggag    3000 cagggggccct ggtgttgcat ttagccctgg ggcatggagc tgaacagtac ttgtgcagga    3060
ttgttgtggc tactagagaa caagagggaa agtagggcag aaactggata cagttctgag    3120
gcacagccag acttgctcag ggtggccctg ccacaggctg cagctaccta ggaacattcc    3180
ttgcagaccc cgcattgccc tttggggtg ccctgggatc cctggggtag tccagctctt    3240
cttcatttcc cagcgtggcc ctggttggaa gaagcagctg tcacagctgc tgtagacagc    3300
tgtgttccta caattggccc agcaccctgg ggcacgggag aagggtgggg accgttgctg    3360
tcactactca ggctgactgg ggcctggtca gattacgtat gcccttggtg gtttagagat    3420
aatccaaaat cagggtttgg tttggggaag aaaatcctcc cccttcctcc cccgcccgt    3480 tccctaccgc ctccactcct gccagctcat ttccttcaat ttcctttgac ctataggcta    3540 aaaagaaag gctcattcca gccacagggc agccttccct gggcctttgc ttctctagca    3600
caattatggg ttacttcctt tttcttaaca aaaagaatg tttgatttcc tctgggtgac    3660
cttattgtct gtaattgaaa ccctattgag aggtgatgtc tgtgttagcc aatgacccag    3720
gtgagctgct cgggcttctc ttggtatgtc ttgtttggaa aagtggattt cattcatttc    3780
tgattgtcca gttaagtgat caccaaagga ctgagaatct ggagggcaa aaaaaaaaa    3840 aaagtttta tgtgcactta aatttgggga caatttatg tatctgtgtt aaggatatgt    3900
ttaagaacat aattctttg ttgctgtttg tttaagaagc accttagttt gtttaagaag    3960
caccttatat agtataatat atattttttt gaaattacat tgcttgttta tcagacaatt    4020
gaatgtagta attctgttct ggatttaatt tgactgggtt aacatgcaaa aaccaaggaa    4080
aaatatttag tttttttttt tttttttgta tacttttcaa gctaccttgt catgtataca    4140
gtcatttatg cctaaagcct ggtgattatt catttaaatg aagatcacat ttcatatcaa    4200
cttttgtatc cacagtagac aaaatagcac taatccagat gcctattgtt ggatactgaa    4260
tgacagacaa tcttatgtag caaagattat gcctgaaaag gaaaattatt cagggcagct    4320
```

```
aattttgctt ttaccaaaat atcagtagta atattttgg acagtagcta atgggtcagt    4380
gggttctttt taatgtttat acttagattt tcttttaaaa aaattaaaat aaaacaaaaa    4440
aaaatttcta ggactagacg atgtaatacc agctaaagcc aaacaattat acagtggaag    4500
gttttacatt attcatccaa tgtgtttcta ttcatgttaa gatactacta catttgaagt    4560
gggcagagaa catcagatga ttgaaatgtt cgcccagggg tctccagcaa ctttggaaat    4620
ctctttgtat ttttacttga agtgccacta atggacagca gatattttct ggctgatgtt    4680
ggtattgggt gtaggaacat gatttaaaaa aaaactcttg cctctgcttt cccccactct    4740
gaggcaagtt aaaatgtaaa agatgtgatt tatctggggg gctcaggtat ggtggggaag    4800
tggattcagg aatctgggga atggcaaata tattaagaag agtattgaaa gtatttggag    4860
gaaaatggtt aattctgggt gtgcaccagg gttcagtaga gtccacttct gccctggaga    4920
ccacaaatca actagctcca tttacagcca tttctaaaat ggcagcttca gttctagaga    4980
agaaagaaca acatcagcag taaagtccat ggaatagcta gtggtctgtg tttctttcg    5040 ccattgccta gcttgccgta atgattctat aatgccatca tgcagcaatt atgagaggct    5100
aggtcatcca aagagaagac cctatcaatg taggttgcaa aatctaaccc ctaaggaagt    5160
gcagtctttg atttgatttc cctagtaacc ttgcagatat gtttaaccaa gccatagccc    5220
atgccttttg agggctgaac aaataaggga cttactgata atttactttt gatcacatta    5280
aggtgttctc accttgaaat cttatacact gaaatggcca ttgatttagg ccactggctt    5340
agagtactcc ttcccctgca tgacactgat tacaaatact ttcctattca tactttccaa    5400
ttatgagatg gactgtgggt actgggagtg atcactaaca ccatagtaat gtctaatatt    5460
cacaggcaga tctgcttggg gaagctagtt atgtgaaagg caaatagagt catacagtag    5520
ctcaaaaggc aaccataatt ctctttggtg caggtcttgg gagcgtgatc tagattacac    5580
tgcaccattc ccaagttaat cccctgaaaa cttactctca actggagcaa atgaactttg    5640
gtcccaaata tccatctttt cagtagcgtt aattatgctc tgtttccaac tgcatttcct    5700
ttccaattga attaaagtgt ggcctcgttt ttagtcattt aaaattgttt tctaagtaat    5760
tgctgcctct attatggcac ttcaattttg cactgtcttt tgagattcaa gaaaaatttc    5820
tattcttttt tttgcatcca attgtgcctg aacttttaaa atatgtaaat gctgccatgt    5880
tccaaaccca tcgtcagtgt gtgtgtttag agctgtgcac cctagaaaca acatattgtc    5940
ccatgagcag gtgcctgaga cacagacccc tttgcattca cagagaggtc attggttata    6000
gagacttgaa ttaataagtg acattatgcc agtttctgtt ctctcacagg tgataaacaa    6060 tgcttttttgt gcactacata ctcttcagtg tagagctctt gttttatggg aaaaggctca    6120
aatgccaaat tgtgtttgat ggattaatat gcccttttgc cgatgcatac tattactgat    6180
gtgactcggt tttgtcgcag ctttgctttg tttaatgaaa cacacttgta aacctctttt    6240
gcactttgaa aaagaatcca gcgggatgct cgagcacctg taaacaattt tctcaaccta    6300
tttgatgttc aaataaagaa ttaaaactaaa                                   6330
```